(12) United States Patent
Casuscelli et al.

(10) Patent No.: US 8,541,576 B2
(45) Date of Patent: *Sep. 24, 2013

(54) SUBSTITUTED PYRAZOLO-QUINAZOLINE DERIVATIVES AS KINASE INHIBITORS

(75) Inventors: Francesco Casuscelli, Nerviano (IT); Claudia Piutti, Nerviano (IT); Antonella Ermoli, Nerviano (IT); Daniela Faiardi, Nerviano (IT)

(73) Assignee: Nerviano Medical Sciences SRL, Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/327,979

(22) Filed: Dec. 16, 2011

(65) Prior Publication Data

US 2012/0190678 A1    Jul. 26, 2012

(30) Foreign Application Priority Data

Dec. 17, 2010    (EP) .................................. 10195675

(51) Int. Cl.
C07D 487/04    (2006.01)
A61K 31/517    (2006.01)

(52) U.S. Cl.
USPC ........................................ 544/251; 514/267

(58) Field of Classification Search
USPC ........................................ 514/267; 544/251
See application file for complete search history.

(56) References Cited

U.S. PATENT DOCUMENTS

| | | | |
|---|---|---|---|
| 6,057,329 A | 5/2000 | Davis et al. | |
| 6,133,257 A | 10/2000 | Batchelor et al. | |
| 7,482,354 B2 * | 1/2009 | Traquandi et al. | 514/267 |
| 2002/0119975 A1 | 8/2002 | Snow et al. | |
| 2003/0100594 A1 | 5/2003 | Masferrer et al. | |
| 2010/0216808 A1 | 8/2010 | Caruso et al. | |

FOREIGN PATENT DOCUMENTS

| | | |
|---|---|---|
| WO | 96/40142 | 12/1996 |
| WO | 98/58926 | 12/1998 |
| WO | 00/69846 | 11/2000 |
| WO | 01/12188 A1 | 2/2001 |
| WO | 01/12189 A1 | 2/2001 |
| WO | 02/12242 A2 | 2/2002 |
| WO | 02/48114 A1 | 6/2002 |
| WO | 02/070515 A2 | 9/2002 |
| WO | 03/028720 A1 | 4/2003 |
| WO | 03/070706 A1 | 8/2003 |
| WO | 98/28281 | 8/2003 |
| WO | 2004/014352 A2 | 2/2004 |
| WO | 2004/104007 A1 | 2/2004 |
| WO | 2008/074788 A1 | 6/2008 |
| WO | 2009/156315 A1 | 12/2009 |
| WO | 2011/012534 A1 | 2/2011 |

OTHER PUBLICATIONS

Angiolini et al., "Structure-based optimization of potent PDK1 inhibitors" Bioorg Med Chem Lett. 20(14):4095-9 (2010).

(Continued)

*Primary Examiner* — Timothy Thomas
*Assistant Examiner* — Rayna B Rodriguez
(74) *Attorney, Agent, or Firm* — Alex Andrus; Genentech, Inc.

(57) ABSTRACT

The present invention relates to substituted pyrazolo[4,3-h] quinazoline compounds which modulate the activity of protein kinases and are therefore useful in treating diseases caused by dysregulated protein kinase activity, in particular PIM kinases. The present invention also provides methods for preparing these compounds, pharmaceutical compositions comprising these compounds, and methods of treating diseases utilizing such these compounds or the pharmaceutical compositions containing them.

2 Claims, 2 Drawing Sheets

(56) References Cited

OTHER PUBLICATIONS

Beria et al., "Identification of 4,5-dihydro-1H-pyrazolo[4,3-h]quinazoline derivatives as a new class of orally and selective Polo-like kinase 1 inhibitors" J Med Chem. 53(9):3532-51 (2010).

Beria, "4-5-Dihydro-1H-pyrazolo[4,3-h]quinazolines as potent and selective Polo-like kinase 1 (PLK1) inhibitors" Bioorg Med Chem Lett. 20(22):6489-94 (2010).

Brasca et al., "Idenification of N,1,4,4-tetramethyl-8-{[4-(4-methylpiperazin-1-yl)phenyl]amino}-4,5-dihydro-1H-pyrazolo[4,3-h]quinazoline-3-carboxamide (PHA-848125), a potent, oally available cyclin dependent kinase inhibitor" J Med Chem. 52(16):5152-63 (2009).

PCT ISR for PCT/IB2011/055743.

Pihan et al., "Centrosome defects can account for cellular and genetic changes that characterize prostate cancer progression" Cancer Res. 61(5):2212-9 (2001).

Traquandi et al., "Identification of potent pyrazolo[4,3,-h]quinazoline-3-carboxamides as multi-cyclin-dependent kinase inhibitors" J Med Chem. 53(5):2171-87 (2010).

\* cited by examiner

SUBSTITUTED PYRAZOLO-QUINAZOLINE DERIVATIVES AS KINASE INHIBITORS

This application claims the benefit under 35 USC §119(a) of European Patent Application No. 10195675.3 filed on 17 Dec. 2010, which is incorporated by reference in entirety

FIELD OF THE INVENTION

The present invention relates to certain substituted pyrazolo[4,3-h]quinazoline compounds, which modulate the activity of protein kinases and in particular, Pim kinase (Pim-1, Pim-2, and/or Pim-3) inhibitors. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

BACKGROUND OF THE INVENTION

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3, 459-465 and Carcinogenesis 2008, 29, 1087-1091.

Originally identified as activated genes by proviral mutagenesis in a lymphoma mouse model, PIMs (PIM1, PIM2 and/or PIM-3 throughout this application) are protein-serine/threonine kinases. PIM kinases are poorly expressed in normal tissues, and overexpressed or even mutated in a discrete number of human cancers, including Lymphoma, Leukaemia, Prostate, Pancreas and Gastric cancers [Shah et al. *Eur. J. Cancer*, 44, 2144-51, (2008)].

PIM kinases are constitutively active and their activity supports in vitro and in vivo tumor cell growth and survival through modification of an increasing number of common as well as isoform-specific substrates including several cell cycle regulators and apoptosis mediators. PIM1 but not PIM2 seems also to mediate homing and migration of normal and malignant hematopoietic cells by regulating chemokine receptor surface expression [Brault et al. *Haematologica* 95 1004-1015 (2010)].

There is increasing evidence that PIM1 and PIM2 kinases may be involved in mediating the oncogenic effects of some acute myelogenous leukemias (AML)-associated oncogenes. In particular, the oncogenic role of FLT3-mutations (ITD and KD mut., present in 30% of AMLs) and/or translocations involving the MLL gene (occurring in 20% of AMLs), (Kumar, et al. (2005) *J. Mol. Biol.* 348, 183-193). PIM1 is more expressed in FLT3-ITD-transformed AML cells than in WT bone marrow cells. Data suggest that PIM1 as well as PIM2 inhibition may mediate FLT3ITD-dependent death of AML cells. Interestingly, cells transformed by FLT3 mutations that confer resistance to small-molecule tyrosine kinase inhibitors were still sensitive to knockdown of PIM2, or PIM-1 and PIM-2 by RNAi (Kim et al. (2005) *Blood* 105:1759-67).

Moreover, PIM2 has been reported being over-expressed and associated with progression of several malignancies that originate from the B-cell lineage such as chronic lymphocytic leukemia (CLL), diffuse large B-cell lymphoma (DLBCL), mantle cell lymphoma (MCL) or myeloma (Cohen et al. (2004) *Leuk. Lymphoma* 94:51; Huttmann et al (2006) *Leukemia* 20 1774).

Interestingly, PIM and AKT/PKB seem to play partly redundant roles in mediating growth and survival of hematopoietic cells most probably due to overlapping substrates like BAD, $p21^{WAF1/CIP1}$, $p27^{KIP1}$, or Cot/Tp1-2 [Choudhary et al., *Mol Cell.* 36 326-39 (2009)].

PIM kinases have been shown to control mTOR inhibition (rapamycin) resistant, proliferation and survival. Therefore, a combination of small molecule inhibitors targeting several survival kinases might be essential for a powerful cancer therapeutic platform [Amaravadi R., et al. *J. Clin. Invest.* 2005, 115 (10) 2618-24]. Oncogenic protein synthesis through eIF4E binding protein 1 (4E-BP1) seems to be mTOR-independent and controlled by PIM-2. This observations suggest that the oncogenic eIF4F translation-initiating complex could be blocked with small molecules PIM-2 inhibitors [Tamburini J. et al. Blood 2009, 114 (8), 1718-27 and Brault L. et al. Haematologica 2010, 95 (6) 1004-1015].

Pyrazolo-quinazoline derivatives possessing kinase inhibitory activity have been also disclosed in WO 04/104007, in the name of Pharmacia Italia S.P.A. Some specific compounds of the aforementioned WO 04/104007 are excluded from the present general formula.

Despite these developments, there is still need for effective agents for said diseases.

SUMMARY OF THE INVENTION

A new class of substituted pyrazolo[4,3-h]quinazoline compounds has now been identified endowed with a higher activity than previously achieved in the prior art. These compounds were found able to prevent the proliferation of human tumor cells at a remarkably low concentration, thereby maximizing the antitumor efficacy while simultaneously reducing risk of the side effects linked to the administration of higher amounts of drugs.

The new compounds have the structure shown in formula (I)

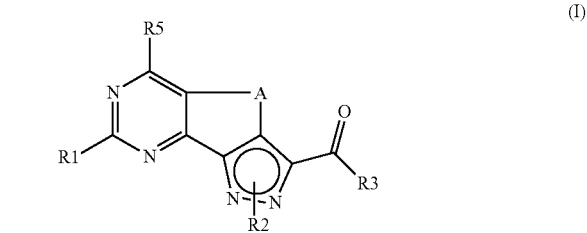

wherein
R1 is hydrogen, CN, an optionally substituted group selected from straight or branched $C_1$-$C_6$ alkyl,
$C_3$-$C_7$ cycloalkyl, cycloalkylalkyl, aryl, arylalkyl, heterocyclyl and heterocyclylalkyl, or a group XR4, wherein
X is a divalent radical selected from O, S, SO, $SO_2$ and NR6, wherein R6 is an optionally substituted straight or branched $C_1$-$C_6$ alkyl or, together with the nitrogen atom to which they are bound, R6 and R4 may form a 5 to 6 membered heteroaryl or heterocyclyl group optionally containing one additional heteroatom selected from N, O and S;

R2 is hydrogen or an optionally substituted group selected from straight or branched $C_1$-$C_6$ alkyl, straight or branched $C_2$-$C_6$ alkenyl, $C_3$-$C_7$ cycloalkyl, cycloalkylalkyl, aryl, arylalkyl, heterocyclyl and heterocyclylalkyl;

R3 is a group selected from NR'R" and N(OH)R', wherein R' and R" are each independently, hydrogen or an optionally substituted group selected from straight or branched $C_1$-$C_6$ alkyl, $C_3$-$C_7$ cycloalkyl, cycloaklylalkyl, aryl, arylalkyl, heterocyclyl and heterocyclylalkyl;

R4 is a group selected from optionally substituted straight or branched $C_1$-$C_6$ alkyl, $C_3$-$C_7$ cycloalkyl, cycloalkylalkyl, aryl, arylalkyl, heterocyclyl and heterocyclylalkyl;

R5 is hydrogen or NR'R" wherein R' and R" are each independently, hydrogen or an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or together with the nitrogen atom to which they are bound, R' and R" may form a 5 to 6 membered heteroaryl or heterocyclyl group optionally containing one additional heteroatom selected from N, O and S;

A is a divalent group selected from —($CH_2$)$_2$— and —CH=CH—; and the pharmaceutically acceptable salts thereof, with the exception of:

1-methyl-8-(piperidin-1-yl)-4,5-dihydro-1H-pyrazolo[4,3-h]quinazoline-3-carboxamide, 1-methyl-8-(methylsulfanyl)-4,5-dihydro-1H-pyrazolo[4,3-h]quinazoline-3-carboxamide and 1-methyl-8-(methylsulfonyl)-4,5-dihydro-1H-pyrazolo[4,3-h]quinazoline-3-carboxamide.

The present invention also provides methods of synthesizing the substituted pyrazolo[4,3-h]quinazoline compounds, represented by the formula (I), prepared through a process consisting of standard synthetic transformations and isomers, tautomers, hydrates, solvates, complexes, metabolites, prodrugs, carriers, N-oxides.

The present invention also provides a method for treating diseases caused by and/or associated with dysregulated protein kinase activity, particularly human PIM-1, PIM-2, PIM-3, Flt-3, c-Kit, MPS1 (TTK), PLK family members, protein kinase C in different isoforms, Met, PAK-4, PAK-5, PERK, STLK-2, DDR-2, Aurora 1, Aurora 2, Bub-1, Chk1, Chk2, HER2, C-raf, B-raf raf1, Melk, PDK1, MEK1, MAPK, EGF-R, PDGF-R, FGF-R, IGF-R, PI3K, weel kinase, Src, Abl, Akt, MAPK, ILK, MK-2, IKK-2, Cdc7, Nek, Cdk/cyclin kinase family, more particularly human PIM-1, PIM-2, PIM-3, which comprises administering to a mammal, in need thereof, an effective amount of a substituted pyrazolo[4,3-h] quinazoline compound represented by the formula (I) as defined above.

A method of the present invention is to treat a disease caused by and/or associated with dysregulated protein kinase activity selected from the group consisting of cancer, cell proliferative disorders and immune cell-associated diseases and disorders.

Another method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma and others.

Another method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another method of the present invention is to treat immune cell-associated diseases and disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

In addition, the method of the present invention also provides tumor angiogenesis and metastasis inhibition as well as the treatment of organ transplant rejection and host versus graft disease.

The present invention also provides a pharmaceutical composition comprising one or more compounds of the formula (I) or a pharmaceutically acceptable salt thereof and a pharmaceutically acceptable excipient, carrier or diluent.

The present invention further provides a pharmaceutical composition comprising a compound of the formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The present invention further provides an in vitro method for inhibiting PIM-1, PIM-2, PIM-3 protein kinase activity which comprises contacting the kinase with an effective amount of a compound of formula (I) as defined above.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

DETAILED DESCRIPTION OF EXEMPLARY EMBODIMENTS

Figure 1:
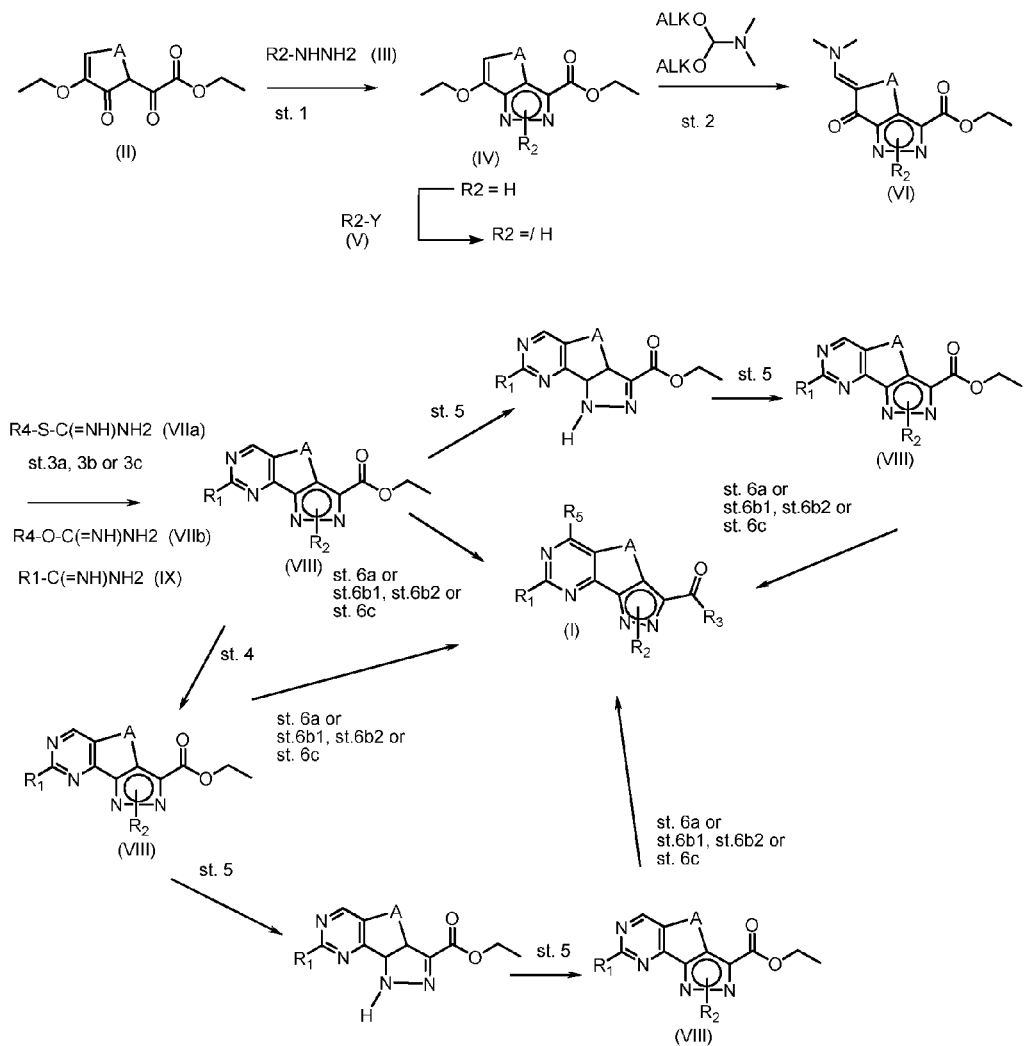
FIG. 1 shows conversions of compounds I-VIII, including the preparation of a compound of formula (I) where R1 is hydrogen, an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group SR4 or OR4; and R2, R3, R4, R5, R', R" and A are as defined above.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this application is based on IUPAC systematic nomenclature, unless indicated otherwise.

Unless otherwise specified, when referring to the compounds of the formula (I) per se as well as to any pharmaceutical composition thereof or to any therapeutic treatment comprising them, the present invention includes all of the isomers, tautomers, hydrates, solvates, complexes, metabolites, prodrugs, carriers, N-oxides and pharmaceutically acceptable salts of the compounds of this invention.

In other words, if easily obtainable from the compounds of the formula (I) as defined above, also their isomers, tautomers, hydrates, solvates, complexes, metabolites, prodrugs, carriers and N-oxides are object of the present invention.

A metabolite of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

Prodrugs are any covalently bonded compounds, which release in vivo the active parent drug according to the formula (I).

N-oxides are compounds of the formula (I) wherein nitrogen and oxygen are tethered through a dative bond.

In formula (I)

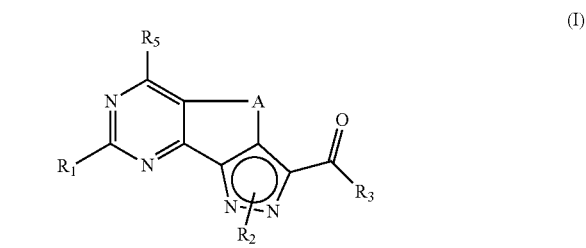

R2 can be bound to any one of the nitrogen atoms of the pyrazole ring as per formula (Ia) and (Ib),

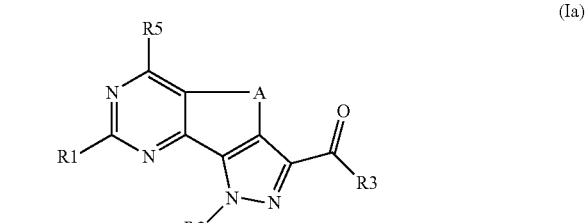

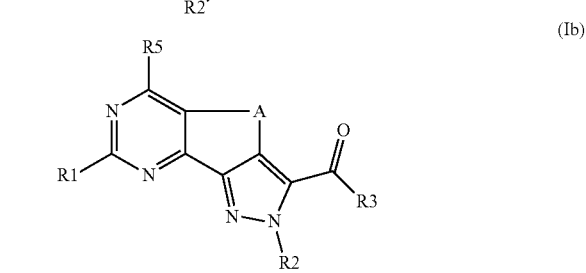

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

As such, unless otherwise provided, when in compounds of formula (I) R2 is hydrogen, only one of the following tautomeric forms of formula (Ia') or (Ib') is indicated, the remaining one has still to be intended as comprised within the scope of the invention:

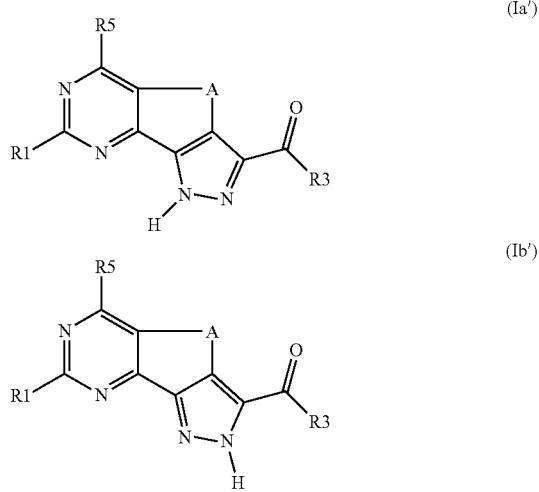

In cases wherein compounds may exist in other tautomeric forms, such as keto-enol tautomers, each tautomeric form is contemplated as being included within this invention whether existing in equilibrium or predominantly in one form.

The term aryl includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected from N, O and S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

The term "heterocyclyl" (also known as "heterocycloalkyl") means a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "$C_3$-$C_7$ cycloalkyl", hence comprehensive of $C_4$-$C_7$ cycloalkyl, means, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloheptane, cycloheptene, cycloheptadiene.

The term "straight or branched $C_1$-$C_6$ alkyl", hence comprehensive of $C_1$-$C_4$ alkyl, means any of the groups such as, for instance, methyl, ethyl, n-propyl, isopropyl, n-butyl, isobutyl, tert-butyl, sec-butyl, n-pentyl, n-hexyl, and the like.

The term "straight or branched $C_2$-$C_6$ alkenyl" means any of the groups such as, for instance, vinyl, allyl, 1-propenyl, isopropenyl, 1-butenyl, 2-butenyl, 3-butenyl, 2-pentenyl, 1-hexenyl, and the like.

According to the present invention and unless otherwise provided, any of the above R1, R2, R4, R6, R' and R" group may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, the term "halogen atom" means a fluorine, chlorine, bromine or iodine atom.

The term "cyano" means a —CN residue.

The term "nitro" means a —$NO_2$ group.

The terms "alkenyl" and "alkynyl" means any of the aforementioned straight or branched $C_2$-$C_6$ alkyl groups further bearing a double or triple bond, respectively. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

The term "polyfluorinated alkyl" or "polyfluorinated alkoxy" means any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

The terms "alkoxy", "aryloxy", "heterocyclyloxy" and derivatives thereof means any of the above $C_1$-$C_6$ alkyl, aryl or heterocyclyl groups linked to the rest of the molecule through an oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of the formula (I) are the compounds wherein:

R1 is CN, an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group XR4, wherein X is a divalent radical selected from O, S, SO, $SO_2$ and NR6, wherein R6 is an optionally substituted straight or branched $C_1$-$C_6$ alkyl or, together with the nitrogen atom to which they are bound, R6 and R4 may form a 5 to 6 membered heteroaryl or heterocyclyl group optionally containing one additional heteroatom selected from N, O and S;

R2 is an optionally substituted group selected from straight or branched $C_1$-$C_6$ alkyl, straight or branched $C_2$-$C_6$ alkenyl, $C_3$-$C_7$ cycloalkyl, cycloalkylalkyl, aryl, arylalkyl, heterocyclyl and heterocyclylalkyl;

R5 is hydrogen or NR'R" wherein

R' and R" hydrogen, and R3, R4 and A are as defined above.

Another preferred class of compounds of formula (I) are the compounds wherein:

R1 is an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group XR4, wherein X is a divalent radical selected from O, S, SO, $SO_2$ and NR6, wherein R6 is an optionally substituted straight or branched $C_1$-$C_6$ alkyl or, together with the nitrogen atom to which they are bound, R6 and R4 may form a 5 to 6 membered heteroaryl or heterocyclyl group optionally containing one additional heteroatom selected from N, O and S;

R2 is an optionally substituted group selected from straight or branched $C_1$-$C_6$ alkyl, heterocyclyl and heterocyclylalkyl;

R3 is a group selected from NR'R" and N(OH)R', wherein

R' and R" are hydrogen, and R4, R5 and A are as defined above.

A further preferred class of compounds of formula (I) are the compounds wherein:

R1 is an optionally substituted group selected from straight or branched $C_1$-$C_6$ alkyl, aryl and heterocyclyl or a group XR4, wherein X is a divalent radical selected from O, S, and NR6, wherein R6 is an optionally substituted straight or branched $C_1$-$C_6$ alkyl or, together with the nitrogen atom to which they are bound, R6 and R4 may form a 5 to 6 membered heteroaryl or heterocyclyl group optionally containing one additional heteroatom selected from N, O and S;

R3 is NR'R", wherein

R' and R" are hydrogen;

R4 is a group selected from optionally substituted straight or branched $C_1$-$C_6$ alkyl, aryl, arylalkyl, and heterocyclyl;

R5 is hydrogen, and R2 and A are as defined above.

A particularly preferred class of compounds of formula (I) are the compounds wherein:

R1 is an optionally substituted group selected from straight or branched $C_1$-$C_6$ alkyl, and aryl, or a group XR4, wherein X is a divalent radical selected from O, S, and NR6, wherein R6 is an optionally substituted straight or branched $C_1$-$C_6$ alkyl or, together with the nitrogen atom to which they are bound, R6 and R4 may form a 5 to 6 membered heteroaryl or heterocyclyl group optionally containing one additional heteroatom selected from N, O and S;

R4 is a group selected from optionally substituted straight or branched $C_1$-$C_6$ alkyl, aryl, and heterocyclyl;

A is a divalent group —CH=CH—, and R2, R3 and R5 are as defined above.

Biological Evaluation

Determination of the Pim kinase activity of a formula (I) compound is possible by a number of direct and indirect detection methods. Certain exemplary compounds described herein were assayed for their Pim kinase binding activity, including isoforms Pim-1, Pim-2, and Pim-3, (Example 901) and in vitro activity against tumor cells (Example 902). Certain exemplary compounds of the invention had Pim binding activity $IC_{50}$ values less than about 1 micromolar (μM). Certain compounds of the invention had tumor cell-based activity $EC_{50}$ values less than about 1 micromolar (μM). Formula (I) compounds having $Ki/IC_{50}/EC_{50}$ of less than 1 μM in assays described in Examples 901 and 902 may be useful therapeutically as Pim kinase inhibitors (Pim-1, Pim-2 and/or Pim-3).

Exemplary formula (I) compounds in Table 1 were made, characterized, and tested for inhibition of Pim kinase according to the methods of this invention, and have the following structures and corresponding names (ChemBioDraw Ultra, Version 11.0, CambridgeSoft Corp., Cambridge Mass.).

TABLE 1

| No. | Structure | Name |
|-----|-----------|------|
| 1. | 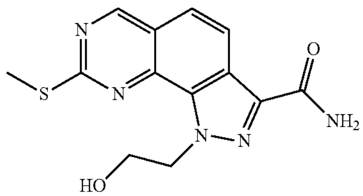 [SMILES: CSc1ncc2ccc3c(C(N)=O)nn(CCO)c3c2n1] | 1-(2-hydroxyethyl)-8-(methylsulfanyl)-1H-pyrazolo[4,3-h]quinazoline-3-carboxamide |
| 2. | 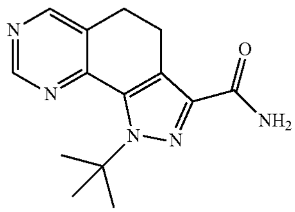 [SMILES: CC(C)(C)n1nc(C(N)=O)c2c1-c1ncncc1CC2] | 1-tert-butyl-4,5-dihydro-1H-pyrazolo[4,3-h]quinazoline-3-carboxamide |
| 3. | 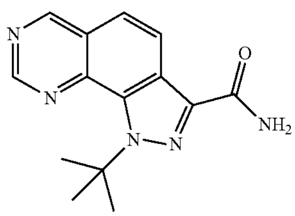 [SMILES: CC(C)(C)n1nc(C(N)=O)c2ccc3cncnc3c21] | 1-tert-butyl-1H-pyrazolo[4,3-h]quinazoline-3-carboxamide |
| 4. | 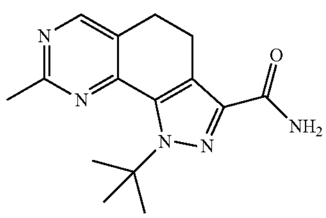 [SMILES: Cc1ncc2c(n1)-c1c(c(C(N)=O)nn1C(C)(C)C)CC2] | 1-tert-butyl-8-methyl-4,5-dihydro-1H-pyrazolo[4,3-h]quinazoline-3-carboxamide |
| 5. | 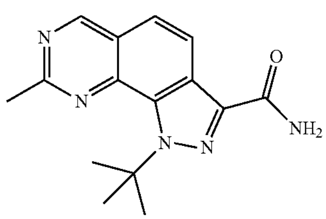 [SMILES: Cc1ncc2ccc3c(C(N)=O)nn(C(C)(C)C)c3c2n1] | 1-tert-butyl-8-methyl-1H-pyrazolo[4,3-h]quinazoline-3-carboxamide |
| 6. | 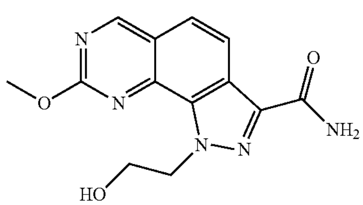 | 1-(2-hydroxyethyl)-8-methoxy-1H-pyrazolo[4,3-h]quinazoline-3-carboxamide |
| 7. | 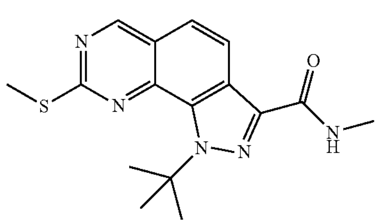 | 1-tert-butyl-N-methyl-8-(methylsulfanyl)-1H-pyrazolo[4,3-h]quinazoline-3-carboxamide |

TABLE 1-continued

| No. | Structure | Name |
|---|---|---|
| 8. | 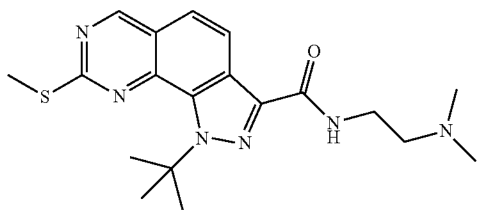 | 1-tert-butyl-N-[2-(dimethylamino)ethyl]-8-(methylsulfanyl)-1H-pyrazolo[4,3-h]quinazoline-3-carboxamide |
| 9. | 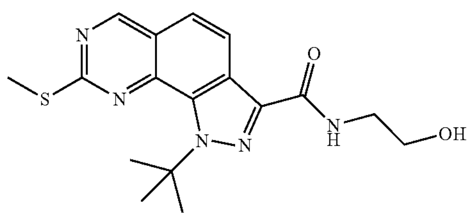 [SMILES: CSc1ncc2ccc3c(C(=O)NCCO)nn(C(C)(C)C)c3c2n1] | 1-tert-butyl-N-(2-hydroxyethyl)-8-(methylsulfanyl)-1H-pyrazolo[4,3-h]quinazoline-3-carboxamide |
| 10. | 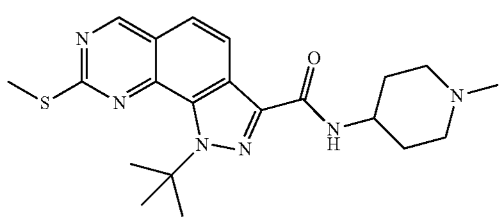 | 1-tert-butyl-N-(1-methylpiperidin-4-yl)-8-(methylsulfanyl)-1H-pyrazolo[4,3-h]quinazoline-3-carboxamide |
| 11. | 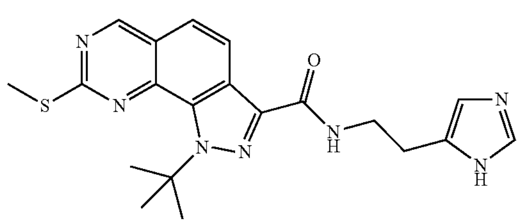 [SMILES: CSc1ncc2ccc3c(C(=O)NCCc4cnc[nH]4)nn(C(C)(C)C)c3c2n1] | 1-tert-butyl-N-[2-(1H-imidazol-5-yl)ethyl]-8-(methylsulfanyl)-1H-pyrazolo[4,3-h]quinazoline-3-carboxamide |
| 12. | 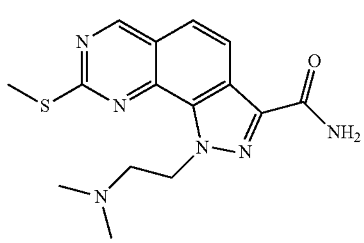 [SMILES: CSc1ncc2ccc3c(C(N)=O)nn(CCN(C)C)c3c2n1] | 1-[2-(dimethylamino)ethyl]-8-(methylsulfanyl)-1H-pyrazolo[4,3-h]quinazoline-3-carboxamide |
| 13. | 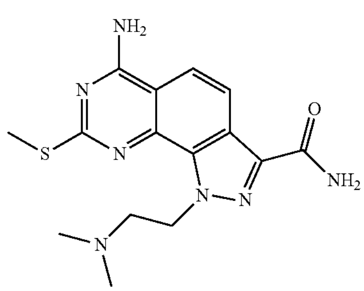 [SMILES: CSc1nc(N)c2ccc3c(C(N)=O)nn(CCN(C)C)c3c2n1] | 6-amino-1-[2-(dimethylamino)ethyl]-8-(methylsulfanyl)-1H-pyrazolo[4,3-h]quinazoline-3-carboxamide |

TABLE 1-continued

| No. | Structure | Name |
|---|---|---|
| 14. | 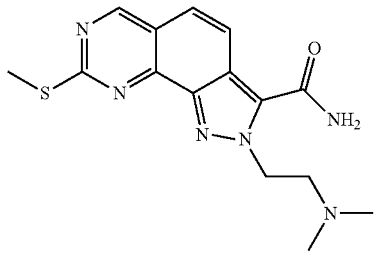 | 2-[2-(dimethylamino)ethyl]-8-(methylsulfanyl)-2H-pyrazolo[4,3-h]quinazoline-3-carboxamide |
| 15. | 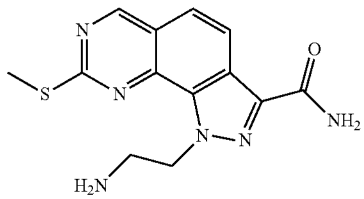 [SMILES: CSc1ncc2ccc3c(C(N)=O)nn(CCN)c3c2n1] | 1-(2-aminoethyl)-8-(methylsulfanyl)-1H-pyrazolo[4,3-h]quinazoline-3-carboxamide |
| 16. | 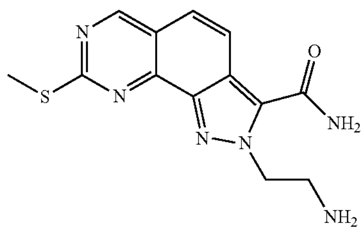 [SMILES: CSc1ncc2ccc3c(C(N)=O)n(CCN)nc3c2n1] | 2-(2-aminoethyl)-8-(methylsulfanyl)-2H-pyrazolo[4,3-h]quinazoline-3-carboxamide |
| 17. | 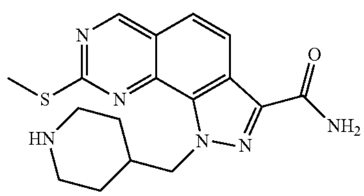 [SMILES: CSc1ncc2ccc3c(C(N)=O)nn(CC4CCNCC4)c3c2n1] | 8-(methylsulfanyl)-1-(piperidin-4-ylmethyl)-1H-pyrazolo[4,3-h]quinazoline-3-carboxamide |
| 18. | 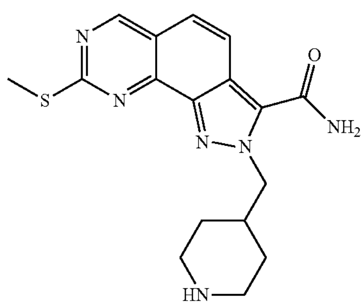 [SMILES: CSc1ncc2ccc3c(C(N)=O)n(CC4CCNCC4)nc3c2n1] | 8-(methylsulfanyl)-2-(piperidin-4-ylmethyl)-2H-pyrazolo[4,3-h]quinazoline-3-carboxamide |
| 19. | 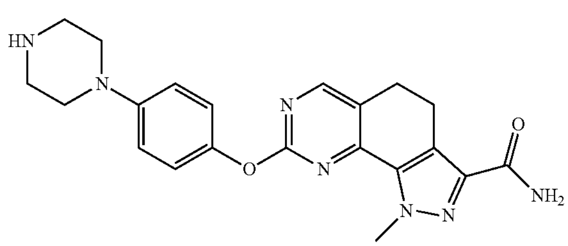 [SMILES: Cn1nc(C(N)=O)c2c1-c1nc(Oc3ccc(N4CCNCC4)cc3)ncc1CC2] | 1-methyl-8-[4-(piperazin-1-yl)phenoxy]-4,5-dihydro-1H-pyrazolo[4,3-h]quinazoline-3-carboxamide |

TABLE 1-continued

| No. | Structure | Name |
| --- | --- | --- |
| 20. | 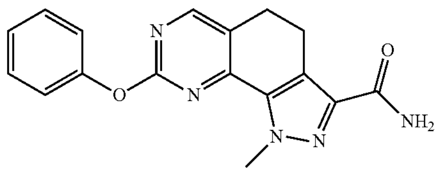 [SMILES: Cn1nc(C(N)=O)c2c1-c1nc(Oc3ccccc3)ncc1CC2] | 1-methyl-8-phenoxy-4,5-dihydro-1H-pyrazolo[4,3-h]quinazoline-3-carboxamide |
| 21. | 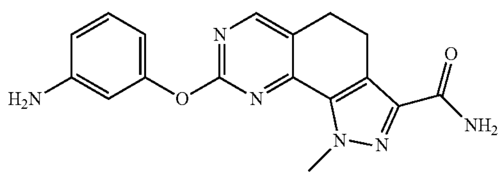 [SMILES: Cn1nc(C(N)=O)c2c1-c1nc(Oc3cccc(N)c3)ncc1CC2] | 8-(3-aminophenoxy)-1-methyl-4,5-dihydro-1H-pyrazolo[4,3-h]quinazoline-3-carboxamide |
| 22. | 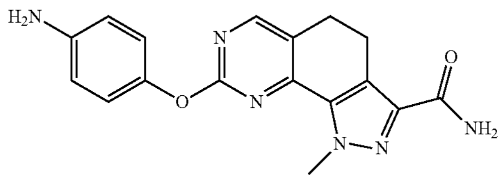 [SMILES: Cn1nc(C(N)=O)c2c1-c1nc(Oc3ccc(N)cc3)ncc1CC2] | 8-(4-aminophenoxy)-1-methyl-4,5-dihydro-1H-pyrazolo[4,3-h]quinazoline-3-carboxamide |
| 23. | 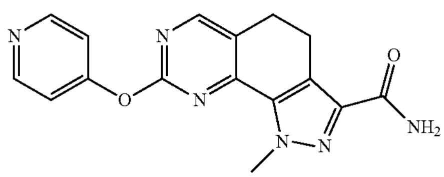 [SMILES: Cn1nc(C(N)=O)c2c1-c1nc(Oc3ccncc3)ncc1CC2] | 1-methyl-8-(pyridin-4-yloxy)-4,5-dihydro-1H-pyrazolo[4,3-h]quinazoline-3-carboxamide |
| 24. | 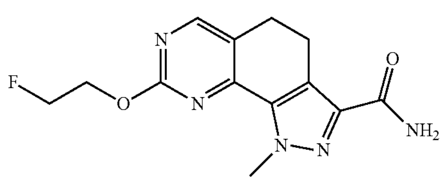 [SMILES: Cn1nc(C(N)=O)c2c1-c1nc(OCCF)ncc1CC2] | 8-(2-fluoroethoxy)-1-methyl-4,5-dihydro-1H-pyrazolo[4,3-h]quinazoline-3-carboxamide |
| 25. | 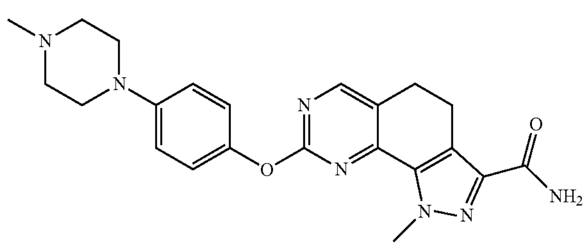 [SMILES: CN1CCN(c2ccc(Oc3ncc4c(n3)-c3c(c(C(N)=O)nn3C)CC4)cc2)CC1] | 1-methyl-8-[4-(4-methylpiperazin-1-yl)phenoxy]-4,5-dihydro-1H-pyrazolo[4,3-h]quinazoline-3-carboxamide |
| 26. | 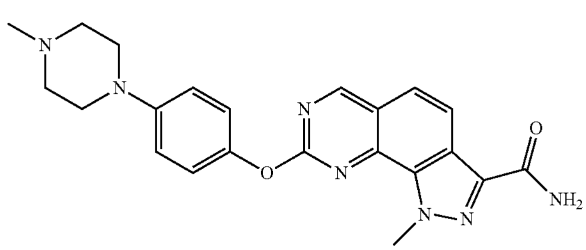 [SMILES: CN1CCN(c2ccc(Oc3ncc4ccc5c(C(N)=O)nn(C)c5c4n3)cc2)CC1] | 1-methyl-8-[4-(4-methylpiperazin-1-yl)phenoxy]-1H-pyrazolo[4,3-h]quinazoline-3-carboxamide |

TABLE 1-continued

| No. | Structure | Name |
|---|---|---|
| 27. | 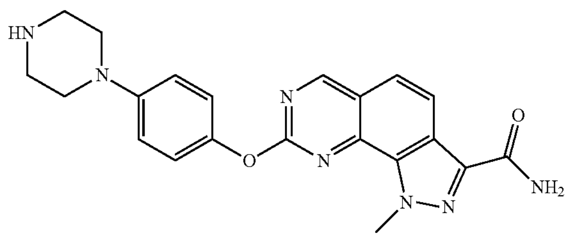 [SMILES: Cn1nc(C(N)=O)c2ccc3cnc(Oc4ccc(N5CCNCC5)cc4)nc3c21] | 1-methyl-8-[4-(piperazin-1-yl)phenoxy]-1H-pyrazolo[4,3-h]quinazoline-3-carboxamide |
| 28. | 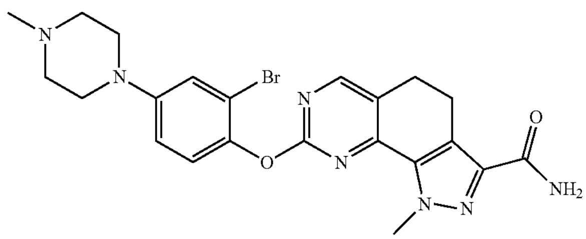 | 8-[2-bromo-4-(4-methylpiperazin-1-yl)phenoxy]-1-methyl-4,5-dihydro-1H-pyrazolo[4,3-h]quinazoline-3-carboxamide |
| 29. | 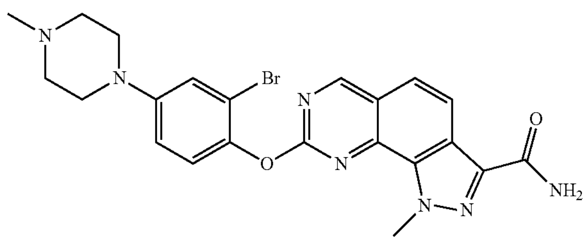 [SMILES: CN1CCN(c2ccc(Oc3ncc4ccc5c(C(N)=O)nn(C)c5c4n3)c(Br)c2)CC1] | 8-[2-bromo-4-(4-methylpiperazin-1-yl)phenoxy]-1-methyl-1H-pyrazolo[4,3-h]quinazoline-3-carboxamide |
| 30. | 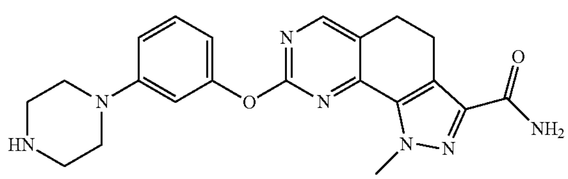 [SMILES: Cn1nc(C(N)=O)c2c1-c1nc(Oc3cccc(N4CCNCC4)c3)ncc1CC2] | 1-methyl-8-[3-(piperazin-1-yl)phenoxy]-4,5-dihydro-1H-pyrazolo[4,3-h]quinazoline-3-carboxamide |
| 31. | 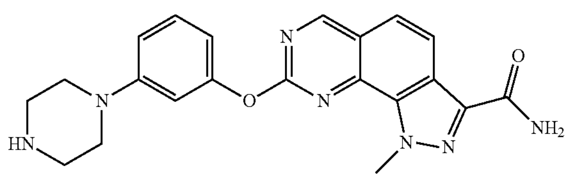 [SMILES: Cn1nc(C(N)=O)c2ccc3cnc(Oc4cccc(N5CCNCC5)c4)nc3c21] | 1-methyl-8-[3-(piperazin-1-yl)phenoxy]-1H-pyrazolo[4,3-h]quinazoline-3-carboxamide |
| 32. | 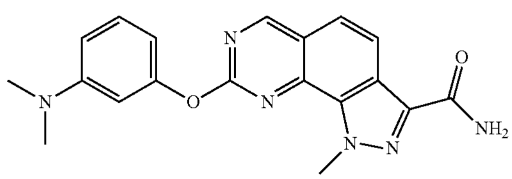 [SMILES: CN(C)c1cccc(Oc2ncc3ccc4c(C(N)=O)nn(C)c4c3n2)c1] | 8-[3-(dimethylamino)phenoxy]-1-methyl-1H-pyrazolo[4,3-h]quinazoline-3-carboxamide |
| 33. | 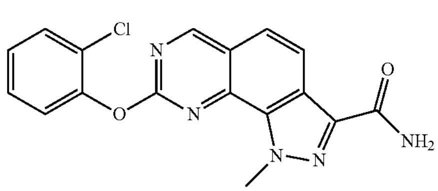 | 8-(2-chlorophenoxy)-1-methyl-1H-pyrazolo[4,3-h]quinazoline-3-carboxamide |

TABLE 1-continued

| No. | Structure | Name |
|---|---|---|
| 34. | 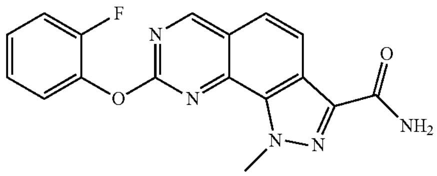 [SMILES: Cn1nc(C(N)=O)c2ccc3cnc(Oc4ccccc4Cl)nc3c21] | 8-(2-fluorophenoxy)-1-methyl-1H-pyrazolo[4,3-h]quinazoline-3-carboxamide |
| 35. | 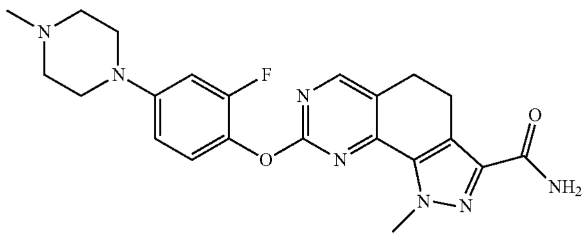 [SMILES: CN1CCN(c2ccc(Oc3ncc4c(n3)-c3c(c(C(N)=O)nn3C)CC4)c(F)c2)CC1] | 8-[2-fluoro-4-(4-methylpiperazin-1-yl)phenoxy]-1-methyl-4,5-dihydro-1H-pyrazolo[4,3-h]quinazoline-3-carboxamide |
| 36. | 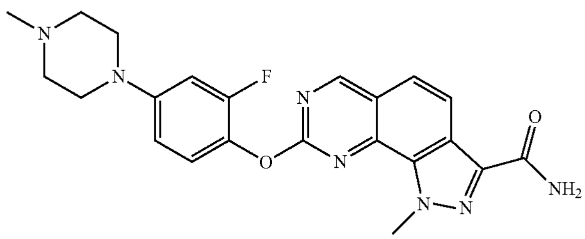 [SMILES: CN1CCN(c2ccc(Oc3ncc4ccc5c(C(N)=O)nn(C)c5c4n3)c(F)c2)CC1] | 8-[2-fluoro-4-(4-methylpiperazin-1-yl)phenoxy]-1-methyl-1H-pyrazolo[4,3-h]quinazoline-3-carboxamide |
| 37. | 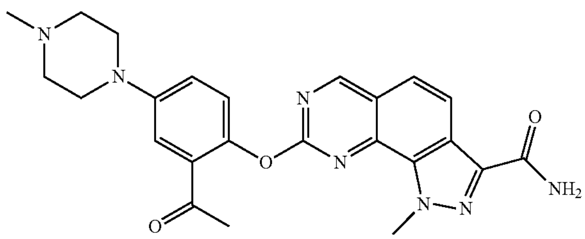 [SMILES: CC(=O)c1cc(N2CCN(C)CC2)ccc1Oc1ncc2ccc3c(C(N)=O)nn(C)c3c2n1] | 8-[2-acetyl-4-(4-methylpiperazin-1-yl)phenoxy]-1-methyl-1H-pyrazolo[4,3-h]quinazoline-3-carboxamide |
| 38. | 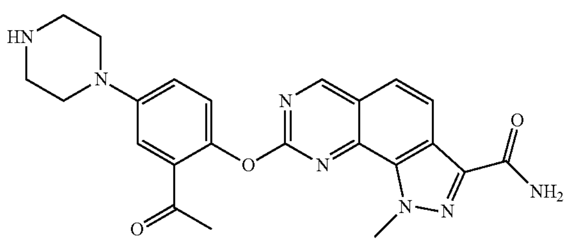 [SMILES: CC(=O)c1cc(N2CCNCC2)ccc1Oc1ncc2ccc3c(C(N)=O)nn(C)c3c2n1] | 8-[2-acetyl-4-(piperazin-1-yl)phenoxy]-1-methyl-1H-pyrazolo[4,3-h]quinazoline-3-carboxamide |
| 39. | 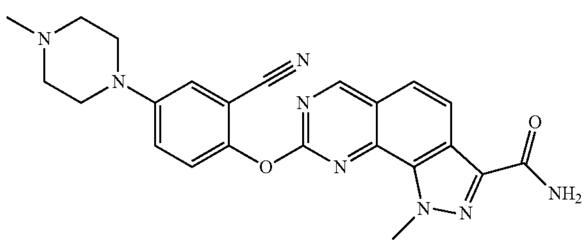 [SMILES: CN1CCN(c2ccc(Oc3ncc4ccc5c(C(N)=O)nn(C)c5c4n3)c(C#N)c2)CC1] | 8-[2-cyano-4-(4-methylpiperazin-1-yl)phenoxy]-1-methyl-1H-pyrazolo[4,3-h]quinazoline-3-carboxamide |
| 40. | 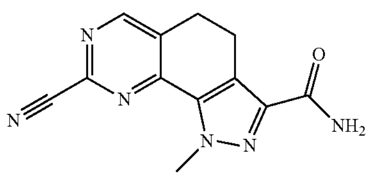 [SMILES: Cn1nc(C(N)=O)c2c1-c1nc(C#N)ncc1CC2] | 8-cyano-1-methyl-4,5-dihydro-1H-pyrazolo[4,3-h]quinazoline-3-carboxamide |

TABLE 1-continued

| No. | Structure | Name |
|---|---|---|
| 41. | 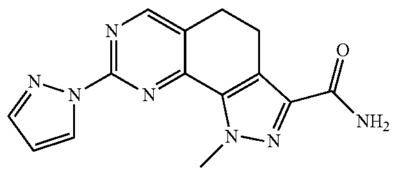 [SMILES: Cn1nc(C(N)=O)c2c1-c1nc(-n3cccn3)ncc1CC2] | 1-methyl-8-(1H-pyrazol-1-yl)-4,5-dihydro-1H-pyrazolo[4,3-h]quinazoline-3-carboxamide |
| 42. | 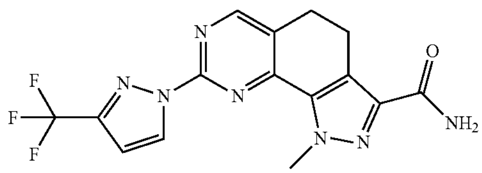 [SMILES: Cn1nc(C(N)=O)c2c1-c1nc(-n3ccc(C(F)(F)F)n3)ncc1CC2] | 1-methyl-8-[3-(trifluoromethyl)-1H-pyrazol-1-yl]-4,5-dihydro-1H-pyrazolo[4,3-h]quinazoline-3-carboxamide |
| 43. | 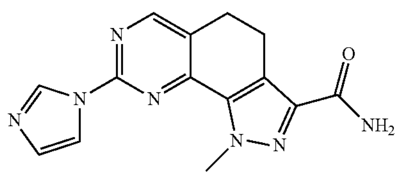 [SMILES: Cn1nc(C(N)=O)c2c1-c1nc(-n3ccnc3)ncc1CC2] | 8-(1H-imidazol-1-yl)-1-methyl-4,5-dihydro-1H-pyrazolo[4,3-h]quinazoline-3-carboxamide |
| 44. | 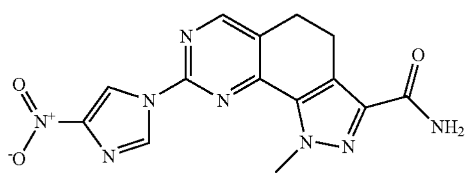 | 1-methyl-8-(4-nitro-1H-imidazol-1-yl)-4,5-dihydro-1H-pyrazolo[4,3-h]quinazoline-3-carboxamide |
| 45. | 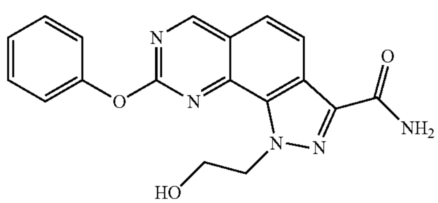 [SMILES: NC(=O)c1nn(CCO)c2c1ccc1cnc(Oc3ccccc3)nc12] | 1-(2-hydroxyethyl)-8-phenoxy-1H-pyrazolo[4,3-h]quinazoline-3-carboxamide |
| 46. | 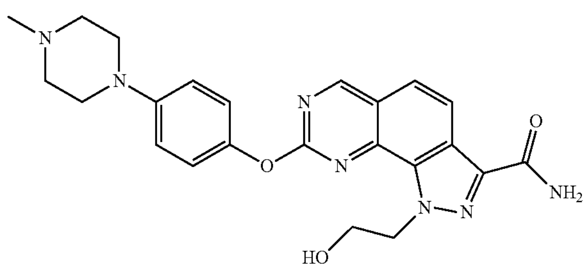 [SMILES: CN1CCN(c2ccc(Oc3ncc4ccc5c(C(N)=O)nn(CCO)c5c4n3)cc2)CC1] | 1-(2-hydroxyethyl)-8-[4-(4-methylpiperazin-1-yl)phenoxy]-1H-pyrazolo[4,3-h]quinazoline-3-carboxamide |
| 47. | 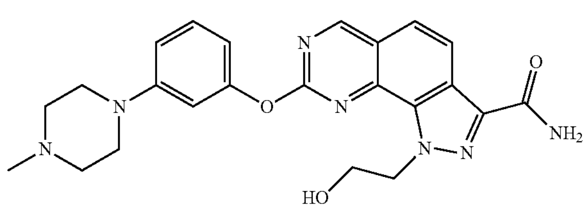 [SMILES: CN1CCN(c2cccc(Oc3ncc4ccc5c(C(N)=O)nn(CCO)c5c4n3)c2)CC1] | 1-(2-hydroxyethyl)-8-[3-(4-methylpiperazin-1-yl)phenoxy]-1H-pyrazolo[4,3-h]quinazoline-3-carboxamide |
| 48. | 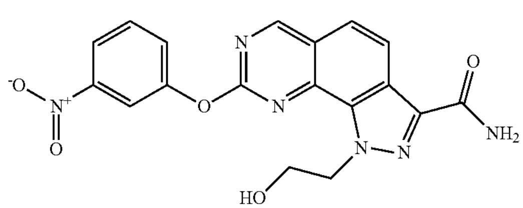 | 1-(2-hydroxyethyl)-8-(3-nitrophenoxy)-1H-pyrazolo[4,3-h]quinazoline-3-carboxamide |

TABLE 1-continued

| No. | Structure | Name |
|---|---|---|
| 49. | 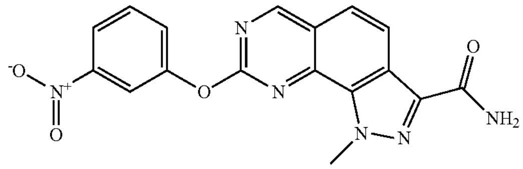 | 1-methyl-8-(3-nitrophenoxy)-1H-pyrazolo[4,3-h]quinazoline-3-carboxamide |
| 50. | 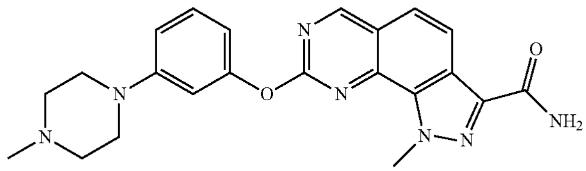 [SMILES: CN1CCN(c2cccc(Oc3ncc4ccc5c(C(N)=O)nn(C)c5c4n3)c2)CC1] | 1-methyl-8-[3-(4-methylpiperazin-1-yl)phenoxy]-1H-pyrazolo[4,3-h]quinazoline-3-carboxamide |
| 51. | 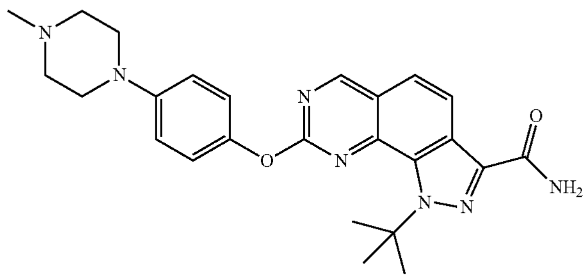 [SMILES: CN1CCN(c2ccc(Oc3ncc4ccc5c(C(N)=O)nn(C(C)(C)C)c5c4n3)cc2)CC1] | 1-tert-butyl-8-[4-(4-methylpiperazin-1-yl)phenoxy]-1H-pyrazolo[4,3-h]quinazoline-3-carboxamide |
| 52. | 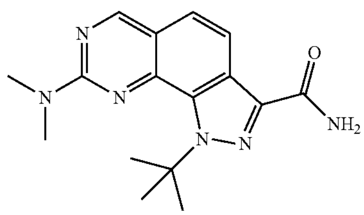 [SMILES: CN(C)c1ncc2ccc3c(C(N)=O)nn(C(C)(C)C)c3c2n1] | 1-tert-butyl-8-(dimethylamino)-1H-pyrazolo[4,3-h]quinazoline-3-carboxamide |
| 53. | 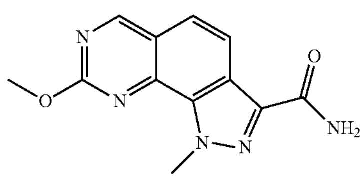 [SMILES: COc1ncc2ccc3c(C(N)=O)nn(C)c3c2n1] | 8-methoxy-1-methyl-1H-pyrazolo[4,3-h]quinazoline-3-carboxamide |
| 54. | 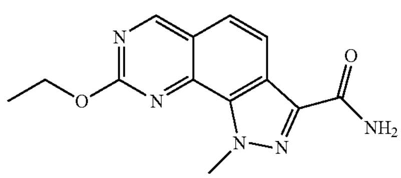 [SMILES: CCOc1ncc2ccc3c(C(N)=O)nn(C)c3c2n1] | 8-ethoxy-1-methyl-1H-pyrazolo[4,3-h]quinazoline-3-carboxamide |
| 55. | 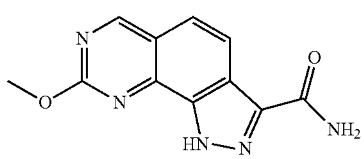 | 8-methoxy-1H-pyrazolo[4,3-h]quinazoline-3-carboxamide |
| 56. | 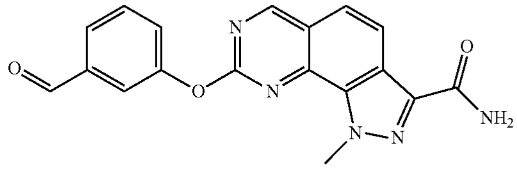 [SMILES: Cn1nc(C(N)=O)c2ccc3cnc(Oc4cccc(C=O)c4)nc3c21] | 8-(3-formylphenoxy)-1-methyl-1H-pyrazolo[4,3-h]quinazoline-3-carboxamide |

TABLE 1-continued

| No. | Structure | Name |
|---|---|---|
| 57. | 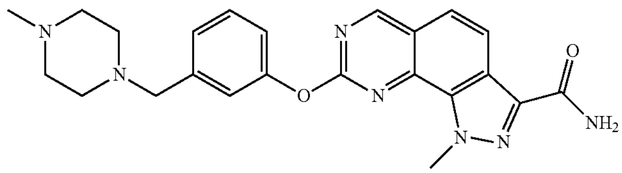 [SMILES: CN1CCN(Cc2cccc(Oc3ncc4ccc5c(C(N)=O)nn(C)c5c4n3)c2)CC1] | 1-methyl-8-{3-[(4-methylpiperazin-1-yl)methyl]phenoxy}-1H-pyrazolo[4,3-h]quinazoline-3-carboxamide |
| 58. | 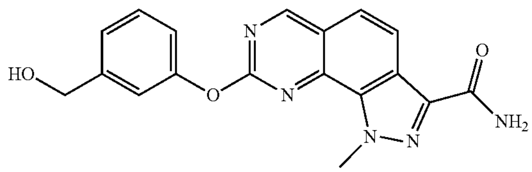 [SMILES: Cn1nc(C(N)=O)c2ccc3cnc(Oc4cccc(CO)c4)nc3c21] | 8-[3-(hydroxymethyl)phenoxy]-1-methyl-1H-pyrazolo[4,3-h]quinazoline-3-carboxamide |
| 59. | 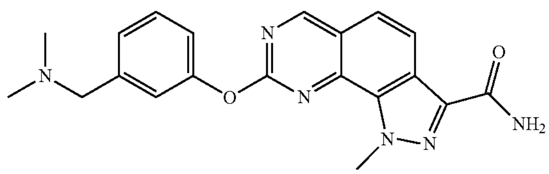 [SMILES: CN(C)Cc1cccc(Oc2ncc3ccc4c(C(N)=O)nn(C)c4c3n2)c1] | 8-{3-[(dimethylamino)methyl]phenoxy}-1-methyl-1H-pyrazolo[4,3-h]quinazoline-3-carboxamide |
| 60. | 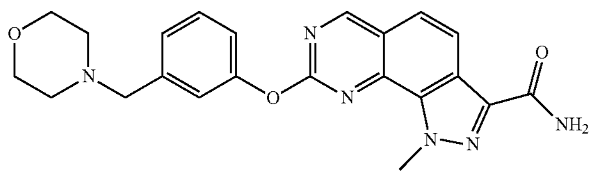 [SMILES: Cn1nc(C(N)=O)c2ccc3cnc(Oc4cccc(CN5CCOCC5)c4)nc3c21] | 1-methyl-8-[3-(morpholin-4-ylmethyl)phenoxy]-1H-pyrazolo[4,3-h]quinazoline-3-carboxamide |
| 61. | 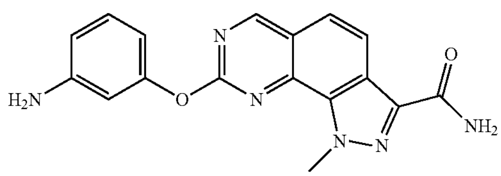 [SMILES: Cn1nc(C(N)=O)c2ccc3cnc(Oc4cccc(N)c4)nc3c21] | 8-(3-aminophenoxy)-1-methyl-1H-pyrazolo[4,3-h]quinazoline-3-carboxamide |
| 62. | 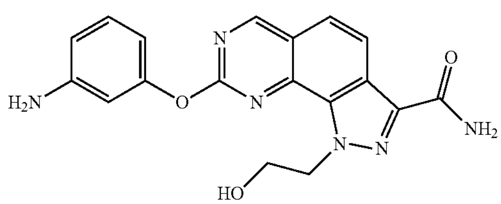 [SMILES: NC(=O)c1nn(CCO)c2c1ccc1cnc(Oc3cccc(N)c3)nc12] | 8-(3-aminophenoxy)-1-(2-hydroxyethyl)-1H-pyrazolo[4,3-h]quinazoline-3-carboxamide |
| 63. | 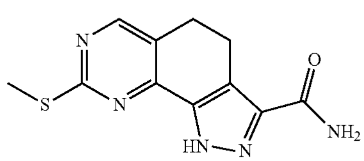 [SMILES: CSc1ncc2c(n1)-c1[nH]nc(C(N)=O)c1CC2] | 8-(methylsulfanyl)-4,5-dihydro-1H-pyrazolo[4,3-h]quinazoline-3-carboxamide |
| 64. | 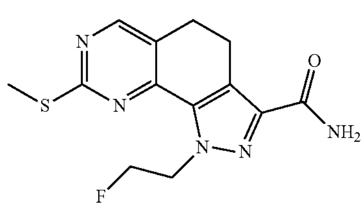 [SMILES: CSc1ncc2c(n1)-c1c(c(C(N)=O)nn1CCF)CC2] | 1-(2-fluoroethyl)-8-(methylsulfanyl)-4,5-dihydro-1H-pyrazolo[4,3-h]quinazoline-3-carboxamide |

TABLE 1-continued

| No. | Structure | Name |
|---|---|---|
| 65. | 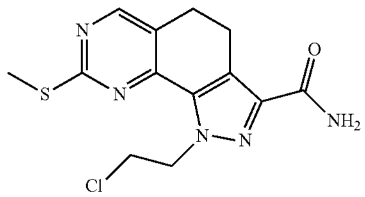 [SMILES: CSc1ncc2c(n1)-c1c(c(C(N)=O)nn1CCCl)CC2] | 1-(2-chloroethyl)-8-(methylsulfanyl)-4,5-dihydro-1H-pyrazolo[4,3-h]quinazoline-3-carboxamide |
| 66. | 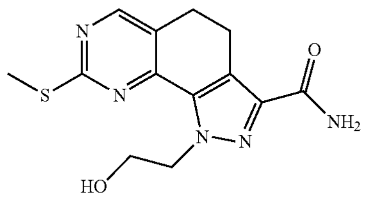 [SMILES: CSc1ncc2c(n1)-c1c(c(C(N)=O)nn1CCO)CC2] | 1-(2-hydroxyethyl)-8-(methylsulfanyl)-4,5-dihydro-1H-pyrazolo[4,3-h]quinazoline-3-carboxamide |
| 67. | 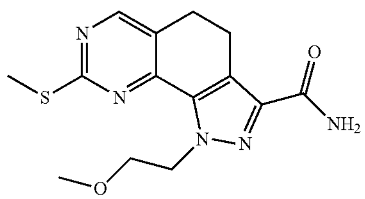 [SMILES: COCCn1nc(C(N)=O)c2c1-c1nc(SC)ncc1CC2] | 1-(2-methoxyethyl)-8-(methylsulfanyl)-4,5-dihydro-1H-pyrazolo[4,3-h]quinazoline-3-carboxamide |
| 68. | 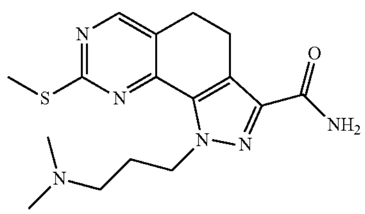 [SMILES: CSc1ncc2c(n1)-c1c(c(C(N)=O)nn1CCCN(C)C)CC2] | 1-[3-(dimethylamino)propyl]-8-(methylsulfanyl)-4,5-dihydro-1H-pyrazolo[4,3-h]quinazoline-3-carboxamide |
| 69. | 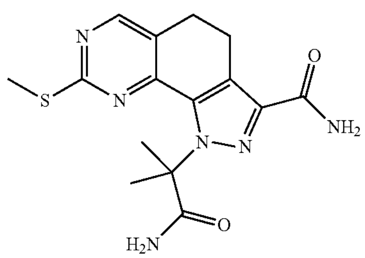 [SMILES: CSc1ncc2c(n1)-c1c(c(C(N)=O)nn1C(C)(C)C(N)=O)CC2] | 1-(1-amino-2-methyl-1-oxopropan-2-yl)-8-(methylsulfanyl)-4,5-dihydro-1H-pyrazolo[4,3-h]quinazoline-3-carboxamide |
| 70. | 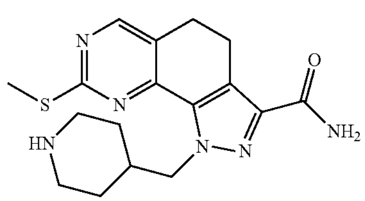 [SMILES: CSc1ncc2c(n1)-c1c(c(C(N)=O)nn1CC1CCNCC1)CC2] | 8-(methylsulfanyl)-1-(piperidin-4-ylmethyl)-4,5-dihydro-1H-pyrazolo[4,3-h]quinazoline-3-carboxamide |
| 71. | 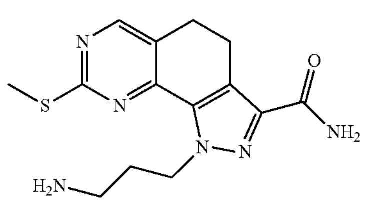 [SMILES: CSc1ncc2c(n1)-c1c(c(C(N)=O)nn1CCCN)CC2] | 1-(3-aminopropyl)-8-(methylsulfanyl)-4,5-dihydro-1H-pyrazolo[4,3-h]quinazoline-3-carboxamide |

TABLE 1-continued

| No. | Structure | Name |
| --- | --- | --- |
| 72. | 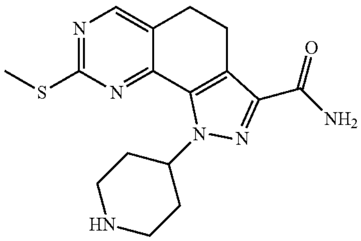 [SMILES: CSc1ncc2c(n1)-c1c(c(C(N)=O)nn1C1CCNCC1)CC2] | 8-(methylsulfanyl)-1-(piperidin-4-yl)-4,5-dihydro-1H-pyrazolo[4,3-h]quinazoline-3-carboxamide |
| 73. | 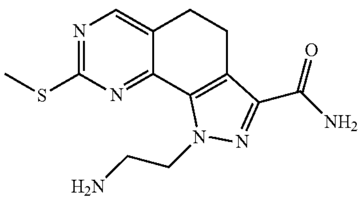 [SMILES: CSc1ncc2c(n1)-c1c(c(C(N)=O)nn1CCN)CC2] | 1-(2-aminoethyl)-8-(methylsulfanyl)-4,5-dihydro-1H-pyrazolo[4,3-h]quinazoline-3-carboxamide |
| 74. | 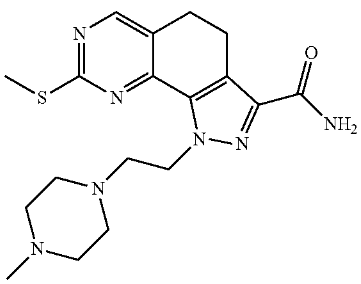 [SMILES: CSc1ncc2c(n1)-c1c(c(C(N)=O)nn1CCN1CCN(C)CC1)CC2] | 1-[2-(4-methylpiperazin-1-yl)ethyl]-8-(methylsulfanyl)-4,5-dihydro-1H-pyrazolo[4,3-h]quinazoline-3-carboxamide |
| 75. | 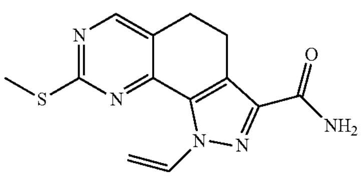 [SMILES: C=Cn1nc(C(N)=O)c2c1-c1nc(SC)ncc1CC2] | 1-ethenyl-8-(methylsulfanyl)-4,5-dihydro-1H-pyrazolo[4,3-h]quinazoline-3-carboxamide |
| 76. | 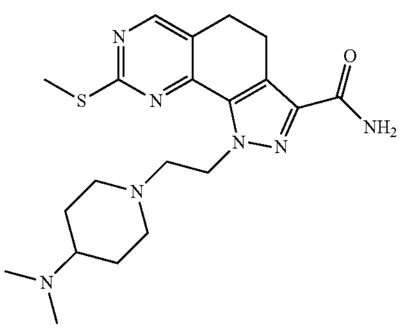 [SMILES: CSc1ncc2c(n1)-c1c(c(C(N)=O)nn1CCN1CCC(N(C)C)CC1)CC2] | 1-{2-[4-(dimethylamino)piperidin-1-yl]ethyl}-8-(methylsulfanyl)-4,5-dihydro-1H-pyrazolo[4,3-h]quinazoline-3-carboxamide |
| 77. | 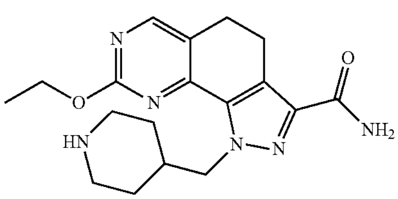 [SMILES: CCOc1ncc2c(n1)-c1c(c(C(N)=O)nn1CC1CCNCC1)CC2] | 8-ethoxy-1-(piperidin-4-ylmethyl)-4,5-dihydro-1H-pyrazolo[4,3-h]quinazoline-3-carboxamide |

TABLE 1-continued

| No. | Structure | Name |
|---|---|---|
| 78. | 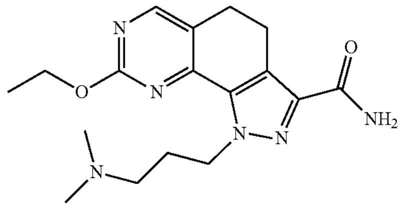 [SMILES: CCOc1ncc2c(n1)-c1c(c(C(N)=O)nn1CCCN(C)C)CC2] | 1-[3-(dimethylamino)propyl]-8-ethoxy-4,5-dihydro-1H-pyrazolo[4,3-h]quinazoline-3-carboxamide |
| 79. | 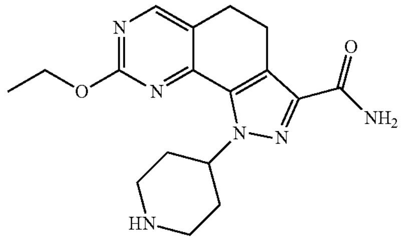 [SMILES: CCOc1ncc2c(n1)-c1c(c(C(N)=O)nn1C1CCNCC1)CC2] | 8-ethoxy-1-(piperidin-4-yl)-4,5-dihydro-1H-pyrazolo[4,3-h]quinazoline-3-carboxamide |
| 80. | 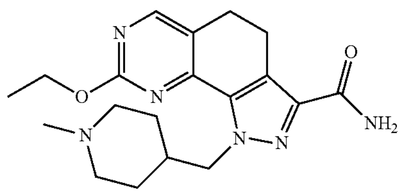 [SMILES: CCOc1ncc2c(n1)-c1c(c(C(N)=O)nn1CC1CCN(C)CC1)CC2] | 8-ethoxy-1-[(1-methylpiperidin-4-yl)methyl]-4,5-dihydro-1H-pyrazolo[4,3-h]quinazoline-3-carboxamide |
| 81. | 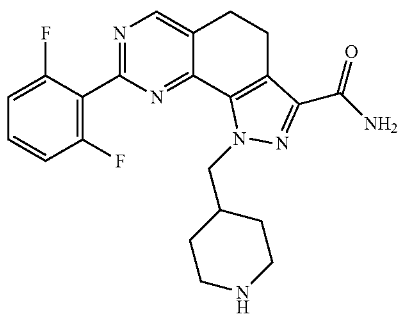 [SMILES: NC(=O)c1nn(CC2CCNCC2)c2c1CCc1cnc(-c3c(F)cccc3F)nc1-2] | 8-(2,6-difluorophenyl)-1-(piperidin-4-ylmethyl)-4,5-dihydro-1H-pyrazolo[4,3-h]quinazoline-3-carboxamide |
| 82. | 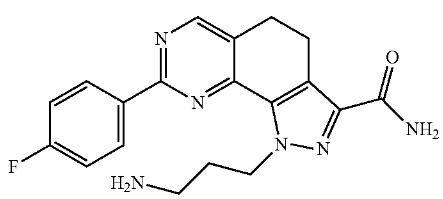 [SMILES: NCCCn1nc(C(N)=O)c2c1-c1nc(-c3ccc(F)cc3)ncc1CC2] | 1-(3-aminopropyl)-8-(4-fluorophenyl)-4,5-dihydro-1H-pyrazolo[4,3-h]quinazoline-3-carboxamide |
| 83. | 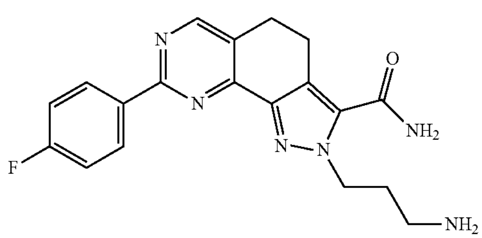 [SMILES: NCCCn1nc2c(c1C(N)=O)CCc1cnc(-c3ccc(F)cc3)nc1-2] | 2-(3-aminopropyl)-8-(4-fluorophenyl)-4,5-dihydro-2Hpyrazolo[4,3-h]quinazoline-3-carboxamide |
| 84. | 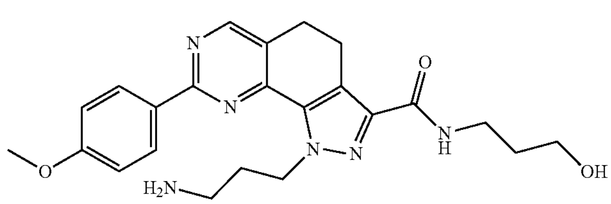 [SMILES: COc1ccc(-c2ncc3c(n2)-c2c(c(C(=O)NCCCO)nn2CCCN)CC3)cc1] | 1-(3-aminopropyl)-N-(3-hydroxypropyl)-8-(4-methoxyphenyl)-4,5-dihydro-1H-pyrazolo[4,3-h]quinazoline-3-carboxamide |

TABLE 1-continued

| No. | Structure | Name |
|---|---|---|
| 85. | 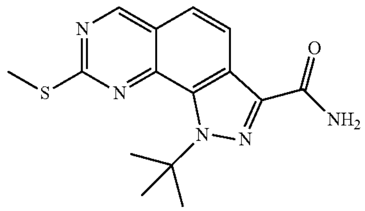 [SMILES: CSc1ncc2ccc3c(C(N)=O)nn(C(C)(C)C)c3c2n1] | 1-tert-butyl-8-(methylsulfanyl)-1H-pyrazolo[4,3-h]quinazoline-3-carboxamide |
| 86. | 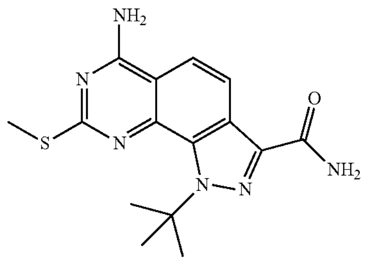 [SMILES: CSc1nc(N)c2ccc3c(C(N)=O)nn(C(C)(C)C)c3c2n1] | 6-amino-1-tert-butyl-8-(methylsulfanyl)-1H-pyrazolo[4,3-h]quinazoline-3-carboxamide |
| 87. | 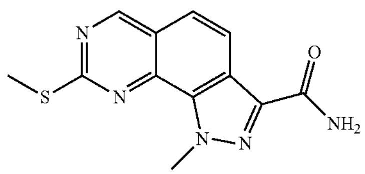 [SMILES: CSc1ncc2ccc3c(C(N)=O)nn(C)c3c2n1] | 1-methyl-8-(methylsulfanyl)-1H-pyrazolo[4,3-h]quinazoline-3-carboxamide |
| 88. | 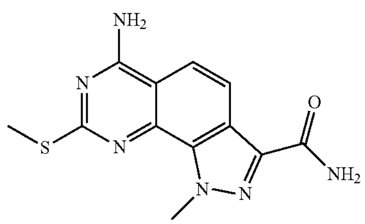 [SMILES: CSc1nc(N)c2ccc3c(C(N)=O)nn(C)c3c2n1] | 6-amino-1-methyl-8-(methylsulfanyl)-1H-pyrazolo[4,3-h]quinazoline-3-carboxamide |
| 89. | 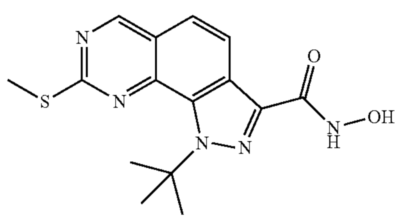 [SMILES: CSc1ncc2ccc3c(C(=O)NO)nn(C(C)(C)C)c3c2n1] | 1-tert-butyl-N-hydroxy-8-(methylsulfanyl)-1H-pyrazolo[4,3-h]quinazoline-3-carboxamide |
| 90. | 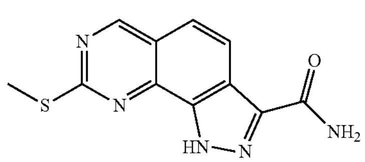 | 8-(methylsulfanyl)-1H-pyrazolo[4,3-h]quinazoline-3-carboxamide |
| 91. | 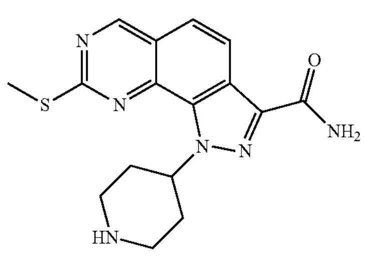 | 8-(methylsulfanyl)-1-(piperidin-4-yl)-1H-pyrazolo[4,3-h]quinazoline-3-carboxamide |

TABLE 1-continued

| No. | Structure | Name |
|---|---|---|
| 92. | 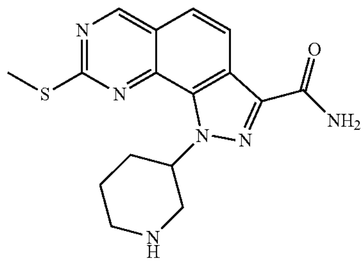 [SMILES: CSc1ncc2ccc3c(C(N)=O)nn(C4CCCNC4)c3c2n1] | 8-(methylsulfanyl)-1-(piperidin-3-yl)-1H-pyrazolo[4,3-h]quinazoline-3-carboxamide |
| 93. | 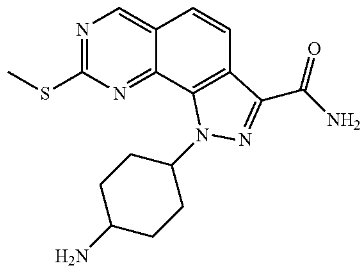 [SMILES: CSc1ncc2ccc3c(C(N)=O)nn(C4CCC(N)CC4)c3c2n1] | 1-(4-aminocyclohexyl)-8-(methylsulfanyl)-1H-pyrazolo[4,3-h]quinazoline-3-carboxamide |
| 94. | 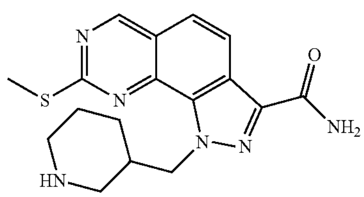 [SMILES: CSc1ncc2ccc3c(C(N)=O)nn(CC4CCCNC4)c3c2n1] | 8-(methylsulfanyl)-1-(piperidin-3-ylmethyl)-1H-pyrazolo[4,3-h]quinazoline-3-carboxamide |
| 95. | 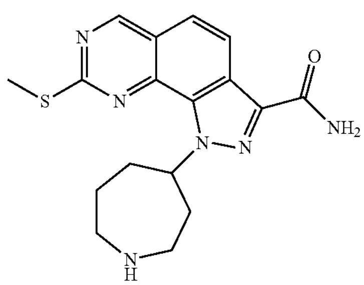 [SMILES: CSc1ncc2ccc3c(C(N)=O)nn(C4CCCNCC4)c3c2n1] | 1-(azepan-4-yl)-8-(methylsulfanyl)-1H-pyrazolo[4,3-h]quinazoline-3-carboxamide |
| 96. | 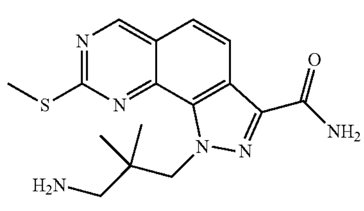 [SMILES: CSc1ncc2ccc3c(C(N)=O)nn(CC(C)(C)CN)c3c2n1] | 1-(3-amino-2,2-dimethylpropyl)-8-(methylsulfanyl)-1H-pyrazolo[4,3-h]quinazoline-3-carboxamide |
| 97. | 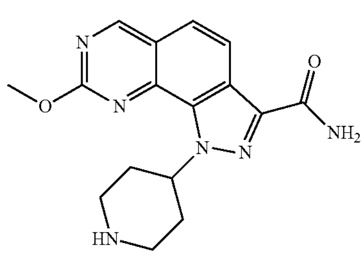 [SMILES: COc1ncc2ccc3c(C(N)=O)nn(C4CCNCC4)c3c2n1] | 8-methoxy-1-(piperidin-4-yl)-1H-pyrazolo[4,3-h]quinazoline-3-carboxamide |

TABLE 1-continued

| No. | Structure | Name |
|---|---|---|
| 98. | 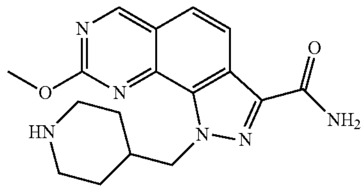 [SMILES: COc1ncc2ccc3c(C(N)=O)nn(CC4CCNCC4)c3c2n1] | 8-methoxy-1-(piperidin-4-ylmethyl)-1H-pyrazolo[4,3-h]quinazoline-3-carboxamide |
| 99. | 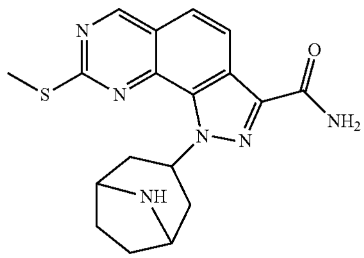 [SMILES: CSc1ncc2ccc3c(C(N)=O)nn(C4CC5CCC(C4)N5)c3c2n1] | 1-[(3-exo)-8-azabicyclo[3.2.1]oct-3-yl]-8-(methylsulfanyl)-1H-pyrazolo[4,3-h]quinazoline-3-carboxamide |
| 100. | 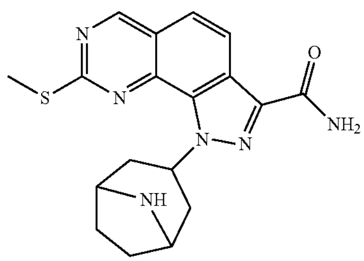 [SMILES: CSc1ncc2ccc3c(C(N)=O)nn(C4CC5CCC(C4)N5)c3c2n1] | 1-[(3-endo)-8-azabicyclo[3.2.1]oct-3-yl]-8-(methylsulfanyl)-1H-pyrazolo[4,3-h]quinazoline-3-carboxamide |
| 101. | 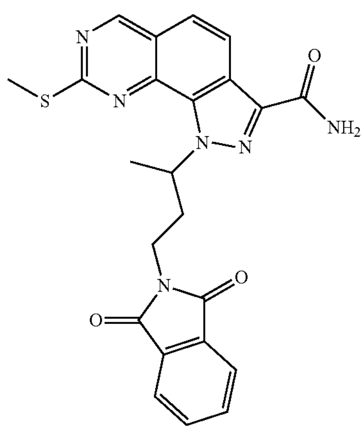 [SMILES: CSc1ncc2ccc3c(C(N)=O)nn(C(C)CCN4C(=O)c5ccccc5C4=O)c3c2n1] | 1-[4-(1,3-dioxo-1,3-dihydro-2H-isoindol-2-yl)butan-2-yl]-8-(methylsulfanyl)-1H-pyrazolo[4,3-h]quinazoline-3-carboxamide |
| 102. | 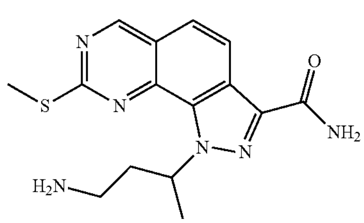 [SMILES: CSc1ncc2ccc3c(C(N)=O)nn(C(C)CCN)c3c2n1] | 1-(4-aminobutan-2-yl)-8-(methylsulfanyl)-1H-pyrazolo[4,3-h]quinazoline-3-carboxamide |

TABLE 1-continued

| No. | Structure | Name |
|---|---|---|
| 103. | 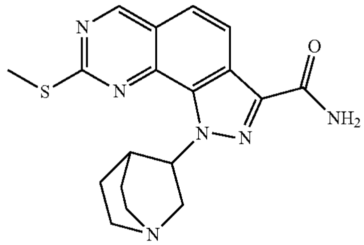 [SMILES: CSc1ncc2ccc3c(C(N)=O)nn(C4CN5CCC4CC5)c3c2n1] | 1-(1-azabicyclo[2.2.2]oct-3-yl)-8-(methylsulfanyl)-1H-pyrazolo[4,3-h]quinazoline-3-carboxamide |
| 104. | 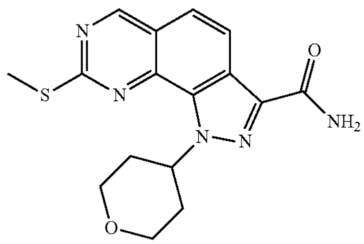 [SMILES: CSc1ncc2ccc3c(C(N)=O)nn(C4CCOCC4)c3c2n1] | 8-(methylsulfanyl)-1-(tetrahydro-2H-pyran-4-yl)-1H-pyrazolo[4,3-h]quinazoline-3-carboxamide |
| 105. | 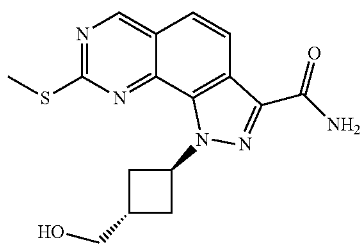 [SMILES: CSc1ncc2ccc3c(C(N)=O)nn([C@H]4C[C@H](CO)C4)c3c2n1] | 1-[trans-3-(hydroxymethyl)cyclobutyl]-8-(methylsulfanyl)-1H-pyrazolo[4,3-h]quinazoline-3-carboxamide |
| 106. | 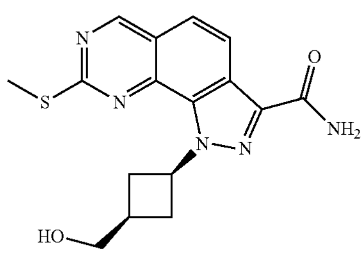 [SMILES: CSc1ncc2ccc3c(C(N)=O)nn([C@H]4C[C@@H](CO)C4)c3c2n1] | 1-[cis-3-(hydroxymethyl)cyclobutyl]-8-(methylsulfanyl)-1H-pyrazolo[4,3-h]quinazoline-3-carboxamide |
| 107. | 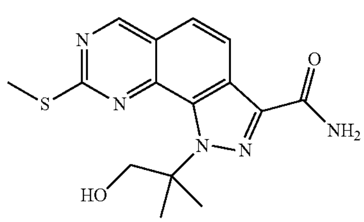 [SMILES: CSc1ncc2ccc3c(C(N)=O)nn(C(C)(C)CO)c3c2n1] | 1-(1-hydroxy-2-methylpropan-2-yl)-8-(methylsulfanyl)-1H-pyrazolo[4,3-h]quinazoline-3-carboxamide |
| 108. | 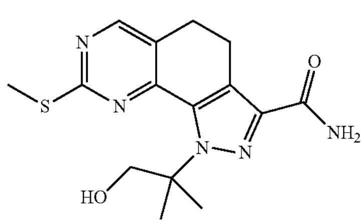 [SMILES: CSc1ncc2c(n1)-c1c(c(C(N)=O)nn1C(C)(C)CO)CC2] | 1-(1-hydroxy-2-methylpropan-2-yl)-8-(methylsulfanyl)-4,5-dihydro-1H-pyrazolo[4,3-h]quinazoline-3-carboxamide |

TABLE 1-continued

| No. | Structure | Name |
|---|---|---|
| 109. | 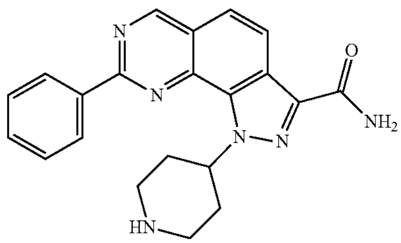 [SMILES: NC(=O)c1nn(C2CCNCC2)c2c1ccc1cnc(-c3ccccc3)nc12] | 8-phenyl-1-(piperidin-4-yl)-1H-pyrazolo[4,3-h]quinazoline-3-carboxamide |
| 110. | 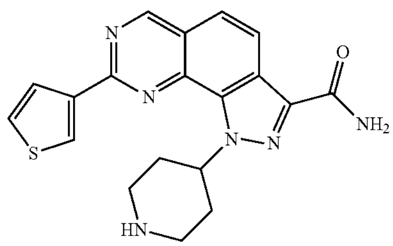 [SMILES: NC(=O)c1nn(C2CCNCC2)c2c1ccc1cnc(-c3ccsc3)nc12] | 1-(piperidin-4-yl)-8-(thiophen-3-yl)-1H-pyrazolo[4,3-h]quinazoline-3-carboxamide |
| 111. | 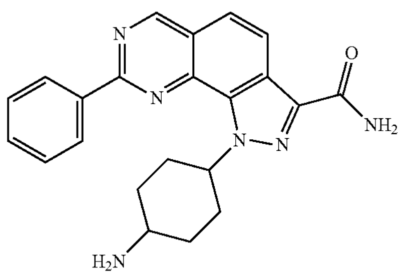 [SMILES: NC(=O)c1nn(C2CCC(N)CC2)c2c1ccc1cnc(-c3ccccc3)nc12] | 1-(4-aminocyclohexyl)-8-phenyl-1H-pyrazolo[4,3-h]quinazoline-3-carboxamide |
| 112. | 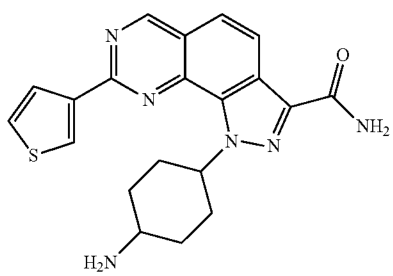 [SMILES: NC(=O)c1nn(C2CCC(N)CC2)c2c1ccc1cnc(-c3ccsc3)nc12] | 1-(4-aminocyclohexyl)-8-(thiophen-3-yl)-1H-pyrazolo[4,3-h]quinazoline-3-carboxamide |
| 113. | 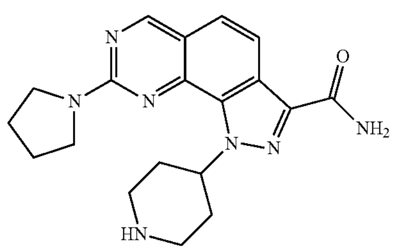 [SMILES: NC(=O)c1nn(C2CCNCC2)c2c1ccc1cnc(N3CCCC3)nc12] | 1-(piperidin-4-yl)-8-(pyrrolidin-1-yl)-1H-pyrazolo[4,3-h]quinazoline-3-carboxamide |
| 114. | 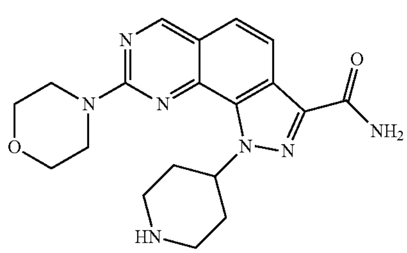 [SMILES: NC(=O)c1nn(C2CCNCC2)c2c1ccc1cnc(N3CCOCC3)nc12] | 8-(morpholin-4-yl)-1-(piperidin-4-yl)-1H-pyrazolo[4,3-h]quinazoline-3-carboxamide |

TABLE 1-continued

| No. | Structure | Name |
|---|---|---|
| 115. | 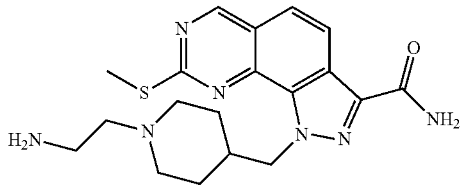 [SMILES: CSc1ncc2ccc3c(C(N)=O)nn(CC4CCN(CCN)CC4)c3c2n1] | 1-{[1-(2-aminoethyl)piperidin-4-yl]methyl}-8-(methylsulfanyl)-1H-pyrazolo[4,3-h]quinazoline-3-carboxamide |
| 116. | 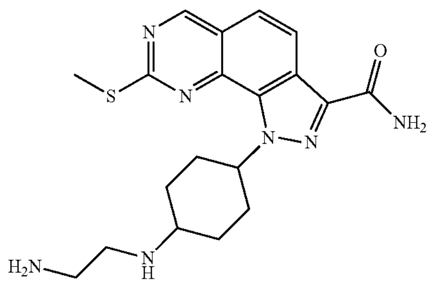 [SMILES: CSc1ncc2ccc3c(C(N)=O)nn(C4CCC(NCCN)CC4)c3c2n1] | 1-{4-[(2-aminoethyl)amino]cyclohexyl}-8-(methylsulfanyl)-1H-pyrazolo[4,3-h]quinazoline-3-carboxamide |
| 117. | 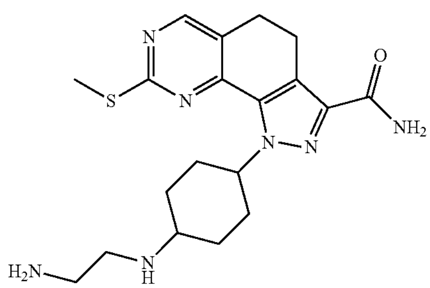 [SMILES: CSc1ncc2c(n1)-c1c(c(C(N)=O)nn1C1CCC(NCCN)CC1)CC2] | 1-{4-[(2-aminoethyl)amino]cyclohexyl}-8-(methylsulfanyl)-4,5-dihydro-1H-pyrazolo[4,3-h]quinazoline-3-carboxamide |
| 118. | 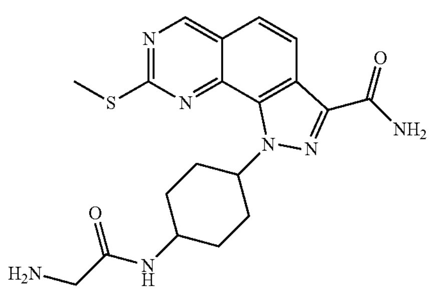 [SMILES: CSc1ncc2ccc3c(C(N)=O)nn(C4CCC(NC(=O)CN)CC4)c3c2n1] | 1-[4-(glycylamino)cyclohexyl]-8-(methylsulfanyl)-1H-pyrazolo[4,3-h]quinazoline-3-carboxamide |
| 119. | 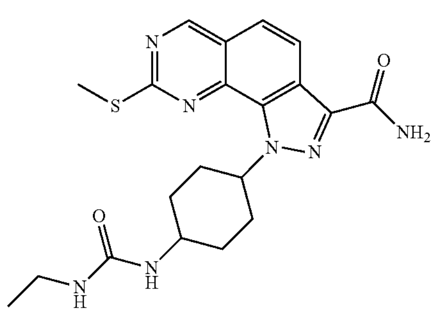 [SMILES: CCNC(=O)NC1CCC(n2nc(C(N)=O)c3ccc4cnc(SC)nc4c32)CC1] | 1-{4-[(ethylcarbamoyl)amino]cyclohexyl}-8-(methylsulfanyl)-1H-pyrazolo[4,3-h]quinazoline-3-carboxamide |

TABLE 1-continued

| No. | Structure | Name |
|---|---|---|
| 120. | 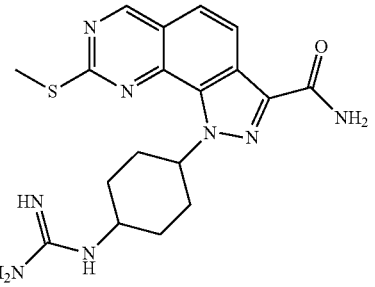 | 1-(4-carbamimidamidocyclohexyl)-8-(methylsulfanyl)-1H-pyrazolo[4,3-h]quinazoline-3-carboxamide |
| 121. | 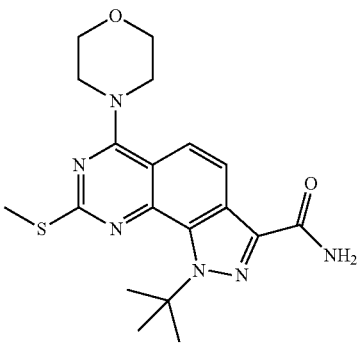 [SMILES: CSc1nc(N2CCOCC2)c2ccc3c(C(N)=O)nn(C(C)(C)C)c3c2n1] | 1-tert-butyl-8-(methylsulfanyl)-6-(morpholin-4-yl)-1H-pyrazolo[4,3-h]quinazoline-3-carboxamide |
| 122. | 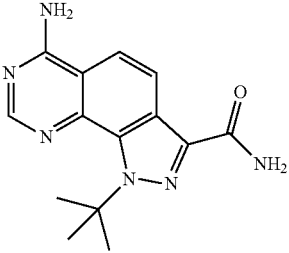 [SMILES: CC(C)(C)n1nc(C(N)=O)c2ccc3c(N)ncnc3c21] | 6-amino-1-tert-butyl-1H-pyrazolo[4,3-h]quinazoline-3-carboxamide |

For a reference to any specific compound of the formula (I) of the invention, optionally in the form of a pharmaceutically acceptable salt, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

FIG. 1 shows the preparation of a compound of formula (I) where R1 is hydrogen, an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group SR4 or OR4; and R2, R3, R4, R5, R', R" and A are as defined above.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises:

st.1) mixing a compound of the formula (II):

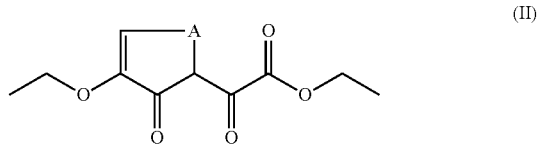

(II)

wherein A is —(CH$_2$)$_2$— with an hydrazine derivative of formula (III):

R2-NHNH$_2$     (III)

wherein R2 is as defined above, under acidic conditions to give a compound of formula (IV):

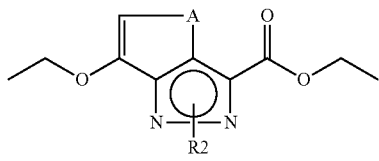

(IV)

wherein A is —(CH$_2$)$_2$— and R2 is as defined above; or st.1a) mixing a compound of formula (IV) wherein R2 is hydrogen with a compound of formula (V):

R2-Y  (V)

wherein R2 is as defined above but not hydrogen and Y represents a suitable leaving group such as iodo, bromo, chloro or a sulfonate group (e.g. —OS(O)$_2$CF$_3$, —OS(O)$_2$CH$_3$ or —OS(O)$_2$PhMe), to give a compound of formula (IV) wherein R2 is as defined above but not hydrogen;

st. 2) mixing the resulting compound of formula (IV) with dimethylformamide-di-alkylacetal to give a compound of formula (VI):

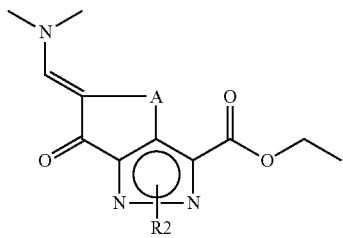

(VI)

wherein A is —(CH$_2$)$_2$— and R2 is as defined above;

st.3) reacting the resulting compound of formula (VI) according to any one of the alternative steps (st.3a), (st. 3b) or (st.3c):

st.3a) with an isothiourea of formula (VIIa) or a salt thereof:

R4-S—C(=NH)NH$_2$  (VIIa)

wherein R4 is as defined above, st.3b) with an isourea of formula (VIIb) or a salt thereof:

R4-O—C(=NH)NH$_2$  (VIIb)

wherein R4 is as defined above, st.3c) with a suitable amidine of formula (IX) or a salt thereof:

R1-C(=NH)NH$_2$  (IX)

wherein R1 is hydrogen or an optionally substituted group selected from straight or branched C$_1$-C$_6$ alkyl, C$_3$-C$_7$ cycloalkyl, cycloalkylalkyl, aryl, arylalkyl, heterocyclyl and heterocyclylalkyl, to give a compound of formula (VIII):

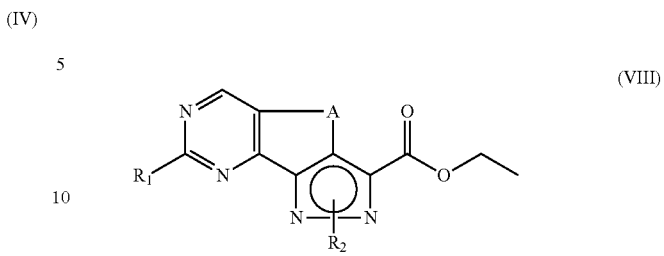

(VIII)

wherein R1 is respectively SR4, OR4, hydrogen or an optionally substituted group selected from straight or branched C$_1$-C$_6$ alkyl, C$_3$-C$_7$ cycloalkyl, cycloalkylalkyl, aryl, arylalkyl, heterocyclyl and heterocyclylalkyl, A is —(CH$_2$)$_2$— and R2 and R4 are as defined above;

st.4) mixing the resultant compound of formula (VIII) with an oxidizing agent, or under dehydrogenating operative conditions in the presence of a Pd or Pt catalyst to give a compound of formula (VIII) wherein R1 is respectively SR4, OR4, hydrogen or an optionally substituted group selected from straight or branched C$_1$-C$_6$ alkyl, C$_3$-C$_7$ cycloalkyl, cycloalkylalkyl, aryl, arylalkyl, heterocyclyl and heterocyclylalkyl, A is —CH=CH—, and R2 and R4 are as defined above;

st. 5) reacting a compound of formula (VIII) obtained as described in step st.3a), st.3b), st.3c) or st.4) and wherein R2 is a protecting group such as t-butyl or trityl under acidic conditions, to obtain a compound of formula (VIII) wherein R2 is hydrogen, converting the resulting compound of formula (VIII) into a mixture of two compounds of formula (VIIIa) and formula (VIIIb) wherein R2 is as defined above but not hydrogen, through reaction with a compound of formula (V):

R2-Y  (V)

wherein Y is as defined above and R2 is as defined above but not hydrogen:

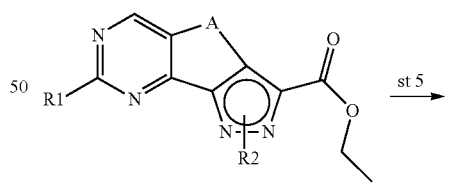

(VIII)

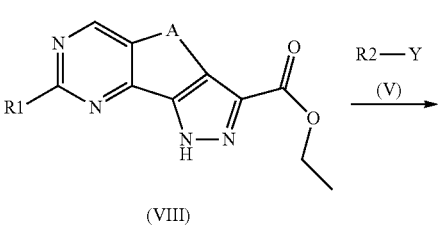

(VIII)

-continued

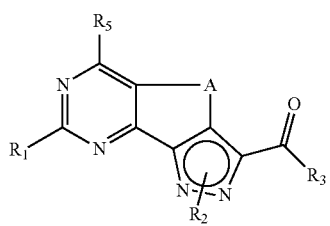

(VIIIa)

+

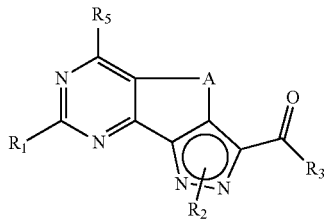

(VIIIb)

st. 6) reacting a compound of formula (VIII) obtained as described in step st.3a), st.3b), st.3c), st.4) or st.5) according to any one of the alternative steps st. 6a), st. 6b) or st. 6c):

st. 6a) with ammonium hydroxide or an amine of formula (XII):

R'R"—NH  (XII):

wherein R' and R" are as defined above, to obtain a compound of formula (I):

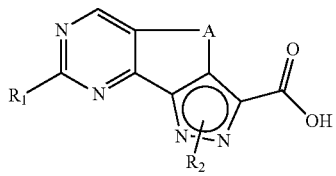

(I)

wherein R1 is hydrogen, an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group SR4 or OR4; R3 is NR'R", R5 is hydrogen and R2, R4 and A are as defined above;

st. 6b1) under acidic or basic hydrolytic conditions to give a compound of formula (XI) or a salt thereof:

(XI)

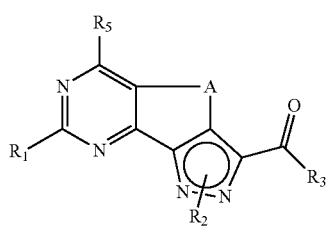

wherein R1 is hydrogen, an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group SR4 or OR4; and R2, R4 and A are as defined above;

st. 6b2) mixing the resulting compound of formula (XI) or a salt thereof with an ammonium salt or a derivative of formula (XII) or a derivative of formula (X):

R'NHOH  (X):

under basic conditions and in the presence of a suitable condensing agent, to give a compound of formula (I):

(I)

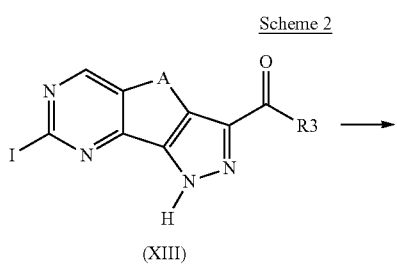

wherein R1 is hydrogen, an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group SR4 or OR4; R5 is hydrogen and R2, R4, R3 and A are as defined above;

st. 6c) with an ammonium salt or a suitable amine of formula (XII) in the presence of a strong base, to give a compound of formula (I):

(I)

wherein R1 is hydrogen, an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, or a group SR4 or OR4; R3 is NR'R", and R2, R4, R5, A, R' and R" are as defined above;

optionally converting a compound of the formula (I) into another different compound of the formula (I), and, if desired, converting a compound of the formula (I) into a pharmaceutically acceptable salt thereof or converting a salt into the free compound (I).

The present invention further provides an alternative process for the preparation of a compound of formula (I) as defined above, reported in Scheme 2 below.

Scheme 2

(XIII)

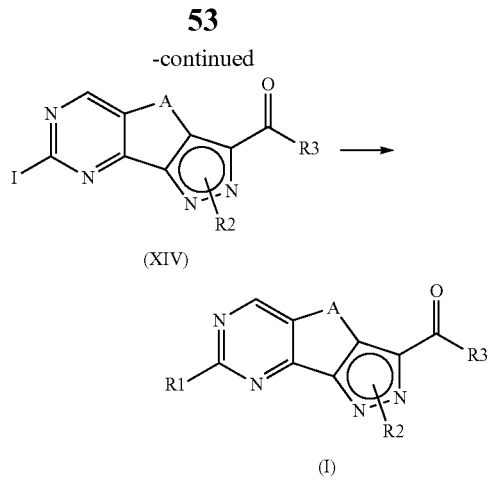

(XIV)

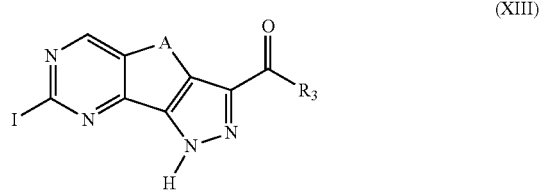

(I)

In the above scheme R1 is an optionally substituted group selected from straight or branched $C_1$-$C_6$ alkyl, $C_3$-$C_7$ cycloalkyl, aryl, and heterocyclyl, R2 is as defined above but not hydrogen, R3 and A are as defined above; this alternative process comprises the following steps:

st. 7) reacting a compound of formula (XIII):

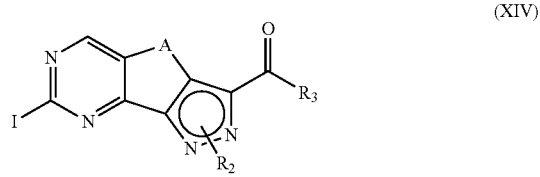

(XIII)

wherein R3 and A are as defined above, with a compound of formula (V):

R2-Y (V)

wherein Y is a defined above and R2 is as defined above but not hydrogen;

st. 8) reacting the resulting compound of formula (XIV):

(XIV)

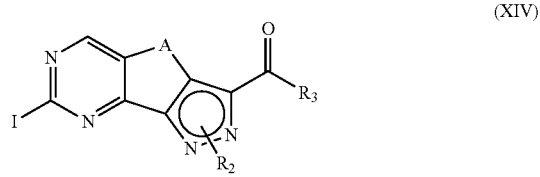

wherein R2 is as defined above but not hydrogen and R3 and A are as defined above, with a compound of formula (XV):

R1-Q (XV)

wherein R1 is an optionally substituted group selected from straight or branched $C_1$-$C_6$ alkyl, $C_3$-$C_7$ cycloalkyl, aryl, and heterocyclyl, and Q is a suitable group such as —B(OH)$_2$, —B(OAlk)$_2$, —Sn(Alk)$_4$, —Al(Alk)$_3$, ZnHal, MgHal, or ZrCp$_2$Hal, which can undergo palladium mediated carbon bond formation, to give a compound of formula (I):

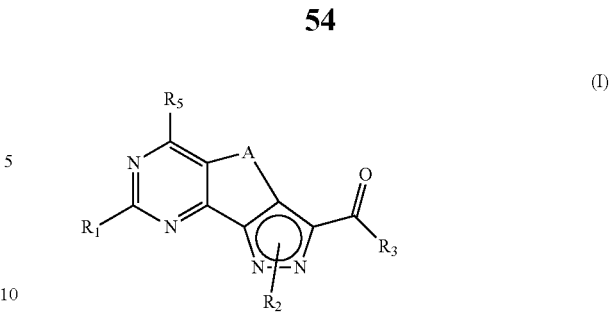

(I)

wherein R1 is an optionally substituted group selected from straight or branched $C_1$-$C_6$ alkyl, $C_3$-$C_7$ cycloalkyl, aryl and heterocyclyl, R2 is as defined above but not hydrogen, R3 and A are as defined above and R5 is hydrogen;

optionally converting a compound of the formula (I) into another different compound of the formula (I), and, if desired, converting a compound of the formula (I) into a pharmaceutically acceptable salt thereof or converting a salt into the free compound (I).

The present invention further provides an alternative process for the preparation of a compound of formula (VIII) as defined above, reported in Scheme 3 below.

Scheme 3

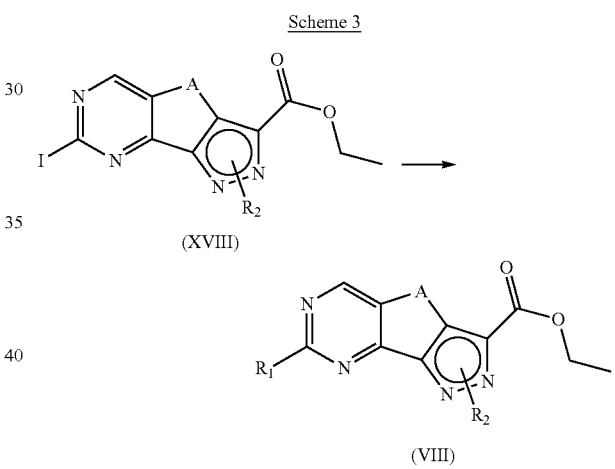

(XVIII)

(VIII)

In the above scheme R1 is an optionally substituted group selected from straight or branched $C_1$-$C_6$ alkyl, $C_3$-$C_7$ cycloalkyl, aryl, and heterocyclyl, R2 is as defined above but not hydrogen and A is as defined above; this alternative process comprises the following step:

st. 9) reacting the compound of formula (XVIII):

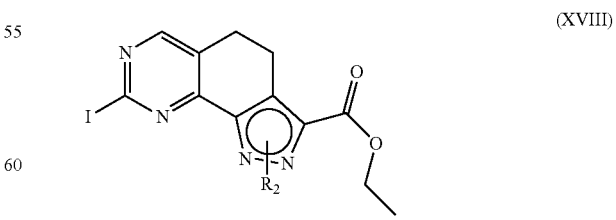

(XVIII)

wherein R2 is as defined above but not hydrogen and A is as defined above with a compound of formula R1-Q (XV):

R1-Q (XV):

wherein R1 is an optionally substituted group selected from straight or branched $C_1$-$C_6$ alkyl, $C_3$-$C_7$ cycloalkyl, aryl, and heterocyclyl, and Q is as defined above, which can undergo palladium mediated carbon bond formation, to give a compound of formula (VIII).

As defined above, the compounds of formula (I) which are prepared according to the process object of the invention, can be conveniently converted into other compounds of formula (I) by operating according to well-known synthetic conditions, the following being examples of possible conversions:

Conv. a) converting a compound of formula (I) wherein R1 is a group such as R4-S—, wherein R4 is as defined above, into a compound of formula (I) wherein R1 is a group R4-S$(O)_2$—, under oxidative condition:

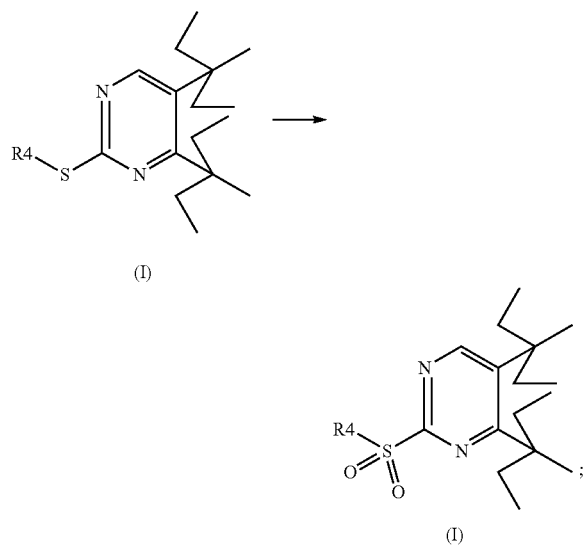

Conv. b) converting a compound of formula (I) wherein R1 is a group such as R4-S$(O)_2$—, wherein R4 is as defined above, into a compound of formula (I) wherein R1 is a group R4-O—, by reacting the sulfonyl derivative with a compound of formula R4-OH (XVI):

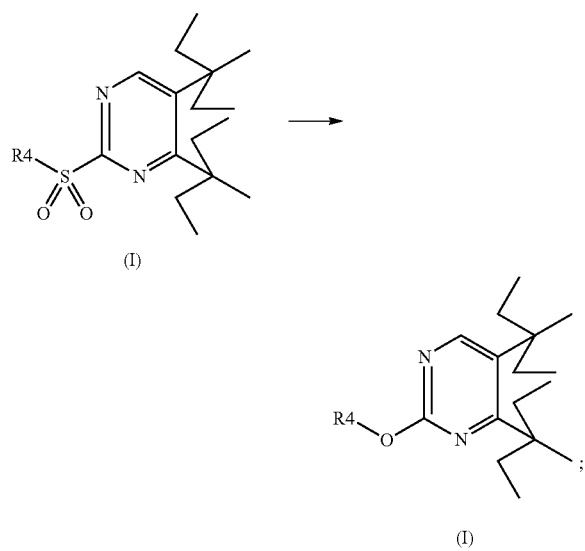

Conv. c) converting a compound of formula (I) wherein R1 is a group such as R4-S$(O)_2$— into a compound of formula (I) wherein R1 is a group R4-NR6 wherein R4 and R6 are as defined above, by reacting the sulfonyl derivative with a compound of formula R4R6-NH (XVII):

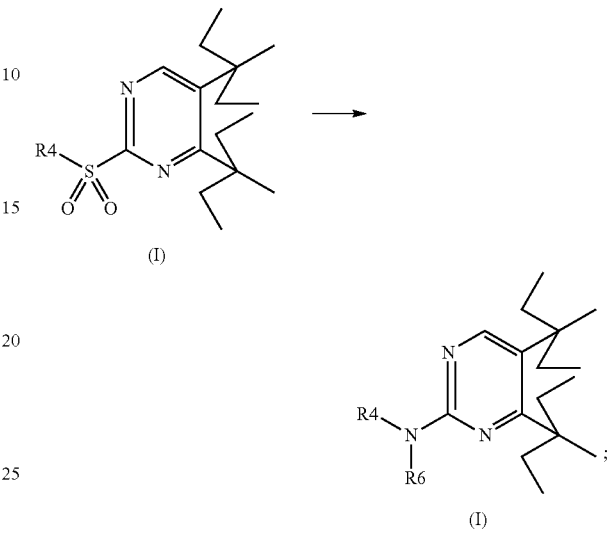

wherein R4 and R6 are as defined above,

Conv. d) converting a compound of formula (I) wherein R1 is a group such as R4-S(O)2- into a compound of formula (I) wherein R1 is —CN, by reacting the sulfonyl derivative with sodium cyanide (NaCN) or potassium cyanide (KCN):

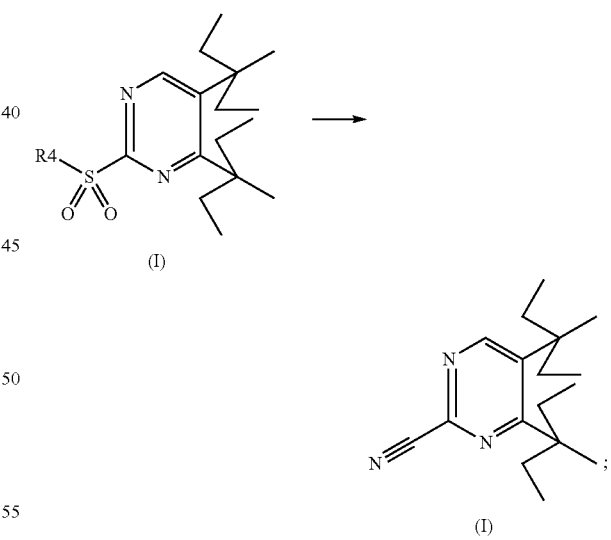

Conv. e) converting a compound of formula (I) wherein R1, R3 and A are as defined above and R2 is hydrogen, into a compound of formula (I) wherein R2 is as defined above but not hydrogen, through reaction with a compound of formula (V):

wherein Y' is OH or a group that optionally upon activation, may work as a suitable leaving group such as iodo, bromo, chloro or a sulfonate group (e.g. —OS(O)$_2$CF$_3$, —OS(O)$_2$CH$_3$ or —OS(O)$_2$PhMe), and R2 is as defined above but not hydrogen,

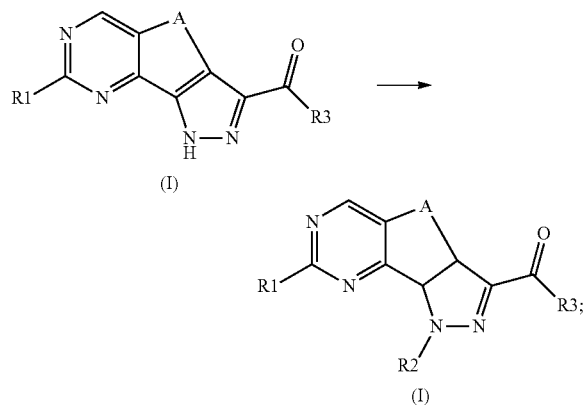

Conv. f) converting a compound of formula (I) wherein R2 is an haloethyl into a compound of formula (I) wherein R2 is vinyl, by applying basic conditions:

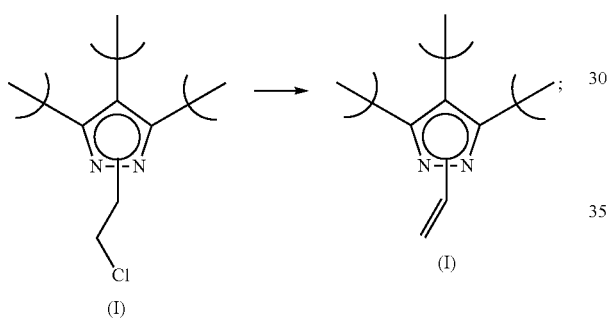

Conv. g) converting a compound of formula (I) wherein R2 is a group of formula L-CH$_2$Cl wherein L is an optionally substituted group selected from straight or branched C$_1$-C$_6$ alkyl, C$_3$-C$_7$ cycloalkyl, cycloalkylalkyl, aryl, arylalkyl, heterocyclyl and heterocyclylalkyl, substituted with a chloro by reacting with a compound of formula R'R"NH (XII), to give a compound of formula (I) wherein R2 is a group L-CH$_2$NR'R", R' and R" are as defined above:

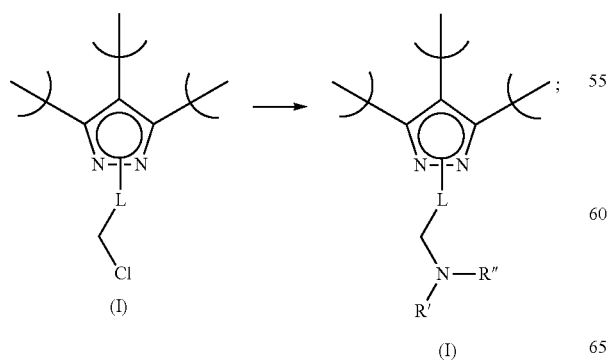

Conv. h) converting a compound of formula (I) wherein R2 is a group of formula L-CH$_2$OH wherein L is as defined above, into a compound of formula (I) wherein R2 is a group L-CH$_2$NR'R" by first converting the group CH$_2$OH into CHO and by then reacting the resulting aldehyde derivative with a compound of formula R'R"NH (XII), in the presence of a suitable reducing agents:

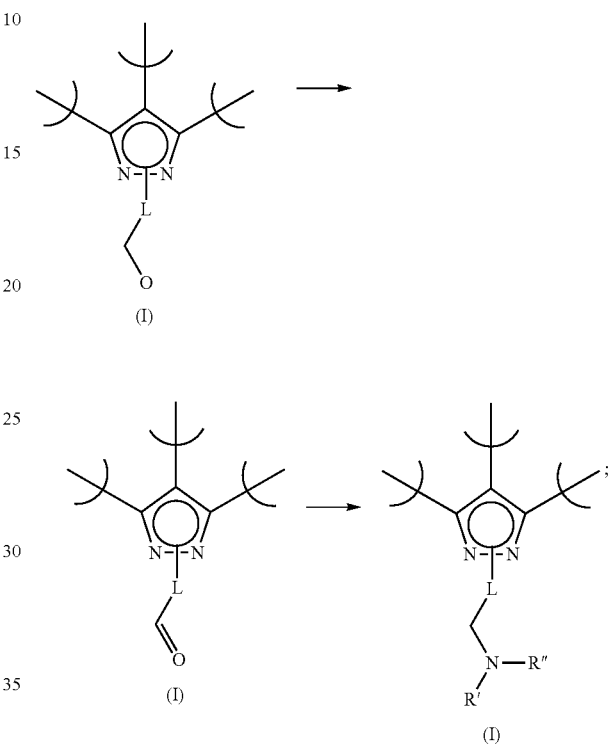

Conv. i) converting a compound of formula (I) wherein R2 is a group of formula L-COOalkyl wherein L is as defined above, into a compound of formula (I) wherein R2 is a L-CH$_2$OH by reacting with a suitable reducing reagent:

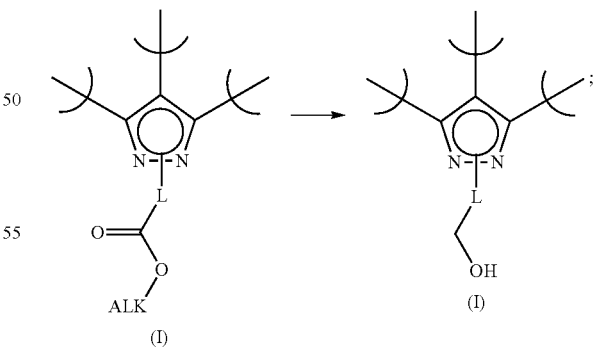

Conv. j) converting a compound of formula (I) wherein X is O and R4 is an aryl, i.e. phenyl, substituted by —CHO, into another compound of formula (I) wherein R4 is an aryl, i.e. phenyl, substituted by CH$_2$NR'R", wherein R' and R" are as defined above, by treatment with an amine of formula R'R"—NH (XII), in the presence of a suitable reducing agents:

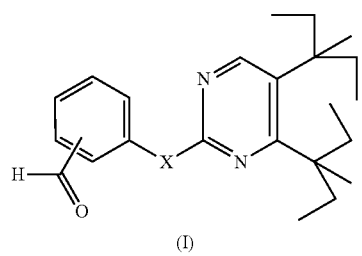

(I)

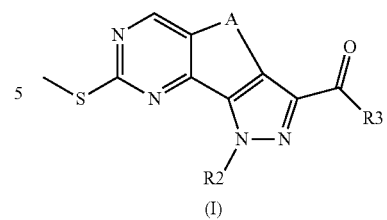

(I)

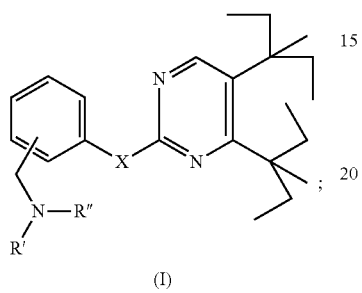

(I)

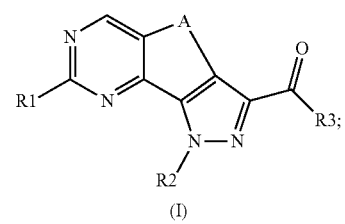

(I)

Conv. k) converting a compound of formula (I) wherein X is O and R4 is an aryl, i.e. phenyl, substituted by —NO₂, into another compound of formula (I) wherein R4 is an aryl, i.e. phenyl, substituted by NH₂, by treatment with a suitable reducing agent:

Conv. m) converting a compound of formula (I) wherein R1 and R2 are as defined above, R5 is hydrogen and A is —CH=CH—, into a compound of formula (I) wherein R5 is NR'R", by reaction with an ammonium salt or a suitable amine of formula R'R"NH (XII) in the presence of a strong base;

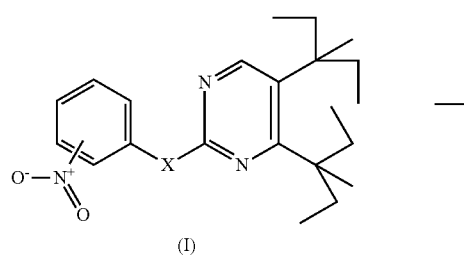

(I)

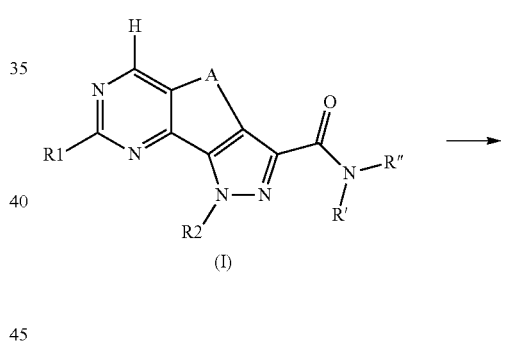

(I)

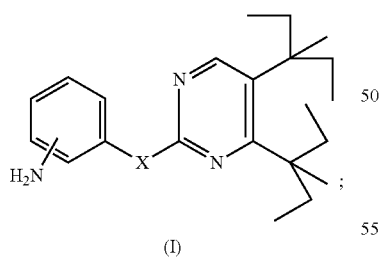

(I)

Conv. l) converting a compound of formula (I) wherein R2, R3 an A are as defined above and R1 is a group such as Me-S— into a compound of formula (I) wherein R1 is an optionally substituted group selected from straight or branched C₁-C₆ alkyl, C₃-C₇ cycloalkyl, aryl, and heterocyclyl, by reacting with a compound of formula R1-Q' (XV) wherein R1 is as defined above and Q' is a suitable group such as —B(OH)₂, —MgHal, —ZnHal, which can undergo palladium mediated carbon bond formation:

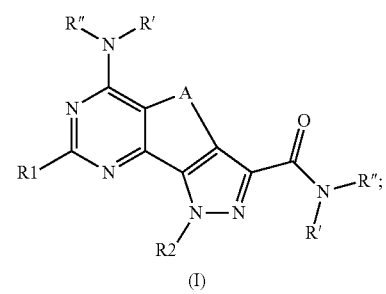

(I)

Conv. n) converting a compound of formula (I) wherein R2 is a group of formula L-N(H)R' wherein L and R' are as defined above, by treatment with a compound of formula R"—CHO (XIX) under conditions such that is formed a compound of formula (I) wherein R2 is a group of formula L-NR'R", wherein R' and R" are as defined above:

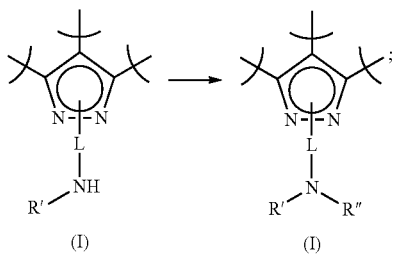

Conv. o) converting a compound of formula (I) wherein R2 is a group of formula L-N(H)R' wherein L and R' are as defined above, by treatment with a compound of formula R7-COW (XX) wherein R7 is an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, wherein W is hydroxyl or halogen, under conditions such that is formed a compound of formula (I) wherein R2 is a group of formula L-N(R')COR7, wherein R' is as defined above:

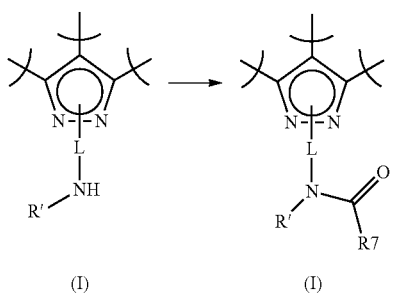

Conv. p) converting a compound of formula (I)) wherein R2 is a group of formula L-N(H)R' wherein L and R' are as defined above, by treatment with a compound of formula R8-N=C=O (XXI) wherein R8 is an optionally substituted group selected from straight or branched $C_1$-$C_6$ alkyl, $C_3$-$C_7$ cycloalkyl, cycloalkylalkyl, aryl, arylalkyl, heterocyclyl and heterocyclylalkyl, under conditions such that is formed a compound of formula (I) wherein R2 is a group of formula L-N(R')CONHR8, wherein R' is as defined above:

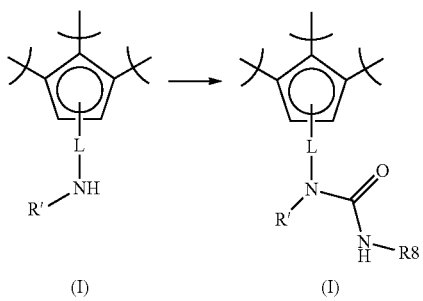

Conv. q) converting a compound of formula (I)) wherein R2 is a group of formula L-N(H)R' wherein L and R' are as defined above, by treatment with a compound of formula R8-NHC(NH)G (XXII) wherein R8 is as defined above and G is a suitable leaving group under conditions such that is formed a compound of formula (I) wherein R2 is a group of formula L-N(R')NHCNHR8, wherein R' is as defined above:

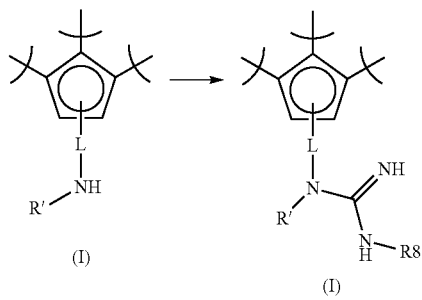

Conv. r) converting a compound of formula (I) wherein R1, R2 and R3 are as defined above and A is a divalent group such as —$CH_2$—$CH_2$— into a compound of formula (I) wherein A is a —CH=CH— group, by treatment with an oxidizing agent, or under dehydrogenating operative conditions in the presence of a Pd or Pt catalyst:

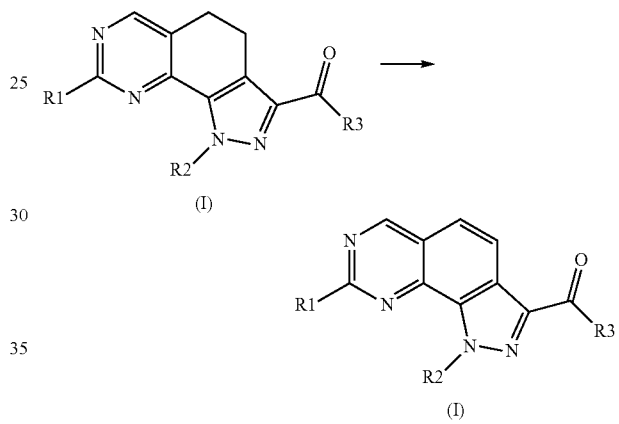

The synthesis of a compound of formula (I), according to the synthetic process described before, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

According to step (st. 1) of the process, the compound of formula (II) is reacted with hydrazine or an hydrazine derivative of formula (III) in a solvent such as ethanol, in the presence of acetic acid, the reaction is carried out at a temperature ranging from room temperature to 80° C., so as a compound of formula (IV) is obtained.

Optionally, the compound of formula (IV) wherein R2 is hydrogen is dissolved in a suitable solvent for instance acetonitrile, tetrahydrofuran, dimethylformamide, or the like, and a suitable base such as sodium hydride, or cesium carbonate is added therein. The compound of general formula R2Y (V) is then added and the mixture stirred for a time of about 2 hours to about 15 hours, at a temperature ranging from about 20° C. to about 80° C.

According to step (st. 2) of the process, the synthesis of the enaminone derivative of formula (IV) is accomplished using a N,N-dimethylformamide dialkyl acetal, such as, for instance dimethylformamide-di-tert-butylacetal, dimethylformamide-diethylacetal and the like in a suitable solvent such as N,N-dimethylformamide, N,N-dimethylacetamide, toluene, or the like at a temperature ranging from room temperature to 100° C., and for a time ranging from 30 minutes to about 24 hours.

According to one of the alternative steps, (st. 3a), (st.3b) or (st. 3c) of the process, the conversion of a compound of formula (VI) into a compound of formula (VIII) is accomplished by using an isothiourea of formula (VIIa), or isourea of formula (VIIb), or a suitable amidine of formula (IX). Any of the above reactions is carried out according to conventional methods. As an examples, the reaction with methylisothiourea or salts thereof such as sulphate is carried out in a suitable solvent such as N,N-dimethylformamide, tetrahydrofuran, acetonitrile and the like, in the presence of a base such as potassium acetate, sodium bicarbonate, sodium or potassium carbonate and the like, at a temperature ranging from 50° C. to 100° C. and for a time ranging from 2 hours to about 48 hours.

According to step (st. 4) of the process, the compound of formula (VIII) can undergo dehydrogenation in the presence of an optionally supported palladium or platinum or 2,3-Dichloro-5,6-dicyano-1,4-benzoquinone (DDQ), so as to obtain the corresponding aromatic derivative of formula (VIII), by operating in a suitable solvent such as toluene, 1,4-dioxane, chlorobenzene, dichlorobenzene, at a temperature ranging from 90° C. to reflux, for a time varying between 2 hours to 8 hours.

According to step (st. 5) of the process a compound of formula (VIII) wherein R2 is a protecting group such as t-butyl or trityl the cleavage of them can be accomplished in a variety of ways according to conventional methods. Preferably is carried out by mixing with hydrochloride acid, trifluoroacetic acid in the presence of a suitable solvent as dichloromethane and the like, so as to give raise a compound of formula (VIII) wherein R2 is hydrogen.

Therefore, the obtained compound of formula (VIII) is reacted with compound of formula R2Y (V) wherein R2 is as defined above but not hydrogen and Y is as defined above, in the presence of a base such as potassium or cesium carbonate, in a suitable solvent such as acetonitrile, N,N-dimethylformamide. The latter reaction could yield a mixture of regioisomers of formula (VIIIa) and (VIIIb), which can be resolved by known methods such as silica gel chromatography or preparative HPLC.

According to step (st. 6a) of the process, the compound of formula (VIII) is transformed into the compound of formula (I) according to methods well-known in the art to convert carboxyester groups (—COOEt) into carboxamides (—CONH$_2$), N-substituted carboxamides (—CONHR'), N,N-disubstituted carboxamides (—CONR'R"). Preferably the reaction is carried out with ammonium hydroxide in a methanol/N,N-dimethylformamide mixture, at a temperature ranging from about 50° C. to about 100° C.

Analogous operative conditions are applied in the preparation of N-substituted carboxamides or N,N-disubstituted carboxamides wherein a suitable primary or secondary amine are used in place of ammonia or ammonium hydroxide.

Preferably according to step (st. 6b1) of the process, the hydrolysis of a compound of formula (VIII), to give the corresponding carboxylic acid of compound of formula (XI) is carried out under acidic or basic conditions. Preferably, the reaction is carried out with aqueous alkaline solutions such as aqueous lithium, sodium or potassium hydroxide in the presence of a suitable solvent such as a lower alcohol, tetrahydrofuran, N,N-dimethylformamide or mixtures thereof; preferably the reaction is carried out with potassium hydroxide in a methanol/N,N-dimethylformamide mixture, at a temperature ranging from about room temperature to about 100° C. According to the operative conditions being employed, the compound of formula (XI) could be obtained either in its acidic form or, alternatively, as a salt.

Preferably according to step (st. 6b2) of the process, the amidation of a carboxylic acid of formula (XI) to give the corresponding compound of formula (I), is carried out in the presence of ammonium chloride or a suitable primary or secondary amine of formula R'R"NH (XII) or a substituted hydroxylamine derivative of formula R'NHOH (X), under basic conditions, preferably with N,N-diisopropyl-N-ethylamine or triethylamine, in a suitable solvent such as dichloromethane, N,N-dimethylformamide, tetrahydrofuran, 1,4-dioxane, or N,N-dimethylacetamide, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-Benzotriazole-1-yl)-1,1,3,3-tetramethyluronium hexafluorophosphate (HBTU). The said reaction is optionally carried out in the presence of a suitable catalyst such as the 4-dimethylaminopyridine, or in the presence of a further coupling reagent such as N-hydroxybenzotriazole. Alternatively, this same reaction is also carried out, for example through a mixed anhydride method, by using an alkyl chloroformate such as ethyl, iso-propyl, benzyl chloroformate, in the presence of a tertiary amine such as triethylamine, N,N-diisopropylethylamine, or pyridine, in a suitable solvent such as, for instance toluene, dichloromethane, tetrahydrofuran, N,N-dimethylformamide and the like, at a room temperature.

According to step (st. 6c) of the process the carboxyester group of the compound of formula (VIII) may be converted into carboxamide or N-substituted carboxamides or N,N-disubstituted carboxamides under basic conditions such as lithium bis-trimethylsilylamide 1 N in THF, using ammonium chloride or a suitable primary or secondary amine; preferably the reaction is carried out in tetrahydrofuran at a temperature ranging from 0° C. to reflux.

Interestingly, in this reaction when A is —CH=CH— a mixture of desired products of formula (I) were obtained, wherein R3 is R'R"N—, and R5 is hydrogen or a group R'R"N—. These two derivatives are then resolved from the reaction mixture according to conventional methods, for instance by chromatography or by preparative HPLC.

According to step (st. 7) of the process the compound of formula (XIII) is reacted with compound of formula R2Y (V) wherein R2 is as defined above but not hydrogen and Y is as defined above, in the presence of a base such as potassium or cesium carbonate, in a suitable solvent such as acetonitrile, dimethylformamide, to obtain the derivatives of formula (XIV).

According to step (st. 8) of the process the compound of formula (XIV) can be transformed into a compound of formula (I) by exploiting any of the cross-coupling reactions suitable for the formation of carbon-carbon bonds. Said reactions, which are well known in the art, imply coupling with a suitable organometal reagent such as for instance organoboron (Suzuki reaction), organotin (Stille reaction), organomagnesium (Kumada reaction), organozinc, or organoaluminium, or organozirconium (Negishi reaction) and the like. Preferred reaction is the Suzuki reaction where the appropriate aryl or heteroarylboronic derivative is used in the presence of a palladium based catalyst such as [1,1'-bis(diphenylphosphino)ferrocene]palladium(II) dichloride dichloromethane complex (PdCl$_2$(dppf)$_2$.CH$_2$Cl$_2$) and a base such as sodium or cesium carbonate, in a mixture of solvents, such as dimethoxyethane and water, at a temperature varying from room temperature to 80° C. and for a time between 2 hours and overnight.

According to step (st. 9) of the process the compound of formula (XVIII) can be transformed into a compound of formula (VIII) by exploiting any of the cross-coupling reactions suitable for the formation of carbon-carbon bonds, such as already described in st. 8.

According to conversion (conv. a) of the process, the transformation of thio group into the sulfonyl group can be obtained by reaction with an oxidant agent well-known to those skilled in the art, such as for instance, oxone in a suitable solvent such as tetrahydrofuran, 1,4-dioxane, acetone, optionally in the presence of water as co-solvent or m-chloroperbenzoic acid in the presence of a suitable solvent preferably DCM at room temperature.

According to conversion (conv. b) of the process, a compound of the formula (I) wherein R4 is as defined above and X is —O— may be easily obtained by reacting the corresponding sulfonyl derivative with a derivative of formula (XVI) R4-OH. The reaction may be carried out in the presence of a base such as potassium or sodium carbonate, sodium or lithium hydroxide or the like, in a suitable solvent such as acetonitrile, N,N-dimethylformamide or dimethylsulfoxide, and by working at a temperature ranging from room temperature to about 100° C.

Interestingly, when this reaction is carried out with compound of formula (I) wherein A is —CH$_2$—CH$_2$— a mixture of desired products of formula (I) were obtained, wherein A is a group —CH$_2$—CH$_2$—, or —CH=CH—. These two derivatives are then resolved from the reaction mixture according to conventional methods, for instance by chromatography or by preparative HPLC.

According to conversion (conv. c) of the process, the sulfonyl derivative of formula (I) is treated with a suitable nucleophile such as secondary amine of formula R4R6NH, to give rise a compound of formula (I) wherein R1 is R4R6N—. The said reaction is accomplished with an excess of the same amine or alternatively in a suitable solvent such as for instance acetonitrile, N,N-dimethylformamide, dimethylsulfoxide, and by working at a temperature ranging from room temperature to about 100° C., form 2 hours to 24 hours.

According to conversion (conv. d) of the process, the conversion of sulfonyl derivative of formula (I) into the compound of formula (I) wherein R1 is —CN, can be accomplished for instance using sodium cyanide in a suitable solvent such as acetonitrile, N,N-dimethylformamide, or mixture thereof, at a temperature ranging from 20° C. to reflux for a time from 2 hours to 24 hours.

According to conversion (conv. e) of the process, the conversion of compound of formula (I) into another compound of formula (I) can be accomplished using a compound of formula R2-Y' (V) wherein Y' is OH, in which case the Mitsunobu conditions can be employed, or Y is a group that optionally upon activation, may work as a leaving group, such as a halogen atom, a tosylate, mesylate or triflate.

In the former instance, that is, when a Mitsunobu protocol is employed, the reaction can be accomplished using a dialkyl azodicarboxylate, such as diethylazodicarboxylate (DEAD), diisopropyl azodicarboxylate (DIAD) or the like, in the presence of a trialkyl or triaryl phosphine, preferably triphenyl phosphine in a suitable solvent such as tetrahydrofuran, 1,4-dioxane, 1,2-dimethoxyethane, acetonitrile. When Y is a halogen or a group such as tosylate, mesylate or triflate or the like the conversion can be accomplished using a suitable base such as, for instance, NaH, K$_2$CO$_3$, Cs$_2$CO$_3$, DBU, KO-t-Bu and the like, in a suitable solvent such as tetrahydrofuran, acetonitrile, N,N-dimethylformamide, N,N-dimethylacetamide and the like. Said reactions can be carried out at temperatures ranging from 0° C. to reflux and for a time ranging from 30 minutes to about 48 hours.

According to conversion (conv. f) of the process, the compound of formula (I) wherein R2 is an haloethyl, preferably chloroethyl, is treated with a base, preferably 1,8-Diazabicyclo[5.4.0]undec-7-ene (DBU), at a temperature ranging from 20° C. to 80° C., so as to obtain the corresponding compound of formula (I) wherein R2 is vinyl.

According to conversion (conv. g) of the process, the compound of formula (I) wherein R2 is a group of formula L-CH$_2$Cl, when mixed with a suitable nucleophile such as a primary or secondary amine of formula (XII) NHR'R", in the presence of a base such as for instance potassium carbonate, cesium carbonate, triethylamine, DBU in a suitable solvent such as tetrahydrofuran, acetonitrile, N,N-dimethylformamide and a mixture thereof, at a temperature ranging from 50° C. to 100° C. and for a suitable time, for instance 2 hours to 24 hours.

According to conversion (conv. h) of the process, the conversion of the compound of formula (I) wherein R2 is a group L-CH$_2$OH into a compound of formula (I) wherein R2 is a group L-CH$_2$NR'R" can be accomplished in a number of ways and operative conditions well established among those skilled in the art. Just as an example a two-step sequence involving at the first the formation of an aldehyde of formula (I) wherein R2 is a group L-CHO which is afterwards reacted under reductive amination conditions with amine of formula (XII) NHR'R", is reported here. Accordingly the compound of formula (I) with a group L-CH$_2$OH is at the first converted into the corresponding aldehyde by treatment with an oxidant agent such as for instance 2-Iodoxybenzoic acid (IBX) in a suitable solvent such as ethyl acetate, tetrahydrofuran, and the like, at a temperature ranging from 50° C. to reflux for a suitable time for instance 30 minutes to 4 hours. The obtained aldehyde is afterwards reacted with a suitable amine of formula (XII) NHR'R", in the presence of a reducing agent, such as for instance, sodium cyanoborohydride, sodium triacetoxyborohydride, or tetamethylammonium triacetoxyborohydride in a suitable solvent such as tetrahydrofuran, 1,4-dioxane, N,N-dimethylformamide, or mixtures thereof, at a temperature ranging between 0° C. and room temperature, for 30 minutes to 6 hours.

According to conversion (conv. i) of the process, reduction of a carboxylic ester to the corresponding primary alcohol is accomplished by using a suitable reducing agent, such as for instance lithium aluminium hydride, lithium borohydride, sodium borohydride or the like, in a suitable solvent such as tetrahydrofuran, diethylether, toluene, ethanol and the like, at a temperature ranging from 0° C. to room temperature, for a suitable reaction time, between 30 minutes and 24 hours.

According to conversion (conv. j) of the process, transformation of the aldehyde residue into the corresponding alkylamine derivatives —CH$_2$NR'R", wherein R' and R" are as defined above, can be obtained by reaction of the aldehyde derivative with an amine of the formula (XII) as defined above, under reductive amination conditions, preferably with reducing agent, such as for instance, sodium cyanoborohydride, sodium triacetoxyborohydryde, or tetramethylammonium triacetoxyborohydride in a suitable solvent such as tetrahydrofuran, 1,4-dioxane, N,N-dimethylformamide, or mixtures thereof, at a temperature ranging between 0° C. and room temperature, for 30 minutes to 6 hours.

According to conversion (conv. k) of the process, a compound of formula (I) with a nitro group was converted into a compound of formula (I) with an amino group under reductive conditions, preferably with reducing agent, such as for instance, zinc dust, in the presence of ammonium chloride in a suitable solvent such as tetrahydrofuran, 1,4-dioxane, ethanol and water, or mixtures thereof, at a temperature ranging between 50° C. and reflux, for 30 minutes to 6 hours.

According to conversion (conv. l) of the process, the transformation of the compound of formula (I) wherein R1 is Me-S— into a compound of formula (I) wherein R1 is for example aryl or heteroaryl is accomplished by reaction with a suitable organometal reagent, such as for instance an organoboronic acid of formula R1-B(OH)$_2$. The reaction is a Pd-catalyzed Cu-mediated desulfitative C—C cross coupling generally known as "Liebeskind-Srogl reaction". The said reaction is accomplished in the presence of a suitable palladium source such as for instance, tetrakis triphenylphosphino palladium [Pd(PPh$_3$)$_4$] or the like, a copper$^{(I)}$-carboxylate as metal co-factor such as copper thiophen-2-carboxylate, in a suitable solvent such as tetrahydrofuran, 1,4-dioxane, N,N-dimethylformamide, at reflux temperature, for 30 minutes to 6 hours.

According to conversion (conv. m) of the process, the compound of formula (I) wherein R5 is hydrogen may be converted into a compound of formula (I) wherein R5 is R'R"N— under strong basic conditions such as lithium bis-trimethyl-silylamide 1 N in THF, using ammonium chloride or a suitable primary or secondary amine; preferably the reaction is carried out in tetrahydrofuran at a temperature ranging from 0° C. to reflux.

According to conversion (conv. n) of the process, a compound of formula (I) wherein is present a primary or secondary amino group such as L-N(H)R', is transformed into the corresponding secondary or tertiary amino derivative. Preferably, the reaction is carried out with an aldehyde of formula R"CHO (XIX), under reductive amination conditions, preferably with reducing agent, such as for instance, sodium cyanoborohydride, sodium triacetoxyborohydryde, or tetramethylammonium triacetoxyborohydride in a suitable solvent such as tetrahydrofuran, 1,4-dioxane, N,N-dimethylformamide, or mixtures thereof, at a temperature ranging between 0° C. and room temperature, for 30 minutes to 6 hours.

According to conversion (conv. o) of the process, a compound of formula (I) wherein is present a primary or secondary amino group such as L-N(H)R', is transformed into the corresponding carboxamide derivative, by reaction with a compound of formula R7-COW (XX). It is clear to the skilled person that this reaction can be accomplished in a variety of ways and operative conditions, which are widely known in the art for the preparation of carboxamides. As an example, when W is an halogen such as chloride, the reaction is performed in a suitable solvent such as for instance, dichloromethane, tetrahydrofuran, 1,4-dioxane, acetonitrile, or N,N-dimethylformamide or the like at a temperature ranging from about −10° C. to reflux and for a suitable time, for instance from about 30 minutes to about 96 hours. The reaction is carried out in the presence of an opportune proton scavenger such as triethylamine, N,N-diisopropylethylamine or pyridine. When W is an hydroxyl group, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propylmethyl polystyrene or N-cyclohexylcarbodiimide-N'-methyl polystyrene, in a suitable solvent such as, for instance, dichloromethane, tetrahydrofuran, 1,4-dioxane, acetonitrile, N,N-dimethylformamide at a temperature ranging from about −10° C. to reflux and for a suitable time, for instance from about 30 minutes to about 48 hours. The said reaction is optionally carried out in the presence of a suitable catalyst, for instance 4-dimethylaminopyridine, or in the presence of a further coupling agent such as N-hydroxybenzotriazole.

According to the step (conv. p) of the process, a compound of formula (I) wherein is present a primary or secondary amino group such as L-N(H)R', is transformed into the corresponding urea derivative by reaction with an appropriate isocyanate of formula R8-N=C=O (XXI) to yield the corresponding urea. The reaction is preferably carried out in as suitable solvent such as dichloromethane, tetrahydrofuran or the like, at a temperature ranging from about 20° C. to reflux and for a time varying from about 30 minutes to about 48 hours.

According to conversion (conv. q) of the process, a compound of formula (I) wherein is present a primary or secondary amino group such as L-N(H)R', is transformed into the corresponding guanidine derivative by reaction with a compound of formula R8NHC(NH)-G wherein G is a suitable leaving group such as —S-Me, N—S(O)$_2$CF$_3$, or 1H-pyrazolyl. As an example, this reaction may be carried out under basic conditions, for instance in the presence of triethylamine, or potassium carbonate, in a suitable solvent such as methanol, ethanol, N,N-dimethylformamide, and a mixtures thereof. Preferentially, the reaction is carried out at a temperature ranging from room temperature to about 80° C. and for a time varying from about 30 minutes to about 24 hours.

According to conversion (conv. r) of the process, a compound of formula (I) wherein A is —(CH$_2$)$_2$— can undergo dehydrogenation in the presence of an optionally supported palladium or platinum or 2,3-Dichloro-5,6-dicyano-1,4-benzoquinone (DDQ), so as to obtain the corresponding aromatic derivative of formula (I), by operating in a suitable solvent such as toluene, 1,4-dioxane, chlorobenzene, dichlorobenzene, at a temperature ranging from 90° C. to reflux, for a time varying between 2 hours to 8 hours.

Needless to say, also any of the intermediates of the above described processes could be converted into a different intermediate, if wanted and necessary, by operating in an analogous way as in any one of the conversion reaction here above described.

From all of the above it is clear to the skilled person that any compound of the formula (I) bearing a functional group which can be further derivatized to another functional group, by working according to methods well known in the art thus leading to other compounds of the formula (I), is intended to be comprised within the scope of the present invention.

It is also clear to the skilled person that when necessary reactive groups that may be protected and then removed according to methods well known in the literature e.g. protective groups in organic synthesis.

According to any variant of the process for preparing the compounds of the formula (I), the starting materials and any other reactants are known or easily prepared according to known methods.

The compound of the formula (II) can be prepared as described in WO 2004/104007.

The compounds of the formula (XIII) and (XVIII), can be prepared as described in WO 2008/074788.

Compounds of the formula (III), (VIIa), (VIIb), (IX), (X), (XII), (XV), (XVII), (XIX), (XX), (XXI) and (XXII) are either commercially available or can be prepared with known methods.

Compounds of the formula (V) and (XVI) are either commercially available or can be prepared with known methods or can be prepared as described in the experimental part below (Preparation O to Preparation R).

From all of the above, it is clear to the skilled person that when preparing the compounds of the formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of the formula (I) prepared according to the process described above are obtained as mixture of isomers, their separation using conventional techniques into the single isomers of the formula (I), is within the scope of the present invention.

Conventional techniques for racemate resolution include, for instance, partitioned crystallization of diastereoisomeric salt derivatives or preparative chiral HPLC.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

Experimental Section

Pharmacology

The compounds of the formula (I) are active as protein kinase inhibitors and are therefore useful, for instance, to restrict the unregulated proliferation of tumor cells.

In therapy, they may be used in the treatment of various tumors, such as those formerly defined, as well as in the treatment of other cell proliferative disorders and immune cell-associated diseases and disorders.

The inhibiting activity of PIM-1 and 2 inhibitors and the potency of selected compounds were determined through the assays below described.

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| | |
|---|---|
| BSA | bovine serum albumin |
| Tris | 2-Amino-2-(hydroxymethyl)-1,3-propanediol |
| Hepes | N-(2-Hydroxyethyl)piperazine-N'-(2-ethanesulfonic acid) |
| THF | tetrahydrofuran |
| MTBE | methyl tertiary butyl ether |
| DIPEA | N,N-diisopropylethylamine |
| PyBOP | benzotriazol-1-yloxytris(pyrrolidino)phosphonium hexafluorophosphate |
| EDC | 1-ethyl-3-(3'-dimethylaminopropyl)carbodiimide |
| DHBT | 3,4-dihydro-3-hydroxy-4-oxo-1,2,3-benzotriazine |

| | -continued | | |
|---|---|---|---|
| HBTU | 2-(1H-Benzotriazole-1-yl)-1,1,3,3-tetramethyluronium hexafluorophosphate | | |
| TFA | trifluoroacetic acid | TMOF | trimethylorthoformate |
| DCE | dichloroethane | DCM | dichloromethane |
| DMF | N,N-dimethylformammide | DMA | N,N-dimethylacetamide |
| DMSO | dimethylsulfoxide | KDa | kiloDalton |
| mg | milligram | µg | microgram |
| ng | nanogram | L | liter |
| ml | milliliter | µL | microliter |
| M | molar | mM | millimolar |
| µM | micromolar | nM | nanomolar |
| MHz (Mega-Hertz) | | Hz (Hertz) | |
| min (minutes) | | mol (moles) | |
| TLC (thin layer chromatography) | | r.t. (room temperature) | |
| TEA (triethylamine) | | Hex (hexane) | |
| MeOH (Methanol) | | bs (broad singlet) | |
| Ac (acetyl) | | BOC (tert-butyloxycarbonyl) | |
| Ac$_2$O acetic anhydride | | ESI = electrospray ionization | |
| NaH = sodium hydride, 60% in mineral oil | | NMP = N-methyl-pyrrolidone | |
| RP-HPLC (reverse phase high performance liquid chromatography) | | | |

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society or the Journal of Biological Chemistry.*

Unless otherwise noted, all materials were obtained from commercial suppliers, of the best grade and used without further purification. Anhydrous solvent such as DMF, THF, CH$_2$Cl$_2$ and toluene were obtained from the Aldrich Chemical Company. All reactions involving air- or moisture-sensitive compounds were performed under nitrogen or argon atmosphere.

Biochemical assay for inhibitors of PIM-1 kinase activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange Dowex® resin; the resin then settles down to the bottom of the reaction plate by gravity.

Supernatant is subsequently withdrawn and transferred into a counting plate, then evaluated by β-counting.

Reagents/Assay Conditions

Dowex® Resin Preparation:

500 g of wet resin (SIGMA, custom prepared resin DOWEX® 1×8 200-400 mesh, 2.5 Kg) are weighed out and diluted to 2 l in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00

The washed resin is stable for more than one week; the stock resin is kept at 4° C. before use.

Kinase Buffer (KB):

The buffer for PIM-1 assay was composed of HEPES 50 mM, at pH 7.5, with 10 mM MgCl$_2$, 1 mM DTT, 3 µM NaVO$_3$, and 0.2 mg/ml BSA Full-length human PIM-1 was expressed and purified as described in Bullock A N, et al., J. Biol. Chem. 2005, 280, 41675-82.

The enzyme showed a linear kinetic after a step of pre-activation by auto-phosphorylation in the following conditions:

1.7 µM PIM1 was incubated 1 hour RT at 28° C. in the presence of 125 µM ATP

Assay Conditions:

ATP concentration: 200 µM $^{33}$P-γ-ATP: 6 nM

Enzyme concentration: 1 nM

Substrate concentration Aktide (Chemical Abstract Service Registry Number 324029-01-8): 25 µM Robotized Dowex® Assay:

The test mix consisted of:

1) 3× Enzyme mix (done in Kinase Buffer 3×), 5 µL/well 2) 3× substrate and ATP mix (done in ddH2O), together with $^{33}$P-γ-ATP, 5 µL/well 3) 3× test compounds (diluted into ddH2O—3% DMSO)-5 µL/well See below for compound dilution and assay scheme Dilution of Compounds For IC$_{50}$ determination, test compounds are received as a 1 mM solution in 100% DMSO and distributed into 96-well plates: compounds are then plated into the first column of a new 96-well plate (A1 to G1), 100 µl/well.

An automated station (Biomek FX®, Beckman) is used for serial dilutions, producing 1:3 dilutions in 100% DMSO, from line A1 to A10, for all the compounds in the column. Moreover, 4-5 copies of daughter plates are prepared by reformatting 5 µL of this first set of 100% DMSO dilution plates into 384-deep well plates: one copy of these serial dilution plates with the test compounds is thawed on the day of study, reconstituted at the working concentration (3-fold the final concentration) with 162 µL/well of water and used for IC$_{50}$ determination assays. In a standard experiment, the highest concentration (3×) of compounds is typically 30 µM, while the lowest one is typically 1.5 nM.

Each 384-well plate generates at least one curve of the standard inhibitor staurosporine and reference wells (total enzyme activity vs. no enzymatic activity) for evaluation of Z' and signal to background (S/B) ratio.

Assay Scheme:

384-well plates, V bottom (test plates) are prepared with 5 µl of compound diluted as previously described (3×) and then placed onto a PlateTrak® 12 robotized station (Perkin Elmer; the robot has one 384-tip pipetting head for assay start, plus one 96-tip head for dispensing resin) together with one reservoir for Enzyme mix (3×) and one for ATP mix (3×).

Data are analyzed by an internally customized version of the "Assay Explorer®" SW package, which provides sigmoidal fitting of the ten-dilution curves for IC50 determination in secondary assay/hit confirmation routines.

Method for PIM-2 Kinase Inhibition Assay: Dowex Technique

Kinase Buffer (KB):

The buffer for PIM-2 assay was composed of HEPES 50 mM, at pH 7.5, with 1 mM MgCl$_2$, 1 mM DTT, 3 µM Na$_3$VO$_4$, and 0.2 mg/ml BSA Full-length human PIM-2 was expressed and purified as described in Fedorov O, et al. (2007) PNAS 104, 51, 20523-28.

Assay Conditions (Final Concentrations):

Enzyme concentration=1.5 nM

Aktide substrate (Chemical Abstract Service Registry Number 324029-01-8)=5 µM

ATP=4 µM
$^{33}$P-γ-ATP=1 nM
Robotized Dowex Assay:
See above: same procedure as described for PIM-1.
In Vitro Cell Proliferation Assay:

MV-4-11 (biphenotypic B myelomonocytic leukemia) cells (1250 cells/well) were seeded in white 384 well-plates in complete medium (RPMI 1640 or EMEM plus 10% Fetal bovine serum) and treated with compounds dissolved in 0.1% DMSO, 24 h after seeding. The cells were incubated at 37° C. and 5% $CO_2$ and after 72 hours the plates were processed using CellTiter-Glo® assay (Promega) following the manufacturer's instruction. CellTiter-Glo® is a homogenous method based on the quantification of the ATP present, an indicator of metabolically active cells. ATP is quantified using a system based on luciferase and D-luciferin resulting into light generation. The luminescent signal is proportional to the number of cells present in culture.

Briefly 25 µl/well reagent solution was added to each wells and after 5 minutes shacking microplates were red by Envision® (PerkinElmer) luminometer. The luminescent signal was proportional to the number of cells present in culture.

Inhibitory activity was evaluated comparing treated versus control data using Assay Explorer (MDL) program. $IC_{50}$ was calculated using sigmoidal interpolation curve.

Given the above inhibition assays, the compounds of the formula (I) of the invention resulted to possess a good PIM-1 inhibitory activity, typically with an $IC_{50}$ well below 1 microM and a good PIM-2 inhibitory activity, typically with $IC_{50}$ below 10 microM. Moreover, the compounds of the formula (I) of the invention show good cellular proliferation inhibitory activity, typically with an $IC_{50}$ in the range of from 0.010 to 2 µM in MV-4-11 cells.

The following Table A reports the experimental data of some representative compounds of the invention of formula (I) being tested on the PIM-1, and 2 enzyme in the specific in vitro kinase assay above described ($IC_{50}$ microM).

The following Table A also reports the inhibitory activity against PIM-1 and PIM-2 of some of the closest compounds of the prior art.

Ref. compound 1 is 1-methyl-8-(piperidin-1-yl)-4,5-dihydro-1H-pyrazolo[4,3-h]quinazoline-3-carboxamide, the compound coded B76-X06-M00(C01)-D03; and Ref. compound 2 is 1-methyl-8-(methylsulfanyl)-4,5-dihydro-1H-pyrazolo[4,3-h]quinazoline-3-carboxamide, the compound coded B67-X04-M00(C01-D03) in the patent application WO 2004/104007 cited above. Ref. compounds 1 and 2 are the first and to the second disclaimed compounds of the present invention respectively.

Following Table A also reports the antiproliferative activity of some representative compounds of the invention against myelomonocytic leukemia MV-4-11 cells.

TABLE A

| Compound | PIM-1 $IC_{50}$ µM | PIM-2 $IC_{50}$ µM | MV-4-11 $IC_{50}$ µM |
|---|---|---|---|
| Ref. Compound 1 | >10 | >10 | — |
| Ref. Compound 2 | 1.006 | >10 | — |
| 1 | 0.050 | 0.221 | 0.992 |
| 7 | 0.041 | 0.156 | 1.758 |
| 15 | 0.143 | 0.282 | 1.428 |
| 17 | 0.009 | 0.160 | 1.541 |
| 25 | 0.776 | >10 | >10 |
| 26 | 0.033 | 0.861 | 0.520 |
| 27 | 0.004 | 0.498 | 0.308 |
| 29 | 0.021 | 2.400 | 0.758 |
| 36 | 0.116 | 0.694 | 0.940 |
| 37 | 4.12 | >1 | — |

TABLE A-continued

| Compound | PIM-1 $IC_{50}$ µM | PIM-2 $IC_{50}$ µM | MV-4-11 $IC_{50}$ µM |
|---|---|---|---|
| 38 | 0.020 | 0.527 | 0.308 |
| 46 | 0.081 | 1.303 | 0.673 |
| 51 | 0.004 | 0.015 | 0.192 |
| 52 | 0.013 | 0.021 | 0.866 |
| 72 | 0.270 | 0.313 | 1.780 |
| 85 | 0.001 | 0.002 | 0.103 |
| 87 | 0.123 | 0.888 | 1.940 |
| 91 | 0.019 | 0.046 | 1.438 |
| 92 | 0.022 | 0.021 | 0.147 |
| 93 | 0.001 | 0.001 | 0.448 |
| 94 | 0.080 | 0.311 | 0.534 |
| 97 | 0.154 | 0.271 | 0.294 |
| 99 | 0.016 | 0.033 | 0.102 |
| 102 | 0.001 | 0.001 | 0.035 |
| 103 | 0.015 | 0.028 | 0.221 |
| 104 | 0.014 | 0.035 | 0.185 |
| 105 | 0.003 | 0.014 | 0.0168 |
| 106 | 0.003 | 0.013 | 0.021 |
| 111 | 0.40 | 0.21 | — |
| 112 | 0.30 | 0.043 | — |

Surprisingly, the PIM-1 and PIM-2 inhibitory activity of the compounds of the present invention resulted to be markedly superior to that of the reference compounds.

The novel compounds of the invention are unexpectedly endowed with a PIM-1 and PIM-2 inhibitory activity significantly higher than that of the structurally closest prior art compounds of the aforementioned WO 2004/104007 and are thus particularly advantageous, in therapy, against proliferative disorders associated with an altered kinase activity.

To further establish that the cytotoxicity of the compounds of the present invention resulted from the inhibition of PIM kinases, we examined the phosphorylation of the pro-apoptotic protein BAD by PIM kinases in the presence or absence of PIM inhibitors in MV-4-11 leukemia cell lines.

BAD, a downstream target of the PIM kinases, has been demonstrated to be directly phosphorylated at Ser112 by PIM-1, PIM-2 and PIM-3 (Pogacic V. et al (2007) Cancer Research, 67(14); 6916-24).

Figure 2:
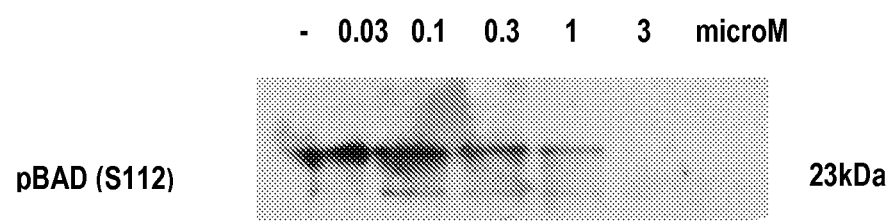
FIG. 2 shows levels of pBAD (s112) by western blots analysis that measures the dose dependent reduction of BAD protein (phosphoBAD) in MV-4-11 cells (human leukemic cell line containing the FLT3/ITD mutation) when treated with compounds of formula (I), exemplified by compound 85, compared to DMSO treated cells (control first lane).

It was found that the compounds of the present invention efficiently and dose-dependently inhibited the phosphorylation of BAD at Ser 112 in MV-4-11 thus confirming that these compounds are PIM inhibitors, results are shown in FIG. 2.

MV-4-11 cells were plated in 6 well plates at 1.5×106 cells/ml and treated with different concentrations of PIM-inhibitors for 3 hours. Cells were harvested, washed with PBS buffer and lysed with lysis buffer (2% SDS, 100 mM Tris ph 7.5, 1:100 Phosphatase Inhibitor Cocktail 1 (SIGMA) and 1:100 Phosphatase Inhibitor Cocktail 2(SIGMA) and Complete Protease Inhibitor (Roche). The protein concentration in the lysates was quantified using the BCA Protein Assay Kit (Pierce). Equal amounts of protein were loaded onto 4-12% gradient Tri-glycine gel for SDS-PAGE analysis. Then the proteins were transferred to PVDF membranes (Millipore) for Western Blotting. Membranes were probed with the antibody for phospho-Bad (Ser112) (Cell Signaling Technologies).

EXAMPLES

The synthetic preparation of some compounds of the formula (I) of the invention is described in the following examples.

The compounds of the present invention, as prepared according to the following examples, were also characterized by $^1$H NMR or by HPLC/MS analytical data; HPLC/MS data were collected following any one of methods 1, 2, 3 and 4.

HPLC MS Analytic Method 1

The HPLC equipment consisted of a Waters Acquity™ HPLC system equipped with a 2996 Waters PDA detector and Micromass mod. ZQ single quadrupole mass spectrometer, equipped with an electrospray (ESI) ion source. Instrument control, data acquisition and data processing were provided by Empower® and MassLynx® 4.0 software.

HPLC was carried out at 45° C. at a flow rate of 0.8 mL/min using a BEH C18 1.7 micron Waters Acquity® HPLC (2.1× 50 mm) column. Mobile phase A was formic acid 0.1% pH=3.3 buffer with acetonitrile (98:2), and mobile phase B was $H_2O$/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytic Method 2

HPLC-MS analyses were performed on a Finnigan MAT mod. LCQ® ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC was carried out at 40° C. at a flow rate of 1.0 mL/min using a Phenomenex Gemini C18, 3 μm, 50×4.6 mm column. Mobile phase A was Acetate Buffer 5 mM pH 4.5: acetonitrile 95:5 (v:v), and mobile phase B was Acetate Buffer 5 mM pH 4.5: acetonitrile 5:95 (v:v) the gradient was from 0 to 100% B in 7 minutes then hold 100% B for 2 minutes before equilibration. Total LC time was 10 minutes. The injection volume was 10 μl.

MS conditions: the LCQ mass spectrometer operates with electrospray ionization (ESI) interface in positive and negative ion mode. ESI sprayer voltage 4.0 kV, heated capillary temperature 255° C., sheath gas nitrogen with a pressure of 5.0 Bar. A full scan detection mode (from 50 to 1000 amu) was used.

MS/MS experiments were performed on the most intense ion of each scan automatically by Xcalibur® software. A 45% collision energy was used for the fragmentation of the precursor ions.

HPLC/MS Analytic Method 3

The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were provided by Empower® and MassLynx® 4.0 software.

HPLC was carried out at 30° C. at a flow rate of 1.0 mL/min using a C18, 3 micron Phenomenex (4.6×50 mm) column. Mobile phase A was ammonium acetate 5 mM pH=5.2 buffer with acetonitrile (95:5), and mobile phase B was $H_2O$/acetonitrile (5:95); the gradient was from 10 to 90% B in 8 minutes then ramp to 100% B in 1.0 minutes. The injection volume was 10 microL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytical Method 4

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 1 mL/min using a RP18 Waters×Terra (3.0×20 mm) column. Mobile phase A was ammonium hydroxide 0.05% pH=10 buffer with acetonitrile (95:5), and Mobile phase B was $H_2O$/acetonitrile (5:95); the gradient was from 10 to 90% B in 4 minutes then hold 90% B 1 minutes. The injection volume was 10 microL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of the invention of the formula (I), as prepared according to the following examples, were purified by preparative HPLC.

The operative conditions are defined below:

HPLC/MS Preparative Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters×Terra 10 micron (19×250 mm) column. Mobile phase A was ammonium hydroxide 0.05% pH=10 buffer with acetonitrile (95:5), and Mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

HPLC/MS Preparative Method 2

The HPLC equipment consisted of a Waters 2790 HPLC system equipped with 996 Waters PDA detector and Micromass mod. ZQ single quadripole mass spectrometer, equipped with electrospray (ESI) ion source. Instrument control, data acquisition and data processing were provided by Empower and MassLynx 4.0 software.

HPLC was carried out at 25° C. at a flow rate of 20 ml/min using a RP18 Waters×Terra 10 micron (19×250 mm) column. Mobile phase A was 0.1% trifluoroacetic acid in water/acetonitrile (95:5), and mobile phase B was acetonitrile; the gradient was from 10 to 90% B in 15 minutes then hold 90% B 3 minutes. The injection volume was 10 μl.

The mass spectrometer was operated in positive and in negative ion mode, the capillary voltage was set-up at 2.5 KV; the source temperature was 120° C.; cone was 10V; full scan, mass range from 100 to 800 amu was set up.

Exact MS

Exact mass data ESI($^+$) were obtained on a Waters Q-T of Ultima® directly connected with micro HPLC 1100 Agilent as previously described (M. Colombo, F. Riccardi-Sirtori, V. Rizzo, *Rapid Commun. Mass Spectrom.* 2004, 18, 511-517).

$^1$H-NMR spectrometry was performed on a Bruker AVANCE® 400 MHz single bay instrument with gradients. It was equipped with a QNP probe (interchangeable 4 nuclei probe—$^1$H, 13C, 19F and 31P) (NMR method 1) or on a Mercury VX 400 operating at 400.45 MHz equipped with a 5 mm double resonance probe [1H (15N-31P) ID_PFG Varian].

Preparation A

Ethyl 1-tert-butyl-7-oxo-4,5,6,7-tetrahydro-1H-indazole-3-carboxylate

[(IV), R2=t-butyl, A=—(CH$_2$)$_2$—]

st. 1

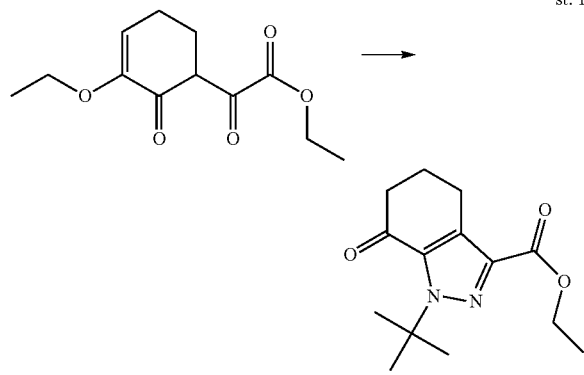

To a solution of ethyl (3-ethoxy-2-oxocyclohex-3-en-1-yl)(oxo)acetate 10 g (42.6 mmol) and acetic acid 5 ml in absolute ethanol (150 ml) at room temperature was added tert-butyl hydrazine hydrochloride 6 g (48 mmol). The mixture was stirred at 60° C. for 3 hours. The volatiles were removed under vacuum, the residue was diluted with DCM and washed with sat. aqueous solution of NaHCO$_3$, and with brine. The organic phase was dried with sodium sulfate, filtered, and concentrated. The crude material was purified by silica gel column chromatography eluting with ethyl acetate and hexane (1:2) to give ethyl 1-tert-butyl-7-oxo-4,5,6,7-tetrahydro-1H-indazole-3-carboxylate in 90% yield. LC/MS (254 nm) HPLC method 2 Rt 6.08 min. $^1$H NMR (400 MHz, DMSO-d$_6$) δ ppm 4.18 (q, J=6.83 Hz, 2H) 2.93-2.30 (3 m, 6H) 1.58 (s, 9H), 1.16 (t, J=6.83 Hz, 3H). HRMS (ESI) calcd for C14H20N2O3 [M+H]$^+$ 287.1366 found 287.1356.

According to the same method, but employing hydrazine, the following compound was prepared:

Ethyl 7-oxo-4,5,6,7-tetrahydro-1H-indazole-3-carboxylate [(IV), R2=H, A=—(CH$_2$)$_2$—]. $^1$H NMR (400 MHz, DMSO-d$_6$) δ ppm 14.39 (s, 1H), 4.27 (q, J=7.11 Hz, 2H), 2.87 (t, J=6.10 Hz, 2H), 2.51 (m, 2H), 2.04 (m, 2H), 1.28 (t, J=7.07 Hz, 3H).

Preparation B

Ethyl 1-(4-methoxybenzyl)-7-oxo-4,5,6,7-tetrahydro-1H-indazole-3-carboxylate

[(IVa), R2=p methoxybenzyl, A=—(CH$_2$)$_2$—] and ethyl 2-(4-methoxybenzyl)-7-oxo-4,5,6,7-tetrahydro-2H-indazole-3-carboxylate [(IVb), R2=p methoxybenzyl, A=—(CH$_2$)$_2$—].

st. 1a

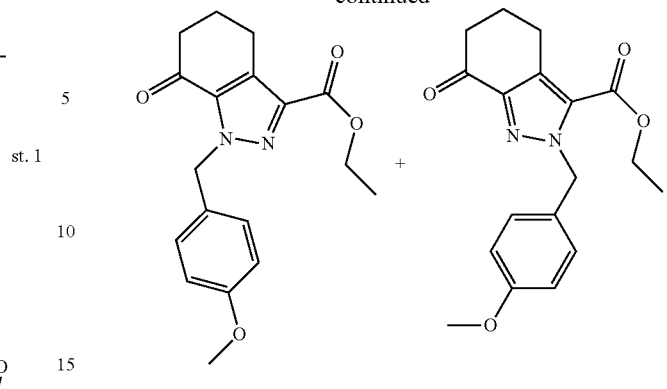

50 mg of ethyl 7-oxo-4,5,6,7-tetrahydro-1H-indazole-3-carboxylate and cesium carbonate 120 mg (0.37 mmol) were dissolved in 1 ml of anhydrous DMF, 42 µl of p-methoxybenzyl bromide (0.288 mmol) was added and stirred at r.t. overnight. The mixture was partitioned between H$_2$O and DCM. The organic layer was washed with brine dried over Na$_2$SO$_4$, filtered and concentrated under reduced pressure. The residue was purified by flash column chromatography (DCM/Acetone 95/5) to provide the two regioisomers:

Ethyl 1-(4-methoxybenzyl)-7-oxo-4,5,6,7-tetrahydro-1H-indazole-3-carboxylate 20% yield. $^1$H NMR (400 MHz, DMSO-d$_6$) δ ppm 7.10-7.30 (m, 2H), 6.75-6.96 (m, 2H), 5.64 (s, 2H), 4.29 (q, J=7.16 Hz, 2H), 3.71 (s, 3H), 2.93 (t, J=6.10 Hz, 2H), 2.55 (dd, J=5.55, 7.26 Hz, 2H), 1.90-2.15 (m, 2H), 1.30 (t, J=7.14 Hz, 3H).

Ethyl 2-(4-methoxybenzyl)-7-oxo-4,5,6,7-tetrahydro-2H-indazole-3-carboxylate 25% yield. $^1$H NMR (401 MHz, DMSO-d6) δ 7.12-7.32 (m, 2H), 6.76-6.97 (m, 2H), 5.70 (s, 2H), 4.32 (q, J=7.12 Hz, 2H), 3.71 (s, 3H), 2.91 (t, J=6.10 Hz, 2H), 2.52-2.57 (m, 2H), 1.97-2.09 (m, 2H), 1.30 (t, J=7.08 Hz, 3H).

Preparation C

Ethyl (6E)-1-tert-butyl-6-[(dimethylamino)methylidene]-7-oxo-4,5,6,7-tetrahydro-1H-indazole-3-carboxylate [(VI), R2=t-butyl, A=—(CH$_2$)$_2$—]

st. 2

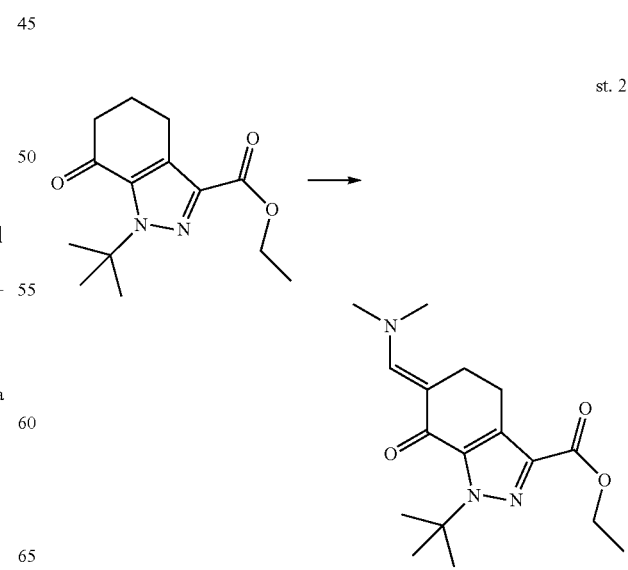

The intermediate ethyl 1-tert-butyl-7-oxo-4,5,6,7-tetrahydro-1H-indazole-3-carboxylate 10 g (37.8 mmol) was dissolved in 50 ml of N,N-dimethylformamide dimethyl acetal and stirred at 110° C. The reaction was stirred at that temperature for 16 hours. The reaction mixture was concentrated and then partitioned between $H_2O$ and DCM. The organic layer was washed with brine dried over $Na_2SO_4$, filtered and concentrated under reduced pressure to afford the title compound in quantitative yield. LC/MS (254 nm) HPLC method 2 Rt 5.85 min. $^1$H NMR (401 MHz, DMSO-d6) δ 7.55 (s, 1H), 4.22-4.33 (m, 2H), 3.11 (s, 6H), 2.82 (s, 4H), 1.66 (s, 9H), 1.25-1.32 (m, 3H).

Preparation D

Ethyl 1-tert-butyl-8-(methylsulfanyl)-4,5-dihydro-1H-pyrazolo[4,3-h]quinazoline-3-carboxylate [(VIII), R1=Me-S—, R2=t-Butyl, A=—(CH$_2$)$_2$—]

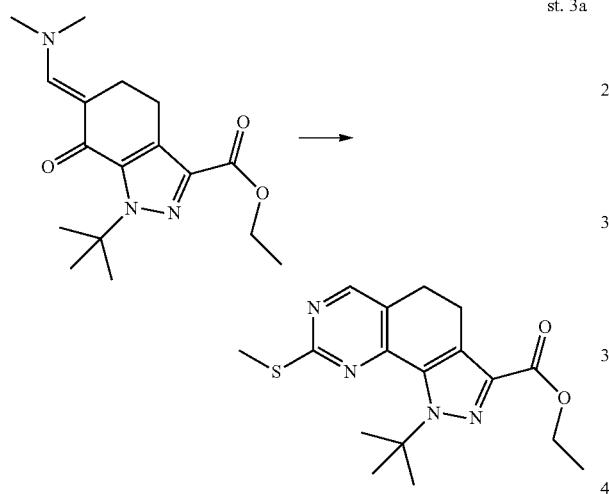

To a solution of 9 g (28.17 mmol) of ethyl (6E)-1-tert-butyl-6-[(dimethylamino)methylidene]-7-oxo-4,5,6,7-tetrahydro-1H-indazole-3-carboxylate in 50 ml of anhydrous DMF, and 9.2 g (112 mmol) of anhydrous potassium acetate and 23.52 g (84.51 mmol) of methylisothiourea sulfate were added. The reaction was stirred at 100° C. for 8 hours. The mixture was diluted with ethyl acetate, washed with $H_2O$, dried over $Na_2SO_4$, filtered and evaporated. The crude was purified by silica gel chromatography (ethyl acetate:hexane 1:3) to give the title compound (50%). LC/MS (254 nm) HPLC method 2 Rt 7.46 min. $^1$H NMR (401 MHz, DMSO-d6) δ 8.58 (s, 1H), 4.22-4.38 (m, 2H), 2.95-3.01 (m, 2H), 2.80-2.86 (m, 2H), 2.57 (s, 2H), 1.76-1.83 (m, 9H). HRMS (ESI) calcd for C17H22N4O2S [M+H]$^+$ 347.1536 found 347.1523.

Applying the same method, the following compounds were prepared:

Ethyl 8-(methylsulfanyl)-1-trityl-4,5-dihydro-1H-pyrazolo[4,3-h]quinazoline-3-carboxylate [(VIII), R1=Me-S—, R2=trityl, A=—(CH$_2$)$_2$—]. $^1$H NMR (401 MHz, DMSO-d6) δ 7.19-7.35 (m, 10H), 6.92-7.01 (m, 6H), 4.22-4.31 (m, 2H), 3.04 (t, J=6.59 Hz, 1H), 2.55-2.60 (m, 2H), 2.41 (s, 3H), 1.22-1.30 (m, 4H).

Ethyl 1-methyl-8-(methylsulfanyl)-4,5-dihydro-1H-pyrazolo[4,3-h]quinazoline-3-carboxylate [(VIII), R1=Me-S—, R2=methyl, A=—(CH$_2$)$_2$—]. $^1$H NMR (401 MHz, DMSO-d6) δ 8.55 (s, 1H), 4.33 (s, 3H), 4.29 (q, J=7.08 Hz, 2H), 2.97-3.04 (m, J=1.10, 6.84 Hz, 2H), 2.88-2.95 (m, 2H), 2.56 (s, 3H), 1.31 (t, J=7.08 Hz, 3H).

Ethyl 1-(2-hydroxyethyl)-8-(methylsulfanyl)-4,5-dihydro-1H-pyrazolo[4,3-h]quinazoline-3-carboxylate [(VIII), R1=Me-S—, R2=2-hydroxyethyl, A=—(CH$_2$)$_2$—]. LC/MS (254 nm) HPLC method 2 Rt 5.27 min. $^1$H NMR (401 MHz, DMSO-d6) δ 8.55 (s, 1H), 4.87 (br. s., 1H), 4.83 (t, J=6.04 Hz, 2H), 4.30 (q, J=7.08 Hz, 2H), 3.82 (t, J=5.80 Hz, 2H), 2.97-3.06 (m, 2H), 2.85-2.95 (m, 2H), 2.55 (s, 3H), 1.32 (t, J=7.08 Hz, 3H). HRMS (ESI) calcd for C15H18N4O3S [M+H]$^+$ 335.1172 found 335.1175.

Preparation E

Ethyl 1-methyl-4,5-dihydro-1H-pyrazolo[4,3-h]quinazoline-3-carboxylate [(VIII), R1=H, R2=Me, A=—(CH$_2$)$_2$—]

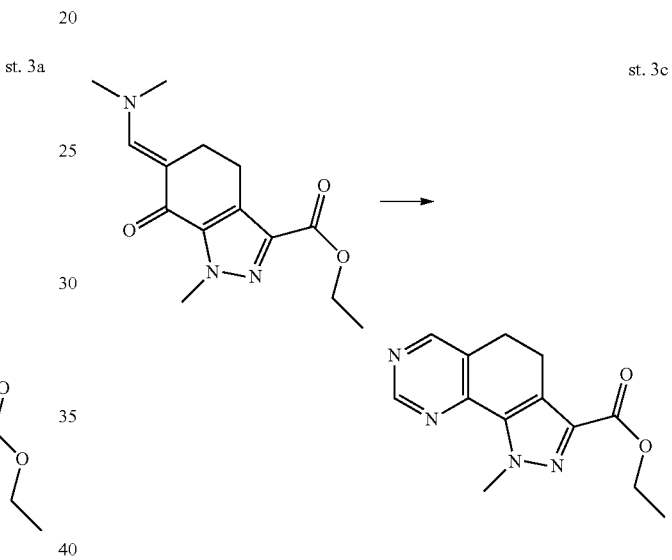

To a solution of 0.5 g (1.80 mmol) of ethyl (6E)-6-[(dimethylamino)methylidene]-1-methyl-7-oxo-4,5,6,7-tetrahydro-1H-indazole-3-carboxylate in 20 ml of anhydrous DMF, and 746 mg (5.4 mmol) of potassium carbonate and 510 mg (5.4 mmol) of formamidine acetate were added. The reaction was stirred at 100° C. for 8 hours. The mixture was diluted with ethyl acetate washed with $H_2O$, dried over $Na_2SO_4$, filtered and evaporated. The residue was triturated with diethyl ether to give the title compound 450 mg (95%). $^1$H NMR (401 MHz, DMSO-d6) δ 9.09 (s, 1H), 8.74 (s, 1H), 4.35 (s, 3H), 4.31 (q, J=7.08 Hz, 2H), 2.98-3.05 (m, 4H), 1.33 (t, J=7.08 Hz, 3H).

Applying the same method, the following compounds were prepared:

Ethyl 1-tert-butyl-4,5-dihydro-1H-pyrazolo[4,3-h]quinazoline-3-carboxylate [(VIII), R1=H, R2=tert-butyl, A=—(CH$_2$)$_2$—]. LC/MS (m/z): 301.1 [M+H]$^+$, HPLC (254 nm) method 2 Rt 5.89 min. $^1$H NMR (500 MHz, DMSO-d$_6$) δ 9.13 (s, 1H), 8.75 (s, 1H), 4.31 (q, J=7.14 Hz, 2H), 2.95-3.06 (m, 2H), 1.81 (s, 9H), 2.85-2.95 (m, 2H), 1.31 (t, J=7.14 Hz, 3H). HRMS (ESI) calcd for C16H20N4O2 [M+H]$^+$ 301.1659 found 301.1663

Prepared as described in preparation E using acetamidine in place of formamidine:

Ethyl 1,8-dimethyl-4,5-dihydro-1H-pyrazolo[4,3-h]quinazoline-3-carboxylate [(VIII), R1=Me, R2=Me, A=—(CH$_2$)$_2$—]. $^1$H NMR (401 MHz, DMSO-d6) δ 8.62 (s, 1H), 4.36 (s, 3H), 4.30 (q, J=7.08 Hz, 2H), 2.91-3.05 (m, 4H), 2.65 (s, 3H), 1.32 (t, J=7.08 Hz, 3H).

Ethyl 1-tert-butyl-8-methyl-4,5-dihydro-1H-pyrazolo[4,3-h]quinazoline-3-carboxylate [(VIII), R1=Me, R2=tert-butyl, A=—(CH$_2$)$_2$—]. LC/MS (m/z): 315.3 [M+H]$^+$, HPLC (254 nm) method 3 Rt 6.52 min.

Preparation F

Ethyl 1-tert-butyl-8-(methylsulfanyl)-1H-pyrazolo[4,3-h]quinazoline-3-carboxylate [(VIII), R1=Me-S—, R2=t-butyl, A=—CH=CH—]

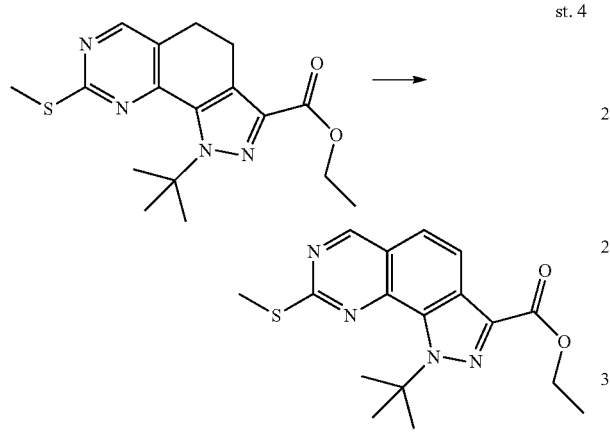

st. 4

A solution of ethyl 1-tert-butyl-8-(methylsulfanyl)-4,5-dihydro-1H-pyrazolo[4,3-h]quinazoline-3-carboxylate 1.5 g (4.35 mmol) and 1.97 g (8.7 mmol) of DDQ in chlorobenzene was heated at reflux for 4 hours. The volatiles were removed in vacuo, the residue was dissolved with ethyl acetate, and washed with sat. aqueous solution of NaHCO$_3$. The organic phase was dried with Na$_2$SO$_4$, filtered and concentrated. The crude material was purified by silica gel column chromatography eluting with ethyl acetate and hexane (1:4) yielding the title compound 1.19 g (80%). LC/MS (254 nm) HPLC method 2 Rt 7.78 min. $^1$H NMR (401 MHz, DMSO-d6) δ 9.52 (s, 1H), 8.18-8.43 (m, 1H), 7.89 (d, J=8.79 Hz, 1H), 4.24-4.61 (m, 2H), 2.74 (s, 3H), 2.00 (s, 9H), 1.40 (t, J=7.08 Hz, 3H). HRMS (ESI) calcd for C17H20N4O2S [M+H]$^+$ 345.1380 found 345.1371.

Using the same methods to those described in the above example, the following analogs were also synthesized:

Ethyl 1-methyl-8-(methylsulfanyl)-1H-pyrazolo[4,3-h]quinazoline-3-carboxylate [(VIII), R1=Me-S—, R2=methyl, A=—CH=CH—]. $^1$H NMR (401 MHz, DMSO-d6) Shift 9.49 (s, 1H), 8.15 (d, J=8.79 Hz, 1H), 7.82 (d, J=8.79 Hz, 1H), 4.74 (s, 3H), 4.44 (q, J=7.20 Hz, 2H), 2.73 (s, 3H), 1.40 (t, J=7.14 Hz, 3H)

Ethyl 1-(2-hydroxyethyl)-8-(methylsulfanyl)-1H-pyrazolo[4,3-h]quinazoline-3-carboxylate [(VIII), R1=Me-S—, R2=2-hydroxyethyl, A=—CH=CH—]. LC/MS (254 nm) HPLC method 2 Rt 5.49 min. $^1$H NMR (401 MHz, DMSO-d6) δ 9.49 (s, 1H), 8.17 (d, J=8.67 Hz, 1H), 7.83 (d, J=8.79 Hz, 1H), 5.24 (t, J=5.92 Hz, 2H), 4.39-4.49 (m, 2H), 3.98 (t, J=5.80 Hz, 2H), 2.70 (s, 3H), 1.41 (t, J=7.14 Hz, 3H). HRMS (ESI) calcd for C15H16N4O3S [M+H]$^+$ 333.1016 found 333.1017.

Ethyl 1-tert-butyl-8-methyl-1H-pyrazolo[4,3-h]quinazoline-3-carboxylate [(VIII), R1=Me-, R2=tert-butyl, A=—CH=CH—]. LC/MS (m/z): 313.2 [M+H]$^+$, HPLC (254 nm) method 2 Rt 6.79. $^1$H NMR (401 MHz, DMSO-d$_6$) δ 9.62 (s, 1H), 8.33 (d, J=8.67 Hz, 1H), 7.92 (d, J=8.79 Hz, 1H), 4.39-4.50 (m, 2H), 2.92 (s, 3H), 2.02 (s, 9H), 1.41 (t, J=7.08 Hz, 3H). HRMS (ESI) calcd for C17H20N4O2 [M+H]$^+$ 313.1659 found 313.1653.

Ethyl 1-tert-butyl-1H-pyrazolo[4,3-h]quinazoline-3-carboxylate [(VIII), R1=H, R2=tert-butyl, A=—CH=CH—]. LC/MS (m/z): 299.1 [M+H]$^+$, HPLC (254 nm) method 2 Rt 6.36 min. $^1$H NMR (500 MHz, DMSO-d$_6$) δ 9.75 (s, 1H), 9.56 (s, 1H), 8.44 (d, J=8.79 Hz, 1H), 7.98 (d, J=8.79 Hz, 1H), 4.46 (q, J=7.14 Hz, 2H), 2.01 (s, 9H), 1.41 (t, J=7.00 Hz, 3H) HRMS (ESI) calcd for C16H18N4O2 [M+H]$^+$ 299.1503 found 299.1502

Example 1

1-(2-hydroxyethyl)-8-(methylsulfanyl)-1H-pyrazolo[4,3-h]quinazoline-3-carboxamide [(I), R1=Me-S—, R2=2-hydroxyethyl, R3=NH$_2$, A=—CH=CH—]
(cpd 1)

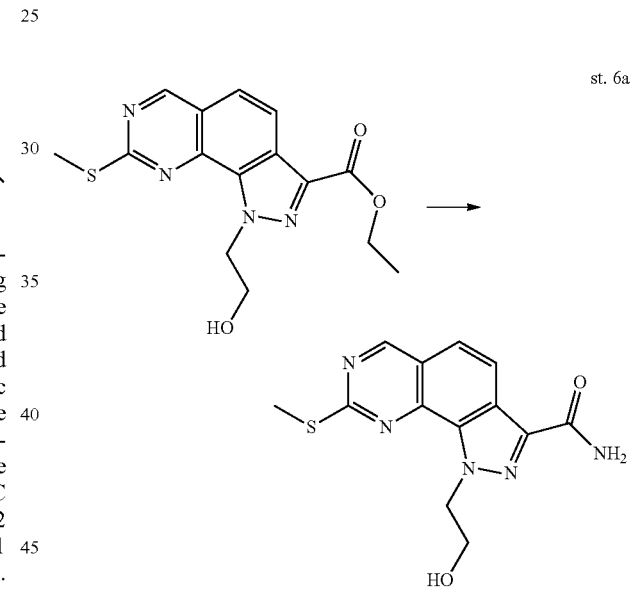

st. 6a

The suspension of 1.2 g (3.61 mmol) of ethyl 1-(2-hydroxyethyl)-8-(methylsulfanyl)-1H-pyrazolo[4,3-h]quinazoline-3-carboxylate in 10 ml of NH$_3$ 7N in methanol was subjected to microwave irradiation at 120° C. for 4 hours. The volatiles were removed under vacuum, the residue was diluted with diethyl ether and the solid filtered to provide the title compound 0.6 g (55%). LC/MS (254 nm) HPLC method 2 Rt 4.29 min. $^1$H NMR (401 MHz, DMSO-d6) δ 9.46 (s, 1H), 8.28 (d, J=8.67 Hz, 1H), 7.84 (s, 1H), 7.73 (d, J=8.79 Hz, 1H), 7.52 (br. s., 1H), 5.21 (t, J=5.98 Hz, 2H), 4.82-4.96 (m, J=0.61 Hz, 1H), 3.94-4.07 (m, 2H), 2.70 (s, 3H). HRMS (ESI) calcd for C13H13N5O2S [M+H]$^+$ 304.0863 found 304.0857.

Using the same methods to those described in the above example, the following analogs were also synthesized:

1-tert-butyl-8-methyl-1H-pyrazolo[4,3-h]quinazoline-3-carboxamide [(I), R1=Me-, R2=tert-butyl, R3=NH$_2$, A=—CH=CH—] (cpd 5) LC/MS (m/z): 284.1 [M+H]$^+$, HPLC (254 nm) method 3 Rt 5.95 min.

1-tert-butyl-1H-pyrazolo[4,3-h]quinazoline-3-carboxamide [(I), R2=tert-butyl, R3=NH$_2$, A=—CH=CH—] (cpd 3) LC/MS (m/z): 270.1 [M+H]$^+$, HPLC (254 nm) method 3 Rt 4.55 min.

Example 2

1-methyl-4,5-dihydro-1H-pyrazolo[4,3-h]quinazoline-3-carboxamide [(I), R1=H, R2=Me, R3=NH$_2$, A=—(CH$_2$)$_2$—]

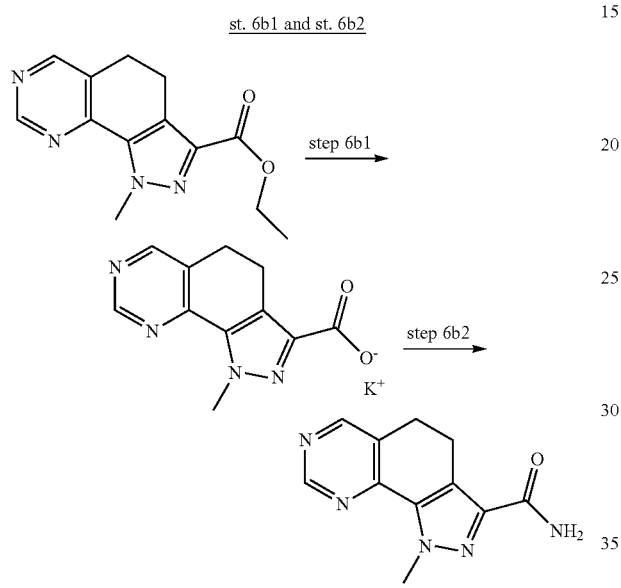

Step a. The suspension of 440 mg (1.74 mmol) of ethyl 1-methyl-4,5-dihydro-1H-pyrazolo[4,3-h]quinazoline-3-carboxylate in ethanol (30 ml) 300 mg (5.2 mmol) of potassium hydroxide was heated at reflux for 2 hours. The volatiles were removed under vacuum, the residue was diluted with ethanol (3 ml) and the solid filtered to provide potassium 1-methyl-4,5-dihydro-1H-pyrazolo[4,3-h]quinazoline-3-carboxylate 374 mg (80%).

Step b. To a suspension of potassium 1-methyl-4,5-dihydro-1H-pyrazolo[4,3-h]quinazoline-3-carboxylate 200 mg (0.74 mmol) in DMF (10 ml), EDCI 286 mg (1.49 mmol), DIPEA 1 ml (10 mmol) HOBt-NH$_4$ 300 mg (1.98 mmol) were added. The mixture was stirred at room temperature for 18 hours, subsequently the solution was diluted with DCM and washed with sat. aqueous solution of NaHCO$_3$. The organic layer was dried over Na$_2$SO$_4$ and evaporated. The crude was purified by flash chromatography eluting with cyclohexane/EtOAc 4/1 to afford the title compound 118 mg (70%) as a white solid. $^1$H NMR (401 MHz, DMSO-d6) δ 9.08 (s, 1H), 8.73 (s, 1H), 7.51 (bs, 2H), 4.33 (s, 3H), 3.05 (m, 2H), 2.97 (m, 2H).

Using the same methods to those described in the above example, the following analog was also synthesized:

1-tert-butyl-4,5-dihydro-1H-pyrazolo[4,3-h]quinazoline-3-carboxamide [(I), R1=H, R2=tert-butyl, R3=NH$_2$, A=—(CH$_2$)$_2$—] (cpd 2) LC/MS (m/z): 272 [M+H]$^+$, HPLC (254 nm) method 2 Rt 4.28 min. $^1$H NMR (500 MHz, DMSO-d$_6$) 9.10 (s, 1H), 8.73 (s, 1H), 7.41 (br. s., 1H), 7.31 (br. s., 1H), 2.97-3.03 (m, 2H), 2.83-2.91 (m, 2H), 1.81 (s, 9H). HRMS (ESI) calcd for C14H17N5O [M+H]+ 272.1506 found 272.1514

Example 3

1-(2-hydroxyethyl)-8-methoxy-1H-pyrazolo[4,3-h]quinazoline-3-carboxamide [(I), R1=R4=Me, X=O, R2=2-hydroxyethyl, R3=NH$_2$, A=—CH=CH—] (cpd 6)

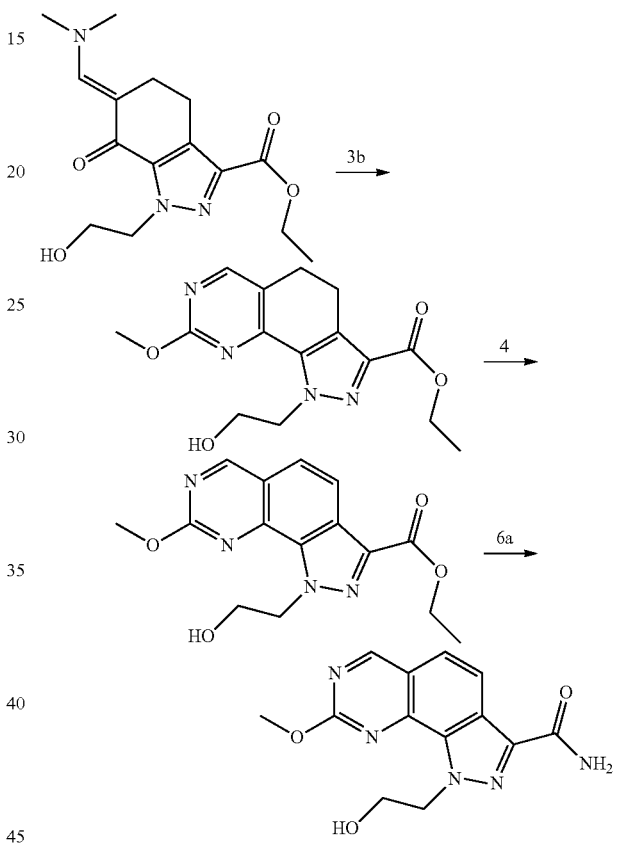

Preparation of ethyl 1-(2-hydroxyethyl)-8-methoxy-4,5-dihydro-1H-pyrazolo[4,3-h]quinazoline-3-carboxylate (St. 3b)

To a solution of ethyl (6E)-6-[(dimethylamino)methylidene]-1-(2-hydroxyethyl)-7-oxo-4,5,6,7-tetrahydro-1H-indazole-3-carboxylate 15 g (49 mmol) in 50 ml of anhydrous DMF, 14.4 g (147 mmol) of anhydrous potassium acetate and 12.60 g (73.0 mmol) of methylisourea sulfate were added. The reaction was stirred at 100° C. for 16 hours. The mixture was diluted with ethyl acetate, washed with H$_2$O, dried over Na$_2$SO$_4$, filtered and evaporated. The crude was purified by column (ethyl acetate:hexane 1:3) to give the title compound 1.2 g (10%). HRMS (ESI) calcd for C15H18N4O4 [M+H]$^+$ 319.3278 found 319.3256.

Preparation of ethyl 1-(2-hydroxyethyl)-8-methoxy-1H-pyrazolo[4,3-h]quinazoline-3-carboxylate. (St. 4)

To a suspension of ethyl 1-(2-hydroxyethyl)-8-methoxy-4,5-dihydro-1H-pyrazolo[4,3-h]quinazoline-3-carboxylate 1.2 g (3.76 mmol) in toluene (20 ml), 500 mg (2.2 mmol) 4,5-dichloro-3,6-dioxocyclohexa-1,4-diene-1,2-dicarbonitrile were added. The mixture was submitted to microwave irradiation at 100° for 3 hours in a sealed vial. The volatiles were evaporated, the crude was dissolved with ethyl acetate and portioned with sat. NaHCO$_3$, the organic layer concentrated to dryness. The residue was purified by chromatography (ethyl acetate/hexane 7/3) to afford the desired compound 520 mg (46%). HRMS (ESI) calcd for C15H16N4O4 [M+H]$^+$ 317.3119 found 317.3126.

Preparation of ethyl 1-(2-hydroxyethyl)-8-methoxy-1H-pyrazolo[4,3-h]quinazoline-3-carboxylate 250 mg (0.79 mmol) was dissolved in NH$_3$ 7 M in Methanol (8 ml). The mixture was submitted to microwave irradiation at 120° for 4 hours in a sealed vial. The volatiles were evaporated and the crude was purified by chromatography eluent DCM/MeOH 95/5 to afford the desired compound 136 mg (60%). LC/MS (254 nm) HPLC method 2 Rt 3.75 min. $^1$H NMR (401 MHz, DMSO-d6) δ 9.51 (s, 1H), 8.20 (d, J=8.67 Hz, 1H), 7.82 (br. s., 1H), 7.74 (d, J=8.79 Hz, 1H), 7.51 (br. s., 1H), 5.19 (t, J=5.92 Hz, 1H), 4.90 (t, J=6.29 Hz, 3H), 4.12 (s, 3H), 3.97-4.07 (m, J=5.00 Hz, 2H). HRMS (ESI) calcd for C13H13N5O3 [M+H]$^+$ 288.1091 found 288.1086.

Preparation G

Potassium 1-tert-butyl-8-(methylsulfanyl)-1H-pyrazolo[4,3-h]quinazoline-3-carboxylate [(XI), R1=Me-S—, R2=tert-butyl, A=—CH=CH—]

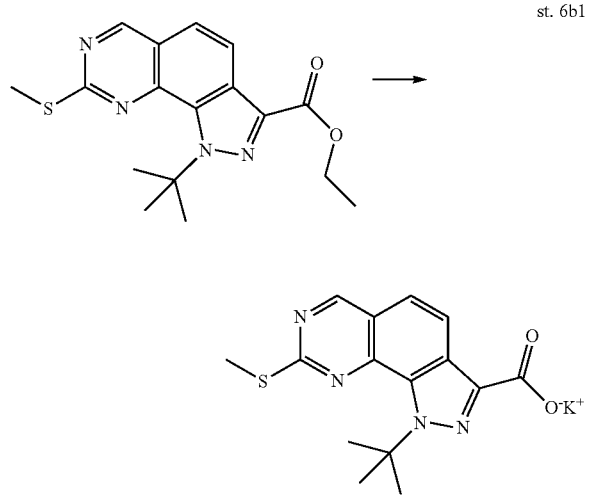

Ethyl 1-tert-butyl-8-(methylsulfanyl)-1H-pyrazolo[4,3-h]quinazoline-3-carboxylate (300 mg 0.87 mmol) was suspended in anhydrous ethanol 2 ml and treated with a 1.5 M solution of potassium hydroxide in ethanol (5 ml, 7.5 mmol) at room temperature, for 2 hours. The resulting precipitate was collected by filtration to give the title compound 215 mg (70%) as an off-white solid. LC/MS (254 nm) HPLC method 2 Rt 4.79 min. $^1$H NMR (401 MHz, DMSO-d$_6$) δ 9.38 (s, 1H), 8.61 (d, J=8.54 Hz, 1H), 7.58 (d, J=8.67 Hz, 1H), 2.72 (s, 3H), 1.95 (s, 9H). HRMS (ESI) calcd for C15H16N4O2S [M+H]$^+$ 317.1067 found 317.1052.

Example 4

1-tert-butyl-N-methyl-8-(methylsulfanyl)-1H-pyrazolo[4,3-h]quinazoline-3-carboxamide [(I), R1=Me-S—, R2=tert-butyl, R'=Me, A=—CH=CH—] (cpd 7)

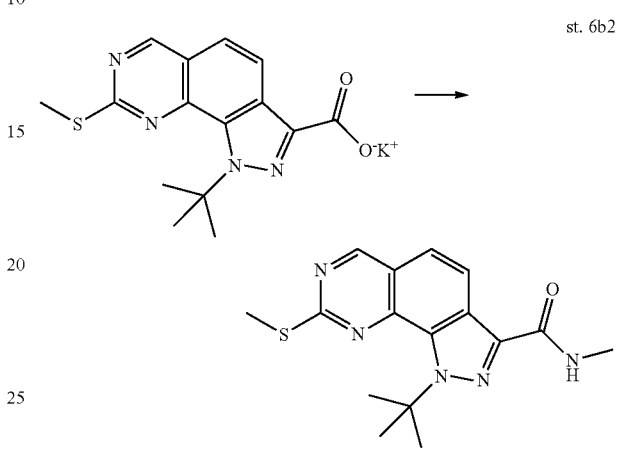

A suspension of potassium 1-tert-butyl-8-(methylsulfanyl)-1H-pyrazolo[4,3-h]quinazoline-3-carboxylate (50 mg 0.142 mmol) in anhydrous N,N-dimethylformamide (2 ml) was treated with 2-(1H-Benzotriazole-1-yl)-1,1,3,3-tetramethyluronium hexafluorophosphate (HBTU) (82 mg 0.255 mmol) and with methylamine hydrochloride (15 mg 0.213 mmol), in the presence of N,N-diisopropylethylamine (100 µl, 0.71 mmol). The reaction was stirred at room temperature for 3 hours. The reaction mixture was portioned between ethyl acetate and water, and the organic layer was dried over Na$_2$SO$_4$, filtered and concentrated. The crude product was purified by column chromatography EtOAc/hexanes 7/3 to provide 20 mg (45%) of the title compound as off-white solid. LC/MS (254 nm) HPLC method 2 Rt 6.89 min. $^1$H NMR (401 MHz, DMSO-d6) δ 9.49 (s, 1H), 8.42 (d, J=8.67 Hz, 1H), 8.32 (d, J=4.52 Hz, 1H), 7.80 (d, J=8.67 Hz, 1H), 2.87 (d, J=4.76 Hz, 3H), 2.74 (s, 3H), 1.98-2.04 (m, 9H). HRMS (ESI) calcd for C16H19N5OS [M+H]$^+$ 330.1383 found 330.1383.

Operating in an analogous way, the following compounds were prepared:

1-tert-butyl-N-[2-(dimethylamino)ethyl]-8-(methylsulfanyl)-1H-pyrazolo[4,3-h]quinazoline-3-carboxamide [(I), R1=Me-S—, R2=tert-butyl, R'=2-(dimethylamino)ethyl, A=—CH=CH—] (cpd 8) LC/MS (254 nm) HPLC method 2 Rt 5.28 min. $^1$H NMR (401 MHz, DMSO-d6) δ 9.49 (s, 1H), 8.43 (d, J=8.67 Hz, 1H), 8.22 (t, J=5.86 Hz, 1H), 7.81 (d, J=8.67 Hz, 1H), 3.44 (q, J=6.59 Hz, 2H), 2.74 (s, 3H), 2.46 (t, J=6.77 Hz, 2H), 2.21 (s, 6H), 2.01 (s, 9H). HRMS (ESI) calcd for C19H26N6OS [M+H]$^+$ 387.1962 found 387.1974.

1-tert-butyl-N-(2-hydroxyethyl)-8-(methylsulfanyl)-1H-pyrazolo[4,3-h]quinazoline-3-carboxamide [(I), R1=Me-S—, R2=tert-butyl, R'=2-hydroxyethyl, A=—CH=CH—] (cpd 9) LC/MS (254 nm) HPLC method 2 Rt 6.07 min. $^1$H NMR (401 MHz, DMSO-d6) δ 9.49 (s, 1H), 8.43 (d, J=8.54 Hz, 1H), 8.22 (t, J=5.92 Hz, 1H), 7.81 (d, J=8.67 Hz, 1H), 4.80 (t, J=5.43 Hz, 1H), 3.58 (q, J=6.02 Hz, 2H), 3.43 (q, J=6.27 Hz, 2H), 2.74 (s, 3H), 2.01 (s, 9H). HRMS (ESI) calcd for C17H21N5O2S [M+H]+360.1489 found 360.1495.

1-tert-butyl-N-(1-methylpiperidin-4-yl)-8-(methylsulfanyl)-1H-pyrazolo[4,3-h]quinazoline-3-carboxamide [R1= [(I), R1=Me-S—, R2=tert-butyl, R'=1-methylpiperidin-4-yl, A=—CH=CH—] (cpd 10) LC/MS (254 nm) HPLC method 2 Rt 5.09 min. ¹H NMR (401 MHz, DMSO-d6) δ 9.48 (s, 1H), 8.40 (d, J=8.67 Hz, 1H), 8.06 (d, J=8.06 Hz, 1H), 7.80 (d, J=8.79 Hz, 1H), 3.84 (dd, J=3.30, 7.57 Hz, 1H), 2.74-2.83 (m, 2H), 2.73 (s, 3H), 2.18 (s, 3H), 2.01 (s, 9H), 1.94-1.99 (m, 2H), 1.63-1.84 (m, 4H). HRMS (ESI) calcd for C21H28N6OS [M+H]+ 413.2118 found 413.2112.

1-tert-butyl-N-[2-(1H-imidazol-5-yl)ethyl]-8-(methylsulfanyl)-1H-pyrazolo[4,3-h]quinazoline-3-carboxamide [R1 [(I), R1=Me-S—, R2=tert-butyl, R'=2-(1H-imidazol-5-yl)ethyl, A=—CH=CH—] (cpd 11) LC/MS (254 nm) HPLC method 2 Rt 5.49 min. ¹H NMR (401 MHz, DMSO-d6) δ 9.49 (s, 1H), 8.55 (d, J=2.93 Hz, 1H), 8.43 (d, J=8.67 Hz, 1H), 7.81 (d, J=8.67 Hz, 1H), 7.57 (d, J=0.98 Hz, 1H), 6.89 (s, 1H), 3.51-3.64 (m, 2H), 2.82 (t, J=7.38 Hz, 2H), 2.70-2.76 (m, 3H), 2.01 (s, 9H). HRMS (ESI) calcd for C20H23N7OS [M+H]+ 410.1758 found 410.1751.

Preparation H

Ethyl 8-(methylsulfanyl)-1H-pyrazolo[4,3-h]quinazoline-3-carboxylate [(VIII), R1=Me-S—, R2=H, A=—CH=CH—]

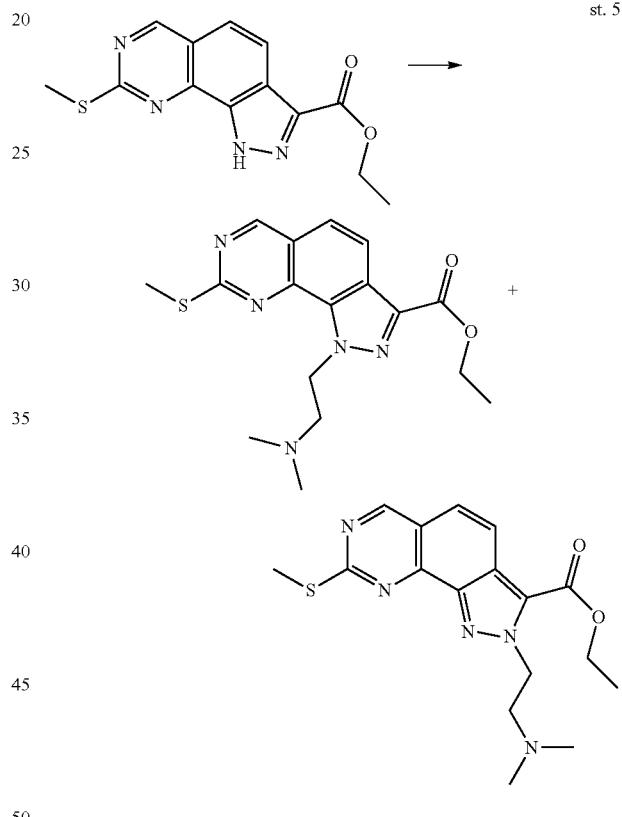

Ethyl 1-tert-butyl-8-(methylsulfanyl)-1H-pyrazolo[4,3-h]quinazoline-3-carboxylate (800 mg, 2.32 mmol) was treated with trifluoroacetic acid (5 ml). The resulting mixture was heated at 70° C. and stirred for 4 hours. Upon removal of the volatiles in vacuo, the residue was dissolved with DCM washed with sat. NaHCO3, dried over Na2SO4, filtered and concentrated to yield the title compound (670 mg>99%) as a light yellow solid. LC/MS (254 nm) HPLC method 2 Rt 5.66 min. ¹H NMR (401 MHz, DMSO-d₆) δ 9.50 (s, 1H), 8.14 (d, J=8.67 Hz, 1H), 7.80 (d, J=8.79 Hz, 1H), 4.41-4.47 (m, 2H), 2.75 (s, 3H), 1.41 (t, J=7.14 Hz, 3H). HRMS (ESI) calcd for C13H12N4O2S [M+H]+ 289.0754 found 289.0752.

Preparation I

Ethyl 1-[2-(dimethylamino)ethyl]-8-(methylsulfanyl)-1H-pyrazolo[4,3-h]quinazoline-3-carboxylate [(VIIIa), R1=Me-S—, R2=2-(dimethylamino)ethyl A=—CH=CH—]

and

Ethyl 2-[2-(dimethylamino)ethyl]-8-(methylsulfanyl)-2H-pyrazolo[4,3-h]quinazoline-3-carboxylate [(VIIIb), R1=Me-S—, R2=2-(dimethylamino)ethyl, A=—CH=CH—]

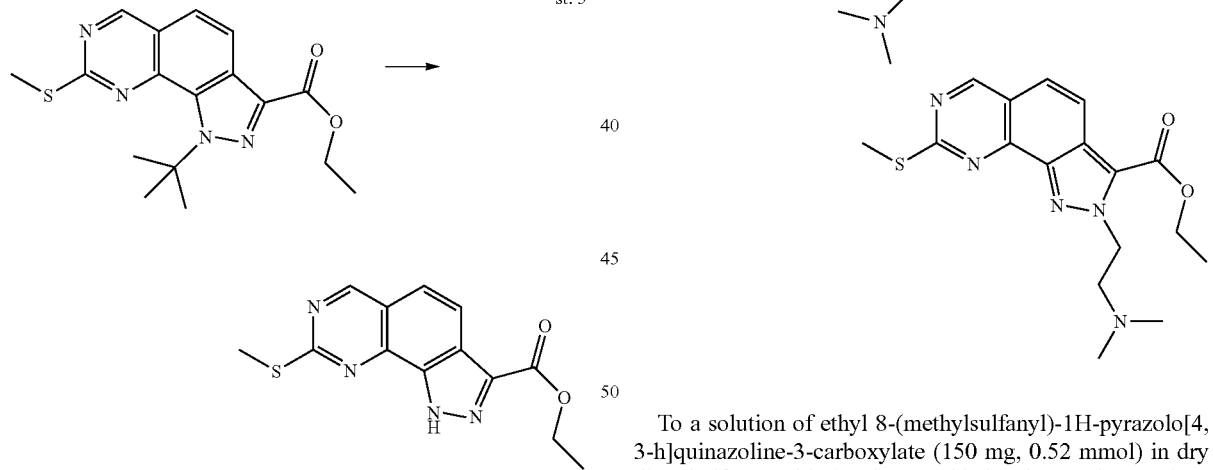

To a solution of ethyl 8-(methylsulfanyl)-1H-pyrazolo[4,3-h]quinazoline-3-carboxylate (150 mg, 0.52 mmol) in dry dimethylformamide (4 ml) was added cesium carbonate (339 mg 1.04 mmol) followed by 2-bromo-N,N-dimethylethanamine (135 mg 0.88 mmol). The heterogeneous mixture was stirred at room temperature for 24 hours. The mixture was treated with water and extracted with EtOAc. The organic layer washed with brine, dried over Na2SO4 and concentrated. The crude was purified by silica gel chromatography eluting with EtOAc/Ethanol 85/15 to give ethyl 1-[2-(dimethylamino)ethyl]-8-(methylsulfanyl)-1H-pyrazolo[4,3-h]quinazoline-3-carboxylate as the major isomer (60 mg 32%) ¹H NMR (401 MHz, DMSO-d6) δ 9.51 (s, 1H), 8.16 (d, J=8.67 Hz, 1H), 7.83 (d, J=8.79 Hz, 1H), 5.29 (t, J=6.59 Hz, 1H), 4.32-4.49 (m, 2H), 2.94 (br. s., 2H), 2.71 (s, 3H), 2.24 (br. s., 6H), 1.41 (t, J=7.08 Hz, 3H); and ethyl 2-[2-(dimethylamino)ethyl]-8-(methylsulfanyl)-2H-pyrazolo[4,3-h]quinazoline-3-carboxylate as minor isomer (20 mg 10%). ¹H NMR (401 MHz, DMSO-d6) δ 9.39 (s, 1H), 8.26 (d, J=8.78 Hz, 1H), 7.87 (d, J=8.78 Hz, 1H), 4.66 (t, J=6.57 Hz, 1H), 4.45 (q, J=7.06 Hz, 2H), 2.71 (br. s., 3H), 2.67 (s, 2H), 2.37 (br. s., 6H), 1.46 (t, J=7.08 Hz, 3H).

Example 5

1-[2-(dimethylamino)ethyl]-8-(methylsulfanyl)-1H-pyrazolo[4,3-h]quinazoline-3-carboxamide [(I), R1=Me-S—, R2=2-(dimethylamino)ethyl, R3=NH₂, A=—CH=CH—] (cpd 12)

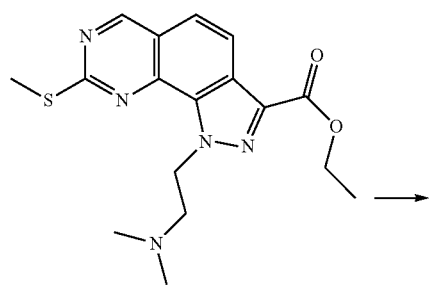

st. 6c

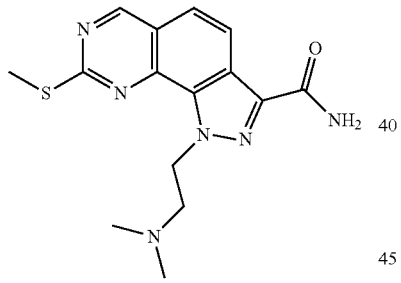

Ethyl 1-[2-(dimethylamino)ethyl]-8-(methylsulfanyl)-1H-pyrazolo[4,3-h]quinazoline-3-carboxylate (46 mg 0.128 mmol) was suspended in 2 ml of tetrahydrofuran. Ammonium chloride (20 mg 0.384 mmol) and LiN(TMS)₂ 1N in THF (0.8 ml 0.8 mmol) were added. The mixture was stirred at room temperature for 1 hour. The solvent was then evaporated to dryness, the residue was purified by flash chromatography on silica gel (eluent: DCM/MeOH/NH₄OH 95/5/0.1) giving 18 mg (42%) of the title compound and 2 mg of a secondary product 6-amino-1-[2-(dimethylamino)ethyl]-8-(methylsulfanyl)-1H-pyrazolo[4,3-h]quinazoline-3-carboxamide. LC/MS (254 nm) HPLC method 2 Rt 3.75 min. ¹H NMR (401 MHz, DMSO-d6) δ 9.48 (s, 1H), 8.27 (d, J=8.67 Hz, 1H), 7.84 (br. s., 1H), 7.74 (d, J=8.67 Hz, 1H), 7.54 (br. s., 1H), 5.25 (t, J=6.71 Hz, 2H), 2.93 (br. s., 2H), 2.71 (s, 3H), 2.23 (br. s., 6H). HRMS (ESI) calcd for C15H18N6OS [M+H]⁺ 331.1336 found 331.1334.

6-amino-1-[2-(dimethylamino)ethyl]-8-(methylsulfanyl)-1H-pyrazolo[4,3-h]quinazoline-3-carboxamide [R1=[(I), R1=Me-S—, R2=2-(dimethylamino)ethyl, R3=NH₂, R5=NH₂, A=—CH=CH—] (cpd 13)

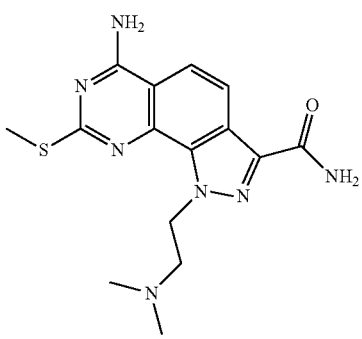 [SMILES: CSc1nc(N)c2ccc3c(C(N)=O)nn(CCN(C)C)c3c2n1]

LC/MS (254 nm) HPLC method 2 Rt 3.97 min. ¹H NMR (401 MHz, DMSO-d6) δ 8.01 (d, J=8.79 Hz, 1H), 7.88 (br. s., 1H), 7.84 (d, J=8.91 Hz, 1H), 7.74 (br. s., 1H), 7.45 (br. s., 1H), 5.22 (t, J=5.61 Hz, 2H), 2.88 (br. s., 2H), 2.58 (s, 3H), 2.15-2.29 (m, J=6.47 Hz, 6H). HRMS (ESI) calcd for C15H19N7OS [M+H]⁺ 346.1445 found 346.1439.

Example 6

2-[2-(dimethylamino)ethyl]-8-(methylsulfanyl)-2H-pyrazolo[4,3-h]quinazoline-3-carboxamide [(I), R1=Me-S—, R2=2-(dimethylamino)ethyl, R3=NH₂, A=—CH=CH—] (cpd 14)

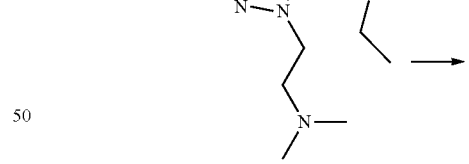

st. 6a

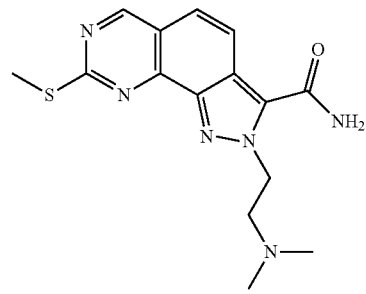

A suspension of 20 mg (0.055 mmol) of ethyl 2-[2-(dimethylamino)ethyl]-8-(methylsulfanyl)-2H-pyrazolo[4,3-h]quinazoline-3-carboxylate in 4 ml of NH₃ 7N in methanol was subjected to microwave irradiation at 120° C. for 4 hours. The volatiles were removed under vacuum, and the residue was purified by silica gel chromatography (eluent DCM/MeOH/NH₃ 97/3/1) to obtain the title compound 2.6 mg (15%). LC/MS (254 nm) HPLC method 2 Rt 3.13 min. ¹H NMR (401 MHz, DMSO-d6) δ 9.34 (s, 1H), 8.34 (br. S., 1H), 8.04 (br. S., 1H), 7.80 (d, J=8.91 Hz, 1H), 7.59 (d, J=9.03 Hz, 1H), 4.89 (t, J=6.47 Hz, 2H), 2.80 (t, J=6.41 Hz, 2H), 2.69 (s, 3H), 2.18 (s, 6H). HRMS (ESI) calcd for C15H18N6OS [M+H]⁺ 331.1336 found 331.1331.

Example 7

Tert-butyl {2-[3-carbamoyl-8-(methylsulfanyl)-1H-pyrazolo[4,3-h]quinazolin-1-yl]ethyl}carbamate [(I), R1=Me-S—, R2=N₁-2-[(tert-butoxycarbonyl)amino]ethyl, R3=NH₂, A=—CH=CH—]

and

Tert-butyl {2-[3-carbamoyl-8-(methylsulfanyl)-2H-pyrazolo[4,3-h]quinazolin-2-yl]ethyl}carbamate [(I), R1=Me-S—, R2=N₂-2-[(tert-butoxycarbonyl)amino]ethyl, R3=NH₂, A=—CH=CH—]

To a solution of ethyl 8-(methylsulfanyl)-1H-pyrazolo[4,3-h]quinazoline-3-carboxylate (200 mg, 0.69 mmol) in dry dimethylformamide (4 ml) was added cesium carbonate (337 mg 1.03 mmol) followed by tert-butyl (2-bromoethyl)carbamate (186 mg 0.83 mmol). The heterogeneous mixture was stirred at room temperature for 48 hours. The mixture was treated with water and extracted with EtOAc. The organic layer washed with brine, dried over Na₂SO₄ and concentrated. The crude was purified by silica gel chromatography eluting with EtOAc/Ethanol 85/15 to give the mixture of two unresolved regioisomers ethyl 1-{2-[(tert-butoxycarbonyl)amino]ethyl}-8-(methylsulfanyl)-1H-pyrazolo[4,3-h]quinazoline-3-carboxylate and ethyl 2-{2-[(tert-butoxycarbonyl)amino]ethyl}-8-(methylsulfanyl)-2H-pyrazolo[4,3-h]quinazoline-3-carboxylate (282 mg 95%).

The obtained mixture of the two regioisomers was suspended in 10 ml of NH₃ 7N in methanol and subjected to microwave irradiation at 120° C. for 5 hours. The volatiles were removed under vacuum, the residue was purified by silica gel chromatography (eluent DCM/MeOH/NH3 97/3/1) to obtain tert-butyl {2-[3-carbamoyl-8-(methylsulfanyl)-1H-pyrazolo[4,3-h]quinazolin-1-yl]ethyl}carbamate as the major isomer 145 mg (55%). LC/MS (254 nm) HPLC method 2 Rt 5.53 min. ¹H NMR (401 MHz, DMSO-d6) δ 9.46 (s, 1H), 8.27 (d, J=8.79 Hz, 1H), 7.74 (s, 2H), 7.54 (br. S., 1H), 6.91 (t, J=6.29 Hz, 1H), 5.21 (t, J=5.86 Hz, 2H), 3.58 (q, J=6.14 Hz, 2H), 2.71 (s, 3H), 1.23 (s, 9H). HRMS (ESI) calcd for C18H22N6O3S [M+H]⁺ 403.1547 found 403.1534; and tert-butyl {2-[3-carbamoyl-8-(methylsulfanyl)-2H-pyrazolo[4,3-h]quinazolin-2-yl]ethyl}carbamate as minor isomer 18 mg (7%) LC/MS (254 nm) HPLC method 2 Rt 5.08 min. ¹H NMR (401 MHz, DMSO-d6) δ 9.33 (s, 1H), 8.08 (d, J=15.01 Hz, 2H), 7.84 (d, J=8.91 Hz, 1H), 7.60 (d, J=8.91 Hz,

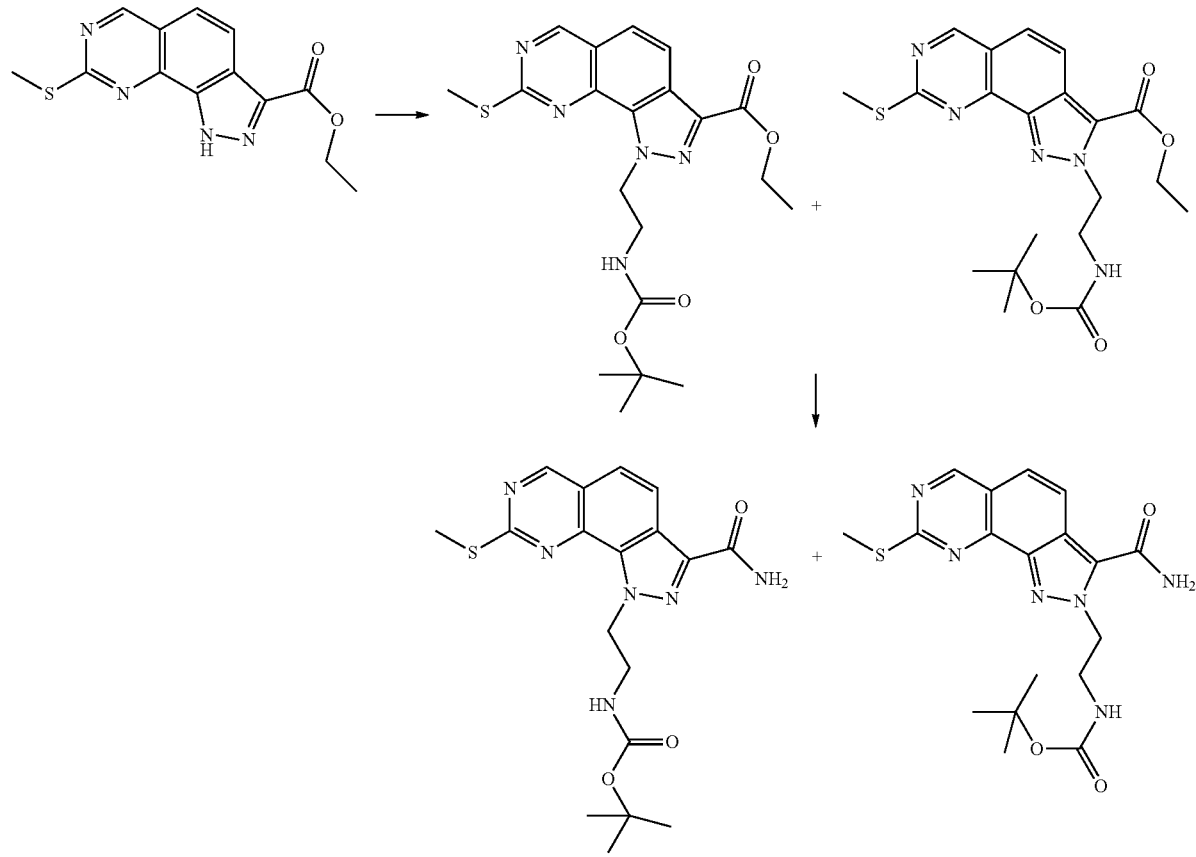

1H), 6.95 (t, J=6.71 Hz, 1H), 4.82 (t, J=6.29 Hz, 2H), 3.49 (q, J=6.51 Hz, 2H), 2.69 (s, 3H), 1.28 (s, 9H). HRMS (ESI) calcd for C18H22N6O3S [M+H]+ 403.1547 found 403.1552.

By working according to this method, the following compound was prepared:

tert-butyl 4-{[3-carbamoyl-8-(methylsulfanyl)-1H-pyrazolo[4,3-h]quinazolin-1-yl]methyl}piperidine-1-carboxylate [(I), R1=Me-S—, R2=$N_1$-tert-butyl 4-methylpiperidin-1-carboxylate, R3=$NH_2$, A=—CH=CH—] LC/MS (254 nm) HPLC method 2 Rt 6.56 min. $^1$H NMR (401 MHz, DMSO-d6) δ 9.47 (s, 1H), 8.28 (d, J=8.79 Hz, 1H), 7.81 (s, 1H), 7.74 (d, J=8.67 Hz, 1H), 7.55 (s, 1H), 5.07 (d, J=7.57 Hz, 2H), 3.90 (d, J=12.08 Hz, 2H), 2.69-2.70 (m, 3H), 2.59-2.68 (m, J=2.01, 3.72 Hz, 2H), 2.22-2.41 (m, 1H), 1.41-1.51 (m, J=6.10 Hz, 2H), 1.38 (s, 9H), 1.22 (dq, J=4.33, 12.31 Hz, 2H). HRMS (ESI) calcd for C22H28N6O3S [M+H]+ 479.1836 found 479.1849.

Example 8

1-(2-aminoethyl)-8-(methylsulfanyl)-1H-pyrazolo[4,3-h]quinazoline-3-carboxamide hydrochloride [(I), R1=Me-S—, R2=$N_1$ 2-aminoethyl, R3=$NH_2$, A=—CH=CH—] (cpd 15)

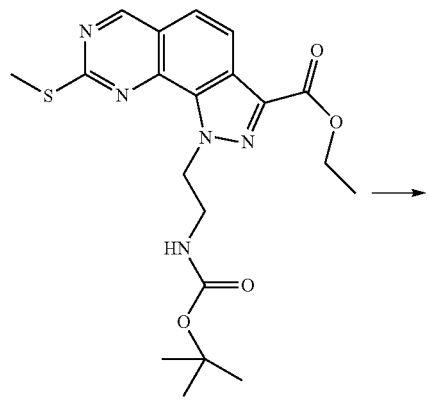

Tert-butyl {2-[3-carbamoyl-8-(methylsulfanyl)-1H-pyrazolo[4,3-h]quinazolin-1-yl]ethyl}carbamate (40 mg 0.1 mmol) was treated with 1 ml of HCl 4M in 1,4-dioxane. The resulting mixture was stirred at room temperature for 1 hour. The volatiles were removed in vacuo, the obtained residue was triturated with diethyl ether, filtered and washed with Et2O and dried in vacuo, to provide 32 mg (97%) of the title compound as a white solid. LC/MS (254 nm) HPLC method 2 Rt 3.59 min. HCl salt, $^1$H NMR (401 MHz, DMSO-d6) δ 9.50 (s, 1H), 8.29 (d, J=8.67 Hz, 1H), 8.12 (br. s., 2H), 8.04 (br. s., 1H), 7.78 (d, J=8.67 Hz, 1H), 7.65 (s, 1H), 5.32-5.58 (m, 2H), 3.57-3.72 (m, 2H), 2.72 (s, 3H). HRMS (ESI) calcd for C13H14N6OS [M+H]+ 303.1023 found 303.1021.

Working according to this method, the following compounds were prepared:

2-(2-aminoethyl)-8-(methylsulfanyl)-2H-pyrazolo[4,3-h]quinazoline-3-carboxamide hydrochloride [(I), R1=Me-S—, R2=$N_2$ 2-aminoethyl, R3=$NH_2$, A=—CH=CH—] (cpd 16) LC/MS (254 nm) HPLC method 2 Rt 3.33 min. HCl salt, $^1$H NMR (401 MHz, DMSO-d6) δ 9.34-9.40 (m, 1H), 7.93-8.29 (m, 5H), 7.85-7.91 (m, 1H), 7.66 (d, J=9.03 Hz, 1H), 5.01 (t, J=6.16 Hz, 2H), 3.43-3.53 (m, 2H), 2.67-2.71 (m, 3H). HRMS (ESI) calcd for C13H14N6OS [M+H]+ 303.1023 found 303.1017;

8-(methylsulfanyl)-1-(piperidin-4-ylmethyl)-1H-pyrazolo[4,3-h]quinazoline-3-carboxamide hydrochloride [(I), R1=Me-S—, $N_1$ R2=piperidin-4-ylmethyl, R3=$NH_2$, A=—CH=CH—] (cpd 17). LC/MS (254 nm) HPLC method 2 Rt 3.94 min. HCl salt, $^1$H NMR (401 MHz, DMSO-d6) δ 9.49 (s, 1H), 8.62 (br. s., 1H), 8.47 (d, J=10.25 Hz, 1H), 8.29 (d, J=8.67 Hz, 1H), 7.81 (s, 1H), 7.76 (d, J=8.67 Hz, 1H), 7.59 (s, 1H), 5.13 (d, J=7.32 Hz, 2H), 3.23 (d, J=12.21 Hz, 2H), 2.81 (q, J=11.76 Hz, 2H), 2.74 (s, 3H), 2.36-2.48 (m, 1H), 1.43-1.68 (m, 4H). HRMS (ESI) calcd for C17H20N6OS [M+H]+ 357.1492 found 357.149; and 8-(methylsulfanyl)-2-(piperidin-4-ylmethyl)-2H-pyrazolo[4,3-h]quinazoline-3-carboxamide hydrochloride [(I), R1=Me-S—, $N_2$ R2=piperidin-4-ylmethyl, R3=$NH_2$, A=—CH=CH—] (cpd 18). LC/MS (254 nm) HPLC method 2 Rt 3.7 min. HCl salt, $^1$H NMR (401 MHz, DMSO-d6) δ 9.36 (s, 1H), 8.64 (d, J=10.37 Hz, 1H), 7.94-8.39 (m, 3H), 7.83 (d, J=9.03 Hz, 1H), 7.62 (d, J=9.03 Hz, 1H), 4.67-4.90 (m, 2H), 2.78-2.94 (m, 2H), 2.69 (s, 3H), 2.34-2.43 (m, 1H), 1.58-1.71 (m, J=12.45 Hz, 2H), 1.41-1.56 (m, 2H). HRMS (ESI) calcd for C17H20N6OS [M+H]+ 357.1492 found 357.1481.

Example 9

1-methyl-8-[4-(piperazin-1-yl)phenoxy]-4,5-dihydro-1H-pyrazolo[4,3-h]quinazoline-3-carboxamide [(I), R1=4-(piperazin-1-yl)phenoxy, R2=methyl, R3=$NH_2$, A=—$(CH_2)_2$—] (cpd 19)

Conv. b

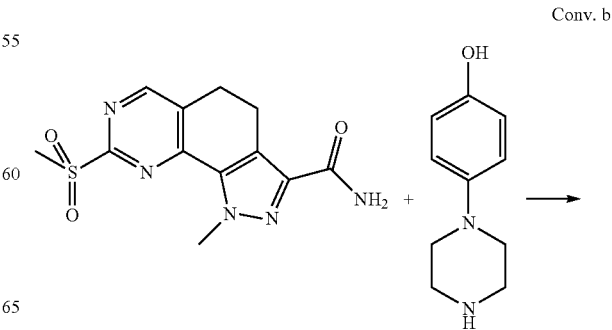

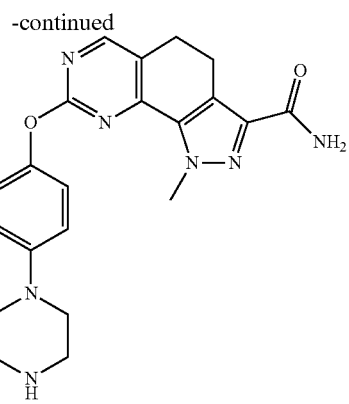

1-methyl-8-(methylsulfonyl)-4,5-dihydro-1H-pyrazolo[4,3-h]quinazoline-3-carboxamide (prepared as described in WO 2004/104007A1) 154 mg (0.5 mmol) and 4-(piperazin-1-yl)phenol 107 mg (0.6 mmol) were reacted in 5 ml of anhydrous DMF in the presence of $Cs_2CO_3$ (0.487 g, 1.5 mmol) at 70° C. for 2 hours. After cooling, the reaction was dried under vacuum, mixed with a spoon of silica and eluted by flash chromatography (DCM/MeOH/$NH_3$ 7N in MeOH 9/1/0.4%) to give the desired product. LC/MS (254 nm) HPLC method 2 Rt 3.73 min. $^1$H NMR (401 MHz, DMSO-d6) δ 8.68 (br. s., 2H), 8.49 (s, 1H), 7.44 (s, 1H), 7.29 (s, 1H), 7.12-7.19 (m, 2H), 7.03-7.08 (m, 2H), 4.06 (s, 3H), 3.20-3.39 (m, 8H), 2.97-3.04 (m, 2H), 2.85-2.92 (m, 2H). HRMS (ESI) calcd for C21H23N7O2 [M+H]$^+$ 406.1986 found 406.19825.

Operating in an analogous way, the following compounds were prepared:

1-methyl-8-phenoxy-4,5-dihydro-1H-pyrazolo[4,3-h]quinazoline-3-carboxamide [(I), R1=phenoxy, R2=methyl, R3=$NH_2$, A=—(CH$_2$)$_2$—] (cpd 20) LC/MS (254 nm) HPLC method 2 Rt 5.23 min. $^1$H NMR (401 MHz, DMSO-d6) δ 8.53 (s, 1H), 7.42-7.49 (m, 3H), 7.22-7.30 (m, 4H), 3.99 (s, 3H), 2.98-3.04 (m, 2H), 2.85-2.93 (m, 2H). HRMS (ESI) calcd for C17H15N5O2 [M+H]$^+$ 322.1299 found 322.1293;

8-(3-aminophenoxy)-1-methyl-4,5-dihydro-1H-pyrazolo[4,3-h]quinazoline-3-carboxamide [(I), R1=3-aminophenoxy, R2=methyl, R3=$NH_2$, A=—(CH$_2$)$_2$—] (cpd 21) LC/MS (254 nm) HPLC method 2 Rt 4.43 min. $^1$H NMR (401 MHz, DMSO-d6) δ 8.51 (s, 1H), 7.45-7.51 (m, 1H), 7.26 (br. s., 1H), 7.04 (t, J=7.99 Hz, 1H), 6.43 (ddd, J=0.85, 2.08, 8.06 Hz, 1H), 6.38 (t, J=2.14 Hz, 1H), 6.32 (ddd, J=0.79, 2.23, 7.96 Hz, 1H), 5.21 (br. s., 2H), 4.06 (s, 3H), 2.98-3.04 (m, 2H), 2.85-2.92 (m, 2H). HRMS (ESI) calcd for C17H16N6O2 [M+H]$^+$ 337.1408 found 337.1411;

8-(4-aminophenoxy)-1-methyl-4,5-dihydro-1H-pyrazolo[4,3-h]quinazoline-3-carboxamide [(I), R1=4-aminophenoxy, R2=methyl, R3=$NH_2$, A=—(CH$_2$)$_2$—] (cpd 22) LC/MS (254 nm) HPLC method 2 Rt 4.23 min. δ H NMR (401 MHz, DMSO-d6) Shift 8.48 (s, 1H), 7.47 (s, 1H), 7.25 (br. s., 1H), 6.84-6.94 (m, 2H), 6.54-6.63 (m, 2H), 4.99 (s, 2H), 4.04 (s, 3H), 2.95-3.04 (m, 2H), 2.83-2.91 (m, 2H). HRMS (ESI) calcd for C17H16N6O2 [M+H]$^+$ 337.1408 found 337.1405;

1-methyl-8-(pyridin-4-yloxy)-4,5-dihydro-1H-pyrazolo[4,3-h]quinazoline-3-carboxamide [(I), R1=pyridin-4-yloxy, R2=methyl, R3=$NH_2$, A=—(CH$_2$)$_2$—] (cpd 23) LC/MS (254 nm) HPLC method 2 Rt 3.68 min. $^1$H NMR (401 MHz, DMSO-d6) δ 8.81-8.86 (m, 2H), 8.79 (s, 1H), 7.53 (s, 1H), 7.32 (br. s., 1H), 6.30-6.36 (m, 2H), 4.36 (s, 3H), 3.04-3.11 (m, 2H), 3.00 (br. s., 2H). HRMS (ESI) calcd for C16H14N6O2 [M+H]$^+$ 323.1251 found 323.1238;

8-ethoxy-1-methyl-4,5-dihydro-1H-pyrazolo[4,3-h]quinazoline-3-carboxamide [(I), R1=ethyl, R2=methyl, R3=$NH_2$, A=—(CH$_2$)$_2$—] LC/MS (254) HPLC method 2 Rt 4.47 min. $^1$H NMR (401 MHz, DMSO-d6) δ 8.48 (s, 1H), 7.45-7.48 (m, 1H), 7.26 (br. s., 1H), 4.39 (q, J=7.04 Hz, 2H), 4.29 (s, 3H), 2.95-3.03 (m, 2H), 2.81-2.90 (m, 2H), 1.36 (t, J=7.02 Hz, 3H). HRMS (ESI) calcd for C13H15N5O2 [M+H]$^+$ 274.1299 found 274.1296;

1-methyl-8-(propan-2-yloxy)-4,5-dihydro-1H-pyrazolo[4,3-h]quinazoline-3-carboxamide [(I), R1=propan-2-yloxy, R2=methyl, R3=$NH_2$, A=—(CH$_2$)$_2$—] LC/MS (254 nm) HPLC method 2 Rt 4.84 min. $^1$H NMR (401 MHz, DMSO-d6) δ 8.47 (s, 1H), 7.47 (br. s., 1H), 7.26 (br. s., 1H), 5.21 (quin, J=6.16 Hz, 1H), 4.28 (s, 3H), 2.96-3.03 (m, 2H), 2.80-2.89 (m, 2H), 1.35 (d, J=6.10 Hz, 6H). HRMS (ESI) calcd for C14H17N5O2 [M+H]$^+$ 288.1455 found 288.144;

1-methyl-8-(2-oxopropoxy)-4,5-dihydro-1H-pyrazolo[4,3-h]quinazoline-3-carboxamide [(I), R1=2-oxopropoxy, R2=methyl, R3=$NH_2$, A=—(CH$_2$)$_2$—] LC/MS (254 nm) HPLC method 2 Rt 3.81 min. $^1$H NMR (401 MHz, DMSO-d6) δ 8.42-8.50 (m, 1H), 7.49 (s, 1H), 7.27 (br. s., 1H), 5.07 (s, 2H), 4.22 (s, 3H), 2.96-3.04 (m, 2H), 2.81-2.89 (m, 2H), 2.14 (s, 3H). HRMS (ESI) calcd for C14H15N5O3 [M+H]$^+$ 302.1248 found 302.1249; and 8-(2-fluoroethoxy)-1-methyl-4,5-dihydro-1H-pyrazolo[4,3-h]quinazoline-3-carboxamide [(I), R1=2-fluoroethoxy, R2=methyl, R3=$NH_2$, A=—(CH$_2$)$_2$—] (cpd 24) LC/MS (254 nm) HPLC method 2 Rt 4.23 min. $^1$H NMR (401 MHz, DMSO-d6) δ 8.51 (s, 1H), 7.41-7.59 (m, 1H), 7.28 (br. s., 1H), 4.80-4.88 (m, 1H), 4.69-4.76 (m, 1H), 4.61-4.67 (m, 1H), 4.53-4.59 (m, 1H), 4.29 (s, 3H), 2.95-3.05 (m, 2H), 2.83-2.92 (m, 2H). HRMS (ESI) calcd for C13H14FN5O2 [M+H]$^+$ 292.1205 found 292.1209.

Example 10

1-methyl-8-[4-(4-methylpiperazin-1-yl)phenoxy]-4,5-dihydro-1H-pyrazolo[4,3-h]quinazoline-3-carboxamide [(I), R1=4-(4-methylpiperazin-1-yl)phenoxy, R2=methyl, R3=$NH_2$, A=—(CH$_2$)$_2$—] (cpd 25)

and 1-methyl-8-[4-(4-methylpiperazin-1-yl)phenoxy]-1H-pyrazolo[4,3-h]quinazoline-3-carboxamide [(I), R1=4-(4-methylpiperazin-1-yl)phenoxy, R2=methyl, R3=$NH_2$, A=—CH=CH—] (cpd 26)

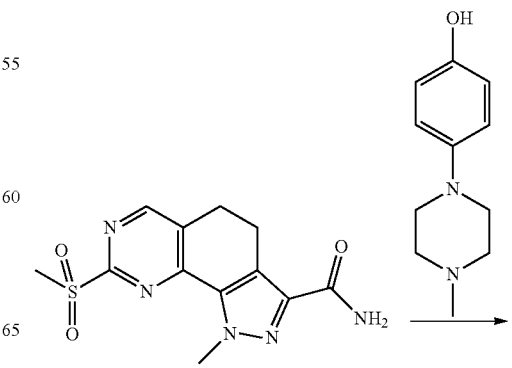

Conv. b

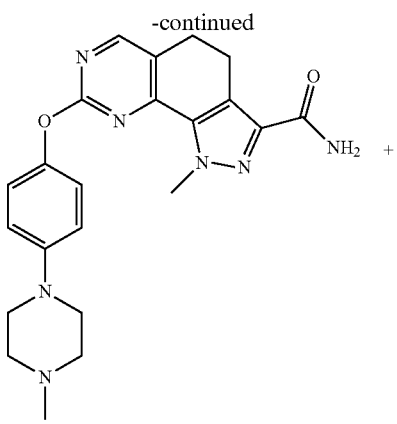

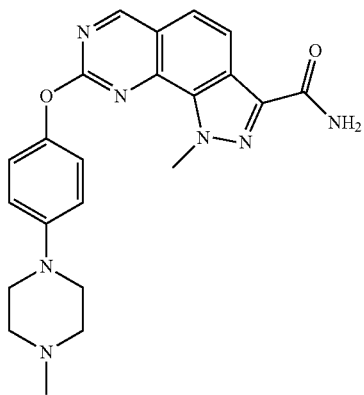

1-methyl-8-(methylsulfonyl)-4,5-dihydro-1H-pyrazolo[4,3-h]quinazoline-3-carboxamide 400 mg (1.3 mmol) and 4-(4-methylpiperazin-1-yl)phenol 360 mg (1.43 mmol) were reacted in 25 ml of anhydrous DMF in the presence of $K_2CO_3$ 717 mg (5.2 mmol) at 70° C. for 4 hours. After cooling, the reaction was dried under vacuum, mixed with a spoon of silica and eluted by flash chromatography (DCM/MeOH/ $NH_3$ 7N in MeOH 9/1/0.4%) to give the mixture 1:1 of the two compounds. Each product was then isolated by preparative HPLC method 2:

1-methyl-8-[4-(4-methylpiperazin-1-yl)phenoxy]-4,5-dihydro-1H-pyrazolo[4,3-h]quinazoline-3-carboxamide. LC/MS (254 nm) HPLC method 2 Rt 3.88 min. $^1$H NMR (401 MHz, DMSO-d6) δ 8.46 (s, 1H), 7.44 (s, 1H), 7.24 (s, 1H), 7.01-7.09 (m, 2H), 6.91-6.98 (m, 2H), 4.02 (s, 3H), 3.06-3.11 (m, 4H), 2.94-3.01 (m, 2H), 2.81-2.88 (m, 2H), 2.42-2.45 (m, 4H), 2.20 (s, 3H). HRMS (ESI) calcd for C22H25N7O2 [M+H]$^+$ 420.2143 found 420.2148; and 1-methyl-8-[4-(4-methylpiperazin-1-yl)phenoxy]-1H-pyrazolo[4,3-h]quinazoline-3-carboxamide. LC/MS (254 nm) HPLC method 2 Rt 4.03 min. $^1$H NMR (401 MHz, DMSO-d6) δ 9.56 (s, 1H), 8.21 (d, J=8.67 Hz, 1H), 7.83 (s, 1H), 7.76 (d, J=8.91 Hz, 1H), 7.49 (s, 1H), 7.18-7.24 (m, 1H), 6.99-7.07 (m, 2H), 4.35 (s, 3H), 3.12-3.19 (m, 4H), 2.45-2.49 (m, 4H), 2.22-2.26 (m, 3H). HRMS (ESI) calcd for C22H23N7O2 [M+H]$^+$ 418.1986 found 418.1985.

According to the same methodology, but employing suitable starting material, the following compounds were prepared:

1-methyl-8-[4-(piperazin-1-yl)phenoxy]-1H-pyrazolo[4,3-h]quinazoline-3-carboxamide trifluoroacetate [(I), R1=4-(4-methylpiperazin-1-yl)phenoxy, R2=methyl, R3=$NH_2$, A=—(CH$_2$)$_2$—] (cpd 27) LC/MS (254 nm) HPLC method 2 Rt 3.91 min. $^1$H NMR (401 MHz, DMSO-d6) δ 9.57 (s, 1H), 8.70 (br. s., 2H), 8.23 (d, J=8.67 Hz, 1H), 7.79 (br. s., 1H), 7.77 (d, J=8.79 Hz, 2H), 7.52 (s, 1H), 7.25-7.31 (m, 2H), 7.09-7.14 (m, 2H), 4.36 (s, 3H), 3.25-3.40 (m, 8H). HRMS (ESI) calcd for C21H21N7O4 [M+H]$^+$ 404.183 found 404.1836;

8-[2-bromo-4-(4-methylpiperazin-1-yl)phenoxy]-1-methyl-4,5-dihydro-1H-pyrazolo[4,3-h]quinazoline-3-carboxamide trifluoroacetate [(I), R1=2-bromo-4-(4-methylpiperazin-1-yl)phenoxy, R2=methyl, R3=$NH_2$, A=—(CH$_2$)$_2$—] (cpd 28) LC/MS (254 nm) HPLC method 2 Rt 4.35 min. TFA salt, $^1$H NMR (401 MHz, DMSO-d6) δ 8.52 (s, 1H), 7.57 (d, J=2.07 Hz, 1H), 7.47 (s, 1H), 7.28 (br. s., 1H), 7.20-7.27 (m, 2H), 4.06 (s, 3H), 2.94-3.04 (m, 6H), 2.84-2.94 (m, 2H), 2.54 (br. s., 4H), 2.26 (s, 3H). HRMS (ESI) calcd for C22H24BrN7O2 [M+H]$^+$ 498.1248 found 498.1239;

8-[2-bromo-4-(4-methylpiperazin-1-yl)phenoxy]-1-methyl-1H-pyrazolo[4,3-h]quinazoline-3-carboxamide trifluoroacetate [(I), R1=2-bromo-4-(4-methylpiperazin-1-yl)phenoxy, R2=methyl, R3=$NH_2$, A=—CH=CH—] (cpd 29). LC/MS (254 nm) HPLC method 2 Rt 4.55 min. TFA salt, $^1$H NMR (401 MHz, DMSO-d6) δ 9.59 (s, 1H), 8.24 (d, J=8.67 Hz, 1H), 7.83 (s, 1H), 7.78 (d, J=8.91 Hz, 1H), 7.73 (d, J=2.69 Hz, 1H), 7.51 (s, 1H), 7.35-7.42 (m, 1H), 7.26-7.32 (m, 1H), 4.36 (s, 2H), 2.95-3.08 (m, 2H), 2.54-2.61 (m, 2H), 2.29 (br. s., 2H). HRMS (ESI) calcd for C22H22BrN7O2 [M+H]$^+$ 496.1091 found 496.1082;

1-methyl-8-[3-(piperazin-1-yl)phenoxy]-4,5-dihydro-1H-pyrazolo[4,3-h]quinazoline-3-carboxamide [(I), R1=3-(piperazin-1-yl)phenoxy, R2=methyl, R3=$NH_2$, A=—(CH$_2$)$_2$—] (cpd 30) LC/MS (254 nm) HPLC method 2 Rt 3.9 min. $^1$H NMR (401 MHz, DMSO-d6) δ 8.51 (s, 1H), 7.47 (br. s., 1H), 7.26-7.28 (m, 1H), 7.17-7.28 (m, 1H), 6.77-6.83 (m, J=1.22, 1.22, 8.42 Hz, 1H), 6.75 (t, J=2.26 Hz, 1H), 6.55-6.63 (m, 1H), 4.03 (s, 3H), 3.05 (dd, J=4.09, 5.92 Hz, 4H), 2.97-3.03 (m, 2H), 2.89 (s, 1H), 2.86-2.93 (m, 2H), 2.77-2.84 (m, J=4.09, 5.92 Hz, 4H). HRMS (ESI) calcd for C21H23N7O2 [M+H]$^+$ 406.1986 found 406.1980;

1-methyl-8-[3-(piperazin-1-yl)phenoxy]-1H-pyrazolo[4,3-h]quinazoline-3-carboxamide trifluoroacetate [(I), R1=3-(piperazin-1-yl)phenoxy, R2=methyl, R3=$NH_2$, A=—CH=CH—] (cpd 31) LC/MS (254 nm) HPLC method 2 Rt 4.1 min. TFA salt, $^1$H NMR (401 MHz, DMSO-d6) δ 9.59 (s, 1H), 8.65 (br. s., 2H), 8.24 (d, J=8.67 Hz, 1H), 7.79 (d, J=8.79 Hz, 2H), 7.51-7.54 (m, 1H), 7.38 (t, J=8.12 Hz, 1H), 7.01 (t, J=2.20 Hz, 1H), 6.96 (d, J=2.44 Hz, 1H), 6.86 (dd, J=1.59, 7.93 Hz, 1H), 4.34 (s, 3H), 3.36-3.41 (m, 4H), 3.22 (br. s., 4H). HRMS (ESI) calcd for C21H21N7O2 [M+H]$^+$ 404.183 found 404.1835;

8-[3-(dimethylamino)phenoxy]-1-methyl-4,5-dihydro-1H-pyrazolo[4,3-h]quinazoline-3-carboxamide [(I), R1=3-(dimethylamino)phenoxy, R2=methyl, R3=$NH_2$, A=—(CH$_2$)$_2$—] LC/MS (254 nm) HPLC method 2 Rt 5.53 min. $^1$H NMR (401 MHz, DMSO-d6) δ 8.51 (s, 1H), 7.47 (br. s., 1H), 7.26 (br. s., 1H), 7.22 (t, J=8.18 Hz, 1H), 6.62 (dd, J=2.08, 8.30 Hz, 1H), 6.57 (t, J=2.20 Hz, 1H), 6.51 (dd, J=1.77, 7.87 Hz, 1H), 4.05 (s, 3H), 2.98-3.04 (m, 2H), 2.85-2.94 (m, 8H). HRMS (ESI) calcd for C19H20N6O2 [M+H]$^+$ 365.1721 found 365.171;

8-[3-(dimethylamino)phenoxy]-1-methyl-1H-pyrazolo[4,3-h]quinazoline-3-carboxamide [(I), R1=3-(dimethylamino)phenoxy, R2=methyl, R3=$NH_2$, A=—CH=CH—] (cpd 32). LC/MS (254 nm) HPLC method 2 Rt 5.8 min. $^1$H NMR (401 MHz, DMSO-d6) δ 9.57 (s, 1H), 8.22 (d, J=8.79 Hz, 1H), 7.83 (br. s., 1H), 7.77 (d, J=8.91 Hz, 1H), 7.45-7.52 (m, 1H), 7.25-7.30 (m, 1H), 6.60-6.74 (m, 3H), 4.35 (s, 3H), 2.92 (s, 6H). HRMS (ESI) calcd for C19H18N6O2 [M+H]$^+$ 363.1564 found 363.1574;

8-(2-chlorophenoxy)-1-methyl-4,5-dihydro-1H-pyrazolo[4,3-h]quinazoline-3-carboxamide [(I), R1=2-chlorophenoxy, R2=methyl, R3=NH$_2$, A=—(CH$_2$)$_2$—] LC/MS (254 nm) HPLC method 2 Rt 5.55 min. $^1$H NMR (401 MHz, DMSO-d6) δ 8.55 (s, 1H), 7.62 (dd, J=0.92, 7.99 Hz, 1H), 7.48 (d, J=2.81 Hz, 1H), 7.40-7.46 (m, 2H), 7.33 (ddd, J=2.75, 6.26, 7.96 Hz, 1H), 7.27 (br. s., 1H), 3.95 (s, 3H), 2.98-3.07 (m, 2H), 2.86-2.94 (m, J=7.93 Hz, 2H). HRMS (ESI) calcd for C17H14ClN5O2 [M+H]$^+$ 356.0909 found 356.0898;

8-(2-chlorophenoxy)-1-methyl-1H-pyrazolo[4,3-h]quinazoline-3-carboxamide [(I), R1=2-chlorophenoxy, R2=methyl, R3=NH$_2$, A=—CH=CH—] (cpd 33). LC/MS (254 nm) HPLC method 2 Rt 5.81 min. $^1$H NMR (401 MHz, DMSO-d6) δ 9.63 (s, 1H), 8.25 (d, J=8.79 Hz, 1H), 7.85 (br. s., 1H), 7.80 (d, J=8.79 Hz, 1H), 7.68 (dd, J=1.46, 7.93 Hz, 1H), 7.55 (dt, J=1.53, 8.15 Hz, 1H), 7.46-7.53 (m, 2H), 7.34-7.43 (m, 1H), 4.23 (s, 3H). HRMS (ESI) calcd for C17H12ClN5O2 [M+H]$^+$ 354.0753 found 354.0746;

8-(2-fluorophenoxy)-1-methyl-4,5-dihydro-1H-pyrazolo[4,3-h]quinazoline-3-carboxamide [(I), R1=2-fluorophenoxy, R2=methyl, R3=NH$_2$, A=—(CH$_2$)$_2$—] LC/MS (254 nm) HPLC method 2 Rt 5.33 min. $^1$H NMR (401 MHz, DMSO-d6) δ 8.55 (s, 1H), 7.48 (br. s., 1H), 7.28-7.46 (m, 4H), 7.26-7.28 (m, 1H), 3.97 (s, 3H), 2.97-3.05 (m, 2H), 2.87-2.94 (m, 2H). HRMS (ESI) calcd for C17H14FN5O2 [M+H]$^+$ 340.1205 found 340.1208;

8-(2-fluorophenoxy)-1-methyl-1H-pyrazolo[4,3-h]quinazoline-3-carboxamide [(I), R1=2-fluorophenoxy, R2=methyl, R3=NH$_2$, A=—CH=CH—] (cpd 34). LC/MS (254 nm) HPLC method 2 Rt 5.58 min. $^1$H NMR (401 MHz, DMSO-d6) δ 9.63 (s, 1H), 8.26 (d, J=8.79 Hz, 1H), 7.85 (s, 1H), 7.80 (d, J=8.79 Hz, 1H), 7.55 (dt, J=1.89, 7.90 Hz, 1H), 7.50 (br. s., 1H), 7.44-7.49 (m, 1H), 7.38-7.44 (m, J=2.14, 4.64, 6.68, 6.68 Hz, 1H), 7.31-7.38 (m, 1H), 4.26 (s, 3H). HRMS (ESI) calcd for C17H12FN5O2 [M+H]$^+$ 338.1048 found 338.1037;

8-[2-fluoro-4-(4-methylpiperazin-1-yl)phenoxy]-1-methyl-4,5-dihydro-1H-pyrazolo[4,3-h]quinazoline-3-carboxamide trifluoroacetate [(I), R1=2-fluoro-4-(4-methylpiperazin-1-yl)phenoxy, R2=methyl, R3=NH$_2$, A=—(CH$_2$)$_2$—] (cpd 35) LC/MS (254 nm) HPLC method 2 Rt 4.06 min. $^1$H NMR (401 MHz, DMSO-d6) δ 9.65 (br. s., 1H), 8.50 (s, 1H), 7.45 (s, 1H), 7.23-7.34 (m, J=9.09, 9.09 Hz, 2H), 7.07 (dd, J=2.81, 13.79 Hz, 1H), 6.87 (dd, J=2.08, 9.03 Hz, 1H), 4.07 (s, 3H), 3.78-3.98 (m, J=13.79 Hz, 2H), 3.46-3.59 (m, 2H), 3.08-3.23 (m, 2H), 2.94-3.07 (m, 4H), 2.84-2.94 (m, 5H). HRMS (ESI) calcd for C22H24FN7O2 [M+H]$^+$ 438.2049 found 438.2039;

8-[2-fluoro-4-(4-methylpiperazin-1-yl)phenoxy]-1-methyl-1H-pyrazolo[4,3-h]quinazoline-3-carboxamide trifluoroacetate [(I), R1=2-fluoro-4-(4-methylpiperazin-1-yl)phenoxy, R2=methyl, R3=NH$_2$, A=—CH=CH—] (cpd 36) LC/MS (254 nm) HPLC method 2 Rt 4.25 min. $^1$H NMR (401 MHz, DMSO-d6) δ 9.68 (br. s., 1H), 9.56-9.61 (m, 1H), 8.25 (d, J=8.67 Hz, 1H), 7.79 (d, J=8.91 Hz, 2H), 7.53 (s, 1H), 7.41 (t, J=9.09 Hz, 1H), 7.14 (dd, J=2.81, 13.79 Hz, 1H), 6.93 (dd, J=2.26, 8.97 Hz, 1H), 4.37 (s, 3H), 3.79-4.05 (m, J=8.79 Hz, 2H), 3.47-3.61 (m, 2H), 3.17 (br. s., 2H), 3.03 (br. s., 2H), 2.88 (s, 3H). HRMS (ESI) calcd for C22H22FN7O2 [M+H]$^+$ 436.1892 found 436.1875;

8-[2-acetyl-4-(4-methylpiperazin-1-yl)phenoxy]-1-methyl-4,5-dihydro-1H-pyrazolo[4,3-h]quinazoline-3-carboxamide trifluoroacetate [(I), R1=2-acetyl-4-(4-methylpiperazin-1-yl)phenoxy, R2=methyl, R3=NH$_2$, A=—(CH$_2$)$_2$—]. LC/MS (254 nm) HPLC method 2 Rt 3.83 min. $^1$H NMR (401 MHz, DMSO-d6) δ 9.57 (br. s., 1H), 8.48 (s, 1H), 7.44 (s, 1H), 7.36 (d, J=2.93 Hz, 1H), 7.27-7.32 (m, 2H), 7.23-7.27 (m, 1H), 4.03 (s, 3H), 3.84-3.96 (m, J=12.45 Hz, 2H), 3.48-3.61 (m, J=11.23 Hz, 2H), 2.98-3.06 (m, J=7.32 Hz, 4H), 2.85-2.92 (m, 5H), 2.45 (s, 3H). HRMS (ESI) calcd for C24H27N7O3 [M+H]$^+$ 462.2248 found 462.2229;

8-[2-acetyl-4-(4-methylpiperazin-1-yl)phenoxy]-1-methyl-1H-pyrazolo[4,3-h]quinazoline-3-carboxamide trifluoroacetate [(I), R1=2-acetyl-4-(4-methylpiperazin-1-yl)phenoxy, R2=methyl, R3=NH$_2$, A=—CH=CH—] (cpd 37) LC/MS (254 nm) HPLC method 2 Rt 3.99 min. $^1$H NMR (401 MHz, DMSO-d6) δ 9.60 (br. s., 1H), 9.57 (s, 1H), 8.24 (d, J=8.79 Hz, 1H), 7.78 (d, J=8.79 Hz, 2H), 7.53 (s, 1H), 7.42 (d, J=2.93 Hz, 1H), 7.36-7.40 (m, 2H), 4.32 (s, 3H), 3.88-4.04 (m, J=15.01 Hz, 2H), 3.47-3.65 (m, J=11.47 Hz, 2H), 2.96-3.12 (m, 2H), 2.90 (br. s., 3H), 2.46 (s, 3H) HRMS (ESI) calcd for C24H25N7O3 [M+H]$^+$ 460.2092 found 460.207;

8-[2-acetyl-4-(piperazin-1-yl)phenoxy]-1-methyl-4,5-dihydro-1H-pyrazolo[4,3-h]quinazoline-3-carboxamide trifluoroacetate [(I), R1=2-acetyl-4-(piperazin-1-yl)phenoxy, R2=methyl, R3=NH$_2$, A=—(CH$_2$)$_2$—]. LC/MS (254 nm) HPLC method 2 Rt 3.75 min. $^1$H NMR (401 MHz, DMSO-d6) δ 8.72 (d, J=5.37 Hz, 2H), 8.49 (s, 1H), 7.44 (s, 1H), 7.35 (d, J=2.93 Hz, 1H), 7.26-7.32 (m, 2H), 7.22-7.26 (m, 1H), 4.02 (s, 3H), 3.37-3.42 (m, 4H), 3.28 (br. s., 4H), 2.98-3.04 (m, 2H), 2.85-2.92 (m, 2H), 2.41-2.46 (m, 3H). HRMS (ESI) calcd for C23H25N7O3 [M+H]$^+$ 448.2092 found 448.2071;

8-[2-acetyl-4-(piperazin-1-yl)phenoxy]-1-methyl-1H-pyrazolo[4,3-h]quinazoline-3-carboxamide trifluoroacetate [(I), R1=2-acetyl-4-(piperazin-1-yl)phenoxy, R2=methyl, R3=NH$_2$, A=—CH=CH—] (cpd 38) LC/MS (254 nm) HPLC method 2 Rt 3.9 min. $^1$H NMR (401 MHz, DMSO-d6) δ 9.57 (s, 1H), 8.74 (br. s., 2H), 8.23 (d, J=8.67 Hz, 1H), 7.78 (d, J=8.91 Hz, 2H), 7.51-7.54 (m, 1H), 7.42 (d, J=2.69 Hz, 1H), 7.37-7.40 (m, 1H), 7.32-7.37 (m, 1H), 4.31 (s, 3H), 3.41-3.45 (m, 4H), 3.30 (d, J=5.13 Hz, 4H), 2.45-2.47 (m, 3H). HRMS (ESI) calcd for C23H23N7O3 [M+H]$^+$ 446.1935 found 446.1927;

8-[2-cyano-4-(4-methylpiperazin-1-yl)phenoxy]-1-methyl-4,5-dihydro-1H-pyrazolo[4,3-h]quinazoline-3-carboxamide trifluoroacetate [(I), R1=2-cyano-4-(4-methylpiperazin-1-yl, R2=methyl, R3=NH$_2$, A=—(CH$_2$)$_2$—] LC/MS (254 nm) HPLC method 2 Rt 4.7 min. $^1$H NMR (401 MHz, DMSO-d6) δ 9.69 (br. s., 1H), 8.54 (s, 1H), 7.53-7.56 (m, 1H), 7.47 (br. s., 1H), 7.42-7.44 (m, 1H), 7.31 (s, 1H), 4.08 (s, 3H), 3.00-3.05 (m, 2H), 2.89-2.95 (m, J=7.81 Hz, 2H), 2.87 (s, 3H). HRMS (ESI) calcd for C23H24N8O2 [M+H]$^+$ 445.2095 found 445.2090; and 8-[2-cyano-4-(4-methylpiperazin-1-yl)phenoxy]-1-methyl-1H-pyrazolo[4,3-h]quinazoline-3-carboxamide trifluoroacetate [(I), R1=2-cyano-4-(4-methylpiperazin-1-yl, R2=methyl, R3=NH$_2$, A=—CH=CH—] (cpd 39) LC/MS (254 nm) HPLC method 2 Rt 4.1 min. $^1$H NMR (401 MHz, DMSO-d6) Shift 9.71 (br. s., 1H), 9.63 (s, 1H), 8.29 (d, J=8.79 Hz, 1H), 7.75-7.87 (m, 2H), 7.60 (d, J=2.93 Hz, 1H), 7.55-7.59 (m, 1H), 7.54 (br. s., 1H), 7.45-7.52 (m, 1H), 4.37 (s, 3H), 3.89-4.05 (m, J=13.79 Hz, 2H), 3.50-3.61 (m, J=14.28 Hz, 2H), 3.19 (br. s., 2H), 3.03-3.13 (m, J=13.43 Hz, 2H), 2.88 (s, 3H). HRMS (ESI) calcd for C23H22N8O2 [M+H]$^+$ 443.1939 found 443.1938.

Example 11

8-(2-acetylphenoxy)-1-methyl-4,5-dihydro-1H-pyrazolo[4,3-h]quinazoline-3-carboxamide and 8-[2-(2-hydroxyphenyl)-2-oxoethyl]-1-methyl-4,5-dihydro-1H-pyrazolo[4,3-h]quinazoline-3-carboxamide. Conv. b

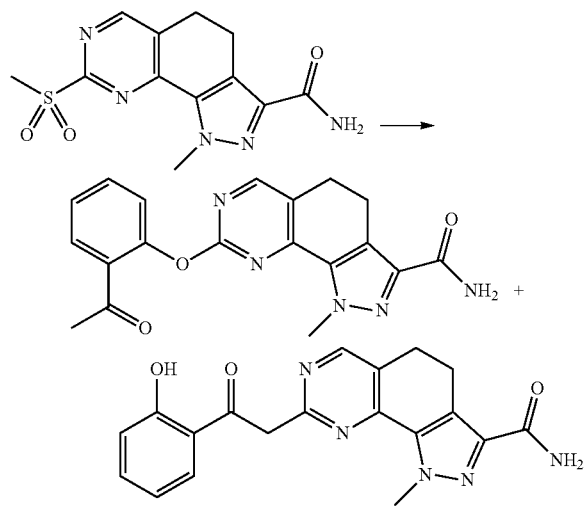

A solution of 1-methyl-8-(methylsulphonyl)-4,5-dihydro-1H-pyrazolo[4,3-h-quinazoline]-3-carboxamide 307 mg (1 mmole), 2-hydroxyacetophenone 322 mg (1.5 mmoles), cesium carbonate 975 mg (3.0 mmoles) in about 15 ml of NMP was heated at 95° C. for 1 hour. After disappearance of s.m., the reaction was cooled down and extracted with water and ethyl acetate. The precipitate formed was isolated by filtration and recovered by preparative reverse phase HPLC leading to two compounds:

8-(2-acetylphenoxy)-1-methyl-4,5-dihydro-1H-pyrazolo[4,3-h]quinazoline-3-carboxamide [(I), R1=2-acetylphenoxy, R2=methyl, R3=NH$_2$, A=—(CH$_2$)$_2$—] LC/MS (254 nm) HPLC method 2 Rt 5.0 min. $^1$H NMR (401 MHz, DMSO-d$_6$) δ 8.52 (s, 1H), 7.87 (dd, J=1.71, 7.81 Hz, 1H), 7.67 (ddd, J=1.71, 7.45, 8.06 Hz, 1H), 7.48 (br. s., 1H), 7.41 (dt, J=1.10, 7.57 Hz, 1H), 7.35 (dd, J=0.85, 8.18 Hz, 1H), 7.26 (br. s., 1H), 3.94 (s, 3H), 2.96-3.06 (m, 2H), 2.89 (t, J=7.90 Hz, 2H), 2.46 (s, 3H). HRMS (ESI) calcd for C19H17N5O3 [M+H]$^+$ 364.1404 found 364.1406; and 8-[2-(2-hydroxyphenyl)-2-oxoethyl]-1-methyl-4,5-dihydro-1H-pyrazolo[4,3-h]quinazoline-3-carboxamide [(I), R1=2-acetylphenoxy, R2=methyl, R3=NH$_2$, A=—(CH$_2$)$_2$—]. LC/MS (254 nm) HPLC method 2 Rt 4.12 min. $^1$H NMR (500 MHz, DMSO-d$_6$) δ 11.62 (s, 1H), 8.66 (s, 1H), 7.92-7.97 (m, 1H), 7.52 (s, 1H), 7.48 (br. s., 1H), 7.27 (br. s., 1H), 6.98 (d, J=7.48 Hz, 1H), 6.94-6.97 (m, 1H), 4.70 (s, 2H), 4.11 (s, 3H), 2.97-3.06 (m, 2H), 2.89-2.95 (m, 2H). HRMS (ESI) calcd for C19H17N5O3 [M+H]$^+$ 363.3770 found 363.3774.

Example 12

8-cyano-1-methyl-4,5-dihydro-1H-pyrazolo[4,3-h]quinazoline-3-carboxamide [(I), R1=CN, R2=Me, R3=NH$_2$, A=—(CH$_2$)$_2$—] (cpd 40)

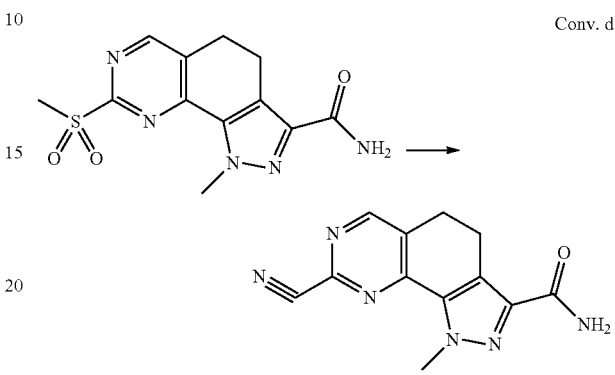

1-methyl-8-(methylsulphonyl)-4,5-dihydro-1H-pyrazolo[4,3-h-quinazoline]-3-carboxamide 136 mg (0.44 mmol) was dissolved in about 8 ml of DMF and heated at 70° C. in the presence of potassium cyanide 116 mg (1.77 mmol). After 30 min the s.m. was disappeared, so the reaction was cooled down and extracted with water and ethyl acetate. The organic phase, dried over Na$_2$SO$_4$ and evaporated, suspended in absolute ethanol and stirred at 65° C. for 2 hours. The product was isolated by filtration as yellowish powder 35 mg (31%). LC/MS (254 nm) HPLC method 2 Rt 3.67 min. $^1$H NMR (401 MHz, DMSO-d$_6$) δ 8.89 (s, 1H), 7.56 (br. s., 1H), 7.33 (br. s., 1H), 4.28 (s, 3H), 3.06 (s, 4H). HRMS (ESI) calcd for C12H10N6O [M+H]$^+$ 255.0989 found 255.0978.

Example 13

1-methyl-8-(1H-pyrazol-1-yl)-4,5-dihydro-1H-pyrazolo[4,3-h]quinazoline-3-carboxamide [(I), R1=1H-pyrazol-1-yl, R2=Me, R3=NH$_2$, A=—(CH$_2$)$_2$—] (cpd 41)

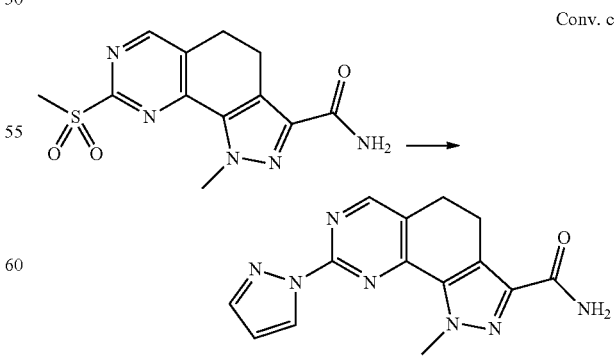

To a solution of 1-methyl-8-(methylsulphonyl)-4,5-dihydro-1H-pyrazolo[4,3-h-quinazoline]-3-carboxamide 100 mg (0.32 mmol) in DMSO (3 ml) was added pyrazole 44 mg (0.65 mmol) and $K_2CO_3$ 134.9 mg (0.976 mmol). The mixture was stirred at 70° C. for 4 hours. The reaction was worked up by addition of water, the precipitate was filtered and washed with water. The solid was washed with hot ethanol and filtered, to obtain the title compound 65 mg (67%). LC/MS (254 nm) HPLC method 2 Rt 3.38 min. $^1$H NMR (401 MHz, DMSO-d6) δ 8.74 (s, 1H), 8.69 (d, J=2.44 Hz, 1H), 7.88 (d, J=0.85 Hz, 1H), 7.51 (br. s., 1H), 7.31 (br. s., 1H), 6.62 (dd, J=1.59, 2.56 Hz, 1H), 4.40 (s, 3H), 3.06 (d, J=6.96 Hz, 2H), 2.97-3.02 (m, 2H). HRMS (ESI) calcd for C14H13N7O [M+H]$^+$ 296.1255 found 296.1261.

According to the same methodology, but employing suitable starting material, the following compounds were prepared:

1-methyl-8-[3-(trifluoromethyl)-1H-pyrazol-1-yl]-4,5-dihydro-1H-pyrazolo[4,3-h]quinazoline-3-carboxamide [(I), R1=3-(trifluoromethyl)-1H-pyrazol-1-yl, R2=Me, R3=NH$_2$, A=—(CH$_2$)$_2$—] (cpd 42) LC/MS (254 nm) HPLC method 2 Rt 4.7 min. $^1$H NMR (401 MHz, DMSO-d6) δ 8.91 (dd, J=0.98, 2.69 Hz, 1H), 8.82 (s, 1H), 7.54 (br. s., 1H), 7.32 (br. s., 1H), 7.10 (d, J=2.56 Hz, 1H), 4.38-4.40 (m, 3H), 2.96-3.15 (m, 4H). HRMS (ESI) calcd for C15H12F3N7O [M+H]$^+$ 364.1128 found 364.1134;

8-(1H-imidazol-1-yl)-1-methyl-4,5-dihydro-1H-pyrazolo[4,3-h]quinazoline-3-carboxamide [(I), R1=1H-imidazol-1-yl, R2=Me, R3=NH$_2$, A=—(CH$_2$)$_2$—] (cpd 43) LC/MS (254 nm) HPLC method 2 Rt 3.33 min. $^1$H NMR (401 MHz, DMSO-d6) δ 8.74 (s, 1H), 8.64 (t, J=0.98 Hz, 1H), 7.99 (t, J=1.34 Hz, 1H), 7.52 (br. s., 1H), 7.31 (br. s., 1H), 7.10-7.21 (m, 1H), 4.34-4.38 (m, 3H), 3.03-3.10 (m, 2H), 2.94-3.02 (m, 2H). HRMS (ESI) calcd for C14H13N7O [M+H]$^+$ 296.1255 found 296.1249; and 1-methyl-8-(4-nitro-1H-imidazol-1-yl)-4,5-dihydro-1H-pyrazolo[4,3-h]quinazoline-3-carboxamide [(I), R1=4-nitro-1H-imidazol-1-yl, R2=Me, R3=NH$_2$, A=—(CH$_2$)$_2$—] (cpd 44) LC/MS (254 nm) HPLC method 2 Rt 3.82 min. $^1$H NMR (401 MHz, DMSO-d6) δ 8.93 (d, J=1.46 Hz, 1H), 8.84 (s, 1H), 8.81 (d, J=1.46 Hz, 1H), 7.51-7.61 (m, 1H), 7.20-7.41 (m, 1H), 4.39 (s, 3H), 3.06 (dd, J=6.23, 12.94 Hz, 4H). HRMS (ESI) calcd for C14H12N8O3 [M+H]$^+$ 341.1105 found 341.1103.

Example 14

1-methyl-8-(methylsulfonyl)-1H-pyrazolo[4,3-h]quinazoline-3-carboxamide [(I), R4=Me, X=SO$_2$—, R2=Me, R3=NH$_2$, A=—CH=CH—]

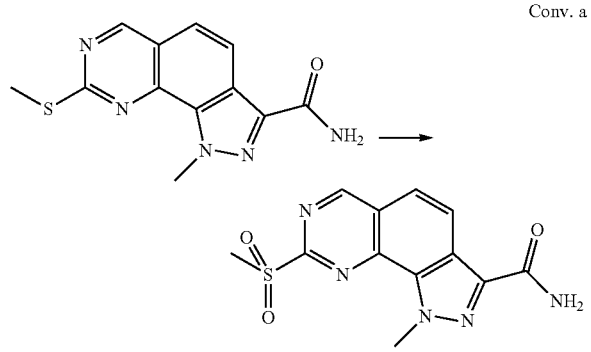

Conv. a 1-methyl-8-(methylsulfanyl)-1H-pyrazolo[4,3-h]quinazoline-3-carboxamide 0.2 g (0.74 mmol) was suspended in 10 ml of DCM and reacted with MCPBA 0.52 g (3.04 mmol) for 3 hours. Water and NaHCO$_3$ were added and the solid separated, filtered and washed with sat. aqueous solution of NaHCO$_3$ to obtain 180 mg (80%) of a white compound. LC/MS (254 nm) HPLC method 2 Rt 3.72 min. $^1$H NMR (401 MHz, DMSO-d6) δ 9.97 (s, 1H), 8.60 (d, J=8.67 Hz, 1H), 7.99 (d, J=8.79 Hz, 2H), 7.63 (br. s., 1H), 4.72 (s, 3H), 3.61 (s, 3H). HRMS (ESI) calcd for C12H11N5O3S [M+H]$^+$ 306.0656 found 306.0645

Operating in an analogous way the following compounds were prepared:

1-(2-hydroxyethyl)-8-(methylsulfonyl)-1H-pyrazolo[4,3-h]quinazoline-3-carboxamide [(I), R4=Me, X=SO$_2$—, R2=2-hydroxyethyl, R3=NH$_2$, A=—CH=CH—] LC/MS (254 nm) HPLC method 2 Rt 3.39. HRMS (ESI) calcd for C13H13N5O4S [M+H]$^+$ 336.0761 found 336.0776;

1-tert-butyl-8-(methylsulfonyl)-1H-pyrazolo[4,3-h]quinazoline-3-carboxamide [(I), R4=Me, X=SO$_2$—, R2=t-butyl, R3=NH$_2$, A=—CH=CH—] LC/MS (m/z): 348.2 [M+H]$^+$, HPLC (254 nm) method 3 Rt 4.59; and 8-(methylsulfonyl)-1H-pyrazolo[4,3-h]quinazoline-3-carboxamide [(I), R4=Me, X=SO$_2$—, R2=H, R3=NH$_2$, A=—CH=CH—] LC/MS (m/z): 292.2 [M+H]$^+$, HPLC (254 nm) method 3 Rt 2.21.

Example 15

1-(2-hydroxyethyl)-8-phenoxy-1H-pyrazolo[4,3-h]quinazoline-3-carboxamide [(I), R1=phenoxy, R2=2-hydroxyethyl, R3=NH$_2$, A=—CH=CH—] (cpd 45)

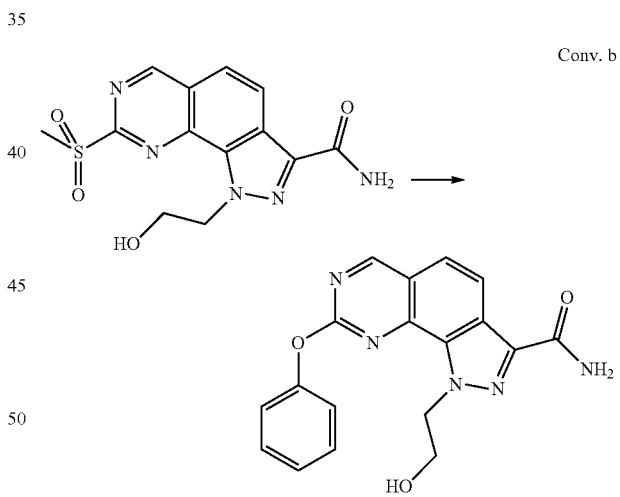

Conv. b

To a solution of 1-(2-hydroxyethyl)-8-(methylsulfonyl)-1H-pyrazolo[4,3-h]quinazoline-3-carboxamide 100 mg (0.298 mmol) in N,N-dimethylformamide (5 ml), potassium carbonate (160 mg, 1.2 mmol) and phenol 35 mg (0.36 mmol) were added. The mixture was stirred at 70° C. for 3 hours, afterwards it was portioned between EtOAc and H$_2$O. The combined organic layers were dried over Na$_2$SO$_4$ and concentrated in vacuo. The crude was purified by chromatography (DCM/MeOH 9/1) to provide the desired product (40 mg 40%). LC/MS (254 nm) HPLC method 2 Rt 4.79 min. $^1$H NMR (401 MHz, DMSO-d6) δ 9.61 (s, 1H), 8.25 (d, J=8.79 Hz, 1H), 7.75-7.84 (m, J=8.79 Hz, 1H), 7.45-7.57 (m, 3H), 7.31-7.40 (m, 3H), 4.69-4.75 (m, 2H), 4.55-4.63 (m, 1H), 3.59 (q, J=5.61 Hz, 2H). HRMS (ESI) calcd for C18H15N5O3 [M+H]⁺ 350.1248 found 350.1247.

Using methods similar to those described in the above example, the following analogs were also synthesized:

1-(2-hydroxyethyl)-8-[4-(4-methylpiperazin-1-yl)phenoxy]-1H-pyrazolo[4,3-h]quinazoline-3-carboxamide [(I), R1=4-(4-methylpiperazin-1-yl)phenoxy, R2=2-hydroxyethyl, R3=NH₂, A=—CH=CH—] (cpd 46) LC/MS (254 nm) HPLC method 2 Rt 3.78 min. ¹H NMR (401 MHz, DMSO-d6) δ 9.57 (s, 1H), 8.23 (d, J=8.79 Hz, 1H), 7.77 (d, J=8.91 Hz, 2H), 7.46-7.53 (m, 1H), 7.16-7.27 (m, 2H), 6.98-7.10 (m, 2H), 4.77 (t, J=5.19 Hz, 2H), 4.55-4.63 (m, 1H), 3.64 (q, J=5.53 Hz, 2H), 3.13-3.21 (m, 4H), 2.52 (br. s., 4H), 2.26 (s, 3H). HRMS (ESI) calcd for C23H25N7O3 [M+H]⁺ 448.2092 found 448.2082;

1-(2-hydroxyethyl)-8-[3-(4-methylpiperazin-1-yl)phenoxy]-1H-pyrazolo[4,3-h]quinazoline-3-carboxamide [(I), R1=3-(4-methylpiperazin-1-yl)phenoxy, R2=2-hydroxyethyl, R3=NH₂, A=—CH=CH—] (cpd 47) LC/MS (254 nm) HPLC method 2 Rt 3.92 min. ¹H NMR (401 MHz, DMSO-d6) δ 9.59 (s, 1H), 8.24 (d, J=8.79 Hz, 1H), 7.79 (s, 1H), 7.77 (s, 2H), 7.48-7.50 (m, 1H), 7.28-7.36 (m, 1H), 6.84-6.93 (m, 2H), 6.68-6.77 (m, 1H), 4.70-4.78 (m, 2H), 4.57 (t, J=5.68 Hz, 1H), 3.62 (q, J=5.53 Hz, 2H), 3.15-3.22 (m, 4H), 2.39-2.47 (m, 4H), 2.21 (s, 3H). HRMS (ESI) calcd for C23H25N7O3 [M+H]⁺ 448.2092 found 448.2086;

1-(2-hydroxyethyl)-8-(3-nitrophenoxy)-1H-pyrazolo[4,3-h]quinazoline-3-carboxamide [(I), R1=3-nitrophenoxy, R2=2-hydroxyethyl, R3=NH₂, A=—CH=CH—] (cpd 48) LC/MS (254 nm) HPLC method 2 Rt 4.9 min. ¹H NMR (401 MHz, DMSO-d6) δ 9.66 (s, 1H), 8.30 (t, J=2.14 Hz, 1H), 8.28 (d, J=8.79 Hz, 1H), 8.20-8.24 (m, 1H), 7.89-7.93 (m, 1H), 7.80-7.86 (m, 2H), 7.50-7.52 (m, 1H), 4.69 (t, J=5.74 Hz, 1H), 4.61-4.65 (m, 1H), 3.57 (q, J=5.45 Hz, 1H). HRMS (ESI) calcd for C18H14N6O5 [M+H]⁺ 395.1099 found 395.1098;

1-methyl-8-(3-nitrophenoxy)-1H-pyrazolo[4,3-h]quinazoline-3-carboxamide [(I), R1=3-nitrophenoxy, R2=methyl, R3=NH₂, A=—CH=CH—] (cpd 49) ¹H NMR (401 MHz, DMSO-d6) δ 9.65 (s, 1H), 8.34 (t, J=2.14 Hz, 1H), 8.27 (d, J=8.67 Hz, 1H), 8.21 (ddd, J=0.98, 2.20, 8.18 Hz, 2H), 7.91-7.95 (m, 2H), 7.86 (br. s., 1H), 7.78-7.85 (m, 4H), 7.51 (br. s., 3H), 4.29 (s, 3H). HRMS (ESI) calcd for C17H12N6O4 [M+H]⁺ 365.0993 found 365.0997;

1-methyl-8-[3-(4-methylpiperazin-1-yl)phenoxy]-1H-pyrazolo[4,3-h]quinazoline-3-carboxamide [(I), R1=3-(4-methylpiperazin-1-yl)phenoxy, R2=methyl, R3=NH₂, A=—CH=CH—] (cpd 50) LC/MS (254 nm) HPLC method 2 Rt 4.24 min. ¹H NMR (401 MHz, DMSO-d6) δ 9.58 (s, 1H), 8.22 (d, J=8.67 Hz, 1H), 7.83 (s, 1H), 7.77 (d, J=8.79 Hz, 1H), 7.49 (s, 1H), 7.31 (t, J=8.18 Hz, 1H), 6.90-6.93 (m, 1H), 6.87 (dd, J=1.77, 8.36 Hz, 1H), 6.71-6.77 (m, 1H), 4.31-4.35 (m, 3H), 3.12-3.20 (m, 4H), 2.44 (d, J=9.28 Hz, 4H), 2.21 (s, 3H). HRMS (ESI) calcd for C22H23N7O2 [M+H]⁺ 418.1986 found 418.1983; and 1-tert-butyl-8-[4-(4-methylpiperazin-1-yl)phenoxy]-1H-pyrazolo[4,3-h]quinazoline-3-carboxamide [(I), R1=4-(4-methylpiperazin-1-yl)phenoxy, R2=tert-butyl, R3=NH₂, A=—CH=CH—] (cpd 51) LC/MS (254 nm) HPLC method 2 Rt 4.63 min. ¹H NMR (401 MHz, DMSO-d6) δ 9.60 (s, 1H), 8.34 (d, J=8.54 Hz, 1H), 7.82 (d, J=8.79 Hz, 1H), 7.67 (s, 1H), 7.43-7.57 (m, 1H), 7.12-7.20 (m, 2H), 6.99-7.09 (m, 2H), 3.09-3.21 (m, 4H), 2.25 (s, 3H), 1.55 (s, 9H). HRMS (ESI) calcd for C25H29N7O2 [M+H]⁺ 460.2456 found 460.2448.

Example 16

1-tert-butyl-8-(dimethylamino)-1H-pyrazolo[4,3-h]quinazoline-3-carboxamide [(I), R1=R4 and R6=Me, X=N, R2=tert-butyl, R3=NH₂, A=—CH=CH—] (cpd 52)

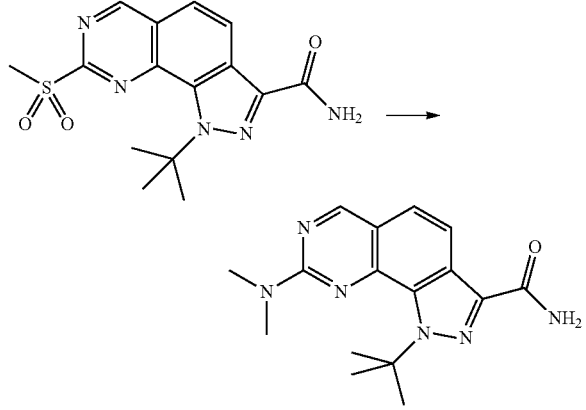

To a solution of 1-tert-butyl-8-(methylsulfonyl)-1H-pyrazolo[4,3-h]quinazoline-3-carboxamide, 10 mg (0.028 mmol) in N,N-dimethylformamide (2 ml), potassium carbonate (160 mg, 0.112 mmol) and 40% aqueous dimethylamine 10 μl mg (0.36 mmol) were added. The mixture was stirred at room temperature for 18 hours, afterwards it was diluted with H₂O. The precipitate was filtered and washed with water, dried in vacuo, to provide the desired product 5 mg (65%). LC/MS (254 nm) HPLC method 2 Rt 6.44 min. ¹H NMR (401 MHz, DMSO-d6) δ 9.23 (s, 1H), 8.05 (d, J=8.54 Hz, 1H), 7.61 (br. s., 1H), 7.56 (d, J=8.67 Hz, 1H), 7.41 (br. s., 1H), 2.00 (s, 9H). HRMS (ESI) calcd for C16H20N6O [M+H]⁺ 313.1772 found 313.1777.

Example 17

8-methoxy-1-methyl-1H-pyrazolo[4,3-h]quinazoline-3-carboxamide [(I), R4=Me, X=O, R2=methyl, A=—CH=CH—] (cpd 53)

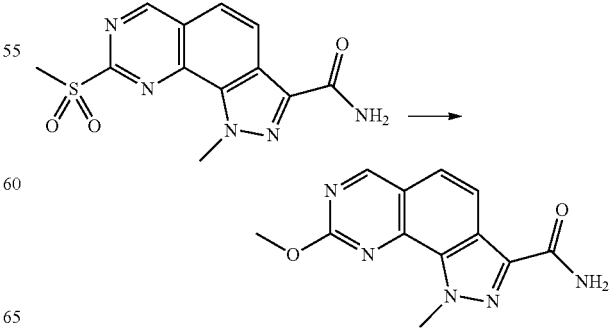

1-methyl-8-(methylsulfonyl)-1H-pyrazolo[4,3-h]quinazoline-3-carboxamide (30 mg 0.1 mmol) was dissolved in 3 ml of methanol, and potassium carbonate (27 mg, 0.2 mmol) was added. The mixture was stirred at room temperature for 1 hour. The solvent was removed under reduced pressure and the residue triturated with diethyl ether, filtered and dried, to obtain the title product 20 mg (80%). LC/MS (254 nm) HPLC method 2 Rt 4.28 min. $^1$H NMR (401 MHz, DMSO-d6) δ 9.51 (s, 1H), 8.18 (d, J=8.67 Hz, 1H), 7.83 (br. s., 1H), 7.73 (d, J=8.67 Hz, 1H), 7.47-7.57 (m, 1H), 4.70 (s, 3H), 4.14 (s, 3H). HRMS (ESI) calcd for C12H11N5O2 [M+H]$^+$ 258.0986 found 258.0987

Operating in an analogous way the following compounds were prepared:

8-ethoxy-1-methyl-1H-pyrazolo[4,3-h]quinazoline-3-carboxamide [(I), R4=Et, X=O, R2=methyl, A=—CH=CH—] (cpd 54) LC/MS (254 nm) HPLC method 2 Rt 4.71 min. $^1$H NMR (401 MHz, DMSO-d6) δ 9.46-9.55 (m, 1H), 8.17 (d, J=8.79 Hz, 1H), 7.79-7.89 (m, 1H), 7.72 (d, J=8.79 Hz, 1H), 7.50 (br. s., 1H), 4.68 (s, 3H), 4.55-4.63 (m, 2H), 1.46 (t, J=7.08 Hz, 3H) HRMS (ESI) calcd for C13H13N5O2 [M+H]$^+$ 272.1142 found 272.1149; and 8-methoxy-1H-pyrazolo[4,3-h]quinazoline-3-carboxamide [(I), R4=Me, X=O, R2=H, A=—CH=CH—] (cpd 55) LC/MS (m/z): 244.2 [M+H]$^+$, HPLC (254 nm) method 3 Rt 2.89 min.

Example 18

8-(3-formylphenoxy)-1-methyl-1H-pyrazolo[4,3-h]quinazoline-3-carboxamide [(I), R4=3-formylphenyl, X=O, R2=methyl, A=—CH=CH—] (cpd 56)

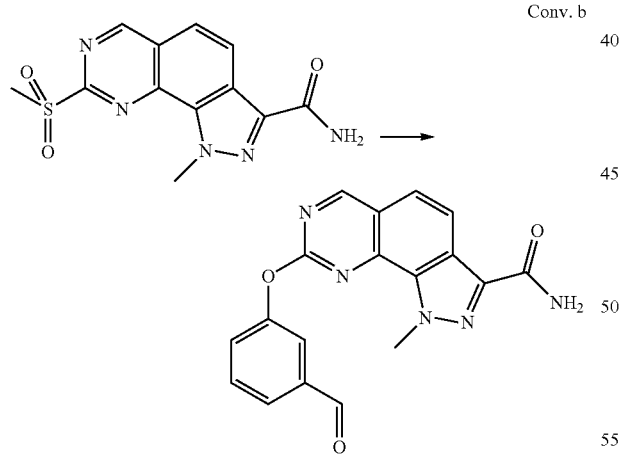

Conv. b

To a solution of 1-methyl-8-(methylsulfonyl)-1H-pyrazolo[4,3-h]quinazoline-3-carboxamide 120 mg (0.39 mmol) in N,N-dimethylformamide (3 ml), potassium carbonate (108 mg, 0.78 mmol) and m-hydroxybenzaldehyde (70 mg, 0.58 mmol) were added. The mixture was stirred at 70° C. for 4 hours, then portioned between EtOAc and H₂O. The combined organic layers were dried over Na₂SO₄ and concentrated in vacuo to provide the desired product (100 mg 74%). LC/MS (m/z): 348.0 [M+H]$^+$, HPLC (254 nm) method 3 Rt 5.05 min.

Example 19

1-methyl-8-{3-[(4-methylpiperazin-1-yl)methyl]phenoxy}-1H-pyrazolo[4,3-h]quinazoline-3-carboxamide [(I), R4=3-[(4-methylpiperazin-1-yl)methyl]phenyl, X=O, R2=methyl, A=—CH=CH—] (cpd 57)

and

8-[3-(hydroxymethyl)phenoxy]-1-methyl-1H-pyrazolo[4,3-h]quinazoline-3-carboxamide [(I), R4=3-hydroxymethylphenyl, X=O, R2=methyl, A=—CH=CH—] (cpd 58)

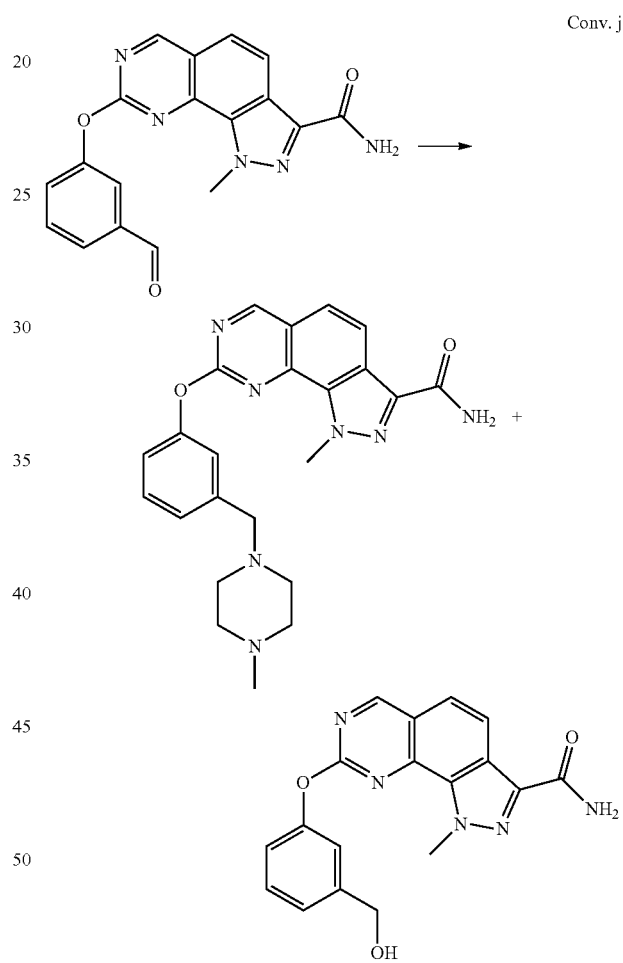

Conv. j

To a solution of 8-(3-formylphenoxy)-1-methyl-1H-pyrazolo[4,3-h]quinazoline-3-carboxamide 30 mg (0.086 mmol) in N,N-dimethylformamide (2 ml) and acetic acid (50 µl), N-methyl piperazine (13 µl, 0.13 mmol), and sodium cyanoborohydride (6 mg, 0.26 mmol) were added. The solution was stirred at r.t. for 3 hours, monitored by both TLC and LC/MS (method 1). The reaction was diluted with ethyl acetate, washed with water and brine, dried over Na₂SO₄ filtered and concentrated. The residue was purified by column (DCM/MeOH/NH₄OH 95/5/0.1) to give 1-methyl-8-{3-[(4-methylpiperazin-1-yl)methyl]phenoxy}-1H-pyrazolo[4,3-h]quinazoline-3-carboxamide as major (15 mg 40%) LC/MS (254 nm) HPLC method 2 Rt 4.14 min. ¹H NMR (401 MHz, DMSO-d6) δ 9.60 (s, 1H), 8.23 (d, J=8.79 Hz, 1H), 7.83 (s, 1H), 7.78 (d, J=8.79 Hz, 1H), 7.49-7.50 (m, 1H), 7.46 (t, J=7.81 Hz, 1H), 7.26 (dt, J=1.71, 7.69 Hz, 3H), 4.27 (s, 3H), 3.53 (s, 2H), 2.30-2.47 (m, 8H), 2.17 (br. s., 3H). HRMS (ESI) calcd for C23H25N7O2 [M+H]⁺ 432.2143 found 432.2141; and 8-[3-(hydroxymethyl)phenoxy]-1-methyl-1H-pyrazolo[4,3-h]quinazoline-3-carboxamide as minor (10 mg 33%) LC/MS (254 nm) HPLC method 2 Rt 4.54 min. ¹H NMR (401 MHz, DMSO-d6) δ 9.60 (s, 1H), 8.23 (d, J=8.79 Hz, 1H), 7.83 (s, 1H), 7.78 (d, J=8.79 Hz, 1H), 7.49 (s, 1H), 7.42-7.48 (m, 1H), 7.30-7.33 (m, J=1.83 Hz, 1H), 7.20-7.28 (m, 2H), 5.27 (t, J=5.80 Hz, 1H), 4.56 (d, J=5.74 Hz, 2H), 4.30 (s, 3H) HRMS (ESI) calcd for C18H15N5O3 [M+H]⁺ 350.1248 found 350.1253.

Working according to the same method the following compounds were prepared:

8-{3-[(dimethylamino)methyl]phenoxy}-1-methyl-1H-pyrazolo[4,3-h]quinazoline-3-carboxamide [(I), R4=3-[(dimethylamino)methyl]phenyl, X═O, R2=methyl, A═—CH═CH—] (cpd 59) LC/MS (254 nm) HPLC method 2 Rt 3.89 min. ¹H NMR (401 MHz, DMSO-d6) δ 9.61 (s, 1H), 8.23 (d, J=8.79 Hz, 1H), 7.82 (s, 1H), 7.78 (d, J=8.91 Hz, 1H), 7.49-7.50 (m, 1H), 7.46 (t, J=7.81 Hz, 1H), 7.29 (d, J=1.46 Hz, 1H), 7.21-7.28 (m, 2H), 4.27 (s, 3H), 3.46 (s, 2H), 2.18 (s, 6H). HRMS (ESI) calcd for C20H20N6O2 [M+H]⁺ 377.1721 found 377.1719; and 1-methyl-8-[3-(morpholin-4-ylmethyl)phenoxy]-1H-pyrazolo[4,3-h]quinazoline-3-carboxamide [(I), R4=3-(morpholin-4-ylmethyl)phenyl, X═O, R2=methyl, A═—CH═CH—] (cpd 60) LC/MS (254 nm) HPLC method 2 Rt 4.72 min. ¹H NMR (401 MHz, DMSO-d6) δ 9.60 (s, 1H), 8.23 (d, J=8.67 Hz, 1H), 7.83 (s, 1H), 7.78 (d, J=8.79 Hz, 1H), 7.49-7.50 (m, 1H), 7.46 (t, J=7.87 Hz, 1H), 7.29-7.32 (m, 1H), 7.23-7.29 (m, 2H), 4.27 (s, 3H), 3.55-3.60 (m, 4H), 3.53 (s, 2H), 2.36-2.41 (m, 4H). HRMS (ESI) calcd for C22H22N6O3 [M+H]⁺ 419.1826 found 419.1815.

Example 20

8-(3-aminophenoxy)-1-methyl-1H-pyrazolo[4,3-h]quinazoline-3-carboxamide [(I), R4=3-aminophenyl, X═O, R2=methyl, A═—CH═CH—] (cpd 61)

Conv. k

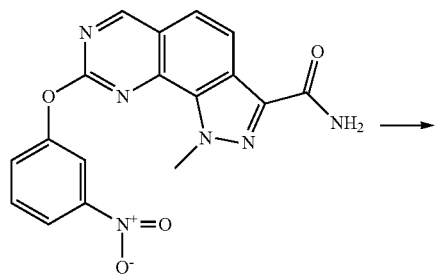

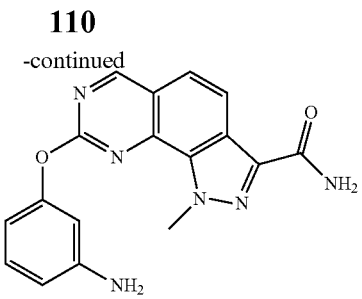

1-methyl-8-(3-nitrophenoxy)-1H-pyrazolo[4,3-h]quinazoline-3-carboxamide 55 mg (0.15 mmol) was suspended in 1,4 dioxane (5 ml) and water (1 ml), zinc dust 43 mg (0.6 mmol), and ammonium chloride 88 mg (1.5 mmol) were added. The mixture was stirred at 100° C. for 2 hours. The volatiles were removed in vacuo, the residue was dissolved with ethyl acetate and water, the organic were extracted and washed with brine, dried over Na₂SO₄ and concentrated. The crude solid was purified by flash chromatography on silica gel (dichloromethane/methanol 95/5) to afford 10 mg (20% yield) of the title compound. LC/MS (254 nm) HPLC method 2 Rt 4.7 min. ¹H NMR (401 MHz, DMSO-d6) δ 9.57 (s, 1H), 8.22 (d, J=8.79 Hz, 1H), 7.84 (s, 1H), 7.77 (d, J=8.79 Hz, 1H), 7.49 (s, 1H), 7.11 (t, J=7.99 Hz, 1H), 6.50-6.53 (m, 1H), 6.41-6.50 (m, J=0.92, 2.23, 8.68, 8.68 Hz, 2H), 5.26 (s, 2H), 4.38 (s, 3H). HRMS (ESI) calcd for C17H14N6O2 [M+H]⁺ 335.1251 found 335.1258.

Working according to the same method the following compound was prepared:

8-(3-aminophenoxy)-1-(2-hydroxyethyl)-1H-pyrazolo[4,3-h]quinazoline-3-carboxamide [(I), R4=3-aminophenyl, X═O, R2=2-hydroxyethyl, A═—CH═CH—] (cpd 62) LC/MS (254 nm) HPLC method 2 Rt 4.26 min. ¹H NMR (401 MHz, DMSO-d6) δ 9.58 (s, 1H), 8.23 (d, J=8.79 Hz, 1H), 7.74-7.83 (m, J=8.79 Hz, 1H), 7.49 (s, 1H), 7.12 (t, J=8.12 Hz, 1H), 6.47-6.55 (m, 2H), 6.40-6.47 (m, 1H), 5.27 (s, 2H), 4.81 (t, J=5.19 Hz, 2H), 4.61 (t, J=5.68 Hz, 1H), 3.69 (q, J=5.57 Hz, 2H) HRMS (ESI) calcd for C18H16N6O3 [M+H]⁺ 365.1357 found 365.1363.

Preparation J

Ethyl 8-(methylsulfanyl)-4,5-dihydro-1H-pyrazolo[4,3-h]quinazoline-3-carboxylate [(VIII), R1=MeS—, R2=H]

st. 5

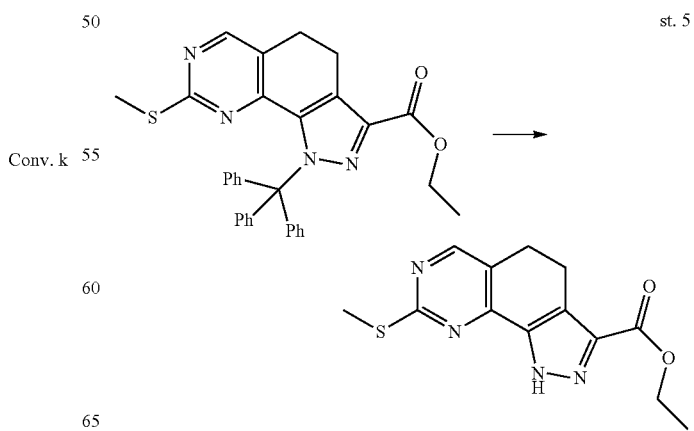

Ethyl 8-(methylsulfanyl)-1-trityl-4,5-dihydro-1H-pyrazolo[4,3-h]quinazoline-3-carboxylate (1.0 g, 1.99 mmol) in DCM (20 ml) was treated with trifluoroacetic acid (5 ml). The resulting mixture was stirred at r.t. for 1 hour and the solvent removed in vacuo. The residue was triturated with diethyl ether filtered and dried to provide the title compound 500 mg (96%). LC/MS (254 nm) HPLC method 2 Rt 3.62 min.

Example 21

8-(methylsulfanyl)-4,5-dihydro-1H-pyrazolo[4,3-h]quinazoline-3-carboxamide [(I), R1=Me-S—, R2=H, R3=NH₂, A=—(CH₂)₂—] (cpd 63)

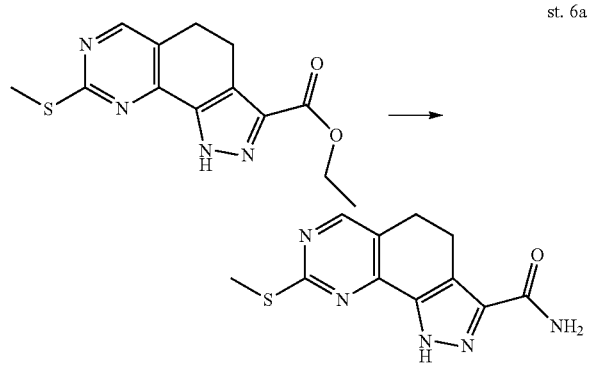

st. 6a

A suspension of 0.5 g (1.91 mmol) of Ethyl 8-(methylsulfanyl)-4,5-dihydro-1H-pyrazolo[4,3-h]quinazoline-3-carboxylate in 5 ml of NH₃ 7N in methanol was heated at 60° C. for 72 hours. The volatiles were removed under vacuum, the residue was triturated with diethyl ether and the solid filtered to provide the title compound 0.4 g (80%). ¹H NMR (401 MHz, DMSO-d6) δ 14.13 (br. s., 1H), 8.52 (s, 1H), 7.53 (br. s., 1H), 7.26 (br. s., 1H), 2.96-3.08 (m, J=7.45 Hz, 2H), 2.83-2.94 (m, 2H), 2.56 (s, 3H) HRMS (ESI) calcd for C11H11N5OS [M+H]⁺ 262.0757 found 262.07575.

Example 22

1-(2-fluoroethyl)-8-(methylsulfanyl)-4,5-dihydro-1H-pyrazolo[4,3-h]quinazoline-3-carboxamide [(I), R1=Me-S—, R2=2-fluoroethyl, R3=NH₂, A=—(CH₂)₂—] (cpd 64)

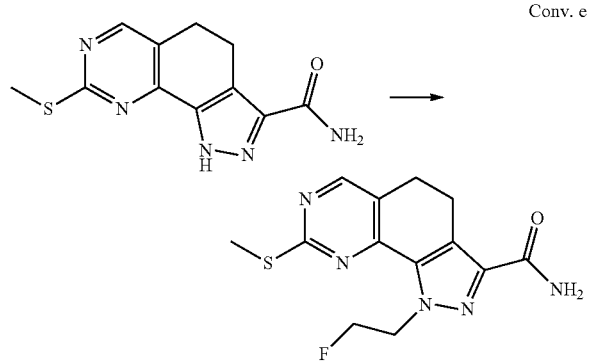

Conv. e

To a solution of 8-(methylsulfanyl)-4,5-dihydro-1H-pyrazolo[4,3-h]quinazoline-3-carboxamide (50 mg 0.191 mmol) in acetonitrile 2-fluoro 1-iodoethane (66.7 mg 0.38 mmol) and cesium carbonate (124 mg 0.38 mmol) were added. The resulting mixture was heated at 60° C. for 4 hours. After cooling to room temperature, the reaction mixture was portioned between ethyl acetate and water. The organic layers were washed with brine, dried over Na₂SO₄ and concentrated. The crude was purified by silica gel chromatography (DCM/EtOH 9/1) to give the title compound. LC/MS (254 nm) HPLC method 2 Rt 4.82 min. ¹H NMR (401 MHz, DMSO-d6) δ 8.52-8.58 (m, 1H), 7.50 (br. s., 1H), 7.33 (br. s., 1H), 5.07-5.15 (m, J=4.88 Hz, 1H), 5.03 (t, J=4.94 Hz, 1H), 4.93-4.99 (m, 1H), 4.85 (t, J=4.88 Hz, 1H), 3.00-3.06 (m, J=7.69 Hz, 2H), 2.85-2.93 (m, J=8.06 Hz, 2H), 2.53 (s, 3H). HRMS (ESI) calcd for C13H14FN5OS [M+H]⁺ 308.0976 found 308.0976.

Working according to the same method the following compounds were prepared:

1-(2-chloroethyl)-8-(methylsulfanyl)-4,5-dihydro-1H-pyrazolo[4,3-h]quinazoline-3-carboxamide [(I), R1=Me-S—, R2=2-chloroethyl, R3=NH₂, A=—(CH₂)₂—] (cpd 65) LC/MS (254 nm) HPLC method 2 Rt 5.25 min. ¹H NMR (401 MHz, DMSO-d6) δ 8.55 (s, 1H), 7.53 (br. s., 1H), 7.35 (br. s., 1H), 5.09 (t, J=6.23 Hz, 2H), 4.11 (t, J=6.29 Hz, 2H), 2.98-3.06 (m, 2H), 2.86-2.92 (m, 2H), 2.56 (s, 3H). HRMS (ESI) calcd for C13H14ClN5OS [M+H]⁺ 324.0681 found 324.0676;

1-(2-hydroxyethyl)-8-(methylsulfanyl)-4,5-dihydro-1H-pyrazolo[4,3-h]quinazoline-3-carboxamide [(I), R1=Me-S—, R2=2-hydroxyethyl, R3=NH₂, —(CH₂)₂—] (cpd 66) LC/MS (254 nm) HPLC method 2 Rt 4.1 min. ¹H NMR (401 MHz, DMSO-d6) δ 8.53 (s, 1H), 7.35-7.60 (m, 1H), 7.28 (br. s., 1H), 4.84-4.90 (m, 1H), 4.79 (t, J=6.16 Hz, 2H), 3.79-3.90 (m, 2H), 2.95-3.08 (m, 2H), 2.82-2.94 (m, 2H), 2.55 (s, 3H) HRMS (ESI) calcd for C13H15N5O2S [M+H]⁺ 306.1019 found 306.1023;

1-(2-methoxyethyl)-8-(methylsulfanyl)-4,5-dihydro-1H-pyrazolo[4,3-h]quinazoline-3-carboxamide [(I), R1=Me-S—, R2=2-methoxyethyl, R3=NH₂, A=—(CH₂)₂—] (cpd 67) LC/MS (254 nm) HPLC method 2 Rt 4.76 min. ¹H NMR (401 MHz, DMSO-d6) δ 8.54 (s, 1H), 7.47 (br. s., 1H), 7.30 (br. s., 1H), 4.90 (t, J=5.86 Hz, 2H), 3.76-3.89 (m, 2H), 3.23 (s, 3H), 2.98-3.06 (m, 2H), 2.84-2.91 (m, 2H), 2.54 (s, 3H) HRMS (ESI) calcd for C14H17N5O2S [M+H]⁺ 320.1176 found 320.1187;

1-[3-(dimethylamino)propyl]-8-(methylsulfanyl)-4,5-dihydro-1H-pyrazolo[4,3-h]quinazoline-3-carboxamide [(I), R1=Me-S—, R2=3-(dimethylamino)propyl, R3=NH₂, A=—(CH₂)₂—] (cpd 68) LC/MS (254 nm) HPLC method 2 Rt 3.69 min. ¹H NMR (401 MHz, DMSO-d6) δ 8.53 (s, 1H), 7.46 (br. s., 1H), 7.29 (br. s., 1H), 4.70-4.77 (m, 2H), 2.97-3.05 (m, 2H), 2.83-2.91 (m, 2H), 2.54-2.58 (m, 3H), 2.22-2.31 (m, 2H), 2.11 (s, 6H), 1.92-2.03 (m, 2H). HRMS (ESI) calcd for C16H22N6OS [M+H]⁺ 347.1649 found 347.1638; and 1-(1-amino-2-methyl-1-oxopropan-2-yl)-8-(methylsulfanyl)-4,5-dihydro-1H-pyrazolo[4,3-h]quinazoline-3-carboxamide [(I), R1=Me-S—, R2=1-amino-2-methyl-1-oxopropan-2-yl, R3=NH₂, A=—(CH₂)₂—] (cpd 69) LC/MS (254 nm) HPLC method 2 Rt 4.13 min. ¹H NMR (401 MHz, DMSO-d6) δ 8.49 (s, 1H), 7.42 (s, 1H), 7.29 (s, 1H), 6.96-7.14 (m, 1H), 2.94-3.05 (m, 2H), 2.75-2.85 (m, 2H), 2.55 (s, 3H), 1.90 (s, 6H). HRMS (ESI) calcd for C15H18N6O2S [M+H]⁺ 347.1285 found 347.1282.

Example 23

8-(methylsulfanyl)-1-(piperidin-4-ylmethyl)-4,5-dihydro-1H-pyrazolo[4,3-h]quinazoline-3-carboxamide hydrochloride [(I), R1=Me-S—, R2=piperidin-4-ylmethyl, R3=NH₂, A=—(CH₂)₂—] (cpd 70)

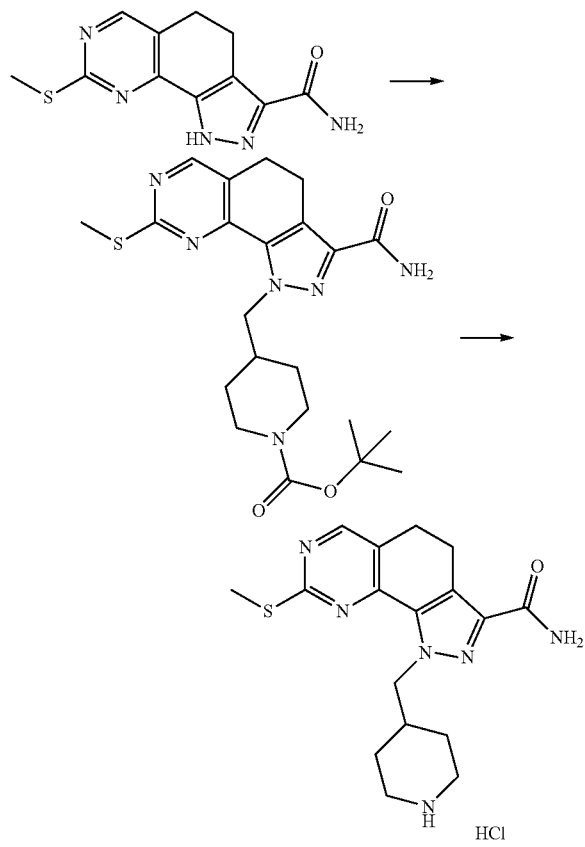

To a solution of 8-(methylsulfanyl)-4,5-dihydro-1H-pyrazolo[4,3-h]quinazoline-3-carboxamide (50 mg 0.191 mmol) in acetonitrile, tert-butyl-piperidin-4-ylmethylbromuro carbamate (105.71 mg 0.38 mmol) and cesium carbonate (124 mg 0.38 mmol) were added. The resulting mixture was heated at 60° C. for 4 hours. After cooling to room temperature, the reaction mixture was portioned between ethyl acetate and water. The organic layers were washed with brine, dried over Na₂SO₄ and concentrated. The crude was purified by silica gel chromatography (DCM/EtOH 9/1) to give tert-butyl 4-{[3-carbamoyl-8-(methylsulfanyl)-4,5-dihydro-1H-pyrazolo[4,3-h]quinazolin-1-yl]methyl}piperidine-1-carboxylate (30 mg 0.65 mmol). The compound was then treated with 2 ml of HCl 4M in 1,4-dioxane. The resulting mixture was stirred at room temperature for 1 hour. The volatiles were removed in vacuo, the obtained residue was triturated with diethyl ether, filtered, washed with Et₂O and dried in vacuo, to provide the title compound 32 mg (97%) as a white solid. LC/MS (254 nm) HPLC method 2 Rt 3.83 min. ¹H NMR (401 MHz, DMSO-d6) δ 8.62 (d, J=10.01 Hz, 1H), 8.55 (s, 1H), 8.27-8.49 (m, J=8.42 Hz, 1H), 7.44 (s, 1H), 7.35 (s, 1H), 4.63-4.78 (m, 2H), 3.18-3.28 (m, J=6.10 Hz, 2H), 2.99-3.07 (m, 2H), 2.85-2.92 (m, J=7.93 Hz, 2H), 2.74-2.85 (m, J=10.38 Hz, 2H), 2.57 (s, 3H), 2.18-2.31 (m, 1H), 1.56-1.70 (m, 2H), 1.37-1.51 (m, J=3.72, 13.98 Hz, 2H). HRMS (ESI) calcd for C17H22N6OS [M+H]⁺ 359.1649 found 359.1634.

Working according to the same method the following compounds were prepared:

1-(3-aminopropyl)-8-(methylsulfanyl)-4,5-dihydro-1H-pyrazolo[4,3-h]quinazoline-3-carboxamide hydrochloride [(I), R1=Me-S—, R2=3-aminopropyl, R3=NH₂, A=—(CH₂)₂—] (cpd 71) LC/MS (254 nm) HPLC method 2 Rt 3.58 min. ¹H NMR (401 MHz, DMSO-d6) δ 8.56 (s, 1H), 7.79 (br. s., 3H), 7.47-7.50 (m, 1H), 7.38 (br. s., 1H), 4.77 (t, J=6.53 Hz, 2H), 2.99-3.06 (m, 2H), 2.86-2.93 (m, 2H), 2.76-2.83 (m, 2H), 2.54-2.59 (m, 3H), 2.17 (br. s., 2H). HRMS (ESI) calcd for C14H18N6OS [M+H]⁺ 319.1336 found 319.1344;

8-(methylsulfanyl)-1-(piperidin-4-yl)-4,5-dihydro-1H-pyrazolo[4,3-h]quinazoline-3-carboxamide trifluoroacetate [(I), R1=Me-S—, R2=piperidin-4-yl, R3=NH₂, A=—(CH₂)₂—] (cpd 72) LC/MS (254 nm) HPLC method 2 Rt 3.65 min. ¹H NMR (401 MHz, DMSO-d6) δ 8.58-8.65 (m, 1H), 8.56 (s, 1H), 8.46 (br. s., 1H), 7.41 (br. s., 1H), 7.38 (br. s., 1H), 5.52-5.73 (m, J=6.84, 6.84 Hz, 1H), 3.46-3.62 (m, 2H), 3.04-3.13 (m, J=6.84 Hz, 2H), 2.97-3.04 (m, 2H), 2.82-2.91 (m, J=8.18 Hz, 2H), 2.58 (s, 3H), 2.19-2.32 (m, J=7.32 Hz, 4H) HRMS (ESI) calcd for C16H20N6OS [M+H]⁺ 345.1492 found 345; and 1-(2-amino ethyl)-8-(methylsulfanyl)-4,5-dihydro-1H-pyrazolo[4,3-h]quinazoline-3-carboxamide trifluoroacetate [(I), R1=Me-S—, R2=2-aminoethyl, R3=NH₂, A=—(CH₂)₂—] (cpd 73) LC/MS (254 nm) HPLC method 2 Rt 3.46 min. ¹H NMR (401 MHz, DMSO-d6) δ 8.58 (s, 1H), 7.92 (br. s., 3H), 7.74 (s, 1H), 7.43 (s, 1H), 4.85-5.09 (m, 2H), 3.42-3.57 (m, J=5.98 Hz, 2H), 2.96-3.09 (m, 2H), 2.80-2.94 (m, 2H), 2.56 (s, 3H) HRMS (ESI) calcd for C13H16N6OS [M+H]⁺ 305.1179 found 305.1191.

Example 24

1-[2-(4-methylpiperazin-1-yl)ethyl]-8-(methylsulfanyl)-4,5-dihydro-1H-pyrazolo[4,3-h]quinazoline-3-carboxamide [(I), R1=Me-S—, R2=2-(4-methylpiperazin-1-yl)ethyl, R3=NH₂, A=—(CH₂)₂—] (cpd 74)

and 1-ethenyl-8-(methylsulfanyl)-4,5-dihydro-1H-pyrazolo[4,3-h]quinazoline-3-carboxamide [(I), R1=Me-S—, R2=ethenyl, R3=NH₂, A=—(CH₂)₂—] (cpd 75)

Conv. f and g

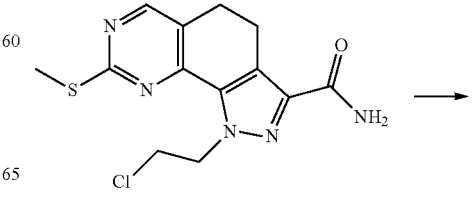

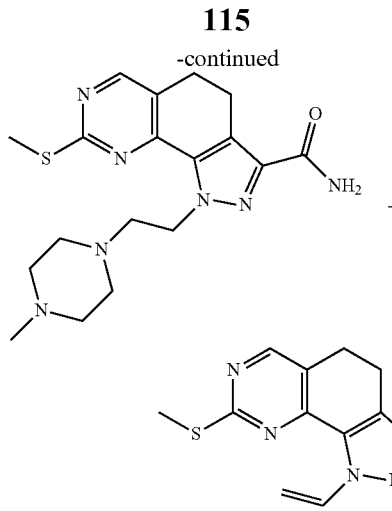

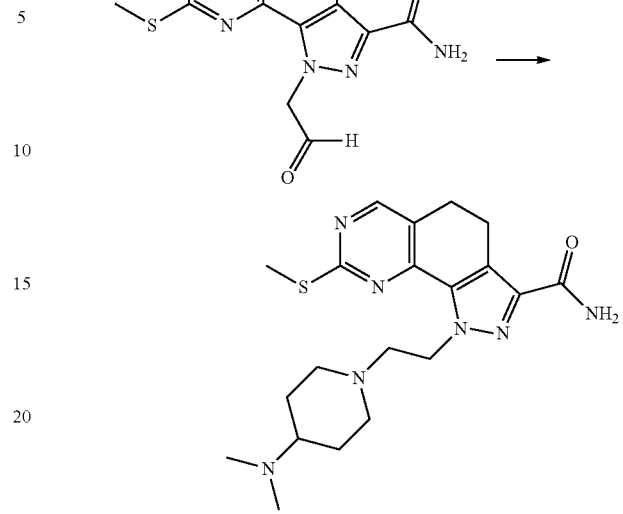

To a solution of 1-(2-chloroethyl)-8-(methylsulfanyl)-4,5-dihydro-1H-pyrazolo[4,3-h]quinazoline-3-carboxamide (50 mg 0.15 mmol) in methanol (3 ml), N-methylpiperazine (62 μl, 0.61 mmol) and cesium carbonate (97 mg, 0.3 mmol), were added. The resulting mixture was heated at 60° C. for 48 hours. The volatiles were removed under vacuum, the crude solid was dissolved with ethyl acetate and water, the organic layer was washed with brine, dried over Na$_2$SO$_4$ and concentrated. The crude was purified by silica gel chromatography (DCM/EtOAc 8/2) to give the compound 1-ethenyl-8-(methylsulfanyl)-4,5-dihydro-1H-pyrazolo[4,3-h]quinazoline-3-carboxamide as a yellow solid (15 mg 35% yield). LC/MS (254 nm) HPLC method 2 Rt 5.34 min. $^1$H NMR (401 MHz, DMSO-d6) δ 8.58 (s, 1H), 8.35 (dd, J=8.73, 15.44 Hz, 1H), 7.71 (s, 1H), 7.46 (br. s., 1H), 5.96 (d, J=15.38 Hz, 1H), 5.15 (d, J=8.67 Hz, 1H), 3.00-3.09 (m, 2H), 2.86-2.94 (m, 2H), 2.56 (s, 3H). HRMS (ESI) calcd for C13H13N5OS [M+H]$^+$ 288.0914 found 288.0913.

Changing the eluent such as DCM/MeOH/NH$_4$OH 9/1/0.1, the polar compound 1-(2-[N-methylpiperazine]ethyl)-8-(methylsulfanyl)-4,5-dihydro-1H-pyrazolo[4,3-h]quinazoline-3-carboxamide was collected as yellow solid (17 mg 30% yield). LC/MS (254 nm) HPLC method 2 Rt 3.79 min. $^1$H NMR (401 MHz, DMSO-d6) δ 8.35 (s, 1H), 7.46 (s, 1H), 7.28 (s, 1H), 4.82 (t, J=6.84 Hz, 2H), 2.98-3.04 (m, 2H), 2.88 (d, J=7.93 Hz, 2H), 2.55 (s, 3H) HRMS (ESI) calcd for C18H25N7OS [M+H]$^+$ 388.1914 found 388.1909

Example 25

1-{2-[4-(dimethylamino)piperidin-1-yl]ethyl}-8-(methylsulfanyl)-4,5-dihydro-1H-pyrazolo[4,3-h]quinazoline-3-carboxamide [(I), R1=Me-S—, R2=2-[4-(dimethylamino)piperidin-1-yl]ethyl, R3=NH$_2$, A=—(CH$_2$)$_2$—] (cpd 76)

To a solution of 1-(2-hydroxyethyl)-8-(methylsulfanyl)-4,5-dihydro-1H-pyrazolo[4,3-h]quinazoline-3-carboxamide (20 mg 0.077 mmol) in ethyl acetate (2 ml), IBX (64 mg, 0.23 mmol) was added. The resulting mixture was heated at 80° C. for 4 hours. After cooling to room temperature, the reaction mixture was filtered and the volatiles removed in vacuo, the aldehyde as crude was used for the next reaction. The aldehyde was dissolved with THF/DMF (3/1 ml), sodium triacetoxyborohydride (49 mg, 0.233 mmol), and 4-dimethylaminopiperidine (20 ul, 0.156 mmol) were added. The reaction mixture was stirred at room temperature for 72 hours. The solvent was evaporated and the obtained crude was purified by chromatography (DCM/MeOH/NH$_4$OH 8/2/0.2) to provide the title compound 15 mg (48%). LC/MS (254 nm) HPLC method 2 Rt 3.93 min. $^1$H NMR (401 MHz, DMSO-d6) δ 8.55 (s, 1H), 7.46 (s, 1H), 7.29 (s, 1H), 4.81 (t, J=6.90 Hz, 2H), 2.96-3.04 (m, 2H), 2.79-2.93 (m, J=8.18 Hz, 5H), 2.71 (t, J=6.59 Hz, 2H), 2.56 (s, 3H), 2.14 (s, 6H), 1.93-2.06 (m, J=16.11 Hz, 3H), 1.53-1.68 (m, J=14.16 Hz, 2H), 1.04-1.20 (m, J=3.17 Hz, 2H) HRMS (ESI) calcd for C20H29N7OS [M+H]$^+$ 416.2227 found 416.2234.

Example 26

8-ethoxy-1-(piperidin-4-ylmethyl)-4,5-dihydro-1H-pyrazolo[4,3-h]quinazoline-3-carboxamide hydrochloride [(I), R4=Et, X=O, R2=2-[4-(dimethylamino)piperidin-1-yl]ethyl, R3=NH$_2$, A=—(CH$_2$)$_2$—] (cpd 77)

Conv. h

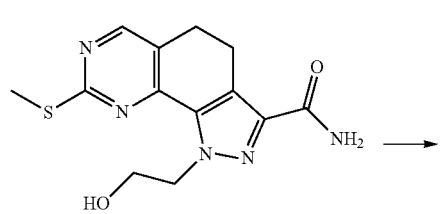

Conv. e

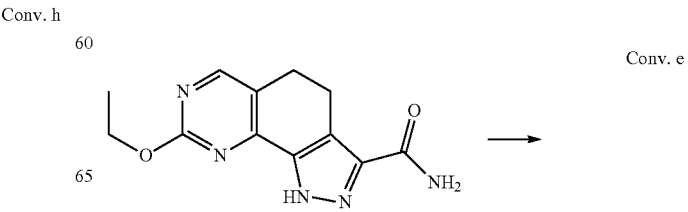

-continued

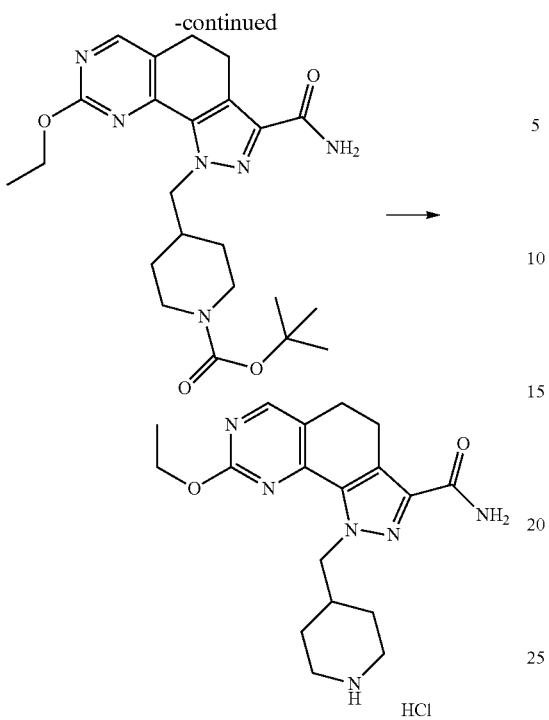

To a solution of 8-ethoxy-4,5-dihydro-1H-pyrazolo[4,3-h]quinazoline-3-carboxamide (40 mg, 0.154 mmol) in DMF (3 ml), tert-butyl-piperidin-4-ylmethylbromuro carbamate (85 mg, 0.308 mmol) and Cs$_2$CO$_3$ (121 mg, 0.370 mmol), were added. The mixture was heated at 70° C. and stirred for 4 hours. The cooled mixture was treated with water (10 ml) and extracted with ethyl acetate. The combined organic phases were washed with water and brine, dried over Na$_2$SO$_4$, and concentrated. The crude material was purified by flash chromatography eluting with DCM/EtOAc/EtOH 7/2/1 to afford the desired product tert-butyl 4-{[3-carbamoyl-8-(methylsulfanyl)-4,5-dihydro-1H-pyrazolo[4,3-h]quinazolin-1-yl]methyl}-piperidine-1-carboxylate 50 mg (70%) as a white solid. The latter product was dissolved in DCM (2 ml), and 4M HCl in 1,4-dioxane (2 ml) was added. The solution was stirred at r.t. for 1 hour, and evaporated to dryness. The solid was triturated with diethyl ether, filtered and dried in vacuo to give the desired product 40 mg (95%). LC/MS (254 nm) HPLC method 2 Rt 3.65 min. $^1$H NMR (401 MHz, DMSO-d6) δ 8.65 (d, J=11.60 Hz, 1H), 8.51 (s, 1H), 8.31-8.46 (m, J=15.38 Hz, 1H), 7.42 (br. s., 1H), 7.34 (s, 1H), 4.69 (d, J=7.20 Hz, 1H), 4.39 (q, J=6.96 Hz, 1H), 3.18-3.27 (m, 2H), 2.97-3.04 (m, 2H), 2.74-2.90 (m, J=7.93 Hz, 4H), 2.18-2.32 (m, J=5.98 Hz, 1H), 1.59-1.70 (m, J=11.84 Hz, 2H), 1.40-1.53 (m, J=4.03 Hz, 2H), 1.38 (t, J=7.02 Hz, 3H) HRMS (ESI) calcd for C18H24N6O2 [M+H]$^+$ 357.2033 found 357.2041

Working according to the same method the following compounds were prepared:

1-[3-(dimethylamino)propyl]-8-ethoxy-4,5-dihydro-1H-pyrazolo[4,3-h]quinazoline-3-carboxamide [(I), R4=Et, X=O, R2=3-(dimethylamino)propyl, R3=NH$_2$, A=—(CH$_2$)$_2$—] (cpd 78) LC/MS (254 nm) HPLC method 2 Rt 3.63 min. $^1$H NMR (401 MHz, DMSO-d6) δ 8.49 (s, 1H), 7.44 (s, 1H), 7.29 (br. s., 1H), 4.67-4.78 (m, 2H), 4.39 (q, J=7.08 Hz, 2H), 2.93-3.05 (m, 2H), 2.81-2.93 (m, 2H), 2.32-2.42 (m, J=1.92, 1.92, 3.72 Hz, 2H), 2.19 (br. s., 6H), 1.90-2.07 (m, 2H), 1.36 (t, J=7.02 Hz, 3H). HRMS (ESI) calcd for C17H24N6O2 [M+H]$^+$ 345.2033 found 345.203; and 8-ethoxy-1-(piperidin-4-yl)-4,5-dihydro-1H-pyrazolo[4,3-h]quinazoline-3-carboxamide hydrochloride [(I), R4=Et, X=O, R2=piperidin-4-yl, R3=NH$_2$, A=—(CH$_2$)$_2$—] (cpd 79) LC/MS (254 nm) HPLC method 2 Rt 3.59 min. $^1$H NMR (401 MHz, DMSO-d6) δ 8.57-8.95 (m, 2H), 8.52 (s, 1H), 7.39 (br. s., 2H), 5.58 (quin, J=7.23 Hz, 1H), 4.36-4.45 (m, 2H), 2.96-3.02 (m, 3H), 2.82-2.89 (m, J=8.18 Hz, 2H), 1.37 (t, J=7.02 Hz, 3H) HRMS (ESI) calcd for C17H22N6O2 [M+H]$^+$ 343.1877 found 343.1876

Example 27

8-ethoxy-1-[(1-methylpiperidin-4-yl)methyl]-4,5-dihydro-1H-pyrazolo[4,3-h]quinazoline-3-carboxamide [(I), R4=Et, X=O, R2=(1-methylpiperidin-4-yl)methyl, R3=NH$_2$, A=—(CH$_2$)$_2$—] (cpd 80)

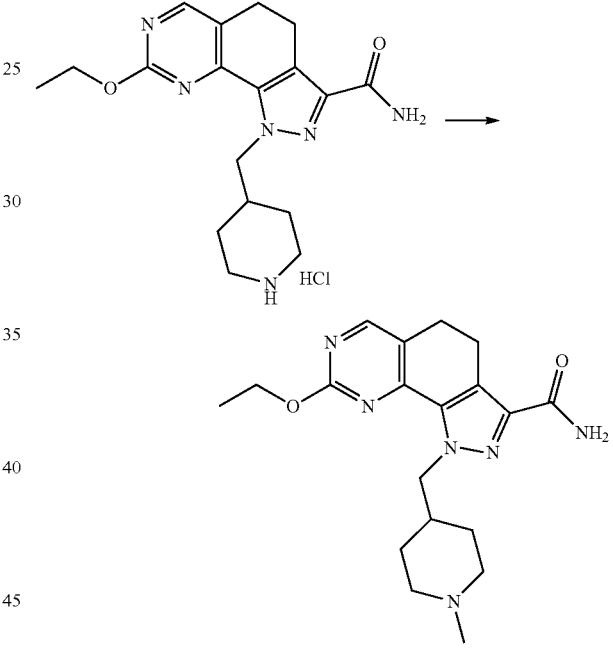

To a solution of 8-ethoxy-1-(piperidin-4-ylmethyl)-4,5-dihydro-1H-pyrazolo[4,3-h]quinazoline-3-carboxamide hydrochloride (30 mg, 0.084 mmol) in DMF (3 ml), formaldehyde 1 ml (37% in water, 12.3 mmol) and sodium triacetoxyborohydride (71 mg, 0.33 mmol) were added. The reaction mixture was stirred at room temperature for 4 hours. The mixture was diluted with water and extracted with ethyl acetate, the organic layer was washed with water and brine, dried over Na$_2$SO$_4$ filtered and concentrated to dryness. The crude mixture was chromatographed on silica eluting with DCM/EtOAc/EtOH 7/2/1 to provide the desired product 20 mg (64%). LC/MS (254 nm) HPLC method 2 Rt 3.7 min. $^1$H NMR (401 MHz, DMSO-d6) δ 8.49 (s, 1H), 7.43 (s, 1H), 7.30 (br. s., 1H), 4.65 (d, J=7.45 Hz, 1H), 4.38 (q, J=7.08 Hz, 2H), 2.97-3.04 (m, 2H), 2.83-2.90 (m, 2H), 2.79 (br. s., 1H), 2.18 (br. s., 2H), 1.86-2.03 (m, 2H), 1.44-1.53 (m, 2H), 1.34-1.39 (m, 3H), 1.29 (d, J=4.03 Hz, 2H). HRMS (ESI) calcd for C19H26N6O2 [M+H]$^+$ 371.219 found 371.2191.

Preparation K

Tert-butyl 4-[(3-carbamoyl-8-iodo-4,5-dihydro-1H-pyrazolo[4,3-h]quinazolin-1-yl)methyl]piperidine-1-carboxylate [(XIV)]

Example 28

8-(2,6-difluorophenyl)-1-(piperidin-4-ylmethyl)-4,5-dihydro-1H-pyrazolo[4,3-h]quinazoline-3-carboxamide hydrochloride [(I), R1=2,6-difluorophenyl, R2=piperidin-4-ylmethyl, R3=NH$_2$, A=—(CH$_2$)$_2$—] (cpd 81)

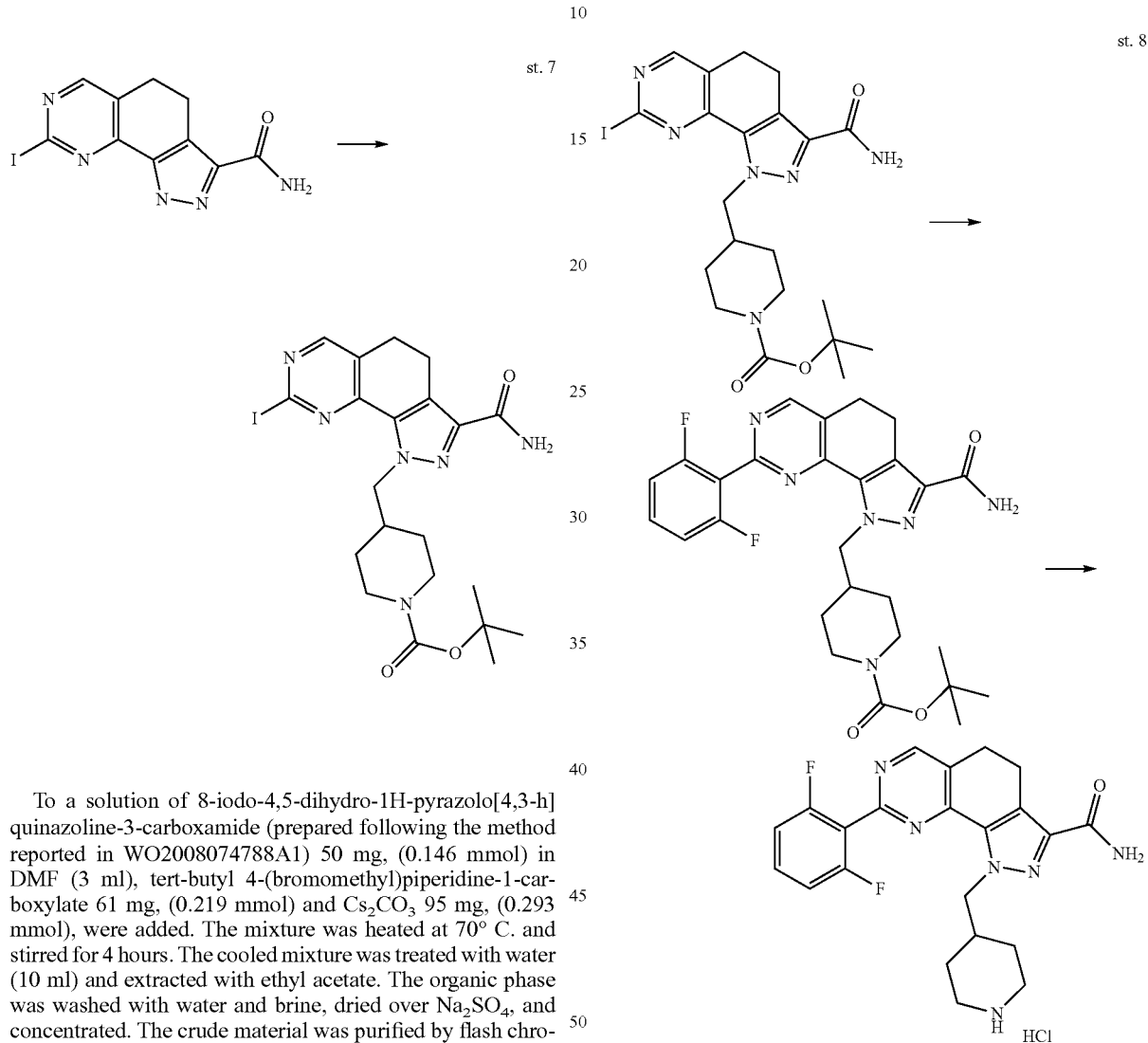

To a solution of 8-iodo-4,5-dihydro-1H-pyrazolo[4,3-h]quinazoline-3-carboxamide (prepared following the method reported in WO2008074788A1) 50 mg, (0.146 mmol) in DMF (3 ml), tert-butyl 4-(bromomethyl)piperidine-1-carboxylate 61 mg, (0.219 mmol) and Cs$_2$CO$_3$ 95 mg, (0.293 mmol), were added. The mixture was heated at 70° C. and stirred for 4 hours. The cooled mixture was treated with water (10 ml) and extracted with ethyl acetate. The organic phase was washed with water and brine, dried over Na$_2$SO$_4$, and concentrated. The crude material was purified by flash chromatography eluting with DCM/EtOH 9/1 to afford the desired title product 63 mg (80%) as a white solid. LC/MS (254 nm) HPLC method 2 Rt 6.51 min. 1H NMR (401 MHz, DMSO-d6) δ 8.46 (s, 1H), 7.47 (s, 1H), 7.32 (s, 1H), 4.50-4.55 (m, 2H), 3.84-3.96 (m, 2H), 2.99-3.07 (m, 2H), 2.84-2.95 (m, 2H), 2.59-2.75 (m, 2H), 2.07 (s, 1H), 1.56 (br. s., 2H), 1.39 (s, 9H), 1.08-1.22 (m, 2H). HRMS (ESI) calcd for C21H27IN6O3 [M+H]$^+$ 539.1262 found 539.1274.

Operating in a way analogous to that described above, the following compounds were prepared:

Ethyl 1-{3-[(tert-butoxycarbonyl)amino]propyl}-8-iodo-4,5-dihydro-1H-pyrazolo[4,3-h]quinazoline-3-carboxylate and Ethyl 2-{3-[(tert-butoxycarbonyl)amino]propyl}-8-iodo-4,5-dihydro-1H-pyrazolo[4,3-h]quinazoline-3-carboxylate. LC/MS (m/z): 528.0 [M+H]+, HPLC (254 nm) method 3 Rt 6.43 min.

To a solution of tert-butyl 4-[(3-carbamoyl-8-iodo-4,5-dihydro-1H-pyrazolo[4,3-h]quinazolin-1-yl)methyl]piperidine-1-carboxylate (30 mg, 0.036 mmol) in 3 ml of 1,4-dioxane and 1 ml of water, under argon atmosphere, 17.6 mg (0.11 mmol) of 2,6-difluorophenylboronic acid 13.7 mg (0.017 mmol) of 1,1'-bis(diphenylphosphino)ferrocenepalladium complex with dichloromethane and 54 mg (0.167 mmol) of cesium carbonate, were successively added. The mixture was submitted to microwave irradiation at 80° for 1 hour in a sealed vial. The reaction was filtered through a celite pad and the solvent evaporated to dryness. The crude was then portioned between ethyl acetate and water, the organic layer dried over sodium sulphate and the solvent removed in vacuo. After purification by flash chromatography on silica gel column (DCM/EtOAc 7/3), 20 mg (70%) of tert-butyl 4-{[3- carbamoyl-8-(2,6-difluorophenyl)-4,5-dihydro-1H-pyrazolo[4,3-h]quinazolin-1-yl]methyl}piperidine-1-carboxylate were obtained. The product was dissolved in DCM (2 ml) and 4M HCl in 1,4-dioxane (2 ml) was added. The reaction was stirred at room temperature for 1 hour, the solvent was evaporated to dryness. The solid was treated with ethyl ether and the precipitate collected by filtration to give the title compound as a pale yellow solid 17 mg (85%). LC/MS (254 nm) HPLC method 2 Rt 4.14 min. $^1$H NMR (401 MHz, DMSO-d6) δ 8.89 (s, 1H), 8.57 (d, J=9.76 Hz, 1H), 8.30 (d, J=10.01 Hz, 1H), 7.55-7.69 (m, 1H), 7.45 (s, 1H), 7.37 (s, 1H), 7.23-7.33 (m, 2H), 4.57-4.66 (m, 2H), 3.16-3.26 (m, 2H), 3.01-3.14 (m, 4H), 2.69-2.85 (m, J=10.74 Hz, 2H), 2.09-2.29 (m, J=7.20 Hz, 1H), 1.56-1.70 (m, J=12.94 Hz, 2H), 1.32-1.48 (m, 2H) HRMS (ESI) calcd for C21H27IN6O3 [M+H]$^+$ 425.1896 found 425.1896

Operating in a way analogous to that described above, the following compound was prepared:

8-(2,6-difluorophenyl)-1-(2-fluoroethyl)-4,5-dihydro-1H-pyrazolo[4,3-h]quinazoline-3-carboxamide [(I), R1=2,6-difluorophenyl, R2=2-fluoroethyl, R3=NH$_2$, A=—(CH$_2$)$_2$—] LC/MS (254 nm) HPLC method 2 Rt 5.31 min. $^1$H NMR (401 MHz, DMSO-d6) δ 8.89 (s, 1H), 7.61 (tt, J=6.44, 8.45 Hz, 1H), 7.53 (br. S., 1H), 7.35 (s, 1H), 7.19-7.32 (m, 2H), 4.96-5.11 (m, 2H), 4.74-4.96 (m, 2H), 2.98-3.18 (m, 4H). HRMS (ESI) calcd for C18H14F3N5O [M+H]$^+$ 374.1223 found 374.1225.

Preparation L

Ethyl 8-(4-fluorophenyl)-1-trityl-4,5-dihydro-1H-pyrazolo[4,3-h]quinazoline-3-carboxylate [(VIII), R1=4-fluorophenyl, R2=trityl, A=—(CH$_2$)$_2$—]

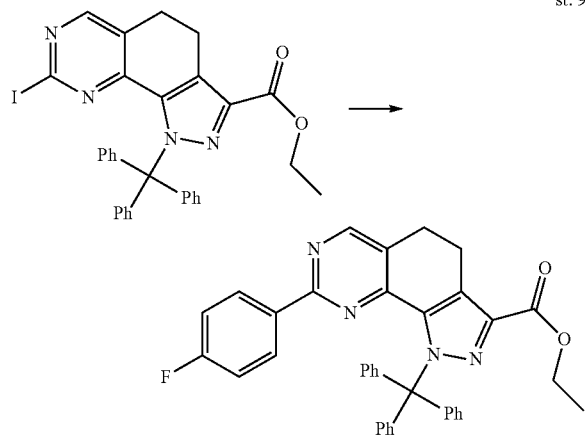

st. 9

To a solution of ethyl 8-iodo-1-trityl-4,5-dihydro-1H-pyrazolo[4,3-h]quinazoline-3-carboxylate 500 mg (0.82 mmol) (prepared according to the method reported in WO2008074788A1) in toluene (10 ml) and 4-fluorobenzeneboronic acid 228 mg (1.63 mmol), lithium chloride 103 mg (2.46 mmol) potassium carbonate 339.8 mg (2.46 mmol) dissolved in water (0.5 ml), were added. The reaction was degassed with argon, then bis (triphenylphosphine)palladium (II) dichloride 22 mg (0.041 mmol 5% mol) were added and the reaction was heated at 100° C. for 60 min. LC/MS analysis indicated complete conversion of the starting material to product. The reaction was cooled to room temperature, then concentrated in vacuo and fused to silica gel. The crude product was purified by flash chromatography eluting with DCM/EtOH 10/0.5 to provide the desired product 380 mg (80%). LC/MS (m/z): 581.2 [M+H]$^+$, HPLC (254 nm) method 3 Rt 9.02.

Operating in a way analogous to that described above, the following compounds were prepared:

Ethyl 8-(4-methoxyphenyl)-1-trityl-4,5-dihydro-1H-pyrazolo[4,3-h]quinazoline-3-carboxylate [(VIII), R1=4-methoxyphenyl, R2=trityl, A=—(CH$_2$)$_2$—] LC/MS (m/z): 593.2 [M+H]$^+$, HPLC (254 nm) method 3 Rt 8.91 min.

Ethyl 1-{3-[(tert-butoxycarbonyl)amino]propyl}-8-(4-fluorophenyl)-4,5-dihydro-1H-pyrazolo[4,3-h]quinazoline-3-carboxylate [(VIII), R1=4-fluorophenyl, R2=3-(tert-butoxycarbonyl)aminopropyl, A=—(CH$_2$)$_2$—] and ethyl 2-{3-[(tert-butoxycarbonyl)amino]propyl}-8-(4-fluorophenyl)-4,5-dihydro-1H-pyrazolo[4,3-h]quinazoline-3-carboxylate [(VIII), R1=4-fluorophenyl, R2=3-(tert-butoxycarbonyl)aminopropyl, A=—(CH$_2$)$_2$—] LC/MS (m/z): 496.1 [M+H]$^+$, HPLC (254 nm) method 3 Rt 7.87 min.

Preparation M 8-(4-fluorophenyl)-1-trityl-4,5-dihydro-1H-pyrazolo[4,3-h]quinazoline-3-carboxylic acid [(XI), R1=4-fluorophenyl, R2=trityl, A=—(CH$_2$)$_2$—]

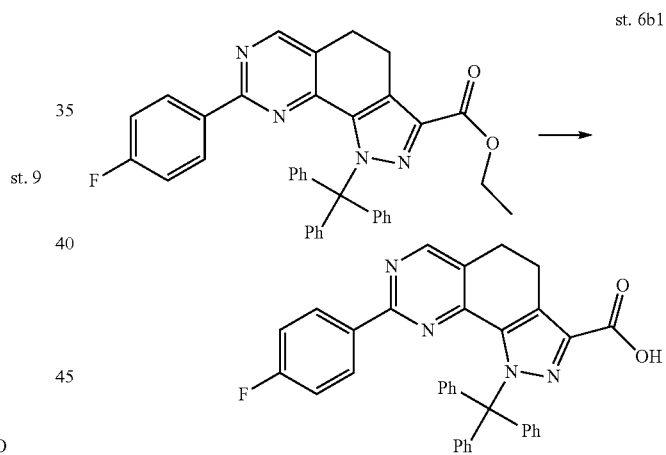

st. 6b1

To a solution of Ethyl 8-(4-fluorophenyl)-1-trityl-4,5-dihydro-1H-pyrazolo[4,3-h]quinazoline-3-carboxylate 380 mg (0.65 mmol) in ethanol (20 ml) was added 2N aqueous NaOH 3 ml (6 mmol). The mixture was heated to 80° C. for 30 min. Upon cooling to room temperature the volatiles were removed in vacuo. The residue was diluted with water and acetic acid pH=4, and the precipitate formed was filtered and washed with ethanol. The solid was dried in oven (40° C. in vacuum) for 2 hours. 360 mg (99%). LC/MS (m/z): 553.1 [M+H]$^+$, HPLC (254 nm) method 3 Rt 5.84.

Operating in a way analogous to that described above, the following compounds were prepared:

8-(4-methoxyphenyl)-1-trityl-4,5-dihydro-1H-pyrazolo[4,3-h]quinazoline-3-carboxylic acid [(XI), R1=4-methoxyphenyl, R2=trityl, A=—(CH$_2$)$_2$—] LC/MS (m/z): 565.2 [M+H]$^+$, HPLC (254 nm) method 3 Rt 6.03;

1-{3-[(tert-butoxycarbonyl)amino]propyl}-8-(4-fluorophenyl)-4,5-dihydro-1H-pyrazolo[4,3-h]quinazoline-3- carboxylic acid [(XI), R1=4-fluorophenyl, R2=3-(tert-butoxycarbonyl)aminopropyl, A=—(CH$_2$)$_2$—]; and 2-{3-[(tert-butoxycarbonyl)amino]propyl}-8-(4-fluorophenyl)-4,5-dihydro-2H-pyrazolo[4,3-h]quinazoline-3-carboxylic acid [(XI), XI R1=4-fluorophenyl, R2=3-(tert-butoxycarbonyl)aminopropyl, A=—(CH$_2$)$_2$—] LC/MS (m/z): 468.1 [M+H]$^+$, HPLC (254 nm) method 3 Rt 4.27 min. (major) and 4.55 min (minor).

Example 29

8-(4-fluorophenyl)-N-(3-hydroxypropyl)-1-trityl-4,5-dihydro-1H-pyrazolo[4,3-h]quinazoline-3-carboxamide [(I), R1=4-fluorophenyl, R2=trityl, R'=3-hydroxypropyl, A=—(CH$_2$)$_2$—]

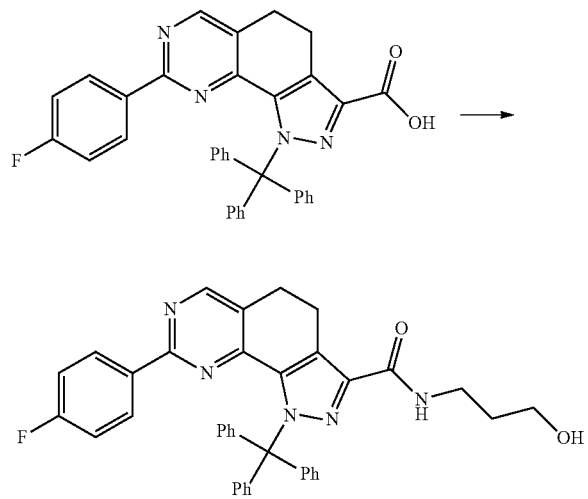 [SMILES: O=C(O)c1nn(C(c2ccccc2)(c2ccccc2)c2ccccc2)c2c1CCc1cnc(-c3ccc(F)cc3)nc1-2 ; O=C(NCCCO)c1nn(C(c2ccccc2)(c2ccccc2)c2ccccc2)c2c1CCc1cnc(-c3ccc(F)cc3)nc1-2]

Example 30

8-(4-fluorophenyl)-N-(3-hydroxypropyl)-4,5-dihydro-1H-pyrazolo[4,3-h]quinazoline-3-carboxamide [(I), R1=4-fluorophenyl, R2=H, R'=hydroxypropyl, A=—(CH$_2$)$_2$—]

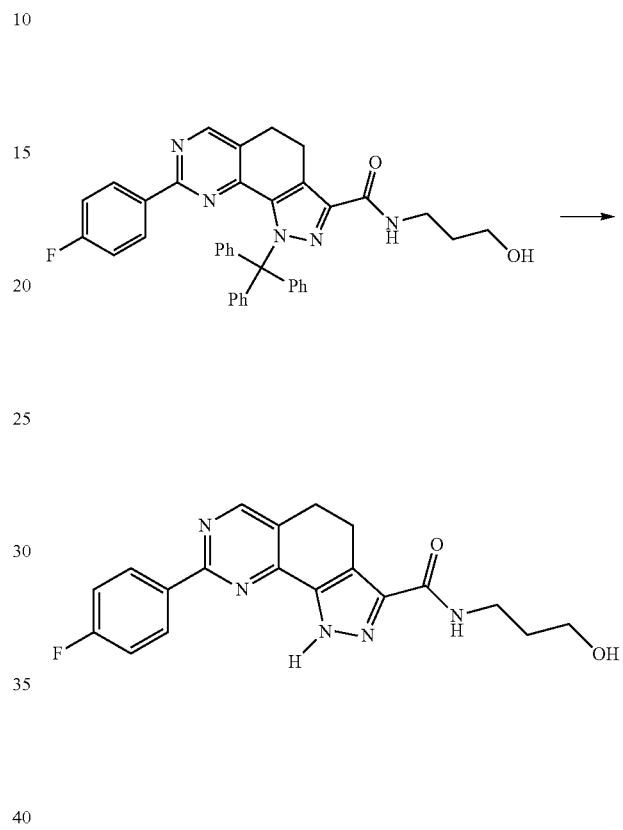

8-(4-fluorophenyl)-1-trityl-4,5-dihydro-1H-pyrazolo[4,3-h]quinazoline-3-carboxylic acid 358 mg (0.65 mmol) were reacted in dry DMF with propanolamine 0.060 ml (0.78 mmol), TBTU 250 mg (0.78 mmol) and DIPEA 0.268 ml (1.5 mmol) at room temperature for 3 hours. The reaction was worked up with water, saturated NaHCO$_3$ and extracted with ethyl acetate. The organic phase, dried on Na$_2$SO$_4$, filtered and evaporated was purified on silica with ethyl acetate/hexane 7/3 to give 300 mg (75%) of clean product. LC/MS (254 nm) HPLC method 2 Rt 8.08 min. $^1$H NMR (401 MHz, DMSO-d$_6$) δ 8.52 (s, 1H), 7.34 (t, J=5.73 Hz, 1H), 6.93-6.99 (m, 2H), 4.52 (t, J=5.00 Hz, 1H), 3.43-3.50 (m, 2H), 3.25-3.32 (m, 2H), 3.10 (d, J=8.05 Hz, 2H), 2.78 (t, J=7.44 Hz, 2H), 1.61 (quin, J=6.40 Hz, 2H) HRMS (ESI) calcd for C38H32FN5O2 [M+H]$^+$ 610.2613 found 610.262.

Operating in a way analogous to that described above, the following compound was prepared:

N-(3-hydroxypropyl)-8-(4-methoxyphenyl)-1-trityl-4,5-dihydro-1H-pyrazolo[4,3-h]quinazoline-3-carboxamide [(I), R1=4-methoxyphenyl, R2=trityl, R'=3-hydroxypropyl, A=—(CH$_2$)$_2$—] LC/MS (m/z): 622.2 [M+H]$^+$ HPLC (254 nm) method 3 Rt 7.07 min.

8-(4-fluorophenyl)-N-(3-hydroxypropyl)-1-trityl-4,5-dihydro-1H-pyrazolo[4,3-h]quinazoline-3-carboxamide 300 mg (0.5 mmol) were dissolved in DCM and reacted with 2 ml of trifluoroacetic acid at room temperature. The reaction was evaporated to dryness and treated with MeOH and saturated NaHCO$_3$ for 30 min. Afterwards, MeOH was evaporated, water phase was acidified with NaH$_2$PO$_3$ to pH=5.0 and extracted with DCM. The dried crude was purified on silica gel with ethyl acetate. LC/MS (254 nm) HPLC method 2 Rt 5.29 min. $^1$H NMR (401 MHz, DMSO-d$_6$) δ 14.20 (s, 1H), 8.77 (s, 1H), 8.52-8.59 (m, 2H), 8.23 (t, J=5.74 Hz, 1H), 7.35-7.43 (m, 2H), 4.51 (t, J=5.25 Hz, 2H), 3.48 (q, J=6.18 Hz, 2H), 3.06-3.11 (m, 2H), 3.00-3.06 (m, 2H), 1.60-1.76 (m, 2H) HRMS (ESI) calcd for C19H18FN5O2 [M+H]$^+$ 368.1518 found 368.153.

Operating in a way analogous to that described above, the following compound was prepared:

N-(3-hydroxypropyl)-8-(4-methoxyphenyl)-4,5-dihydro-1H-pyrazolo[4,3-h]quinazoline-3-carboxamide [(I), R1=4-methoxyphenyl, R2=trityl, R'=3-hydroxypropyl, A=—(CH$_2$)$_2$—] LC/MS (m/z): 380.1 [M+H]+, HPLC (254 nm) method 3 Rt 4.41 min.

Example 31

Tert-butyl {3-[3-carbamoyl-8-(4-fluorophenyl)-4,5-dihydro-1H-pyrazolo[4,3-h]quinazolin-1-yl]propyl}carbamate [(I), R1=4-fluorophenyl, $N_1$ R2=tert-butyl 3-carbamoylpropyl, R3=$NH_2$, A=—($CH_2$)$_2$—]

and

Tert-butyl {3-[3-carbamoyl-8-(4-fluorophenyl)-4,5-dihydro-2H-pyrazolo[4,3-h]quinazolin-2-yl]propyl}carbamate [(I), R1=4-fluorophenyl, $N_2$ R2=tert-butyl 3-carbamoylpropyl, R3=$NH_2$, A=—($CH_2$)$_2$—]

st. 6b2

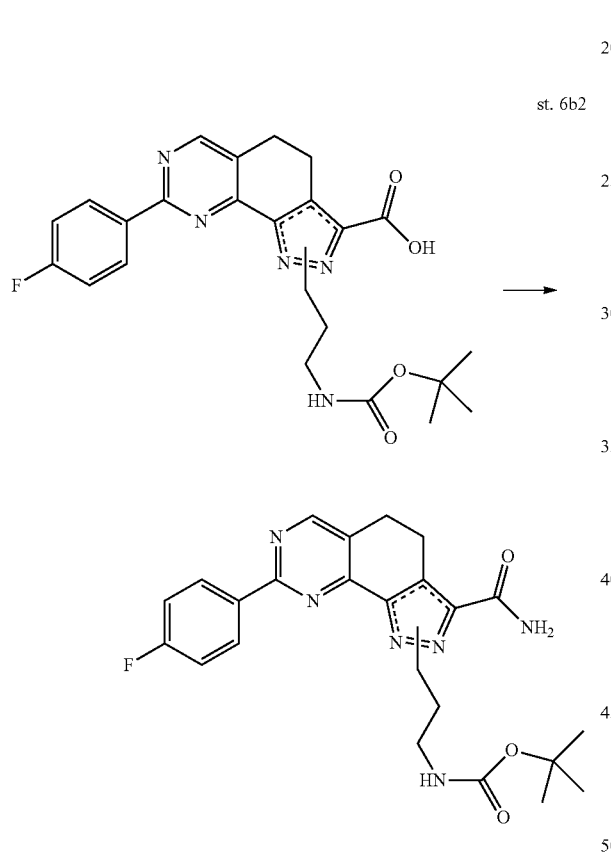

1-{3-[(tert-butoxycarbonyl)amino]propyl}-8-(4-fluorophenyl)-4,5-dihydro-1H-pyrazolo[4,3-h]quinazoline-3-carboxylic acid and 2-{3-[(tert-butoxycarbonyl)amino]propyl}-8-(4-fluorophenyl)-4,5-dihydro-2H-pyrazolo[4,3-h]quinazoline-3-carboxylic acid 358 mg (0.65 mmol) were reacted in dry DMF (5 ml) with HOBt*$NH_4$ 147 mg (0.975 mmol), TBTU 250 mg (0.78 mmol) and DIPEA 0.268 ml (1.5 mmol) at room temperature for 3 hours. The reaction was worked up with water, saturated $NaHCO_3$ and extracted with ethyl acetate. The organic phase, dried on $Na_2SO_4$, filtered and evaporated, was purified on silica with ethyl acetate/hexane 7/3 to give 212 mg (70%) of a clean mixture of the regioisomers. LC/MS (m/z): 467.2 [M+H]$^+$, and 467.2 [M+H]$^+$, HPLC (254 nm) method 3 Rt 5.62 and 6.12 min.

Example 32

1-(3-aminopropyl)-8-(4-fluorophenyl)-4,5-dihydro-1H-pyrazolo[4,3-h]quinazoline-3-carboxamide trifluoroacetate [(I), R1=4-fluorophenyl, $N_1$ R2=3-aminopropyl, R3=$NH_2$, A=—($CH_2$)$_2$—] (cpd 82)

and 2-(3-aminopropyl)-8-(4-fluorophenyl)-4,5-dihydro-2Hpyrazolo[4,3-h]quinazoline-3-carboxamide trifluoroacetate [(I), R1=4-fluorophenyl, $N_2$ R2=3-aminopropyl, R3=$NH_2$, A=—($CH_2$)$_2$—] (cpd 83)

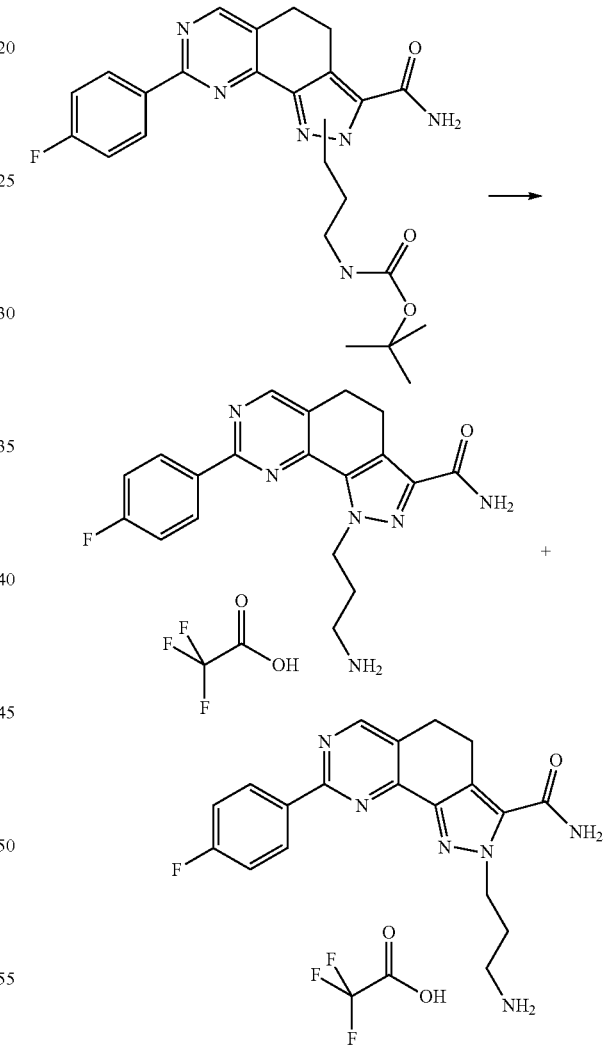

Tert-butyl {3-[3-carbamoyl-8-(4-fluorophenyl)-4,5-dihydro-1H-pyrazolo[4,3-h]quinazolin-1-yl]propyl}carbamate and Tert-butyl {3-[3-carbamoyl-8-(4-fluorophenyl)-4,5-dihydro-2H-pyrazolo[4,3-h]quinazolin-2-yl]propyl}carbamate were suspended in DCM and reacted at 60° C. with 2 ml of TFA. The reaction, complete in 90 min, was evaporated. The crude was purified by prep-HPLC method 2 and the two regioisomers were resolved:

1-(3-aminopropyl)-8-(4-fluorophenyl)-4,5-dihydro-1H-pyrazolo[4,3-h]quinazoline-3-carboxamide trifluoroacetate (major) LC/MS (254 nm) HPLC method 2 Rt 4.32 min. $^1$H NMR (401 MHz, DMSO-$d_6$) δ 8.83 (s, 1H), 8.43 (dd, J=5.68, 8.97 Hz, 2H), 7.64 (br. s., 3H), 7.48 (br. s., 1H), 7.40 (br. s., 1H), 7.38 (t, J=8.85 Hz, 2H), 4.93 (t, J=6.47 Hz, 2H), 3.05-3.13 (m, 2H), 3.01 (t, J=7.20 Hz, 2H), 2.82-2.91 (m, 2H), 2.25 (quin, J=7.20 Hz, 2H) HRMS (ESI) calcd for C19H19FN6O [M+H]$^+$ 367.1677 found 367.16785; and 2-(3-aminopropyl)-8-(4-fluorophenyl)-4,5-dihydro-2Hpyrazolo[4,3-h]quinazoline-3-carboxamide trifluoroacetate (minor) LC/MS (254 nm) HPLC method 2 Rt 4.14 min. $^1$H NMR (401 MHz, DMSO-$d_6$) δ 8.78 (s, 1H), 8.46 (dd, J=5.68, 8.97 Hz, 2H), 7.92 (br. s., 1H), 7.78 (br. s., 1H), 7.74 (br. s., 3H), 7.37 (t, J=8.91 Hz, 2H), 4.53 (t, J=6.84 Hz, 2H), 2.93-3.05 (m, 4H), 2.81-2.92 (m, 2H), 2.16 (quin, J=7.26 Hz, 2H). HRMS (ESI) calcd for C19H19FN6O [M+H]$^+$ 367.1677 found 367.16784.

According to this same methodology, but employing suitable substituted derivative, the following compound was prepared:

1-(3-aminopropyl)-N-(3-hydroxypropyl)-8-(4-methoxyphenyl)-4,5-dihydro-1H-pyrazolo[4,3-h]quinazoline-3-carboxamide trifluoroacetate [(I), R1=4-methoxyphenyl, R2=3-aminopropyl, R'=3-hydroxypropyl, A=—(CH$_2$)$_2$—] (cpd 84) LC/MS (254 nm) HPLC method 2 Rt=3.52 min. $^1$H NMR (401 MHz, DMSO-$d_6$) δ 8.79 (s, 1H), 8.32-8.37 (m, 2H), 8.11 (t, J=5.86 Hz, 1H), 7.67 (br. s., 3H), 7.06-7.14 (m, 2H), 4.94 (t, J=6.53 Hz, 2H), 3.86 (s, 3H), 3.49 (t, J=6.23 Hz, 2H), 3.31 (br. s., 2H), 3.03-3.13 (m, 2H), 3.00 (d, J=7.81 Hz, 2H), 2.81-2.92 (m, 2H), 2.26 (d, J=2.56 Hz, 2H), 1.69 (quin, J=6.56 Hz, 2H). Mass Calc: 437.2296 Mass found: 437.2291.

Preparation N 1-(3-aminopropyl)-8-(4-fluorophenyl)-4,5-dihydro-1H-pyrazolo[4,3-h]quinazoline-3-carboxylic acid trifluoroacetate and 2-(3-aminopropyl)-8-(4-fluorophenyl)-4,5-dihydro-1H-pyrazolo[4,3-h]quinazoline-3-carboxylic acid trifluoroacetate

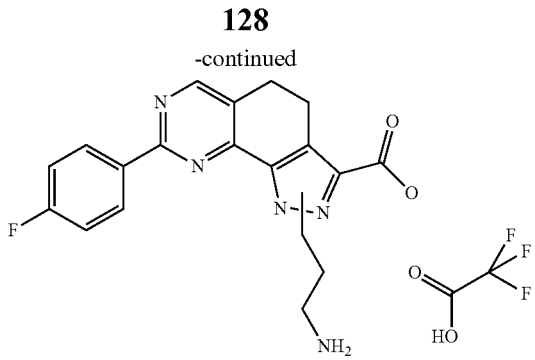

A mixture of 1-{3-[(tert-butoxycarbonyl)amino]propyl}-8-(4-fluorophenyl)-4,5-dihydro-1H-pyrazolo[4,3-h]quinazoline-3-carboxylic acid and 2-{3-[(tert-butoxycarbonyl)amino]propyl}-8-(4-fluorophenyl)-4,5-dihydro-1H-pyrazolo[4,3-h]quinazoline-3-carboxylic acid 165 mg (0.35 mmol) was suspended in DCM and reacted at 60° C. with 2 ml of TFA. The reaction, complete in 90 min, was evaporated. The crude was purified by prep-HPLC method 2 and was delivered as a mixture of the two regioisomers. LC/MS (254 nm) HPLC method 2 Rt 4.2 min same retention time for the two regioisomers. $^1$H NMR (401 MHz, DMSO-$d_6$) δ 8.83 (s, 1H, minor), 8.71 (s, 1H, major), 8.41-8.51 (m, 2H), 8.34 (br. s., 3H), 7.26-7.42 (m, 2H), 4.96 (m, 2H minor), 4.70-4.77 (m, 2H, major), 2.96-3.02 (m, 2H), 2.88-2.95 (m, 2H), 2.61 (t, J=5.92 Hz, 2H), 2.11-2.21 (m, 2H). HRMS (ESI) calcd for C19H18FN5O2 [M+H]$^+$ 368.1518 found 368.153.

Example 33

1-tert-butyl-8-(methylsulfanyl)-1H-pyrazolo[4,3-h]quinazoline-3-carboxamide [(I), R1=Me-S—, R2=tert-butyl, R3=NH$_2$, A=—CH=CH—] (cpd 85)

and 6-amino-1-tert-butyl-8-(methylsulfanyl)-1H-pyrazolo[4,3-h]quinazoline-3-carboxamide [(I), R1=Me-S—, R2=tert-butyl, R3=NH$_2$, R5=NH$_2$, A=—CH=CH—] (cpd 86)

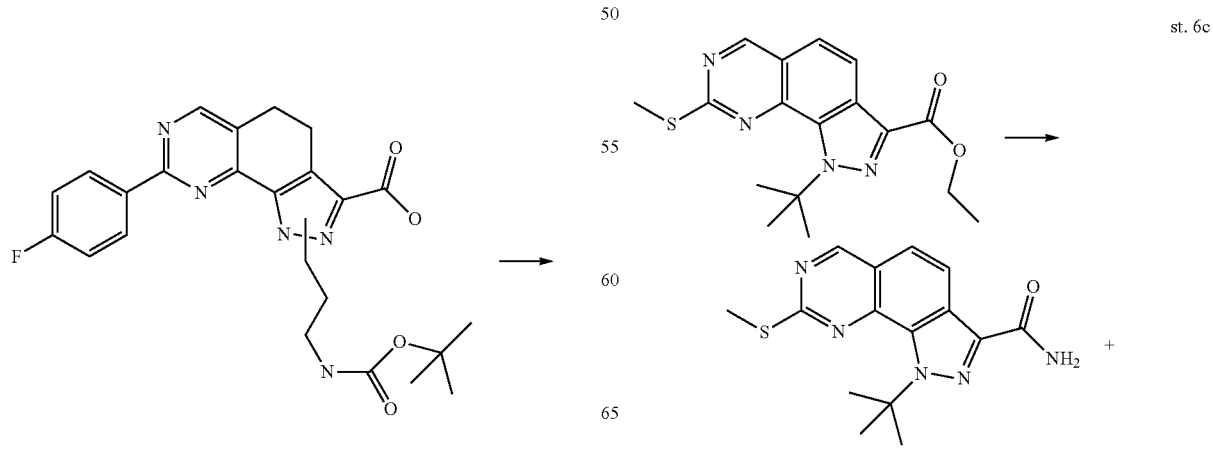

-continued

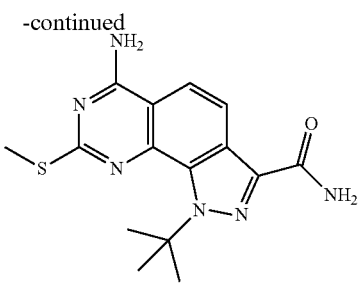

Ethyl 1-tert-butyl-8-(methylsulfanyl)-1H-pyrazolo[4,3-h]quinazoline-3-carboxylate (170 mg 0.494 mmol) was suspended in 4 ml of anhydrous THF and ammonium chloride (80 mg 1.48 mmol) was added. The reaction mixture was cooled to 0° C. and LiN(TMS)$_2$ 1M in THF (3 ml, 3 mmol) was added; the reaction was stirred for 2 hours. The solvent was then evaporated to dryness, the residue suspended in water and filtered. The crude was purified via silica gel column chromatography eluting with DCM/MeOH 97/3 to give 1-tert-butyl-8-(methylsulfanyl)-1H-pyrazolo[4,3-h]quinazoline-3-carboxamide, 100 mg (65% yield), and 6-amino-1-tert-butyl-8-(methylsulfanyl)-1H-pyrazolo[4,3-h]quinazoline-3-carboxamide 10 mg (6%). LC/MS (254 nm) HPLC method 2 Rt 6.07 min. $^1$H NMR (401 MHz, DMSO-d6) δ 9.49 (s, 1H), 8.42 (d, J=8.54 Hz, 1H), 7.80 (d, J=8.79 Hz, 1H), 7.75 (br. s., 1H), 7.53 (br. s., 1H), 2.74 (s, 3H), 2.00 (s, 9H). HRMS (ESI) calcd for C15H17N5OS [M+H]$^+$ 316.1227 found 316.1224.

6-amino-1-tert-butyl-8-(methylsulfanyl)-1H-pyrazolo[4,3-h]quinazoline-3-carboxamide [R1=Me-S—, R2=tert-butyl, R3=NH$_2$, R5=NH$_2$, A=—CH=CH—] LC/MS (254 nm) HPLC method 2 Rt 5.08 min. $^1$H NMR (401 MHz, DMSO-d6) δ 8.16 (d, J=8.79 Hz, 1H), 7.91 (d, J=8.79 Hz, 1H), 7.84 (br. s., 2H), 7.62 (br. s., 1H), 7.42 (br. s., 1H), 2.61 (s, 3H), 1.98 (s, 9H). HRMS (ESI) calcd for C15H18N6OS [M+H]$^+$ 331.1336 found 331.1340

Operating in an analogous way the following compounds were prepared:

1-methyl-8-(methylsulfanyl)-1H-pyrazolo[4,3-h]quinazoline-3-carboxamide [(I), R1=Me-S—, R2=Me, R3=NH$_2$, A=—CH=CH—] (cpd 87) LC/MS (254 nm) HPLC method 2 Rt 4.96 min. $^1$H NMR (401 MHz, DMSO-d6) δ 9.46 (s, 1H), 8.26 (d, J=8.67 Hz, 1H), 7.85 (br. s., 1H), 7.73 (d, J=8.79 Hz, 1H), 7.52 (br. s., 1H), 4.71 (s, 3H), 2.73 (s, 3H). HRMS (ESI) calcd for C12H11N5OS [M+H]$^+$ 274.0757 found 274.0757;

6-amino-1-methyl-8-(methylsulfanyl)-1H-pyrazolo[4,3-h]quinazoline-3-carboxamide [(I), R1=Me-S—, R2=Me, R3=NH$_2$, R5=NH$_2$, A=—CH=CH—] (cpd 88) LC/MS (254 nm) HPLC method 2 Rt 4.59. $^1$H NMR (401 MHz, DMSO-d6) δ 8.00 (d, J=8.91 Hz, 1H), 7.85 (br. s., 1H), 7.83 (d, J=8.91 Hz, 1H), 7.74 (br. s., 1H), 7.42 (br. s., 1H), 4.65 (s, 3H), 2.59 (s, 3H). HRMS (ESI) calcd for C12H12N6OS [M+H]$^+$ 289.0866 found 289.0859;

1-tert-butyl-1H-pyrazolo[4,3-h]quinazoline-3-carboxamide [(I), R1=H, R2=tert-butyl, R3=NH$_2$, A=—CH=CH—] (cpd 3) LC/MS (254 nm) HPLC method 2 Rt 4.63 min. $^1$H NMR (500 MHz, DMSO-d$_6$) δ 9.71 (s, 1H), 9.53 (s, 1H), 8.55 (d, J=8.79 Hz, 1H), 7.89 (d, J=8.78 Hz, 1H), 7.80 (br. s., 1H), 7.58 (br. s., 1H), 2.01 (s, 9H). HRMS (ESI) calcd for C14H15N5O [M+H]$^+$ 270.1350 found 270.1357; and 6-amino-1-tert-butyl-1H-pyrazolo[4,3-h]quinazoline-3-carboxamide [(I), R1=H, R2=tert-butyl, R3=NH$_2$, R5=NH$_2$, A=—CH=CH—] (cpd 122) LC/MS (254 nm) HPLC method 2 Rt 4.29 min. $^1$H NMR (500 MHz, DMSO-d$_6$) δ 8.65 (s, 1H), 8.30 (d, J=9.06 Hz, 1H), 8.12 (br. s., 1H), 8.02 (d, J=8.79 Hz, 1H), 7.70 (br. s., 1H), 7.46-7.52 (m, 1H), 1.98 (s, 9H). HRMS (ESI) calcd for C14H16N6O [M+H]$^+$ 285.1459 found 285.1466.

Example 34

1-tert-butyl-N-hydroxy-8-(methylsulfanyl)-1H-pyrazolo[4,3-h]quinazoline-3-carboxamide [(I), R1=Me-S—, R2=tert-butyl, R3=N(H)OH, A=—CH=CH—] (cpd 89)

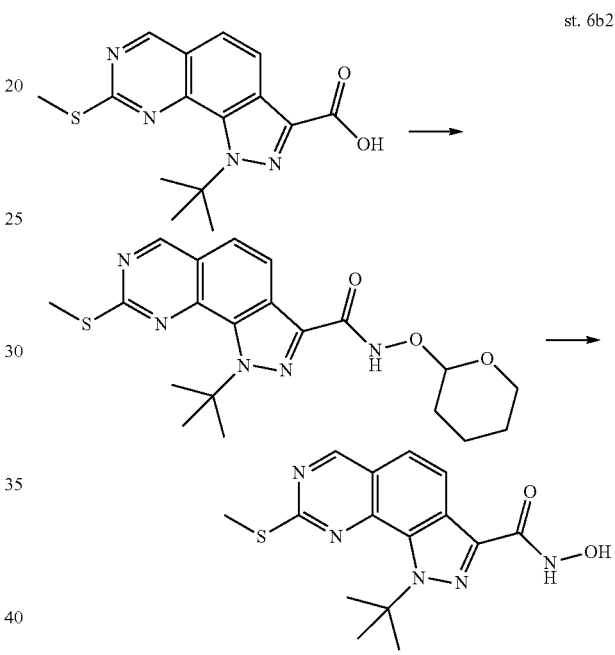

st. 6b2

1-tert-butyl-8-(methylsulfanyl)-1H-pyrazolo[4,3-h]quinazoline-3-carboxylic acid 40 mg (0.112 mmol) was reacted in dry DMF (2 ml) with O-(tetrahydro-2H-pyran-2-yl)hydroxylamine 25 mg (0.21 mmol), TBTU 70 mg (0.21 mmol) and DIPEA 0.110 ml (1.19 mmol) at room temperature for 3 hours. The reaction was worked up with water, saturated NaHCO$_3$ and extracted with ethyl acetate. The organic phase, dried on Na$_2$SO$_4$, filtered and evaporated, was purified on silica with DCM/EtOAc 7/3 to give 23 mg (50%) of 1-tert-butyl-8-(methylsulfanyl)-N-(tetrahydro-2H-pyran-2-yloxy)-1H-pyrazolo[4,3-h]quinazoline-3-carboxamide. LC/MS (m/z): 416.1 [M+H]$^+$, HPLC (254 nm) method 3 Rt 6.94 min.

1-tert-butyl-8-(methylsulfanyl)-N-(tetrahydro-2H-pyran-2-yloxy)-1H-pyrazolo[4,3-h]quinazoline-3-carboxamide was dissolved in methanol (2 ml) and 4 M HCl in dioxane (2 ml) was added. The solution was stirred at room temperature for 2 hours, consequently the volatiles were removed in vacuo. The crude was firstly purified by silica gel eluting with DCM/MeOH 6/1 to obtain the desired product which was submitted to preparative HPLC purification method 1, to afford the title product 5 mg (30%). LC/MS (254 nm) HPLC method 2 Rt 4.95 min. $^1$H NMR (401 MHz, DMSO-d6) δ 11.16 (s, 1H), 9.49 (s, 1H), 9.15 (br. s., 1H), 8.33 (d, J=8.67

Hz, 1H), 7.80 (d, J=8.67 Hz, 1H), 2.73 (s, 3H), 1.99 (s, 9H). HRMS (ESI) calcd for C15H17N5O2S [M+H]+ 332.1176 found 332.1185.

Example 35

8-(methylsulfanyl)-1H-pyrazolo[4,3-h]quinazoline-3-carboxamide [(I), R1=Me-S—, R2=H, R3=NH₂, A=—CH=CH—] (cpd 90)

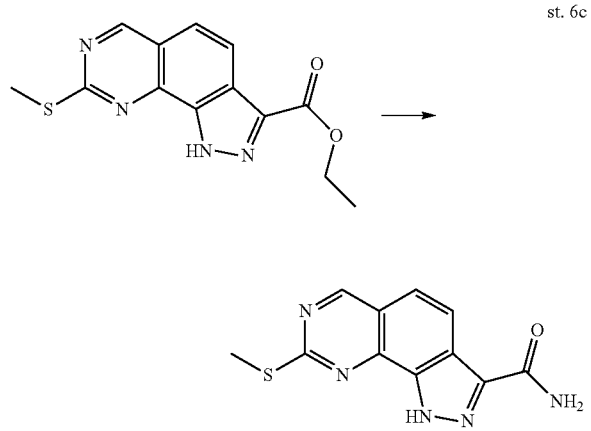

Ethyl 8-(methylsulfanyl)-1H-pyrazolo[4,3-h]quinazoline-3-carboxylate (210 mg 0.76 mmol) was suspended in 4 ml of anhydrous THF, and ammonium chloride (120 mg 2.28 mmol) was added. The reaction mixture was cooled to 0° C. and LiN(TMS)₂ 1M in THF (8 ml, 8.0 mmol) was added to the reaction and stirred for 2 hours. The solvent was then evaporated to dryness, the residue was taken up with DCM and washed with water and brine. The organic layer was dried over Na₂SO₄ filtered and evaporated under vacuum. The crude was purified via silica gel column chromatography eluting with DCM/MeOH 9/1 to give the title compound 180 mg (86% yield). LC/MS (254 nm) HPLC method 2 Rt 4.46 min. ¹H NMR (401 MHz, DMSO-d6) δ 9.48 (s, 1H), 8.24 (d, J=8.79 Hz, 1H), 7.91 (br. s., 1H), 7.71 (d, J=8.67 Hz, 1H), 7.49 (s, 1H), 2.75 (s, 3H) HRMS (ESI) calcd for C11H9N5OS [M+H]+ 260.0601 found 260.0598

Example 36

Tert-butyl 4-[3-carbamoyl-8-(methylsulfanyl)-1H-pyrazolo[4,3-h]quinazolin-1-yl]piperidine-1-carboxylate [(I), R1=Me-S—, R2=tert-butyl 4-piperidine carboxylate, R3=NH₂, A=—CH=CH—]

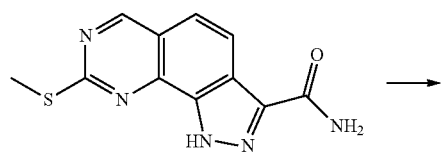

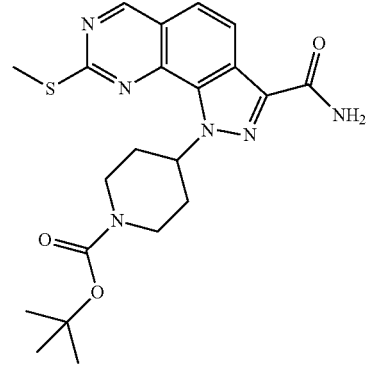

A solution of 8-(methylsulfanyl)-1H-pyrazolo[4,3-h]quinazoline-3-carboxamide 150 mg (0.58 mmol) in DMF (5 ml), tert-butyl 4-bromopiperidine-1-carboxylate 205 mg (1.16 mmol) and cesium carbonate 377 mg (1.16 mmol) was reacted at 80° C. for 18 hours. The mixture was cooled at r.t. and portioned between ethyl acetate and water. The organic phase was washed with brine, dried over Na₂SO₄ and evaporated. The crude was purified by column chromatography eluting with DCM/EtOAc/EtOH 6/4/0.5 to provide the desired compound as a white solid 200 mg (78%). LC/MS (m/z): 443.1 [M+H]+, HPLC (254 nm) method 4 Rt 2.53.

Operating in an analogous way, the following compound was prepared:

tert-butyl 4-(3-carbamoyl-8-methoxy-1H-pyrazolo[4,3-h]quinazolin-1-yl)piperidine-1-carboxylate. LC/MS (m/z): 427.2 [M+H]+, HPLC (254 nm) method 3 Rt 5.61.

Example 37

8-(methylsulfanyl)-1-(piperidin-4-yl)-1H-pyrazolo[4,3-h]quinazoline-3-carboxamide hydrochloride [(I), R1=Me-S—, R2=piperidin-4-yl, R3=NH₂, A=—CH=CH—] (cpd 91)

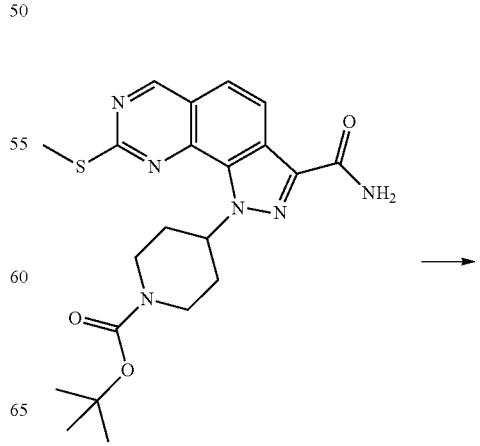

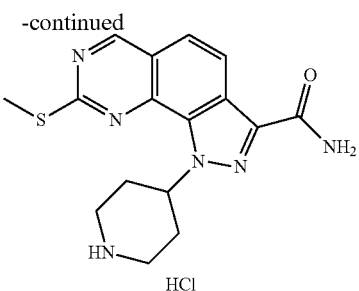

Tert-butyl 4-[3-carbamoyl-8-(methylsulfanyl)-1H-pyrazolo[4,3-h]quinazolin-1-yl]piperidine-1-carboxylate was dissolved in 1,4-dioxane (2 ml) and 4 M HCl in 1,4 dioxane (3 ml) was added. The solution was stirred at room temperature for 1 hour. The volatiles were removed in vacuo and the residue triturated with diethyl ether, filtered and dried in the oven (40° C.) under vacuum for 2 hours, to obtain the title compound 25 mg (99%). LC/MS (254 nm) HPLC method 2 Rt 3.73 min. $^1$H NMR (401 MHz, DMSO-d6) δ 9.50 (s, 1H), 8.85 (br. s., 1H), 8.64-8.78 (m, 1H), 8.29 (d, J=8.67 Hz, 1H), 7.73-7.82 (m, 2H), 7.64 (s, 1H), 6.16 (quin, J=7.05 Hz, 1H), 3.52-3.61 (m, J=13.06 Hz, 2H), 3.08-3.21 (m, 2H), 2.75 (s, 3H), 2.37-2.47 (m, 4H). HRMS (ESI) calcd for C16H18N6OS [M+H]$^+$ 343.1336 found 343.1326.

According to the same methodology, but employing suitable starting material, the following compounds were prepared:

8-(methylsulfanyl)-1-(piperidin-3-yl)-1H-pyrazolo[4,3-h]quinazoline-3-carboxamide hydrochloride [(I), R1=Me-S—, R2=piperidin-3-yl, R3=NH$_2$, A=—CH=CH—] (cpd 92) LC/MS (254 nm) HPLC method 2 Rt 3.86 min. $^1$H NMR (401 MHz, DMSO-d6) δ 9.41-9.59 (m, 1H), 9.27 (br. s., 1H), 8.43 (br. s., 1H), 8.20-8.38 (m, 2H), 7.75-7.84 (m, 1H), 7.69 (s, 1H), 6.30 (t, J=4.88 Hz, 1H), 3.90 (d, J=12.33 Hz, 2H), 3.78 (d, J=4.52 Hz, 2H), 2.74 (br. s., 3H), 2.27-2.42 (m, 3H), 2.14 (dd, J=5.61, 14.16 Hz, 2H), 1.78 (d, J=5.37 Hz, 2H). HRMS (ESI) calcd for C16H18N6OS [M+H]$^+$ 343.1336 found 343.1329;

1-(4-aminocyclohexyl)-8-(methylsulfanyl)-1H-pyrazolo[4,3-h]quinazoline-3-carboxamide hydrochloride [(I), R1=Me-S—, R2=4-aminocyclohexyl, R3=NH$_2$, A=—CH=CH—] (cpd 93) LC/MS (254 nm) HPLC method 2 Rt 4.05 min. $^1$H NMR (401 MHz, DMSO-d6) δ 9.48 (s, 1H), 8.28 (d, J=8.67 Hz, 1H), 8.00 (br. s., 3H), 7.76 (d, J=8.79 Hz, 1H), 7.72 (s, 1H), 7.64 (s, 1H), 6.18 (br. s., 1H), 2.69 (s, 3H), 2.25-2.37 (m, 2H), 2.06-2.19 (m, 4H), 1.79-1.95 (m, 2H). HRMS (ESI) calcd for C17H20N6OS [M+H]$^+$ 357.1492 found 357.1491;

8-(methylsulfanyl)-1-(piperidin-3-ylmethyl)-1H-pyrazolo[4,3-h]quinazoline-3-carboxamide hydrochloride [(I), R1=Me-S—, R2=piperidin-3-ylmethyl, R3=NH$_2$, A=—CH=CH—] (cpd 94) LC/MS (254 nm) HPLC method 2 Rt 3.94 min. $^1$H NMR (401 MHz, DMSO-d6) δ 1H 9.50 (s, 1H), 8.63 (d, J=10.99 Hz, 1H), 8.34-8.40 (m, 1H), 8.30 (d, J=8.67 Hz, 1H), 7.80 (s, 1H), 7.78 (d, J=8.79 Hz, 1H), 7.63 (s, 1H), 5.01-5.19 (m, 2H), 3.20 (d, J=13.79 Hz, 2H), 3.02 (d, J=12.45 Hz, 1H), 2.76-2.88 (m, 2H), 2.74 (s, 3H), 2.55-2.66 (m, 1H), 1.67-1.85 (m, 2H), 1.31-1.64 (m, 2H). HRMS (ESI) calcd for C17H20N6OS [M+H]$^+$ 357.1492 found 357.1489;

1-(azepan-4-yl)-8-(methylsulfanyl)-1H-pyrazolo[4,3-h]quinazoline-3-carboxamide hydrochloride [(I), R1=Me-S—, R2=azepan-4-yl, R3=NH$_2$, A=—CH=CH—] (cpd 95) LC/MS (254 nm) HPLC method 2 Rt 3.94 min. $^1$H NMR (401 MHz, DMSO-d6) δ 9.49 (m, 1H), 8.87 (br. s., 2H), 8.28 (d, J=8.79 Hz, 1H), 7.83 (s, 1H), 7.76 (d, J=8.79 Hz, 1H), 7.63 (s, 1H), 6.05-6.59 (m, 1H), 3.46-3.66 (m, 2H), 3.10-3.24 (m, 1H), 2.72 (s, 3H), 2.53-2.59 (m, 2H), 2.39-2.46 (m, 1H), 2.25-2.35 (m, 1H), 2.04-2.17 (m, 1H), 1.75-1.95 (m, 1H). HRMS (ESI) calcd for C17H20N6OS [M+H]$^+$ 357.1492 found 357.1509;

1-(3-amino-2,2-dimethylpropyl)-8-(methylsulfanyl)-1H-pyrazolo[4,3-h]quinazoline-3-carboxamide hydrochloride [(I), R1=Me-S—, R2=3-amino-2,2-dimethylpropyl, R3=NH$_2$, A=—CH=CH—] (cpd 96) LC/MS (254 nm) HPLC method 2 Rt 4.08 min. $^1$H NMR (401 MHz, DMSO-d6) δ 9.50 (s, 1H), 8.32 (d, J=8.67 Hz, 1H), 7.99 (br. s., 3H), 7.94 (s, 1H), 7.78 (d, J=8.79 Hz, 1H), 7.71 (s, 1H), 5.29 (s, 2H), 2.89 (q, J=6.43 Hz, 1H), 2.75 (s, 3H), 1.02 (s, 6H) HRMS (ESI) calcd for C16H20N6OS [M+H]$^+$ 345.1492 found 345.1502;

8-methoxy-1-(piperidin-4-yl)-1H-pyrazolo[4,3-h]quinazoline-3-carboxamide hydrochloride [(I), R1=Me-O—, R2=piperidin-4-yl, R3=NH$_2$, A=—CH=CH—] (cpd 97) LC/MS (254 nm) HPLC method 2 Rt 3.43 min. $^1$H NMR (401 MHz, DMSO-d6) δ 9.55 (s, 1H), 8.65-8.79 (m, 1H), 8.68 (br. s., 1H), 8.45-8.58 (m, 1H), 8.53 (br. s., 1H), 8.22 (d, J=8.67 Hz, 1H), 7.79 (d, J=8.79 Hz, 1H), 7.75 (s, 1H), 7.62 (s, 1H), 6.10 (quind, J=4.66, 9.67 Hz, 1H), 4.16 (s, 3H), 3.51-3.65 (m, J=12.45 Hz, 1H), 3.18-3.26 (m, 2H), 2.37-2.46 (m, 4H). HRMS (ESI) calcd for C16H18N6O2 [M+H]$^+$ 327.1564 found 327.15575; and 8-methoxy-1-(piperidin-4-ylmethyl)-1H-pyrazolo[4,3-h]quinazoline-3-carboxamide hydrochloride [(I), R1=Me-O—, R2=piperidin-4-ylmethyl, R3=NH$_2$, A=—CH=CH—] (cpd 98) LC/MS (254 nm) HPLC method 2 Rt 3.54 min. $^1$H NMR (401 MHz, DMSO-d6) δ 9.53 (s, 1H), 8.72-8.89 (m, 1H), 8.57-8.70 (m, J=9.52 Hz, 1H), 8.21 (d, J=8.67 Hz, 1H), 7.80 (br. s., 1H), 7.77 (d, J=8.79 Hz, 1H), 7.57 (s, 1H), 5.09 (d, J=7.32 Hz, 2H), 4.16 (s, 3H), 3.18-3.26 (m, J=12.69 Hz, 2H), 2.72-2.89 (m, 2H), 2.40-2.47 (m, 1H), 1.50-1.68 (m, 4H) HRMS (ESI) calcd for C17H20N6O2 [M+H]$^+$ 341.1721 found 341.1721.

Example 38

1-[(3-exo)-8-azabicyclo[3.2.1]oct-3-yl]-8-(methylsulfanyl)-1H-pyrazolo[4,3-h]quinazoline-3-carboxamide [(I), R1=Me-S—, R2=8-azabicyclo[3.2.1]oct-3-yl, R3=NH$_2$, A=—CH=CH—] (cpd 99)

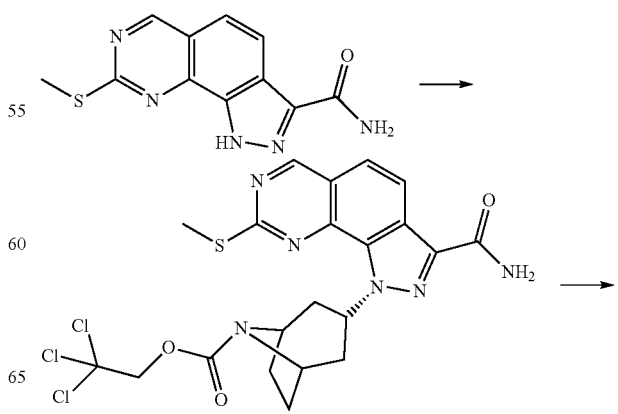

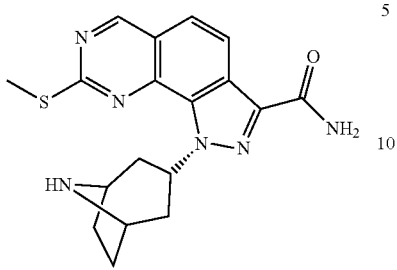

8-(Methylsulfanyl)-1H-pyrazolo[4,3-h]quinazoline-3-carboxamide 50 mg (0.193 mmol) in DMF (8 ml), were reacted with 2,2,2-trichloroethyl 3-[(methylsulfonyl)oxy]-8-azabicyclo[3.2.1]octane-8-carboxylate 200 mg (0.52 mmol) and cesium carbonate 140 mg (0.43 mmol) at 90° C. for 4 hours. The mixture was cooled at r.t. and portioned between ethyl acetate and water. The organic phase was washed with brine, dried over $Na_2SO_4$ and evaporated. The crude was purified by column chromatography eluting with DCM/EtOH 9/1 to provide 2,2,2-trichloroethyl 3-[3-carbamoyl-8-(methylsulfanyl)-1H-pyrazolo[4,3-h]quinazolin-1-yl]-8-azabicyclo[3.2.1]octane-8-carboxylate as a off-white solid 73 mg (70%). The compound (134 mmol) was dissolved in THF (5 ml), acetic acid (5 ml) and zinc dust 35 mg (0.536 mmol) were added. The mixture was heated up to 50° C. and stirred 18 hours. The volatiles were removed in vacuum and the residue was purified by chromatography eluting with DCM/MeOH 95/5. A further purification was required and was performed by prep-HPLC method 1, to obtain the title compound 25 mg (50%). LC/MS (254 nm) HPLC method 2 Rt 4.08 min. $^1$H NMR (401 MHz, DMSO-d6) δ 9.50 (s, 1H), 8.25 (d, J=8.67 Hz, 1H), 7.62-7.79 (m, 3H), 7.52-7.60 (m, 1H), 6.21-6.54 (m, OH), 3.68 (br. s., 2H), 2.76 (s, 2H), 2.22-2.36 (m, 2H), 2.02 (br. s., 2H), 1.78-1.98 (m, 5H). HRMS (ESI) calcd for $C_{18}H_{20}N_6OS$ $[M+H]^+$ 369.1492 found 369.15.

Operating in an analogous way, the following compound was prepared:

1-[(3-endo)-8-azabicyclo[3.2.1]oct-3-yl]-8-(methylsulfanyl)-1H-pyrazolo[4,3-h]quinazoline-3-carboxamide trifluoroacetate [(I), R1=Me-S—, R2=8-azabicyclo[3.2.1]oct-3-yl, R3=$NH_2$, A=—CH=CH—] (cpd 100) LC/MS (254 nm) HPLC method 2 Rt 3.0 min. $^1$H NMR (401 MHz, DMSO-d6) δ 9.49 (s, 1H), 8.66 (br. s., 1H), 8.32 (d, J=8.79 Hz, 1H), 7.85 (s, 1H), 7.79 (d, J=8.79 Hz, 1H), 7.63 (s, 1H), 6.07 (t, J=8.12 Hz, 1H), 4.07 (br. s., 2H), 2.81 (ddd, J=4.09, 8.03, 16.20 Hz, 2H), 2.72 (s, 3H), 2.63 (d, J=16.36 Hz, 2H), 2.05-2.19 (m, 2H), 1.79-1.94 (m, 2H). HRMS (ESI) calcd for $C_{18}H_{20}N_6OS$ $[M+H]^+$ 369.1492 found 369.1484.

Example 39

1-[4-(1,3-dioxo-1,3-dihydro-2H-isoindol-2-yl)butan-2-yl]-8-(methylsulfanyl)-1H-pyrazolo[4,3-h]quinazoline-3-carboxamide [(I), R1=Me-S—, R2=4-(1,3-dioxo-1,3-dihydro-2H-isoindol-2-yl)butan-2-yl, R3=$NH_2$, A=—CH=CH—] (cpd 101)

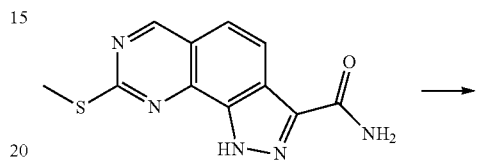

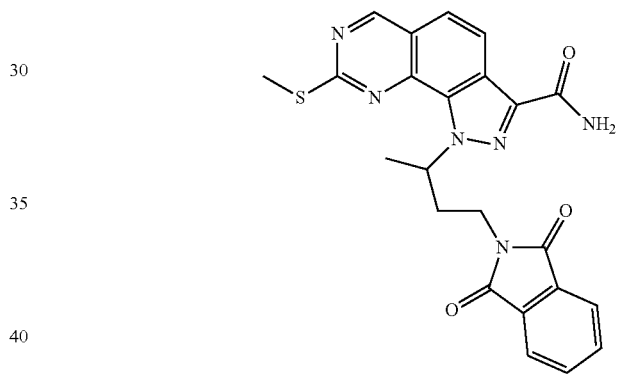

8-(Methylsulfanyl)-1H-pyrazolo[4,3-h]quinazoline-3-carboxamide 50 mg (0.193 mmol) in DMF (3 ml), were reacted with 2-(4-bromo-3-methylbutyl)-1H-isoindole-1,3(2H)-dione 108 mg (0.38 mmol) and cesium carbonate 132 mg (0.38 mmol) at 80° C. for 3 hours. The mixture was cooled at r.t. and portioned between ethyl acetate and water. The organic phase was washed with brine, dried over $Na_2SO_4$ and evaporated. The crude was purified by column chromatography eluting with DCM/EtOH 9/1 to provide the desired compound as a pale yellow solid 57 mg (65%). LC/MS (254 nm) HPLC method 2 Rt 6.01 min. $^1$H NMR (401 MHz, DMSO-d6) δ 9.38 (s, 1H), 8.21 (d, J=8.67 Hz, 1H), 7.71-7.76 (m, 2H), 7.69 (d, J=8.79 Hz, 1H), 7.53-7.60 (m, 2H), 6.29-6.45 (m, 1H), 3.41-3.58 (m, 2H), 2.72 (dt, J=5.25, 9.70 Hz, 1H), 2.45 (d, J=7.57 Hz, 1H), 2.41 (s, 3H), 1.59 (d, J=6.59 Hz, 3H) HRMS (ESI) calcd for $C_{23}H_{20}N_6O_3S$ $[M+H]^+$ 461.1391 found 461.1412.

Example 40

1-(4-aminobutan-2-yl)-8-(methylsulfanyl)-1H-pyrazolo[4,3-h]quinazoline-3-carboxamide [(I), R1=Me-S—, R2=4-aminobutan-2-yl, R3=NH$_2$, A=—CH═CH—] (cpd 02)

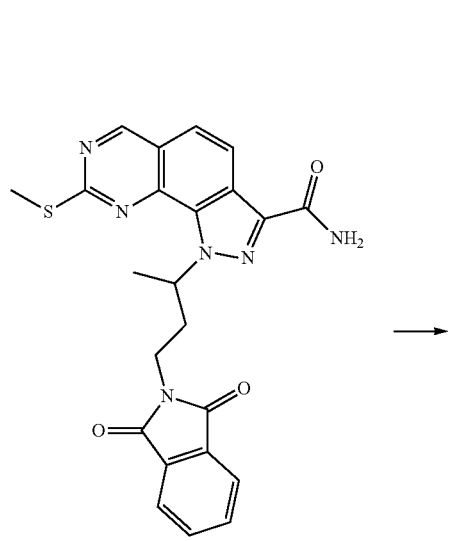

To a solution of 1-[4-(1,3-dioxo-1,3-dihydro-2H-isoindol-2-yl)butan-2-yl]-8-(methylsulfanyl)-1H-pyrazolo[4,3-h]quinazoline-3-carboxamide 45 mg (0.097 mmol) in THF (5 ml), 1M hydrazine in THF (5 ml) was added. The mixture was stirred at 50° C. for 3 hours. The mixture was cooled to r.t. and filtered, the volatiles were removed under vacuum, the crude was submitted to prep-HPLC method 1 to afford the title product 20 mg (60%). LC/MS (254 nm) HPLC method×Rt 3.98 min. $^1$H NMR (401 MHz, DMSO-d6) δ 9.50 (s, 1H), 8.29 (d, J=8.67 Hz, 1H), 7.81 (s, 1H), 7.77 (d, J=8.79 Hz, 1H), 7.62 (d, J=10.25 Hz, 1H), 6.23 (br. s., 1H), 2.87 (td, J=5.66, 11.50 Hz, 1H), 2.71 (s, 3H), 2.61 (dt, J=6.41, 11.81 Hz, 1H), 2.14-2.30 (m, 1H), 1.66 (d, J=6.59 Hz, 3H). HRMS (ESI) calcd for C15H18N6OS [M+H] 331.1336 found 331.134.

Example 41

1-(1-azabicyclo[2.2.2]oct-3-yl)-8-(methylsulfanyl)-1H-pyrazolo[4,3-h]quinazoline-3-carboxamide [(I), R1=Me-S—, R2=azabicyclo[2.2.2]oct-3-yl, R3=NH$_2$, A=—CH═CH—] (cpd 103)

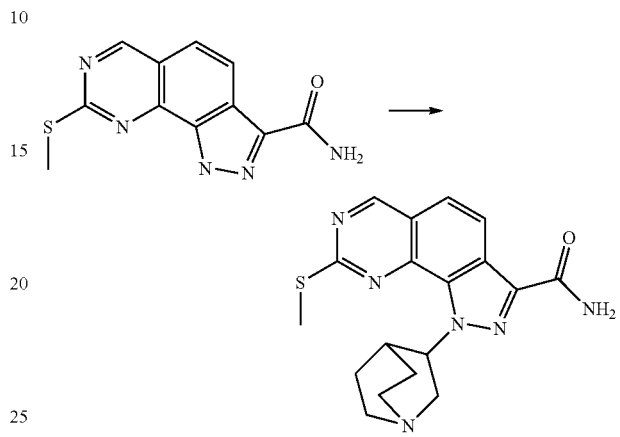

To a solution of 8-(methylsulfanyl)-1H-pyrazolo[4,3-h]quinazoline-3-carboxamide 64 mg (0.247 mmol) in DMF (3 ml) 1-azabicyclo[2.2.2]oct-3-yl 4-methylbenzenesulfonate (prepared following the method described in *Tetrahedron. Lett.* 2000 41 271-274) 300 mg (1.06 mmol) and potassium tert-butoxide 55 mg (0.494 mmol) were added. The mixture was heated up to 100° C. and stirred for 4 hours. The reaction mixture was allowed to cool at room temperature and portioned between ethyl acetate and water. The organic phase was washed with brine, dried over Na$_2$SO$_4$ and evaporated. The crude was purified by column chromatography eluting with DCM/MeOH/NH$_4$OH 9/1/0.5 yielding the desired product 14 mg (15%). LC/MS (254 nm) HPLC method 2 Rt 4.73 min. $^1$H NMR (401 MHz, DMSO-d6) δ 9.46 (s, 1H), 8.17-8.41 (m, 1H), 7.87-8.00 (m, 1H), 7.68-7.80 (m, 1H), 7.54 (s, 1H), 5.94-6.38 (m, 1H), 4.01 (dd, J=4.09, 13.98 Hz, 1H), 3.37-3.48 (m, 1H), 2.75-2.95 (m, 3H), 2.73 (s, 3H), 2.20-2.29 (m, 1H), 1.80-1.95 (m, 1H), 1.75 (ddd, J=4.76, 8.48, 13.12 Hz, 1H), 1.34-1.47 (m, 1H), 1.20-1.35 (m, 1H). HRMS (ESI) calcd for C18H20N6OS [M+H]$^+$ 369.1492 found 369.1508.

Example 42

8-(methylsulfanyl)-1-(tetrahydro-2H-pyran-4-yl)-1H-pyrazolo[4,3-h]quinazoline-3-carboxamide [(I), R1=Me-S—, R2=tetrahydro-2H-pyran-4-yl, R3=NH$_2$, A=—CH═CH—] (cpd 104)

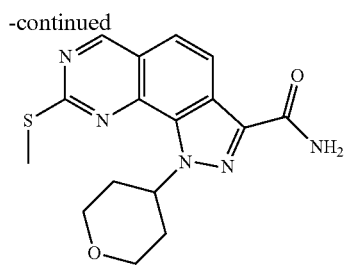

To a solution of 8-(methylsulfanyl)-1H-pyrazolo[4,3-h]quinazoline-3-carboxamide 30 mg (0.247 mmol) in DMF (3 ml), tetrahydro-2H-pyran-4-yl methanesulfonate (prepared according to US 2003/6653489) 62 mg (0.34 mmol) and cesium carbonate 87 mg (0.266 mmol) were added. The mixture was heated up to 80° C. and stirred for 4 hours. The reaction mixture was allowed to cool at room temperature and portioned between ethyl acetate and water. The organic phase was washed with brine, dried over $Na_2SO_4$ and evaporated. The crude was purified by column chromatography eluting with DCM/MeOH/NH$_4$OH 9/1/0.5 yielding 32 mg of the desired product (38%). LC/MS (254 nm) HPLC method 2 Rt 5.41 min. $^1$H NMR (401 MHz, DMSO-d6) δ 9.47 (s, 1H), 8.28 (d, J=8.67 Hz, 1H), 7.84 (br. s., 1H), 7.75 (d, J=8.79 Hz, 1H), 7.54 (s, 1H), 6.25 (tt, J=4.32, 11.37 Hz, 1H), 4.11 (dd, J=4.15, 11.47 Hz, 1H), 3.48-3.65 (m, 1H), 2.75 (s, 3H), 2.23-2.40 (m, 2H), 2.13 (dd, J=2.38, 12.39 Hz, 2H). HRMS (ESI) calcd for C16H17N5O2S [M+H]$^+$ 344.1176 found 344.1166.

Example 43

Methyl 3-[3-carbamoyl-8-(methylsulfanyl)-1H-pyrazolo[4,3-h]quinazolin-1-yl]cyclobutanecarboxylate [(I), R1=Me-S—, R2=methyl 3-cyclobutanecarboxylate, R3=NH$_2$, A=—CH=CH—]

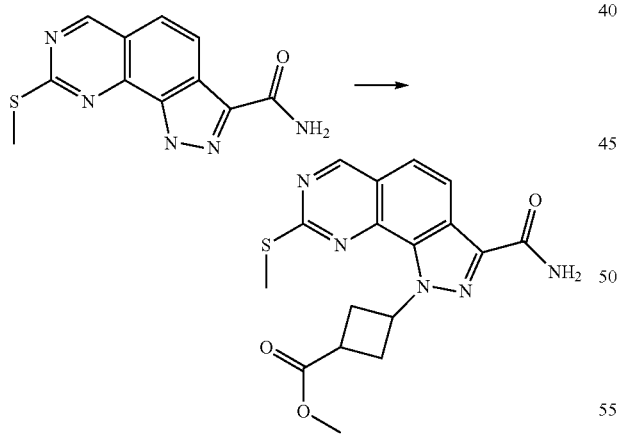

To a solution of 8-(methylsulfanyl)-1H-pyrazolo[4,3-h]quinazoline-3-carboxamide 100 mg (0.38 mmol) in DMF (5 ml), methyl 2-methyl-4-[(methylsulfonyl)oxy]pentanoate (prepared following the method described in WO2009/71509 A1) 200 mg (0.89 mmol) and cesium carbonate 191 mg (0.55 mmol) were added. The mixture was heated up at 90° C. for 18 hours. The mixture was cooled at r.t. and portioned between ethyl acetate and water. The organic phase was washed with brine, dried over $Na_2SO_4$ and evaporated. The crude was purified by column chromatography eluting with DCM/EtOH 9/1 to provide the desired compound as a white solid 100 mg (70%). The product contained a mixture of cis and trans isomers. LC/MS (254 nm) HPLC method 2 Rt 5.55 min. $^1$H NMR (401 MHz, DMSO-d6) δ 9.44-9.51 (m, 1H), 8.26 (dd, J=1.89, 8.73 Hz, 1H), 7.87-8.02 (m, 1H), 7.72-7.77 (m, 1H), 7.58 (br. s., 1H), 6.24-6.93 (m, 1H), 3.66-3.76 (m, 3H), 3.29 (s, 3H), 3.04-3.25 (m, 2H), 2.79-3.02 (m, 3H). HRMS (ESI) calcd for C17H17N5O3S [M+H]$^+$ 372.1125 found 372.1119.

Operating in an analogous way, the following compound was prepared:

methyl 2-[3-carbamoyl-8-(methylsulfanyl)-1H-pyrazolo[4,3-h]quinazolin-1-yl]-2-methylpropanoate LC/MS (m/z): 360.1 [M+H]$^+$, HPLC (254 nm) method 3 Rt 4.75

Example 44

1-[trans-3-(hydroxymethyl)cyclobutyl]-8-(methylsulfanyl)-1H-pyrazolo[4,3-h]quinazoline-3-carboxamide [(I), R1=Me-S—, R2=trans-3-(hydroxymethyl)cyclobutyl, R3=NH$_2$, A=—CH=CH—] (cpd 105)

and

1-[cis-3-(hydroxymethyl)cyclobutyl]-8-(methylsulfanyl)-1H-pyrazolo[4,3-h]quinazoline-3-carboxamide [(I), R1=Me-S—, R2=cis-3-(hydroxymethyl)cyclobutyl, R3=NH$_2$, A=—CH=CH—] (cpd 106)

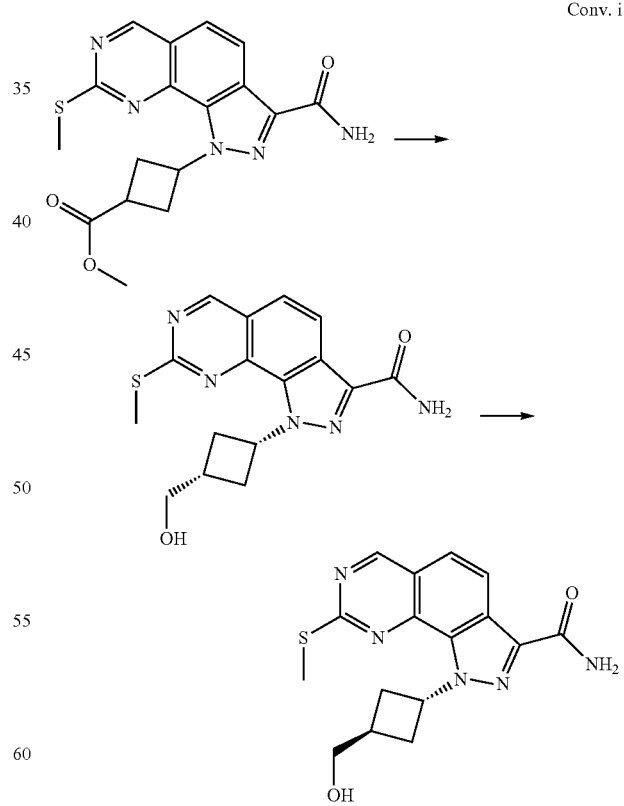

Conv. i

To a solution of methyl 3-[3-carbamoyl-8-(methylsulfanyl)-1H-pyrazolo[4,3-h]quinazolin-1-yl]cyclobutanecarboxylate (cis and trans mixture) 70 mg (0.188 mmol) in ethanol (5 ml), sodium borohydride 30 mg (0.75 mmol) was carefully added. The mixture was stirred at room temperature for 18 hours. After removal of the solvent, the residue was taken up with ethyl acetate (20 ml), water (10 ml) and saturated aqueous NH₄Cl solution (10 ml). The layers were mixed and separated. The organic extract was washed with brine and dried over Na₂SO₄, then filtered and concentrated. The crude product was purified by column chromatography (DCM/EtOAc/EtOH 7/2/1) to provide the product as an off-white solid which was submitted to prep-HPLC for the cis/trans isomers resolution;

1-[cis-3-(hydroxymethyl)cyclobutyl]-8-(methylsulfanyl)-1H-pyrazolo[4,3-h]quinazoline-3-carboxamide LC/MS (254 nm) HPLC method 2 Rt 5.04 min. $^1$H NMR (401 MHz, DMSO-d6) δ 9.46 (s, 1H), 8.26 (d, J=8.67 Hz, 1H), 7.84 (s, 1H), 7.73 (d, J=8.79 Hz, 1H), 7.57 (s, 1H), 6.39 (quin, J=8.33 Hz, 1H), 4.55-4.67 (m, 1H), 3.55 (d, J=6.10 Hz, 2H), 2.73 (s, 3H), 2.57-2.65 (m, J=6.35 Hz, 1H), 2.51-2.54 (m, 2H), 2.31-2.40 (m, 1H). HRMS (ESI) calcd for C16H17N5O2S [M+H]$^+$ 344.1176 found 344.1167; and 1-[trans-3-(hydroxymethyl)cyclobutyl]-8-(methylsulfanyl)-1H-pyrazolo[4,3-h]quinazoline-3-carboxamide LC/MS (254 nm) HPLC method 2 Rt 4.91 min. $^1$H NMR (401 MHz, DMSO-d6) δ 9.39-9.48 (m, 1H), 8.14-8.34 (m, 1H), 7.82-8.00 (m, 1H), 7.73 (d, J=8.79 Hz, 1H), 7.56 (s, 1H), 6.64 (quin, J=7.78 Hz, 1H), 4.71-4.97 (m, 1H), 3.53-3.75 (m, 2H), 2.82-2.97 (m, 2H), 2.73-2.78 (m, 3H), 2.37-2.47 (m, 2H). HRMS (ESI) calcd for C16H17N5O2S [M+H]$^+$ 344.1176 found 344.1174.

Operating in an analogous way, the following compounds were prepared:

1-(1-hydroxy-2-methylpropan-2-yl)-8-(methylsulfanyl)-1H-pyrazolo[4,3-h]quinazoline-3-carboxamide [(I), R1=Me-S—, R2=1-hydroxy-2-methylpropan-2-yl, R3=NH₂, A=—CH=CH—] (cpd 107) LC/MS (m/z): 332.08 [M+H]$^+$, HPLC (254 nm) method 1 Rt 1.14; and 1-(1-hydroxy-2-methylpropan-2-yl)-8-(methylsulfanyl)-4,5-dihydro-1H-pyrazolo[4,3-h]quinazoline-3-carboxamide [(I), R1=Me-S—, R2=1-hydroxy-2-methylpropan-2-yl, R3=NH₂, A=—(CH₂)₂—] (cpd 108) LC/MS (m/z): 334.1 [M+H]$^+$, HPLC (254 nm) method 1 Rt 0.63.

Example 45 tert-butyl 4-(3-carbamoyl-8-phenyl-1H-pyrazolo[4,3-h]quinazolin-1-yl)piperidine-1-carboxylate [(I), R1=phenyl, R2=tert-butyl 4-piperidine-1-carboxylate, R3=NH₂, A=—CH=CH—]

Conv. 1

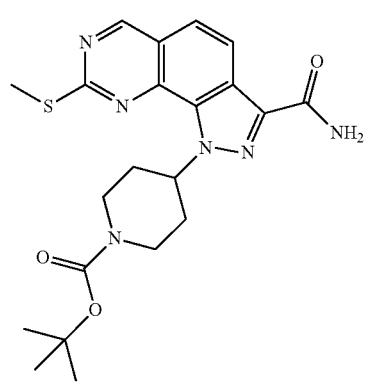

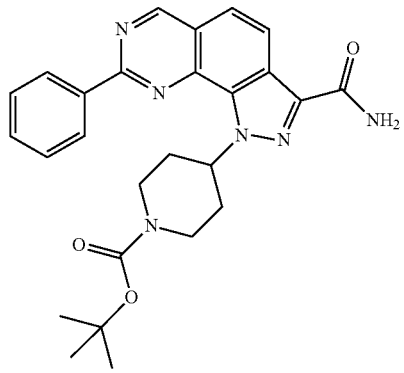

A dry microwave process vial was charged with tert-butyl 4-[3-carbamoyl-8-(methylsulfanyl)-1H-pyrazolo[4,3-h]quinazolin-1-yl]piperidine-1-carboxylate 30 mg (0.068 mmol), 3 ml of dry THF, phenylboronic acid 16.5 mg (0.138 mmol), copper thiophenecarboxylate 38.7 mg (0.203 mmol), and Pd(PPh₃)₄ 7.8 mg (0.007 mmol, 10 mol %). The mixture was subsequently heated in a microwave reactor at 100° C. for 60 min. After cooling, the mixture was diluted with ethyl acetate and washed with 25% aqueous ammonia. The aqueous layer was extracted again with ethyl acetate, the combined organic phases were dried over Na₂SO₄ and the residue, after evaporation, purified by column chromatography on silica gel (DCM/EtOAc/EtOH, 6/4/0.2) to provide 29 mg of the title product (90%) as a white solid. LC/MS (m/z): 473.0 [M+H]$^+$, HPLC (254 nm) method 4 Rt 2.95

Example 46

8-phenyl-1-(piperidin-4-yl)-1H-pyrazolo[4,3-h]quinazoline-3-carboxamide hydrochloride [(I), R1=phenyl, R2=piperidin-4-yl, R3=NH₂, A=—CH=CH—] (cpd 109)

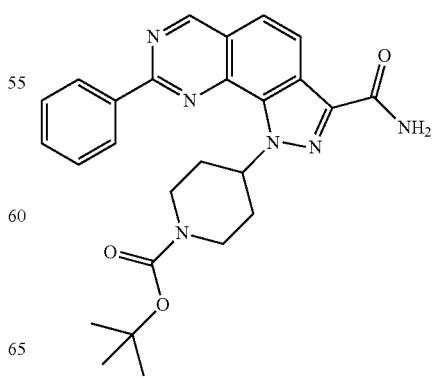

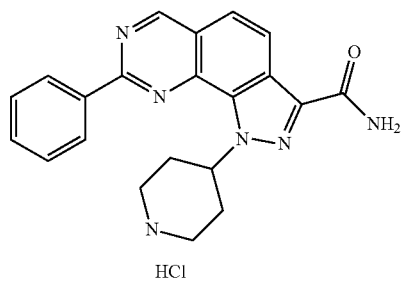

HCl

Tert-butyl 4-(3-carbamoyl-8-phenyl-1H-pyrazolo[4,3-h]quinazolin-1-yl)piperidine-1-carboxylate was dissolved in 1,4-dioxane (2 ml) and 4 M HCl in 1,4 dioxane (3 ml) was added. The solution was stirred at room temperature for 1 hour. The volatiles were removed in vacuo and the residue triturated with diethyl ether, filtered and dried in oven (40° C.) under vacuum for 2 hours, to obtain the title compound 27 mg (99%). LC/MS (254 nm) HPLC method 2 Rt 4.47 min. $^1$H NMR (401 MHz, DMSO-d6) δ 9.82 (s, 1H), 8.94 (br. s., 1H), 8.85 (br. s., 1H), 8.52-8.66 (m, 2H), 8.41 (d, J=8.67 Hz, 1H), 7.89 (d, J=8.67 Hz, 1H), 7.84 (br. s., 1H), 7.57-7.73 (m, 4H), 6.16-6.37 (m, 1H), 3.54-3.67 (m, 2H). HRMS (ESI) calcd for C21H20N6O [M+H]$^+$ 373.1771 found 373.1783

Operating in an analogous way, the following compounds were prepared:

1-(piperidin-4-yl)-8-(thiophen-3-yl)-1H-pyrazolo[4,3-h]quinazoline-3-carboxamide trifluoroacetate [(I), R1=thiophen-3-yl, R2=piperidin-4-yl, R3=NH$_2$, A=—CH═CH—] (cpd 110) LC/MS (254 nm) HPLC method 2 Rt 4.32 min. $^1$H NMR (401 MHz, DMSO-d6) δ 9.74 (s, 1H), 8.69 (br. s., 1H), 8.64 (dd, J=1.10, 3.05 Hz, 1H), 8.59 (br. s., 1H), 8.37 (d, J=8.67 Hz, 1H), 8.03 (dd, J=0.98, 5.00 Hz, 1H), 7.85 (d, J=8.79 Hz, 1H), 7.80 (s, 1H), 7.77 (dd, J=3.05, 5.00 Hz, 1H), 7.65 (s, 1H), 6.11-6.43 (m, 1H), 3.48-3.73 (m, J=12.94 Hz, 2H), 3.35-3.42 (m, 2H). HRMS (ESI) calcd for C19H18N6OS [M+H]$^+$ 379.1336 found 379.1332;

1-(4-aminocyclohexyl)-8-phenyl-1H-pyrazolo[4,3-h]quinazoline-3-carboxamide hydrochloride [(I), R1=phenyl, R2=4-aminocyclohexyl, R3=NH$_2$, A=—CH═CH—] (cpd 111) LC/MS (254 nm) HPLC method 2 Rt 3.91 min. $^1$H NMR (401 MHz, DMSO-d6) δ 9.79 (s, 1H), 8.59 (dd, J=1.89, 7.75 Hz, 2H), 8.40 (d, J=8.67 Hz, 1H), 8.04 (br. s., 3H), 7.86 (d, J=8.79 Hz, 1H), 7.73 (br. s., 1H), 7.69 (br. s., 1H), 7.56-7.67 (m, 3H), 6.32 (quin, J=4.61 Hz, 1H), 2.10-2.46 (m, 6H), 1.85-2.03 (m, J=4.52 Hz, 2H). HRMS (ESI) calcd for C22H22N6O [M+H]$^+$ 387.1928 found 387.1929; and 1-(4-aminocyclohexyl)-8-(thiophen-3-yl)-1H-pyrazolo[4,3-h]quinazoline-3-carboxamide trifluoroacetate [(I), R1=thiophen-3-yl, R2=4-aminocyclohexyl, R3=NH$_2$, A=—CH═CH—] (cpd 112) LC/MS (254 nm) HPLC method 2 Rt 3.73 min. $^1$H NMR (401 MHz, DMSO-d6) δ 9.71 (s, 1H), 8.51-8.69 (m, 1H), 8.36 (d, J=8.67 Hz, 1H), 7.99 (d, J=5.13 Hz, 1H), 7.89 (br. s., 2H), 7.83 (d, J=8.79 Hz, 1H), 7.76 (dd, J=3.05, 5.00 Hz, 2H), 7.58 (s, 1H), 6.27 (quin, J=4.61 Hz, 1H), 3.38-3.46 (m, J=4.64 Hz, 2H), 2.31-2.42 (m, 2H), 2.20-2.31 (m, 2H), 2.04-2.18 (m, 2H), 1.96 (dd, J=5.00, 13.06 Hz, 1H). HRMS (ESI) calcd for C20H20N6OS [M+H]$^+$ 393.1492 found 393.1481.

Example 47

Tert-butyl 4-[3-carbamoyl-8-(methylsulfonyl)-1H-pyrazolo[4,3-h]quinazolin-1-yl]piperidine-1-carboxylate [(I), R4=Me, X═SO$_2$, R2=tert-butyl 4-piperidine-1-carboxylate, R3=NH$_2$, A=—CH═CH—]

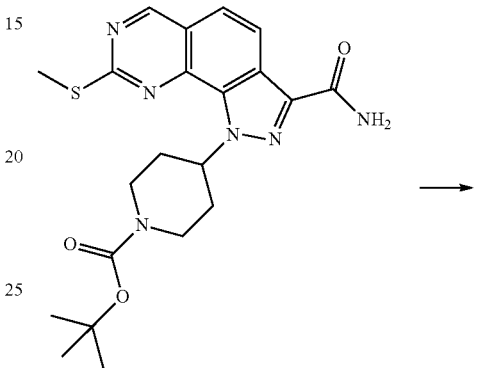

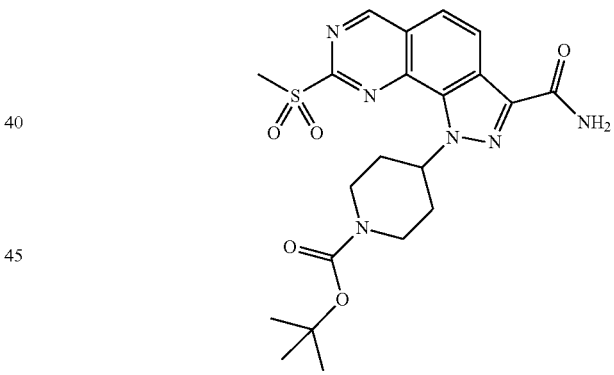

100 mg (0.225 mmol) of tert-butyl 4-[3-carbamoyl-8-(methylsulfanyl)-1H-pyrazolo[4,3-h]quinazolin-1-yl]piperidine-1-carboxylate were dissolved in 10 ml of DCM. 77.3 mg (0.448 mmol) of mCPBA (m-chloroperbenzoic acid) were added at room temperature and stirred at the same temperature for 60 min. 1 ml of saturated aqueous sodium sulfite solution was added and stirred for 30 min. The reaction mixture was washed with brine, dried over Na$_2$SO$_4$ and concentrated under reduced pressure, to provide the title compound 100 mg (94%) as a yellow solid. LC/MS (m/z): 475.0 [M+H]$^+$, HPLC (254 nm) method 4 Rt 2.01 min.

Example 48

1-(piperidin-4-yl)-8-(pyrrolidin-1-yl)-1H-pyrazolo[4,3-h]quinazoline-3-carboxamide hydrochloride [(I), R1=pyrrolidin-1-yl, R2=piperidin-4-yl, R3=NH$_2$, A=—CH=CH—] (compound 113)

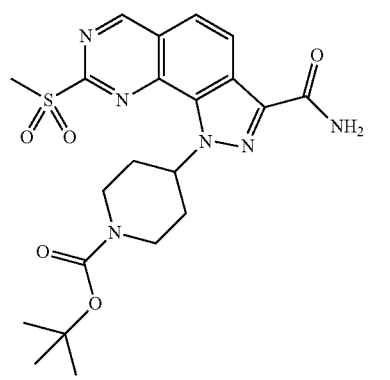

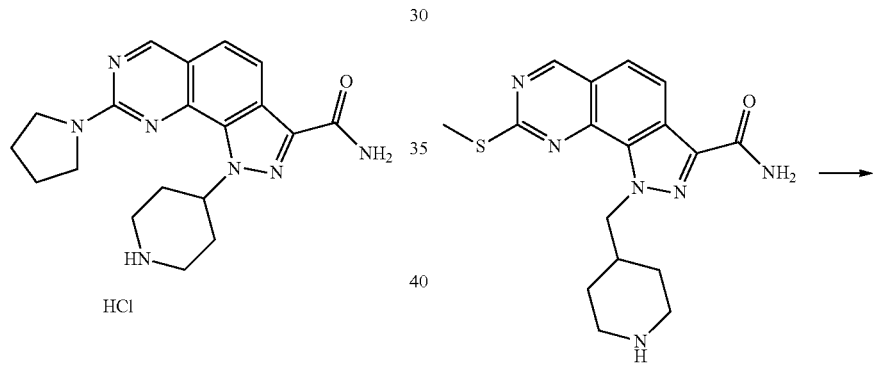

HCl

To a solution of tert-butyl 4-[3-carbamoyl-8-(methylsulfonyl)-1H-pyrazolo[4,3-h]quinazolin-1-yl]piperidine-1-carboxylate 30 mg (0.063 mmol) in THF (3 ml), pyrrolidine 70 μl (1 mmol) was added. The solution was stirred at room temperature for 1 hour and monitored by LC/MS. The reaction mixture was cooled to room temperature; the separated solid was filtered and washed with diethyl ether to afford tert-butyl 4-[3-carbamoyl-8-(pyrrolidin-1-yl)-1H-pyrazolo[4,3-h]quinazolin-1-yl]piperidine-1-carboxylate 15 mg (50%). LC/MS (m/z): 475.0 [M+H]$^+$, HPLC (254 nm) method 4 Rt 2.01 min.

Tert-butyl 4-[3-carbamoyl-8-(pyrrolidin-1-yl)-1H-pyrazolo[4,3-h]quinazolin-1-yl]piperidine-1-carboxylate 15 mg (0.032 mmol) was dissolved in 1,4 dioxane (2 ml) and 4 M HCl in 1,4-dioxane 3 ml (3 mmol) was added. The mixture was stirred at room temperature for 1 h. The volatiles were removed in vacuo and the obtained residue was triturated with diethyl ether, filtered and dried, to afford the title compound 12 mg (93%). LC/MS (254 nm) HPLC method 2 Rt 4.11 min. $^1$H NMR (401 MHz, DMSO-d6) δ 9.11-9.31 (m, 1H), 8.89 (br. s., 1H), 8.57-8.82 (m, 1H), 7.89 (d, J=8.67 Hz, 1H), 7.64 (br. s., 1H), 7.41-7.58 (m, 2H), 5.80-6.23 (m, 1H), 3.69 (br. s., 4H), 3.50-3.62 (m, 2H), 3.07-3.27 (m, 2H), 2.35-2.45 (m, 4H), 1.94-2.15 (m, 4H). HRMS (ESI) calcd for C19H23N7O [M+H]$^+$ 366.2037 found 366.2047.

Operating in an analogous way, the following compound was obtained:

8-(morpholin-4-yl)-1-(piperidin-4-yl)-1H-pyrazolo[4,3-h]quinazoline-3-carboxamide hydrochloride [(I), R1=pyrrolidin-1-yl, R2=piperidin-4-yl, R3=NH$_2$, A=—CH=CH—] (cpd 114) LC/MS (254 nm) HPLC method 2 Rt 3.92 min. $^1$H NMR (401 MHz, DMSO-d6) δ 9.31 (s, 1H), 8.82 (br. s., 1H), 8.73 (br. s., 1H), 7.98 (d, J=8.67 Hz, 1H), 7.64-7.73 (m, 1H), 7.51-7.62 (m, 2H), 5.87-6.09 (m, 1H), 3.85-3.91 (m, 4H), 3.72-3.80 (m, 4H), 3.54 (d, J=13.43 Hz, 2H), 3.18 (d, J=5.86 Hz, 3H), 2.35-2.44 (m, 4H). HRMS (ESI) calcd for C19H23N7O2 [M+H]$^+$ 382.1986 found 382.2004.

Example 49

1-{[1-(2-aminoethyl)piperidin-4-yl]methyl}-8-(methylsulfanyl)-1H-pyrazolo[4,3-h]quinazoline-3-carboxamide hydrochloride [(I), R1=Me-S—, R2=1-(2-aminoethyl)piperidin-4-yl]methyl, R3=NH$_2$, A=—CH=CH—] (cpd 115)

Conv. n

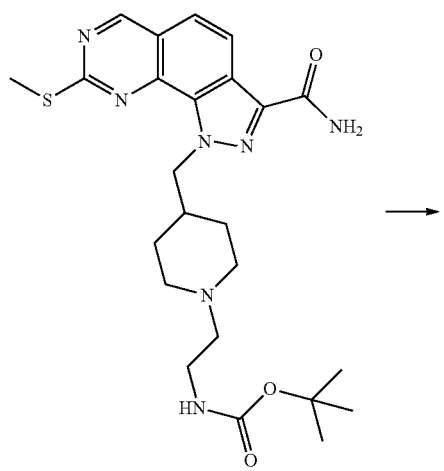

-continued

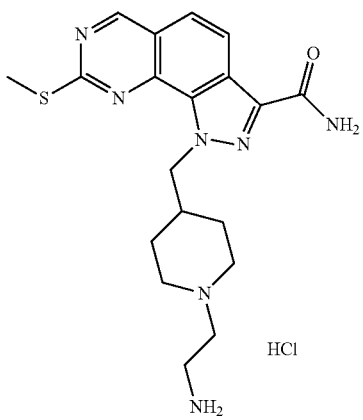

To a solution of 8-(methylsulfanyl)-1-(piperidin-4-ylmethyl)-1H-pyrazolo[4,3-h]quinazoline-3-carboxamide 26 mg (0.073 mmol) in methanol (1.5 ml) and DMF (1 ml), acetic acid 13 μl (0.219 mmol), tert-butyl (2-oxoethyl)carbamate 69.6 mg (0.438 mmol) and NaCNBH₃ 28 mg (0.438 mmol) were added. The mixture was stirred at r.t. for 18 hours, consequently the volatiles were removed in vacuo. The residue was dissolved with ethyl acetate and portioned with water; the organic layer was washed with brine, dried over Na₂SO₄ and concentrated. The crude was purified by flash chromatography (DCM/MeOH 95/5) to give tert-butyl[2-(4-{[3-carbamoyl-8-(methylsulfanyl)-1H-pyrazolo[4,3-h]quinazolin-1-yl]methyl}piperidin-1-yl)ethyl]carbamate 27 mg as a white solid (75%). LC/MS (254) HPLC method 2 Rt 3.86 min. ¹H NMR (401 MHz, DMSO-d6) δ 9.47 (s, 1H), 8.28 (d, J=8.67 Hz, 1H), 7.81 (s, 1H), 7.74 (d, J=8.79 Hz, 1H), 7.54 (br. s., 1H), 6.56 (br. s., 1H), 5.08 (d, J=7.32 Hz, 2H), 2.93-3.05 (m, 2H), 2.76-2.84 (m, J=10.25 Hz, 2H), 2.71 (s, 3H), 2.27 (br. s., 1H), 2.14 (br. s., 1H), 1.75-1.94 (m, 2H), 1.12-1.49 (m, 17H). HRMS (ESI) calcd for C24H33N7O3S [M+H]⁺ 500.2439 found 500.2436.

The obtained tert-butyl[2-(4-{[3-carbamoyl-8-(methylsulfanyl)-1H-pyrazolo[4,3-h]quinazolin-1-yl]methyl}piperidin-1-yl)ethyl]carbamate was dissolved in 4M HCl in 1,4-dioxane 2 ml, stirred at r.t. for 2 hours. Afterwards, the volatiles were removed under vacuum, the residue was suspended with diethyl ether and filtered to give the desired product as a pale yellow solid 14 mg (90%). LC/MS (254) HPLC method 2 Rt 3.29 min. ¹H NMR (401 MHz, DMSO-d6) δ 10.78 (br. s., 1H), 9.49 (s, 1H), 8.30 (d, J=8.67 Hz, 1H), 8.12-8.24 (m, 2H), 7.86 (s, 1H), 7.77 (d, J=8.79 Hz, 1H), 7.58 (s, 1H), 5.12 (d, J=7.32 Hz, 1H), 3.47-3.54 (m, 2H), 3.16-3.28 (m, 3H), 2.85-3.01 (m, 1H), 2.76 (s, 2H), 1.73-1.88 (m, 2H), 1.60-1.71 (m, 2H). HRMS (ESI) calcd for C19H25N7OS [M+H]⁺ 400.1914 found 400.1918.

Operating in an analogous way, the following compounds were obtained:

1-{4-[(2-aminoethyl)amino]cyclohexyl}-8-(methylsulfanyl)-1H-pyrazolo[4,3-h]quinazoline-3-carboxamide Hydrochloride [(I), R1=Me-S—, R2=4-(2-aminoethyl)aminocyclohexyl, R3=NH₂, A=—CH=CH—] (cpd 116) HRMS (ESI) calcd for C19H25N7OS [M+H]⁺ 400.1914 found 400.1908; and 1-{4-[(2-aminoethyl)amino]cyclohexyl}-8-(methylsulfanyl)-4,5-dihydro-1H-pyrazolo[4,3-h]quinazoline-3-carboxamide hydrochloride [(I), R1=Me-S—, R2=4-(2-aminoethyl)aminocyclohexyl, R3=NH₂, A=—(CH₂)₂—] (cpd 117) HRMS (ESI) calcd for C19H27N7OS [M+H]⁺ 402.2071 found 402.2074.

Example 50

1-[4-(glycylamino)cyclohexyl]-8-(methylsulfanyl)-1H-pyrazolo[4,3-h]quinazoline-3-carboxamide hydrochloride [(I), R1=Me-S—, R2=4-(glycylamino)cyclohexyl, R3=NH₂, A=—CH=CH—] (cpd 118)

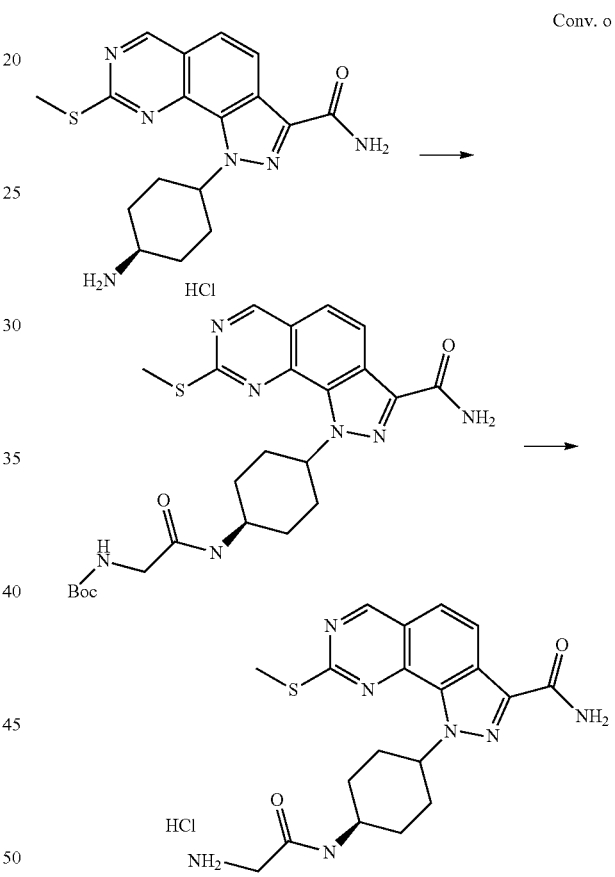

Conv. o 30 mg (0.084 mmol) of 1-(4-aminocyclohexyl)-8-(methylsulfanyl)-1H-pyrazolo[4,3-h]quinazoline-3-carboxamide hydrochloride were dissolved in 2 ml of dimethyl acetamide. To the obtained solution 21 mg (0.126 mmol) of N-(tert-butoxycarbonyl)glycine, 60 μl (0.336 mmol) of DIPEA, 40 mg (0.126 mmol) of TBTU were added. The mixture was stirred at room temperature for 18 hours, the solution was portioned between ethyl acetate and saturated aqueous solution of NaHCO₃, the organic layer was washed with brine, dried over Na₂SO₄ and evaporated under vacuum. The crude was purified by silica gel chromatography (DCM/MeOH/NH₄OH 95/5/0.1) to provide tert-butyl[2-({4-[3-carbamoyl-8-(methylsulfanyl)-1H-pyrazolo[4,3-h]quinazolin-1-yl]cyclohexyl}amino)-2-oxoethyl]carbamate 35 mg (81%) as a white solid. ¹H NMR (401 MHz, DMSO-d6) δ 9.47 (s, 1H), 8.27 (d, J=8.67 Hz, 1H), 7.78 (d, J=6.35 Hz, 1H), 7.74 (d, J=8.67 Hz, 1H), 7.64 (br. s., 1H), 7.55 (br. s., 1H), 6.86 (t, J=5.86 Hz, 1H), 6.00 (br. s., 1H), 3.96 (d, J=2.56 Hz, 1H), 3.62 (d, J=5.61 Hz, 2H), 2.72 (s, 3H), 2.23-2.36 (m, 2H), 1.91-2.11 (m, 4H), 1.68-1.82 (m, 2H), 1.38 (s, 9H).

To a solution of tert-butyl[2-({4-[3-carbamoyl-8-(methylsulfanyl)-1H-pyrazolo[4,3-h]quinazolin-1-yl]cyclohexyl}amino)-2-oxoethyl]carbamate 20 mg (0.039 mmol) 1,4-dioxane (1 ml), 4M HCl in 1,4-dioxane (2 ml 8 mmol) was added. The mixture was stirred at room temperature for 2 hours. The solvent was removed under reduced pressure and the crude was diluted with diethyl ether and filtered, to give the final hydrochloride salt 15 mg as yellow solid (88%). LC/MS (254) HPLC method 2 Rt 3.3 min. $^1$H NMR (401 MHz, DMSO-d6) δ 9.48 (s, 1H), 8.46 (d, J=6.96 Hz, 1H), 8.27 (d, J=8.67 Hz, 1H), 7.93-8.11 (m, 3H), 7.75 (d, J=8.79 Hz, 1H), 7.67 (br. s., 1H), 7.51 (br. s., 1H), 5.83-6.10 (m, 1H), 3.96-4.12 (m, 1H), 3.56-3.71 (m, 2H), 2.73 (s, 3H), 2.25-2.39 (m, 2H), 2.04-2.15 (m, 2H), 1.89-2.04 (m, 3H), 1.75-1.88 (m, 2H). HRMS (ESI) calcd for C19H23N7O2S [M+H]$^+$ 414.1707 found 414.1721.

Example 51

1-{4-[(ethylcarbamoyl)amino]cyclohexyl}-8-(methylsulfanyl)-1H-pyrazolo[4,3-h]quinazoline-3-carboxamide [(I), R1=Me-S—, R2=ethylcarbamoyl)amino]cyclohexyl, R3=NH$_2$, A=—CH=CH—] (cpd 119)

hydrochloride were dissolved in 2 ml of dimethylformamide. To the obtained solution 32 μl (0.42 mmol) of ethylisocyanate, 60 μl (0.336 mmol) of DIPEA, were added. The mixture was stirred at 100° C. for 18 hours, the solution was portioned between ethyl acetate and saturated aqueous solution of NaHCO$_3$, and the organic layer was washed with brine, dried over Na$_2$SO$_4$ and evaporated under vacuum. The crude was purified by silica gel chromatography (DCM/MeOH/NH4OH 95/5/1) to provide 1-{4-[(ethylcarbamoyl)amino]cyclohexyl}-8-(methylsulfanyl)-1H-pyrazolo[4,3-h]quinazoline-3-carboxamide 4 mg (11%) as a white solid. LC/MS (254) HPLC method 2 Rt 4.38 min. $^1$H NMR (401 MHz, DMSO-d6) δ 9.47 (s, 1H), 8.27 (d, J=8.67 Hz, 1H), 7.74 (d, J=8.67 Hz, 1H), 7.59 (s, 2H), 6.06 (d, J=7.08 Hz, 1H), 5.89-6.02 (m, 1H), 5.81 (t, J=5.49 Hz, 1H), 3.78-3.88 (m, 1H), 3.00-3.07 (m, 2H), 2.71-2.74 (m, 3H), 2.15-2.29 (m, 2H), 1.99-2.11 (m, 3H), 1.90 (dd, J=3.54, 13.67 Hz, 2H), 1.65-1.79 (m, 2H), 1.01 (t, J=7.20 Hz, 3H). HRMS (ESI) calcd for C20H25N7O2S [M+H]$^+$ 428.1863 found 428.1852.

Example 52

1-(4-carbamimidamidocyclohexyl)-8-(methylsulfanyl)-1H-pyrazolo[4,3-h]quinazoline-3-carboxamide [(I), R1=Me-S—, R2=4-carbamimidamidocyclohexyl, R3=NH$_2$, A=—CH=CH—] (cpd 120)

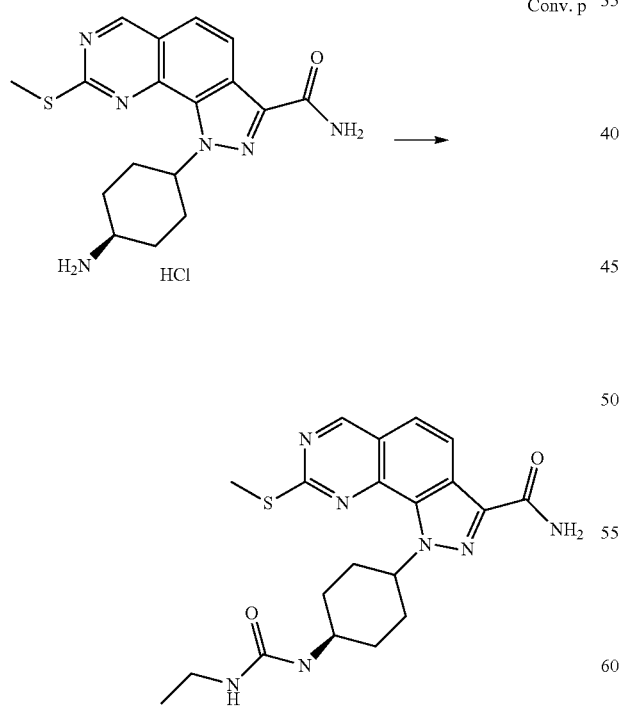

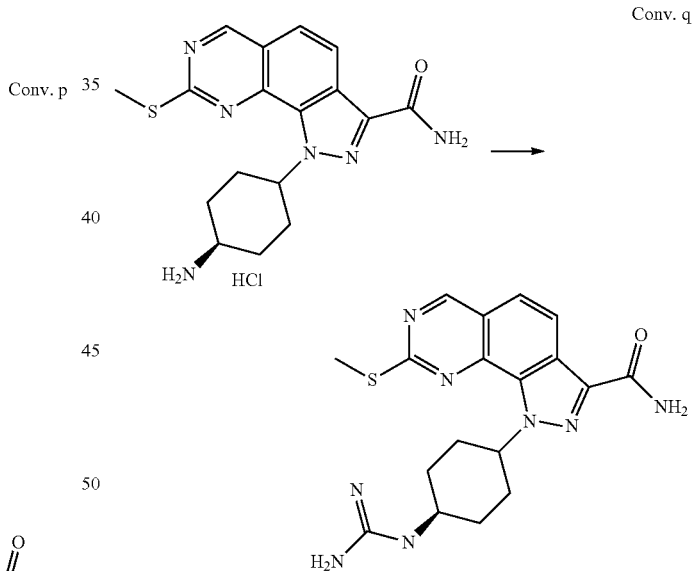

30 mg (0.084 mmol) of 1-(4-aminocyclohexyl)-8-(methylsulfanyl)-1H-pyrazolo[4,3-h]quinazoline-3-carboxamide hydrochloride were dissolved in 2 ml of dimethylformamide. To the obtained solution 70 mg (0.34 mmol) of 3,5-dimethyl-1H-pyrazole-1-carboxylmidamide, 93 μl (0.67 mmol) of TEA, were added. The mixture was stirred at 100° C. for 48 hours, the solution was portioned between ethyl acetate and saturated aqueous solution of NaHCO$_3$, the organic layer was washed with brine, dried over Na$_2$SO$_4$ and evaporated under vacuum. The crude was purified by silica gel chromatography (DCM/MeOH/NH$_4$OH 95/5/1) to provide 1-(4-carbamimidamidocyclohexyl)-8-(methylsulfanyl)-1H-pyrazolo[4,3-h]

quinazoline-3-carboxamide 6 mg (11%) as a yellow solid. LC/MS (m/z): 399.1 [M+H]⁺, HPLC (254 nm) method 3 Rt 4.1 min.

Example 53

1-tert-butyl-8-(methylsulfanyl)-6-(morpholin-4-yl)-1H-pyrazolo[4,3-h]quinazoline-3-carboxamide [(I), R1=Me-S—, R2=tert-butyl, R3=NH₂, R5=morpholin-4-yl, A=—CH=CH—] (cpd 121)

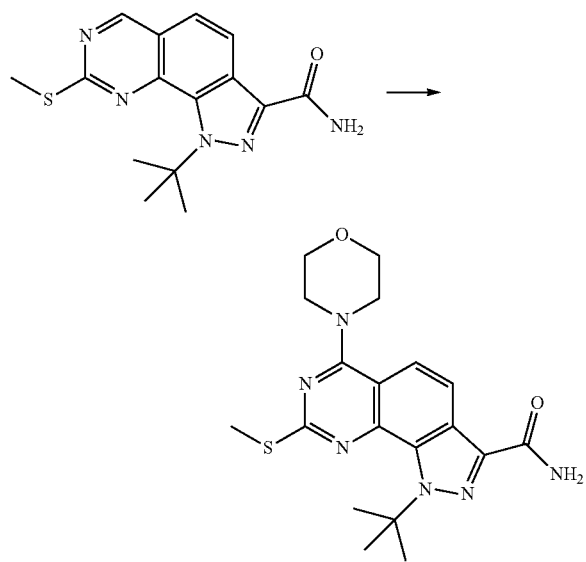

To a solution of 1-tert-butyl-8-(methylsulfanyl)-1H-pyrazolo[4,3-h]quinazoline-3-carboxamide 50 mg (0.158 mmol) in anhydrous THF (2 ml), morpholine 137 ul (1.26 mmol), LiN(TMS)₂ 1M in THF (4 ml, 4 mmol) were added. The mixture was stirred at r.t. for 48 hours, then diluted with cold water and the obtained precipitate was filtered. The crude was submitted to HPLC/MS purification method 1 to obtain the desired product 5 mg (8%). LC/MS (m/z): 401.0 [M+H]⁺, HPLC (254 nm) method 2 Rt 6.39 min. ¹H NMR (401 MHz, DMSO-d6) δ 8.20 (d, J=8.91 Hz, 1H), 7.67 (d, J=8.91 Hz, 2H), 7.44 (s, 1H), 3.75-3.82 (m, 4H), 3.63-3.69 (m, 4H), 2.64 (s, 3H), 1.97 (s, 9H). HRMS (ESI) calcd for C19H25N6O2S [M+H]⁺ 401.1754 found 428.1757.

Preparation O

1-[2-hydroxy-5-(4-methylpiperazin-1-yl)phenyl]ethanone

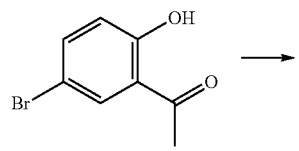

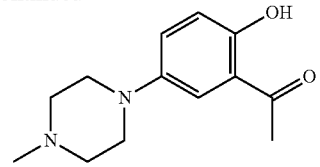

1-(5-bromo-2-hydroxyphenyl)ethanone 1.0 g (4.65 mmol) in THF (10 ml), N-methylpiperazine 0.83 ml (7.45 mmol), LiHMDSA 16.2 ml (16.2 mmol), Pd₂(dba)₃ 68 mg (0.074 mmol) and 2-dicyclohexylphosphino-2'-N,N-dimethylaminobiphenyl 29.3 mg (0.074 mmol) were combined under argon in a capped vial and stirred at 70° C. for 40 minutes. The volatiles were removed in vacuo, the obtained residue was dissolved with water and 1 N HCl (pH=6) and portioned with DCM. The organic phase was washed with brine, dried over Na₂SO₄, filtered and concentrated under reduced pressure. The residue was purified by flash column chromatography (DCM gradient to 10% MeOH/DCM) to provide 532 mg (51%) of desired product as a brown solid. LC/MS (254 nm) HPLC method 2 Rt 3.34 min. ¹H NMR (401 MHz, DMSO-d6) δ 11.45 (s, 1H), 7.21-7.28 (m, 2H), 6.80-6.93 (m, 1H), 2.98-3.10 (m, 4H), 2.63 (s, 3H), 2.44-2.48 (m, 4H), 2.23 (s, 3H). HRMS (ESI) calcd for C13H18N2O2 [M+H]⁺ 235.1441 Found 235.1448.

According to the same methodology, but employing suitable starting material, the following compounds were prepared:

Tert-butyl 4-(3-acetyl-4-hydroxyphenyl)piperazine-1-carboxylate. LC/MS (254 nm) HPLC method 2 Rt 6.61 min. ¹H NMR (401 MHz, DMSO-d6) δ 11.49 (s, 1H), 7.32 (d, J=2.93 Hz, 1H), 7.25-7.30 (m, 1H), 6.88 (d, J=8.91 Hz, 1H), 3.41-3.52 (m, 4H), 2.95-3.05 (m, 4H), 2.64 (s, 3H), 1.42 (s, 9H). HRMS (ESI) calcd for C17H24N2O4 [M+H]⁺ 321.1809 Found 321.1805;

2-hydroxy-5-(4-methylpiperazin-1-yl)benzonitrile. LC/MS (254 nm) HPLC method 2 Rt min. ¹H NMR (401 MHz, DMSO-d6) δ 10.38 (br. s., 1H), 7.18 (dd, J=3.11, 9.09 Hz, 1H), 7.08 (d, J=2.93 Hz, 1H), 6.90 (d, J=9.15 Hz, 1H). HRMS (ESI) calcd for C12H15N3O [M+H]⁺ 218.1288 Found 218.1287; and 2-fluoro-4-(4-methylpiperazin-1-yl)phenol. LC/MS (m/z): 211.1 [M+H]⁺, HPLC (254 nm) method 3 Rt 4.00 min.

Preparation P 4-(4-methylpiperazin-1-yl)phenol

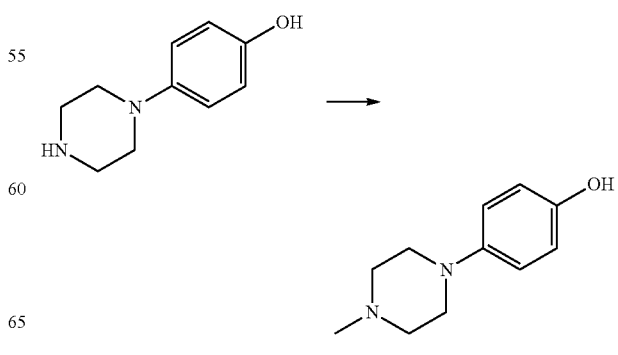

4-(piperazin-1-yl)phenol 2 g (11.24 mmol) and formaldehyde 4.5 ml (37% in water, 56 mmol) were suspended in a mixture of THF/AcOH 5/1 and stirred at room temperature. After 30 minutes, sodium triacetoxyborohydride 4.7 g (22.5 mmol) was added portion-wise. The reaction was let stir a few hours and evaporated down. The crude was purified on silica gel with ethyl acetate/ethanol/NH$_3$ 7 N in methanol 8/2/0.2 to give 2.3 g of pink solid as a free base. LC/MS (254 nm) HPLC method 2 Rt 2.4 min. $^1$H NMR (401 MHz, DMSO-d6) δ 8.78 (s, 1H), 6.71-6.84 (m, 2H), 6.56-6.69 (m, 2H), 2.85-3.03 (m, 4H), 2.46 (br. s., 4H), 2.23 (s, 3H). HRMS (ESI) calcd for C11H16N2O [M+H]$^+$ 193.1336 Found 193.1328.

Operating in an analogous way, the following compound was obtained:

3-(4-methylpiperazin-1-yl)phenol. LC/MS (254 nm) HPLC method 2 Rt min. $^1$H NMR (401 MHz, DMSO-d6) δ 9.07 (s, 1H), 6.96 (t, J=8.12 Hz, 1H), 6.34-6.38 (m, 1H), 6.28 (t, J=2.32 Hz, 1H), 6.19 (ddd, J=0.73, 2.20, 7.93 Hz, 1H), 3.02-3.09 (m, 4H), 2.41-2.46 (m, 4H), 2.22 (s, 3H). HRMS (ESI) calcd for C11H16N2O [M+H]$^+$ 193.1336 Found 193.1329.

Preparation Q

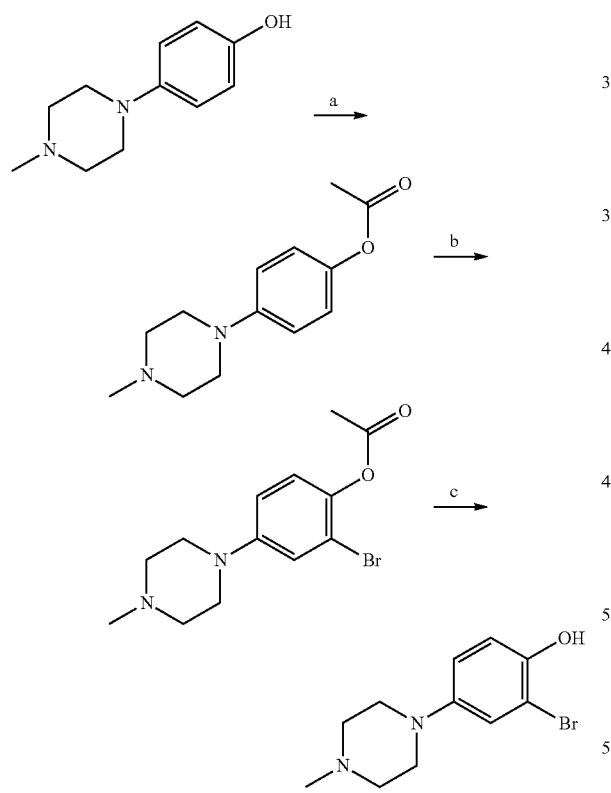

Step a. Preparation of 4-(4-methylpiperazin-1-yl)phenyl acetate

A mixture of 4-(4-methylpiperazin-1-yl)phenol 1.080 mg (5.59 mmol) and TEA 1.72 ml (12.3 mmol) in DCM was cooled in an ice bath and 0.44 ml (6.15 mmol) of acetyl chloride were added dropwise. After completion, the reaction was filtered, the organic phase quickly extracted with water, dried over Na$_2$SO$_4$ and evaporated down to give a light pink solid. LC/MS (m/z): 235.4 [M+H]$^+$, HPLC (254 nm) method 3 Rt 1.89 min.

Step b. Preparation of 2-bromo-4-(4-methylpiperazin-1-yl)phenyl acetate

A solution of 4-(4-methylpiperazin-1-yl)phenyl acetate 247 mg (1.05 mmol) and p-toluenesulfonic acid 209 mg (1.1 mmol) in acetonitrile was cooled in an ice bath and bromine 0.056 ml (1.1 mmol) was added dropwise. The reaction was stirred at room temperature until complete (3-4 hours), was diluted with ethyl acetate and extracted with water and saturated NaHCO$_3$. The organic phase, dried over Na$_2$SO$_4$ and evaporated, was purified by flash chromatography (DCM/MeOH 85/15) to give the product as a dark brown oil. HPLC (254 nm) method 2 Rt 4.05 min. $^1$H NMR (400 MHz, DMSO-d6) δ ppm 2.25 (s, 3H) 2.36 (s, 3H) 2.39 (m, 4H) 3.44 (m, 4H) 6.50 (dd. J=2.1, 8.3 Hz, 1H) 7.03 (d, J=8.3 Hz, 1H) 7.21 (d, J=2.1 Hz, 1H). Mass. Calc. 313.0546 Mass. Found: 313.0538

Step c. Preparation of 2-bromo-4-(4-methylpiperazin-1-yl)phenol 2-bromo-4-(4-methylpiperazin-1-yl)phenyl acetate 280 mg (1.03 mmol) were dissolved in methanol and reacted with 2 ml of 1 N NaOH. After two hours the reaction was acidified with glacial acetic acid, evaporated and purified on silica with DCM/MeOH 9/1 0.4% 7M NH$_3$ in MeOH. LC/MS (m/z): 273.2 [M+H]$^+$, HPLC (254 nm) method 3 Rt 2.96 min.

Preparation R

Tert-butyl 3-[(methylsulfonyl)oxy]azepane-1-carboxylate

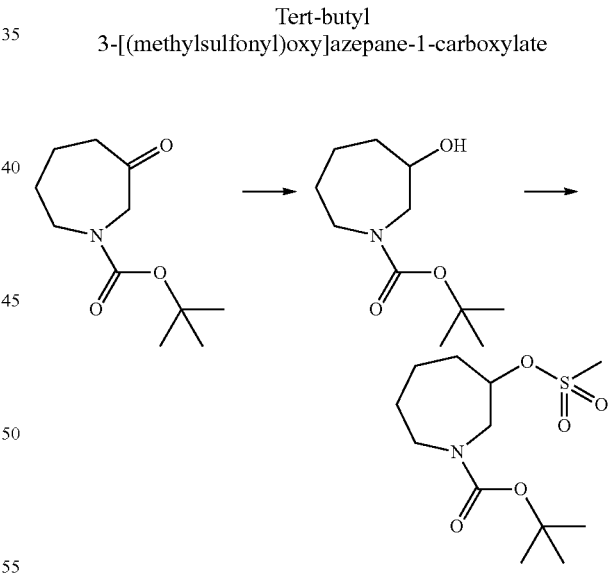

Step a. Preparation of tert-butyl 3-hydroxyazepane-1-carboxylate. A solution of tert-butyl 3-oxoazepane-1-carboxylate 1.07 g (5 mmol) in 50 ml of MeOH was cooled to 0° C. and sodium borohydride 213 mg (6.1 mmol) was added. The solution was slowly warmed to room temperature and stirred for 2 hours. The volatiles were removed under vacuum, the residue was dissolved with ethyl acetate and portioned with water. The organic layer was washed with brine, dried with Na$_2$SO$_4$ and evaporated. The crude was purified by flash chromatography (EtOAc/hexane 3/7) to give tert-butyl 3-hydroxyazepane-1-carboxylate as a white solid 0.75 g (75%).

¹H NMR (401 MHz, DMSO-d6) δ 4.34-4.65 (m, 1H), 3.52-3.80 (m, 1H), 3.05-3.25 (m, 2H), 1.70-1.89 (m, 2H), 1.58-1.69 (m, 1H), 1.43-1.56 (m, 3H), 1.39 (s, 9H).

Step b. Preparation of tert-butyl 3-[(methylsulfonyl)oxy]azepane-1-carboxylate. To a solution of tert-butyl 3-hydroxyazepane-1-carboxylate 200 mg (0.93 mmol) in DCM (10 ml), cooled to 0° C., TEA 190 µl (1.4 mmol) and mesyl chloride 114 µl (1.4 mmol) were added. The solution was let warm to room temperature and stirred for 2 hours. The mixture was diluted with saturated aqueous solution of NaHCO₃, the organic layer was separated and washed with brine, dried over Na₂SO₄ and concentrated under reduced pressure, the obtained thick pale yellow oil, was directly submitted to the next step. LC/MS (m/z): 294.0 [M+H]⁺, HPLC (254 nm) method 3 Rt 5.65 min.

According to the same methodology, but employing suitable starting material, the following compound was prepared:

2,2,2-trichloroethyl (3-exo)-3-[(methylsulfonyl)oxy]-8-azabicyclo[3.2.1]octane-8-carboxylate. LC/MS (m/z): 381.1 [M+H]⁺, HPLC (254 nm) method 3 Rt 5.56 min.

Example 901

Pim Kinase Binding Activity

PIM-1, -2, and -3 enzymes were generated as fusion proteins expressed in bacteria and purified by IMAC column chromatography (Sun, X., Chiu, J. F., and He, Q. Y. (2005) Expert Rev. Proteomics, 2:649-657). A fluorescent-labeled Pim-specific peptide substrate, was custom synthesized by American Peptide Company (Sunnyvale, Calif.). Reaction Buffer contained 10 mM HEPES, pH 7.2, 10 mM MgCl₂, 0.01% Tween 20, 2 mM DTT. Termination Buffer contained 190 mM HEPES, pH 7.2, 0.015% Brij-35, 0.2% Coating Reagent 3 (Caliper Life Sciences, Hopkinton, Mass.), 20 mM EDTA. Separation Buffer contained 100 mM HEPES, pH 7.2, 0.015% Brij-35, 0.1% Coating Reagent 3, 1:200 Coating Reagent 8 (Caliper Life Sciences, Hopkinton, Mass.), 10 mM EDTA and 5% DMSO.

PIM reactions were carried out in a final volume of 10 µL per well in a 384-well plate. A standard enzymatic reaction, initiated by the addition of 5 µL 2×ATP and test compound to 5 µL of 2× enzyme and FAM-peptide, contained 20 pM PIM1, 50 pM PIM2, or 55 pM PIM3, 1 µM FAM-peptide, and 10 µM ATP, in Reaction Buffer. After 90 minutes of incubation at room temperature, the phosphorylation reaction was stopped by the addition of 10 µL Termination Buffer. The product and substrate in each independent reaction were separated on a 12-sipper microfluidic chip (Caliper Life Sciences, Hopkinton, Mass.) run on a Caliper LC3000® (Caliper Life Sciences, Hopkinton, Mass.). The separation of product and substrate was optimized by choosing voltages and pressure using Caliper's Optimizer software (Hopkinton, Mass.). The separation conditions used a downstream voltage of −500V, an upstream voltage of −2150V, and a screening pressure of −1.2 psi. The product and substrate fluorophore were excited at 488 nm and detected at 530 nm. Substrate conversion was calculated from the electropherogram using HTS Well Analyzer software (Caliper Life Sciences, Hopkinton, Mass.). Ki values for the test compound were calculated. See Table 1 for representative PIM1 LC3K Ki in micromolar values of exemplary compounds.

Example 902

In Vitro Cell Proliferation Potency Assays

BaF3 is a murine interleukin-3 dependent pro-B cell line, useful as a model system for assessing both the potency and downstream signaling of kinase oncogenes ("Ba/F3 cells and their use in kinase drug discovery", Warmuth, M, et al, (January 2007) Current Opinion in Oncology, Vol 19(1):55-60). BaF3 parental line was obtained from the DSMZ repository. BaF3 lines transfected with PIM1 or PIM2 were generated. Mouse IL-3 was purchased from R&D Systems. G418 was purchased from Clontech. Media for BaF3 parental line contained RPMI, 10% FBS, 2 mM L-Glutamine, 2 ng/mL mIL-3. Media for BaF3 PIM1 & 2 lines contained RPMI, 10% FBS, 2 mM L-Glutamine, 250 µg/mL. Media for MM1.S (multiple myeloma cells) line contained RPMI, 10% FBS, 2 mM L-Glutamine.

Parental cells, BaF3 PIM1 cells, BaF3 PIM2 cells, and MM1.S (multiple myeloma) cells were seeded at 2 k/well, 5 k/well, 5 k/well, and 10 k/well respectively, in a 384-well plate, at 45 µL/well. Test compound was added at 5 µL/well. BaF3 cells (parental and transfected) were incubated overnight, while MM1.S cells were incubated for 72 hours at 37° C., 5% CO₂. CELL TITER GLO® Reagent (Promega) was added at 50 µL/well, the plates were incubated for 30 minutes, and their luminescence read on an HT Analyst. IC₅₀/EC₅₀ values for the test compound were calculated.

Representative compounds of the present invention were tested as described above and found to exhibit a Ki/IC₅₀/EC₅₀ as shown below in Table 2.

TABLE 2

| No. | Prolif BaF3 IL3 (EC50) µM | Prolif BaF3 PIM1 (EC50) µM |
|---|---|---|
| 51 | 9.3 | 0.21 |
| 85 | 13 | 0.31 |
| 93 | 7.9 | 0.044 |
| 112 | 2 | 1.3 |

The invention claimed is:
1. A compound selected from the group consisting of:
1-(2-hydroxyethyl)-8-(methylsulfanyl)-1H-pyrazolo[4,3-h]quinazoline-3-carboxamide;
1-tert-butyl-N-methyl-8-(methylsulfanyl)-1H-pyrazolo[4,3-h]quinazoline-3-carboxamide;
1-(2-aminoethyl)-8-(methylsulfanyl)-1H-pyrazolo[4,3-h]quinazoline-3-carboxamide;
8-(methylsulfanyl)-1-(piperidin-4-ylmethyl)-1H-pyrazolo[4,3-h]quinazoline-3-carboxamide;
1-(2-hydroxyethyl)-8-[4-(4-methylpiperazin-1-yl)phenoxy]-1H-pyrazolo[4,3-h]quinazoline-3-carboxamide;
1-tert-butyl-8-[4-(4-methylpiperazin-1-yl)phenoxy]-1H-pyrazolo[4,3-h]quinazoline-3-carboxamide;
1-tert-butyl-8-(methylsulfanyl)-1H-pyrazolo[4,3-h]quinazoline-3-carboxamide
8-(methylsulfanyl)-1-(piperidin-4-yl)-1H-pyrazolo[4,3-h]quinazoline-3-carboxamide;
8-(methylsulfanyl)-1-(piperidin-3-yl)-1H-pyrazolo[4,3-h]quinazoline-3-carboxamide;
1-(4-aminocyclohexyl)-8-(methylsulfanyl)-1H-pyrazolo[4,3-h]quinazoline-3-carboxamide;
8-(methylsulfanyl)-1-(piperidin-3-ylmethyl)-1H-pyrazolo[4,3-h]quinazoline-3-carboxamide;
8-methoxy-1-(piperidin-4-yl)-1H-pyrazolo[4,3-h]quinazoline-3-carboxamide;
1-[(3-exo)-8-azabicyclo[3.2.1]oct-3-yl]-8-(methylsulfanyl)-1H-pyrazolo[4,3-h]quinazoline-3-carboxamide;
1-(4-aminobutan-2-yl)-8-(methylsulfanyl)-1H-pyrazolo[4,3-h]quinazoline-3-carboxamide;
1-(1-azabicyclo[2.2.2]oct-3-yl)-8-(methylsulfanyl)-1H-pyrazolo[4,3-h]quinazoline-3-carboxamide;

8-(methylsulfanyl)-1-(tetrahydro-2H-pyran-4-yl)-1H-pyrazolo[4,3-h]quinazoline-3-carboxamide;

1-[trans-3-(hydroxymethyl)cyclobutyl]-8-(methylsulfanyl)-1H-pyrazolo[4,3-h]quinazoline-3-carboxamide; and 1-[cis-3-(hydroxymethyl)cyclobutyl]-8-(methylsulfanyl)-1H-pyrazolo[4,3-h]quinazoline-3-carboxamide.

2. A pharmaceutical composition comprising a therapeutically effective amount of a compound of claim 1, or a pharmaceutically acceptable salt thereof, and at least one pharmaceutically acceptable excipient, carrier and/or diluent.

* * * * *